United States Patent

Mermerian et al.

(10) Patent No.: US 8,674,115 B2
(45) Date of Patent: Mar. 18, 2014

(54) CRTH2 MODULATORS

(75) Inventors: Ara Mermerian, Melrose, MA (US); Bo Peng, Arlington, MA (US); Colleen Hudson, Malden, MA (US); Charles Kim, Cambridge, MA (US); Joel Moore, Lexington, MA (US); Jason Rohde, Andover, MA (US); Kevin Sprott, Needham, MA (US); Regina Graul, Duxbury, MA (US); Takashi Nakai, Newton, MA (US); James Jia, Somerville, MA (US); Wilmin Bartolini, Amesbury, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/969,840

(22) Filed: Dec. 16, 2010

(65) Prior Publication Data

US 2011/0150834 A1   Jun. 23, 2011

Related U.S. Application Data

(60) Provisional application No. 61/289,841, filed on Dec. 23, 2009.

(51) Int. Cl.
*C07D 207/30* (2006.01)
*A61K 31/40* (2006.01)

(52) U.S. Cl.
USPC ........................ 548/561; 514/422

(58) Field of Classification Search
USPC .......................... 548/561; 514/422
See application file for complete search history.

(56) References Cited

U.S. PATENT DOCUMENTS

| | | | |
|---|---|---|---|
| 3,773,919 A | 11/1973 | Boswell et al. | |
| 3,995,631 A | 12/1976 | Higuchi et al. | |
| 4,203,440 A | 5/1980 | Theeuwes | |
| 4,627,850 A | 12/1986 | Deters et al. | |
| 4,672,850 A | 6/1987 | Konersmann | |
| 5,145,684 A | 9/1992 | Liversidge et al. | |
| 5,304,121 A | 4/1994 | Sahatjian | |
| 5,324,280 A | 6/1994 | Wong et al. | |
| 5,859,042 A * | 1/1999 | Lee et al. | 514/400 |
| 5,886,026 A | 3/1999 | Hunter et al. | |
| 6,099,562 A | 8/2000 | Ding et al. | |
| 6,342,249 B1 | 1/2002 | Wong et al. | |
| 6,419,952 B2 | 7/2002 | Wong et al. | |
| 8,022,063 B2 | 9/2011 | Ulven et al. | |

FOREIGN PATENT DOCUMENTS

| | | |
|---|---|---|
| EC | SP06-7115 A | 3/2007 |
| EC | SP06-7104 | 4/2007 |
| EP | 378404 | 8/1994 |
| WO | 9309100 | 5/1993 |
| WO | 0039125 | 7/2000 |
| WO | 02070523 | 9/2002 |
| WO | 03035627 | 5/2003 |
| WO | 03084954 | 10/2003 |
| WO | 2004011443 | 2/2004 |
| WO | 2004014875 | 2/2004 |
| WO | 2004018425 | 3/2004 |
| WO | 2004018435 | 3/2004 |
| WO | 2005011634 | 2/2005 |
| WO | 2005115374 | 12/2005 |
| WO | 2005116001 | 12/2005 |
| WO | 2006063763 | 6/2006 |
| WO | 2008012511 | 1/2008 |

OTHER PUBLICATIONS

Grimstrup et al. (Bioorganic & Medicinal Chemistry Letters, vol. 20, Issue 5, Mar. 1, 2010, pp. 1638-1641).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chapters 9-10 provided.*
Wermuth (The Practice of Medicinal Chemistry, 2nd ed. (2003), 768 pages), chs. 5, 10, 12-15 provided.*
Mai et al. (The International Journal of Biochemistry & Cell Biology 41 (2009) 235-247).*
Pfefferkorn et al. (Bioorg. Med. Chem. Lett. 17 (2007) 4538-4544).*
Delie and Blanco-Prieto 2005 Molecule, 10:65-80.
Steinke and Borish 2001, Respiratory Research, vol. 2, pp. 66-70.
Leckie et al., Dec. 23, 2000, The Lancet, vol. 356, pp. 2144-2148.
International Search Report for PCT/US10/060671 dated Apr. 6, 2011.
O'Neil et al., (2006), The Merck Index, (14th edition), Whitehouse Station, NJ: Merck 7 Co., Inc., p. 684.

* cited by examiner

*Primary Examiner* — Robert Havlin
(74) *Attorney, Agent, or Firm* — Kenyon & Kenyon LLP

(57) ABSTRACT

Modulators of CRTH2, particularly antagonists of CRTH2, that are useful for treating various disorders, including asthma and respiratory disorders are disclosed. The compounds fall within a genus described by formula I:

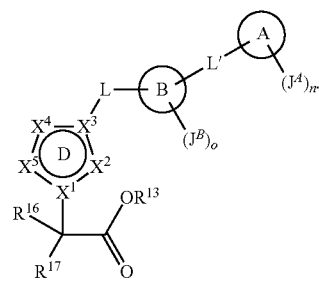

42 Claims, No Drawings

CRTH2 MODULATORS

This application claims the benefit of U.S. Provisional Application No. 61/289,841 filed Dec. 23, 2009.

FIELD OF THE INVENTION

This disclosure relates to modulators of chemoattractant receptor-homologous molecule expressed on T helper type 2 cells (CRTH2), particularly CRTH2 antagonists that are useful for treating various disorders, including asthma and allergic and respiratory disorders.

BACKGROUND

CRTH2 is a $G\alpha_i$ protein-coupled receptor involved in both mediating PGD2-induced chemoattraction and in activation of specific cell types involved in allergic inflammation. CRTH2 is expressed by Th2 cells, eosinophils and basophils, but not by Th1 cells, B cells or NK cells. PGD2 is produced by allergen-activated mast cells and has been implicated as a pro-inflammatory mediator in various allergic diseases, such as asthma, rhinitis and allergies. Thus, blocking binding of $PGD_2$ to CRTH2 is a useful therapeutic strategy for treatment of such diseases.

CRTH2 agonists activate eosinophils, basophils and Th2 cells in vitro, resulting in induction of actin polymerization, calcium influx, CD11b expression and chemotaxis. Injection of a CRTH2 agonist in vivo can elicit transient recruitment of eosinophils from bone marrow into the blood. A genetic study of African American and Chinese cohorts found that polymorphisms in CRTH2 were tightly associated with asthma susceptibility. Thus, it has been suggested that modulators of CRTH2, particularly CRTH2 inhibitors, may be useful in the prevention and/or treatment of allergic asthma and other allergic disorders as recruitment and/or activation of eosinophils, basophils and Th2 cells is a prominent feature of the changes that occur in the asthmatic lung. Similar activation of these cell types, or subsets thereof, is believed to play an important role in the etiology of other diseases, including eosinophilic esophagitis and atopic dermatitis. This fact, combined with the fact that CRTH2 mediates $PGD_2$-induced chemotaxis, suggests that compounds that alter chemotaxis by inhibiting CRTH2 activity could be useful in controlling various diseases and disorders, including, without limitation, allergic asthma, chronic airway inflammation, atopic dermatitis, chronic obstructive pulmonary disease (COPD), and/or eosinophilic esophagitis.

Compounds that alter chemotaxis by inhibiting CRTH2 activity could also be useful in controlling allergic rhinitis, which is classified as either seasonal (SAR) or perennial (PAR) depending upon the type of trigger and duration of symptoms. SAR symptoms occur in the spring, summer and/or early fall and can be triggered by outdoor allergens such as airborne tree, grass and weed pollens while PAR is usually persistent and chronic with symptoms occurring year-round and is commonly associated with indoor allergens such as dust mites, animal dander and/or mold spores. Symptoms of allergic rhinitis may include runny nose, nasal itching, sneezing, watery eyes and nasal congestion.

CRTH2 agonists can induce desensitization of the cell system by promoting internalization and down regulation of the cell surface receptor. For example, certain CRTH2 agonists can induce desensitization of $PGD_2$-responsive cells to subsequent activation by a CRTH2 agonist. Therefore, CRTH2 modulators that are CRTH2 agonists may be therapeutically useful because they can cause the desensitization of $PGD_2$-responsive cells. Importantly, CRTH2 agonists may also cause cross-desensitization. Cross-desensitization, which can occur in many cell-signaling systems, refers to a phenomenon whereby an agonist for one receptor can reduce or eliminate sensitivity of a cell type to an unrelated agonist/receptor signaling system. For example, treatment with the CRTH2 agonist indomethacin reduces expression of CCR3, the receptor for the chemoattractant, eotaxin.

CRTH2 is also found on cell types outside the immune system, including spinal cord neurons and brain. $PGD_2$ activation of CRTH2, e.g., during inflammation, can lead to hyperalgesia, allodynia and neuropathic pain. Thus, inhibitors of CRTH2 may be used to treat hyperalgesia, allodynia and neuropathic pain.

Accordingly, there is a need to develop inhibitors of CRTH2, which could be used to prevent and/or treat disorders such as allergic rhinitis, asthma, chronic airway inflammation, atopic dermatitis, chronic obstructive pulmonary disease (COPD), eosinophilic esophagitis and/or neuropathic pain.

SUMMARY

In a first aspect, compounds disclosed herein and their pharmaceutically acceptable compositions thereof are effective as CRTH2 modulators. These compounds have the general Structural Formula I, or are pharmaceutically acceptable salts thereof:

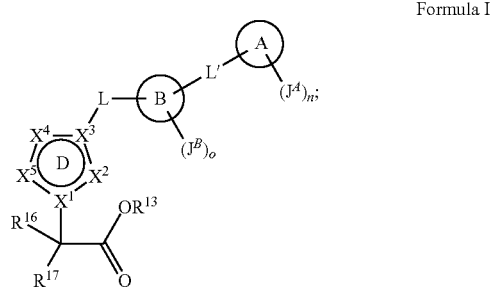

Formula I with the proviso that the compound having Formula I is not a compound selected from 5-[[6-methoxy-3-(4-methoxybenzoyl)-2-methyl-1H-pyrrolo[2,3-b]pyridin-1-yl]methyl]-α,α-dimethyl-2H-Tetrazole-2-acetic acid [CAS Registry No. 1097838-63-5], 5-[[5-(benzoylamino)-2-thiazolyl]thio]-2H-tetrazole-2-acetic acid [CAS Registry No. 1099441-56-1], 2-butyl-1-[[4-[(2-carboxybenzoyl)amino]phenyl]methyl]-5-chloro-1H-imidazole-4-acetic acid [CAS Registry No. 114798-40-2], and 2-butyl-1-[[4-[(2-carboxybenzoyl)amino]phenyl]methyl]-5-chloro-1H-imidazole-4-acetic acid [CAS Registry No. 114773-45-4], or a pharmaceutically acceptable salt thereof; wherein:

Ring A is a monocyclic or bicyclic ring selected from a 6 to 10-membered aryl, a 5 to 10-membered heteroaryl, a $C_{3-10}$ cycloaliphatic and a 4 to 10-membered heterocycle; wherein said heteroaryl or heterocycle contains from 0 to 3 ring heteroatoms independently selected from N, O and S.

Ring B is a monocyclic ring selected from a phenyl and a 5 to 6-membered heteroaryl, wherein said heteroaryl contains up to three ring heteroatoms independently selected from N, O, and S.

Ring D is a 5-membered heteroaryl; wherein $x^1$ is selected from N and C; $x^2$ is selected from N and $C-R^2$; $x^3$ is selected from N and C; $x^4$ is selected from N and $C-R^4$; and $x^5$ is selected from N and C—$R^5$; provided that at least one of $x^1$ or $x^3$ is N, but both are not simultaneously N.

$R^2$ is selected from —H, a halogen, —$NO_2$, —CN, a $C_{1-6}$ aliphatic radical, a $C_{1-6}$ alkoxy and a cyclopropyl ring, wherein $R^2$ is independently substituted with from 0 to 3 instances of $R^A$; wherein each $R^A$ is independently selected from a halogen, —OH, a $C_{1-2}$ alkoxy and a $C_{1-2}$ haloalkoxy.

$R^4$ is selected from a halogen, —$NO_2$, —CN, —$R^6$, —$OR^6$, —$C(O)R^6$, —$C(O)OR^6$, —$N(R^6)_2$, —$S(O)_pR^6$, —$S(O)_2N(R^6)_2$, —$NR^6S(O)_2R^6$, —$C(O)N(R^6)_2$ and —$NR^6C(O)R^6$.

$R^5$ is selected from a halogen, —$NO_2$, —CN, —$R^6$, —$OR^6$, —$C(O)R^6$, —$C(O)OR^6$, —$N(R^6)_2$, —$S(O)_pR^6$, —$S(O)_2N(R^6)_2$, —$NR^6S(O)_2R^6$, —$C(O)N(R^6)_2$ and —$NR^6C(O)R^6$.

p is an integer selected from 0, 1 and 2.

Each $R^6$ is independently selected from —H, a $C_{1-6}$ aliphatic radical, and a monocyclic or bicyclic ring; wherein: the ring is selected from a 6 to 10-membered aryl, a 5 to 10-membered heteroaryl, a $C_{3-10}$ cycloaliphatic and a 4 to 10-membered heterocycle; when $R^6$ is a $C_{1-6}$ aliphatic radical, it is independently substituted with from 0 to 6 instances of $R^7$; when $R^6$ is a non-aromatic ring or a heteroaryl, it is independently substituted with from 0 to 6 instances of $R^8$; and when $R^6$ is an aryl, it is independently substituted with from 0 to 6 instances of $R^{8'}$.

Each $R^7$ is independently selected from a halogen, —CN, oxo, —$OR^9$, —$R^{10}$, —$C(O)R^9$, —$C(O)OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$.

Each $R^8$ is independently selected from a halogen, —CN, —$NO_2$, oxo, a $C_{1-6}$ aliphatic radical, —$R^{10}$, —$C(O)R^9$, —$C(O)OR^9$, —$OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$.

Each $R^{8'}$ is independently selected from a halogen, —CN, —$NO_2$, a $C_{1-6}$ aliphatic radical, —$R^{10}$, —$C(O)R^9$, —$C(O)OR^9$, —$OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$.

Each $R^9$ is independently selected from hydrogen, a $C_{1-6}$ aliphatic radical, and a monocyclic or bicyclic ring, wherein the ring is selected from a 6 to 10-membered aryl, a 5 to 10-membered heteroaryl, a $C_{3-10}$ cycloaliphatic and a 4 to 10-membered heterocycle; when $R^9$ is a $C_{1-6}$ aliphatic radical, it is independently substituted with from 0 to 6 instances of $R^{11}$; and when $R^9$ is a ring, it is independently substituted with from 0 to 3 instances of $R^{12}$.

Each $R^{10}$ is a monocyclic or bicyclic ring independently selected from a 6 to 10-membered aryl, a 5 to 10-membered heteroaryl, a $C_{3-10}$ cycloaliphatic and a 4 to 10-membered heterocycle; and $R^{10}$ is independently substituted with from 0 to 3 instances of $R^{12}$.

Each $R^{11}$ is independently selected from a halogen, —CN, —OH, a $C_{1-4}$ alkoxy and a $C_{1-4}$ haloalkoxy.

Each $R^{12}$ is independently selected from a halogen, —CN, —OH, a $C_{1-4}$ alkyl, a $C_{1-4}$ haloalkyl, a $C_{1-4}$ alkoxy and a $C_{1-4}$ haloalkoxy.

$R^{13}$ is selected from —H, a $C_{1-6}$ aliphatic radical, and a monocyclic or bicyclic ring, wherein the ring is selected from a 6 to 10-membered aryl, a 5 to 10-membered heteroaryl, a $C_{3-10}$ cycloaliphatic and a 4 to 10-membered heterocycle; and when $R^{13}$ is a $C_{1-6}$ aliphatic radical, it is independently substituted with from 0 to 6 instances of $R^{14}$; when $R^{13}$ is a non-aromatic ring or a heteroaryl, it is independently substituted with from 0 to 6 instances of $R^{15}$; and when $R^{13}$ is an aryl, it is independently substituted with from 0 to 6 instances of $R^{15'}$.

Each $R^{14}$ is independently selected from a halogen, —CN, oxo, —$OR^9$, —$R^{10}$, —$C(O)R^9$, —$C(O)OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$.

Each $R^{15}$ is independently selected from a halogen, —CN, —$NO_2$, oxo, a $C_{1-6}$ aliphatic radical, —$R^{10}$, —$C(O)R^9$, —$C(O)OR^9$, —$OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$.

Each $R^{15'}$ is independently selected from a halogen, —CN, —$NO_2$, a $C_{1-6}$ aliphatic radical, —$R^{10}$, —$C(O)R^9$, —$C(O)OR^9$, —$OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$.

$R^{16}$ and $R^{17}$ are each independently selected from —H, deuterium, a $C_{1-6}$ alkyl, a $C_{1-6}$ haloalkyl and a halogen, or, alternatively, $R^{16}$ and $R^{17}$ are independently selected from a $C_{1-6}$ alkyl and a $C_{1-6}$ haloalkyl, and $R^{16}$ and $R^{17}$ taken together with the atom to which they are attached form a cyclopropyl or halocyclopropyl ring.

L is a linker selected from a methylene, —C(O)—, —O—, —$S(O)_m$— and —$NR^1$—; wherein when L is a methylene, it is independently substituted with from 0 to 2 instances of $R^{18}$.

m is 0, 1 or 2.

$R^1$ is selected from —H, a $C_{1-6}$ aliphatic radical, a $C_{3-6}$ cycloaliphatic, —$CO(C_{1-6}$ aliphatic), —$CO(C_{3-6}$ cycloaliphatic), —CO-(phenyl), a benzyl and —CO-(benzyl); wherein when $R^1$ is selected from a $C_{1-6}$ aliphatic radical, —CO-(phenyl), a benzyl and —CO-(benzyl), it is independently substituted with from 0 to 3 instances of $R^B$; wherein each $R^B$ is independently selected from a halogen, a $C_{1-2}$ alkyl and a $C_{1-2}$ alkoxy.

Each $R^{18}$ is independently selected from a halogen, —CN, a $C_{1-6}$ aliphatic radical, a $C_{1-6}$ haloaliphatic radical, and a $C_{3-6}$ cycloaliphatic; or, alternatively, each $R^{18}$ is independently selected from a $C_{1-6}$ aliphatic radical and a $C_{1-6}$ haloaliphatic radical, and two $R^{18}$ groups, taken together with the atom to which they are attached, form a cyclopropyl or halocyclopropyl ring.

o is an integer selected from 0, 1 and 2.

Each $J^B$ is independently selected from a halogen, —$NO_2$, —CN, —$R^{19}$, —C(O)H, —C(O)OH, —$C(O)NH_2$, —OH, —SH, —$NH_2$, —$C(O)R^{19}$, —$C(O)OR^{19}$, —$C(O)N(R^{20})R^{19}$, —$N(R^{20})C(O)R^{19}$, —$OR^{19}$, —$SR^{19}$ and —$NR^{19}R^{20}$; or, alternatively, two $J^B$ groups are attached to two vicinal ring B atoms and, together with said ring atoms, form a 5 to 6-membered heterocycle or a 5 to 6-membered heteroaryl, each of said rings independently substituted with from 0 to 2 instances of $R^E$, wherein each $R^E$ is independently selected from a halogen, a $C_{1-2}$ alkyl, a $C_{1-2}$ alkoxy, —CN and —OH.

Each $R^{20}$ is independently selected from a —H and a $C_{1-6}$ aliphatic radical.

Each $R^{19}$ is independently selected from a $C_{1-6}$ aliphatic radical, a $C_{3-6}$ cycloaliphatic, a phenyl, a benzyl, a 4 to 6-membered heterocycle and a 5 to 6-membered heteroaryl; wherein: when $R^{19}$ is a $C_{1-6}$ aliphatic radical, it is independently substituted with from 0 to 3 instances of $R^C$, wherein each $R^C$ is independently selected from a halogen, —CN, —OH, —$NH_2$, a $C_{3-4}$ cycloalkyl, a $C_{3-4}$ halocycloalkyl, a —$O(C_{1-4}$ alkyl), a —$O(C_{3-4}$ cycloalkyl), a —$O(C_{3-4}$ halocycloalkyl), a —$O(C_{1-4}$ haloalkyl), a —$NH(C_{1-4}$ alkyl), a —$N(C_{1-4}$ alkyl)$_2$, and —$NR^V$; wherein —$NR^V$ is a 4 to 6-membered heterocycle containing a ring N atom linked to $J^B$, and wherein said heterocycle contains from 0 to 2 additional ring heteroatoms selected from O and N; when $R^{19}$ is a heterocycle or a heteroaryl it contains from 1 to 3 ring heteroatoms independently selected from N, O and S; when $R^{19}$ is a phenyl, it is independently substituted with from 0 to 3 instances of $R^D$, wherein each $R^D$ is independently selected from a halogen, a $C_{1-4}$ aliphatic radical, —CN, —OH, —NH$_2$, a —O($C_{1-4}$ alkyl), a —NH($C_{1-4}$ alkyl) and a —N($C_{1-4}$ alkyl)$_2$; and when $R^{19}$ is a non-aromatic ring or a heteroaryl, it is independently substituted with from 0 to 3 instances of $R^{D'}$, wherein each $R^{D'}$ is independently selected from a halogen, oxo, a $C_{1-4}$ aliphatic radical, —CN, —OH, —NH$_2$, a —O($C_{1-4}$ alkyl), a —NH($C_{1-4}$ alkyl) and a —N($C_{1-4}$ alkyl)$_2$.

L' is a linker selected from —Y—SO$_2$—, —NR$^{21}$SO$_2$—, —SO$_2$NR$^{21}$—, —Y—C(O)—, —NR$^{21}$C(O)— and —C(O)NR$^{21}$—; wherein Y is selected from a single bond, a straight $C_{1-2}$ alkylene linker, and a branched $C_2$ alkylene linker, wherein the $C_{1-2}$ alkylene linker is independently substituted with from 0 to 3 halogen atoms.

$R^{21}$ is selected from hydrogen, a $C_{1-6}$ alkyl, a $C_{1-6}$ haloalkyl, and a $C_{3-6}$ cycloalkyl ring.

n is an integer selected from 0, 1, 2 and 3.

Each $J^A$ is independently selected from a halogen, —NO$_2$, —CN, —R$^{22}$, —C(O)H, —C(O)OH, —C(O)NH$_2$, —OH, —SH and —NH$_2$, —C(O)R$^{22}$, —C(O)OR$^{22}$, —C(O)N(R$^{23}$)R$^{22}$, —N(R$^{23}$)C(O)R$^{22}$, —OR$^{22}$, —SR$^{22}$ and —NR$^{22}$R$^{23}$.

Each $R^{23}$ is selected from a —H and a $C_{1-6}$ aliphatic radical.

Each $R^{22}$ is selected from a $C_{1-6}$ aliphatic radical, a $C_{3-6}$ cycloaliphatic ring, a phenyl, a benzyl, a 4 to 6-membered heterocycle and a 5 to 6-membered heteroaryl; wherein, when $R^{22}$ is a $C_{1-6}$ aliphatic radical, it is independently substituted with from 0 to 3 instances of $R^F$, wherein each $R^F$ is independently selected from a halogen, —CN, —OH, —NH$_2$, a $C_{3-4}$ cycloalkyl, a $C_{3-4}$ halocycloalkyl, a —O($C_{1-4}$ alkyl), a —O($C_{3-4}$ cycloalkyl), a —O($C_{3-4}$ halocycloalkyl), a —O($C_{1-4}$ haloalkyl), a —NH($C_{1-4}$ alkyl), a —N($C_{1-4}$ alkyl)$_2$ and —NR$^V$; wherein —NR$^V$ is a 4 to 6-membered heterocycle containing a ring N atom linked to $J^B$, and wherein the heterocycle contains from 0 to 2 additional ring heteroatoms selected from O and N; when $R^{22}$ is a heterocycle or a heteroaryl, the ring contains from 1 to 3 ring heteroatoms independently selected from N, O and S; when $R^{22}$ is a non-aromatic ring or a 5 to 6-membered heteroaryl, it is independently substituted with from 0 to 3 instances of $R^G$, wherein each $R^G$ is independently selected from a halogen, oxo, a $C_{1-4}$ aliphatic radical, —CN, —OH, —NH$_2$, a —O($C_{1-4}$ alkyl), a —NH($C_{1-4}$ alkyl) and a —N($C_{1-4}$ alkyl)$_2$; and when $R^{22}$ is a phenyl 1, it is independently substituted with from 0 to 3 instances of $R^{G'}$, wherein each $R^{G'}$ is independently selected from a halogen, a $C_{1-4}$ aliphatic radical, —CN, —OH, —NH$_2$, —O($C_{1-4}$ alkyl). —NH($C_{1-4}$ alkyl) and —N($C_{1-4}$ alkyl)$_2$.

In another aspect, this disclosure provides compositions comprising a pharmaceutically acceptable carrier and a compound described above.

In another aspect, the disclosure relates to a method for preventing or treating a disease involving a CRTH2 receptor or lessening the severity of a disease involving a CRTH2 receptor, in a patient suffering from such disease. The method comprises administering to the patient a therapeutically effective amount of a compound or pharmaceutical composition described herein, either alone or in combination therapy. Typical diseases that involve the CRTH2 receptor and that can be treated with the compounds and pharmaceutical compositions described herein, either alone or in combination therapy, include, without limitation, asthma, allergic rhinitis and chronic obstructive pulmonary disease (COPD).

DETAILED DESCRIPTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and a material described herein but includes any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Description of Exemplary Compounds:
Definitions and General Terminology

For purposes of this disclosure, the chemical elements are identified in accordance with the Periodic Table of the Elements, CAS version, and the Handbook of Chemistry and Physics, 75.sup.th Ed. 1994. Additionally, general principles of organic chemistry are described in "Organic Chemistry", Thomas Sorrell, University Science Books, Sausalito: 1999, and "March's Advanced Organic Chemistry", 5.sup.th Ed., Smith, M. B. and March, J., eds. John Wiley & Sons, New York: 2001, which are herein incorporated by reference in their entirety.

As described herein, compounds of the invention may optionally be substituted with one or more substituents, such as illustrated generally below, or as exemplified by particular classes, subclasses, and species of the invention. The phrase "optionally substituted" is used interchangeably with the phrase "substituted or unsubstituted." In general, the term "substituted", refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. If a substituent radical or structure is not identified or defined as "optionally substituted", the substituent radical or structure is not substituted. As it will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. It will be understood by one of ordinary skill in the art that when a group is characterized as substituted (as opposed to optionally substituted) with, e.g., "up to 3" substituents, it can only be substituted with 1, 2 or 3 substituents.

When any variable occurs more than one time at any position, its definition on each occurrence is independent from every other occurrence, unless otherwise indicated.

Selection of substituents and combinations envisioned by this disclosure are only those that result in the formation of stable or chemically feasible compounds. Such choices and combinations will be apparent to those of ordinary sill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound or chemically feasible compound is one that is not substantially altered when kept at a temperature of 25° C. or less, in the absence of moisture or other chemically reactive conditions, for at least a week.

A compound, such as the compounds of the invention or other compounds herein disclosed, may be present in its free form (e.g. an amorphous form, a crystalline form or polymorphs). Under certain conditions, compounds may also form salts, and/or other multi-component crystalline forms (e.g. solvates, hydrates and co-crystals). As used herein, the term co-form is synonymous with the term multi-component crystalline form. When one of the components in the co-form has clearly transferred a proton to the other component, the resulting co-form is referred to as a "salt". When both compounds in a multi-component crystalline form are independently solids at room temperature, the resulting co-form is referred to as a "co-crystal". In co-crystals no proton transfer takes place between the different components of the co-form. The formation of a salt or a co-crystal is determined by how large is the difference in the pKas between the partners that form the mixture. As used herein, a "solvate" refers to an association or complex of one or more solvent molecules and a compound disclosed herein (or its salts or co-crystals). A "hydrate" is a particular type of solvate in which the solvent is water. Examples of solvents that can form solvates include, but are not limited to: water, isopropanol, ethanol, methanol, (dimethyl sulfoxide) DMSO, ethyl acetate, acetic acid, ethanolamine, tetrahydrofuran (THF), dichloromethane (DCM), N,N-dimethylformamide (DMF).

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are within the scope of the disclosure.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group" or "aliphatic radical", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like.

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" refers to a linear or branched-chain monovalent hydrocarbon radical with at least one site of unsaturation, i.e., a carbon-carbon, $sp^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances the term can be used in the phrase "aromatic carbocycle", and in this case it refers to an "aryl group" as defined below.

The term "cycloaliphatic" or "cycloaliphatic ring" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_3$-$C_{12}$ hydrocarbon or a bicyclic $C_7$-$C_{12}$ hydrocarbon. In some embodiments, any individual ring in a bicyclic or tricyclic ring system has 3 to 7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

"Heterocycle" (or "heterocyclyl" or "heterocyclic), as used herein, refers to a ring system in which one or more ring atomsatoms are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle"). In some instances the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3 to 18 ring atoms in which one or more ring atoms is a heteroatom independently selected from oxygen, sulfur or nitrogen, and each ring in the system contains 3 to 7 ring atoms. In other embodiments, a heterocycle may be a monocycle having 3-7 ring atoms (2-6 carbon atoms and 1-4 heteroatoms) or a bicycle having 7-10 ring atoms (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo[2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is in the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring atoms. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more ring heteroatoms, wherein each ring in the system contains 3 to 7 ring atoms and which has a single point of attachment to the rest of the molecule. Unless otherwise specified, a heteroaryl ring system may be monocyclic, bicyclic or tricyclic and have a total of five to fourteen ring atoms. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6,5 heteroaromatic system, as used herein, for example, is a six membered heteroaromatic ring fused to a second five membered ring wherein the radical or point of attachment is on the six membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tri-cyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to a bond or an atom or a chain of atoms connecting two different parts of a molecule. The two atoms that are connected through the bridge (usually but not always, two tertiary carbon atoms) are referred to as "bridgeheads". Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl.

"Spiro" bicyclic ring systems share only one ring atom (usually, but not always, a quaternary carbon atom).

The term "ring atom" refers to an atom such as C, N, O or S that is part of the ring of an aromatic ring, a cycloaliphatic ring or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR$^+$ (as in N-substituted pyrrolidinyl).

In some embodiments, two independent occurrences of a variable may be taken together with the atom(s) to which each variable is bound to form a 5 to 8-membered, heterocyclyl, aryl, or heteroaryl ring or a 3 to 8-membered cycloalkyl ring. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, carbocyclyl or aryl ring, wherein the group is attached to the rest of the molecule by a single point of attachment; and b) two independent occurrences of a substituent that are bound to different atoms and are taken together with both of those atoms to form a heterocyclyl, heteroaryl, carbocyclyl or aryl ring, wherein the ring that is formed has two points of attachment with the rest of the molecule. For example, where a phenyl group is substituted with two occurrences of —OR° as in Formula D1:

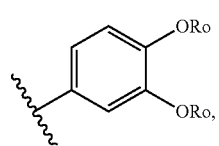

D$_1$ these two occurrences of —OR° may be taken together with the aryl ring carbon atoms to which they are bound to form a fused 6-membered oxygen containing heterocyclic ring as in Formula D2:

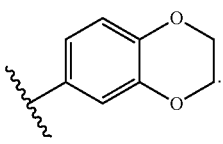

D$_2$

It will be appreciated that a variety of other rings can be formed when two independent occurrences of a substituent are taken together with the atom(s) to which each substituent is bound and that the examples detailed above are not intended to be limiting.

In some embodiments, an alkyl or aliphatic chain can be optionally interrupted with another atom or group. This means that a methylene unit of the alkyl or aliphatic chain can optionally be replaced with said other atom or group. Unless otherwise specified, the optional replacements form a chemically stable compound. Optional interruptions can occur both within the chain and/or at either end of the chain; i.e. both at the point of attachment(s) to the rest of the molecule and/or at the terminal end. Two optional replacements can also be adjacent to each other within a chain so long as it results in a chemically stable compound. Unless otherwise specified, if the replacement or interruption occurs at a terminal end of the chain, the replacement atom is bound to a H on the terminal end. For example, if —CH$_2$CH$_2$CH$_3$ were optionally interrupted with —O—, the resulting chain could be —OCH$_2$CH$_3$, —CH$_2$OCH$_3$, or —CH$_2$CH$_2$OH. In another example, if the divalent linker —CH$_2$CH$_2$CH$_2$— were optionally interrupted with —O—, the resulting linker could be —OCH$_2$CH$_2$—, —CH$_2$OCH$_2$—, or —CH$_2$CH$_2$O—. The optional replacements can also completely replace all of the carbon atoms in a chain. For example, a C$_3$ aliphatic linker can be optionally replaced by —N(R$^\$$)—, —C(O)—, and —N(R$^\$$)— to form —N(R$^\$$)C(O)N(R$^\$$)— (a urea linker).

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent at the end of the substituent bound to the rest of the chemical structure. Alkylcarboxy (e.g., alkyl-C(O)O— or alkyl-O(CO)—) and alkylcarboxyaryl (e.g., alkyl-C(O)O-aryl- or alkyl-O(CO)-aryl-) are examples of carboxy groups used internally.

As described herein, a bond drawn from a substituent to the center of one ring within a multiple-ring system (as shown below), represents substitution with the substituent at any substitutable position in any of the rings within the multiple ring system. For example, formula D3 represents possible substitution with a substituent X at any of the positions shown in formula D4:

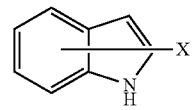

D$_3$

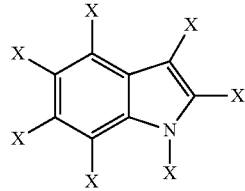

D$_4$

This also applies to multiple ring systems fused to optional ring systems (which would be represented by dotted lines). For example, in Formula D5, X is an optional substituent both for ring A and ring B (ring B being an optional ring).

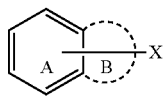

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

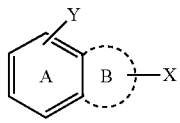

As used herein, the terms "alkoxy" or "alkylthio" refer to an alkyl group, as previously defined, attached to the molecule, or to another chain or ring, through an oxygen ("alkoxy" i.e., —O-alkyl) or a sulfur ("alkylthio" i.e., —S-alkyl) atom.

The terms $C_{n-m}$"alkoxyalkyl", $C_{n-m}$"alkoxyalkenyl", $C_{n-m}$"alkoxyaliphatic", and $C_{n-m}$"alkoxyalkoxy" mean alkyl, alkenyl, aliphatic or alkoxy, as the case may be, substituted with one or more alkoxy groups, wherein the combined total number of carbons of the alkyl and alkoxy groups, alkenyl and alkoxy groups, aliphatic and alkoxy groups or alkoxy and alkoxy groups, combined, as the case may be, is between the values of n and m. For example, a $C_{4-6}$ alkoxyalkyl has a total of 4-6 carbons divided between the alkyl and alkoxy portion; e.g. it can be —CH$_2$OCH$_2$CH$_2$CH$_3$, —CH$_2$CH$_2$OCH$_2$CH$_3$ or —CH$_2$CH$_2$CH$_2$OCH$_3$.

When the moieties described in the preceding paragraph are optionally substituted, they can be substituted in either or both of the portions on either side of the oxygen or sulfur. For example, an optionally substituted $C_4$ alkoxyalkyl could be, for instance, —CH$_2$CH$_2$OCH$_2$(Me)CH$_3$ or —CH$_2$(OH)OCH$_2$CH$_2$CH$_3$; a $C_5$ alkoxyalkenyl could be, for instance, —CH═CHOCH$_2$CH$_2$CH$_3$ or —CH═CHCH$_2$OCH$_2$CH$_3$.

The terms aryloxy, arylthio, benzyloxy or benzylthio, refer to an aryl or benzyl group attached to the molecule, or to another chain or ring, through an oxygen ("aryloxy", benzyloxy e.g., —O-Ph, —OCH$_2$Ph) or sulfur ("arylthio" e.g., —S-Ph, —S—CH$_2$Ph) atom. Further, the terms "aryloxyalkyl", "benzyloxyalkyl" "aryloxyalkenyl" and "aryloxyaliphatic" mean alkyl, alkenyl or aliphatic, as the case may be, substituted with one or more aryloxy or benzyloxy groups, as the case may be. In this case, the number of atoms for each aryl, aryloxy, alkyl, alkenyl or aliphatic will be indicated separately. Thus, a 5-6-membered aryloxy($C_{1-4}$alkyl) is a 5-6 membered aryl ring, attached via an oxygen atom to a $C_{1-4}$ alkyl chain which, in turn, is attached to the rest of the molecule via the terminal carbon of the $C_{1-4}$ alkyl chain.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH$_2$CHF$_2$ and a $C_{1-2}$ haloalkoxy could be —OC(Br)HCHF$_2$. This term includes perfluorinated alkyl groups, such as —CF$_3$ and —CF$_2$CF$_3$.

As used herein, the term "cyano" refers to —CN (or —C≡N).

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a $C_{1-3}$ cyanoalkyl could be —C(CN)$_2$CH$_2$CH$_3$ and a $C_{1-2}$ cyanoalkenyl could be ═CHCH$_2$(CN).

As used herein, an "amino" group refers to —NH$_2$.

The terms "aminoalkyl", "aminoalkenyl", "aminoaliphatic", and "aminoalkoxy" mean alkyl, alkenyl, aliphatic or alkoxy, as the case may be, substituted with one or more amino groups. For example a $C_{1-3}$ aminoalkyl could be —CH(NH$_2$)CH$_2$CH$_2$NH$_2$ and a $C_{1-2}$ aminoalkoxy could be —OCH$_2$CH$_2$NH$_2$.

The term "hydroxyl" or "hydroxy" refer to —OH.

The terms "hydroxyalkyl", "hydroxyalkenyl", "hydroxyaliphatic", and "hydroxyalkoxy" mean alkyl, alkenyl, aliphatic or alkoxy, as the case may be, substituted with one or more —OH groups. For example a $C_{1-3}$ hydroxyalkyl could be —CH$_2$CH$_2$(OH)CH$_3$ and a $C_4$ hydroxyalkoxy could be —OCH$_2$C(CH$_3$)(OH)CH$_3$.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to ═O, wherein oxo is usually, but not always, attached to a carbon atom. An aliphatic chain can be optionally interrupted by a carbonyl group or can optionally be substituted by an oxo group, and both expressions refer to the same: e.g. —CH$_2$—C(O)—CH$_3$.

As used herein, in the context of resin chemistry (e.g. using solid resins or soluble resins or beads), the term "linker" refers to a bifunctional chemical moiety attaching a compound to a solid support or soluble support.

In all other situations, a "linker", as used herein, refers to a divalent group in which the two free valences are on different atoms (e.g. carbon or heteroatom) or are on the same atom but can be substituted by two different substituents. For example, a methylene group can be $C_1$ alkyl linker (—CH$_2$—) which can be substituted by two different groups, one for each of the free valences (e.g. as in Ph-CH$_2$-Ph, wherein methylene acts as a linker between two phenyl rings). Ethylene can be $C_2$ alkyl linker (—CH$_2$CH$_2$—) wherein the two free valences are on different atoms. The amide group, for example, can act as a linker when placed in an internal position of a chain (e.g. —CONH—). A linker can be the result of interrupting an aliphatic chain by certain functional groups or of replacing methylene units on said chain by said functional groups. E.g. a linker can be a $C_{1-6}$ aliphatic chain in which up to two methylene units are substituted by —C(O)— or —NH— (as in —CH$_2$—NH—CH$_2$—C(O)—CH$_2$— or —CH$_2$—NH—C(O)—CH$_2$—). An alternative way to define the same —CH$_2$—NH—CH$_2$—C(O)—CH$_2$— and —CH$_2$—NH—C(O)—CH$_2$— groups is as a $C_3$ alkyl chain optionally interrupted by up to two —C(O)— or —NH— moieties. Cyclic groups can also form linkers: e.g. a 1,6-cyclohexanediyl can be a linker between two R groups, as in

A linker can additionally be optionally substituted in any portion or position.

Divalent groups of the type R—CH= or R₂C=, wherein both free valences are in the same atom and are attached to the same substituent, are also possible. In this case, they will be referred to by their IUPAC accepted names. For instance an alkylidene (such as, for example, a methylidene (=CH$_2$) or an ethylidene (=CH—CH$_3$)) would not be encompassed by the definition of a linker in this disclosure.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999. As used herein, the term "displaceable moiety" or "leaving group" refers to a group that is associated with an aliphatic or aromatic group as defined herein and is subject to being displaced by nucleophilic attack by a nucleophile.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-Ethyl-3-(3-dimethylaminopropyl)carbodiimide), DCC (dicyclohexylcarbodiimide), BOP (Benzotriazol-1-yloxy-tris(dimethylamino)-phosphonium hexafluorophosphate), pyBOP ((Benzotriazol-1-yloxy)tripyrrolidinophosphonium Hexafluorophosphate), 2,4,6-tripropyl-1,3,5,2,4,6-trioxatriphosphorinane-2,4,6-trioxide (T$_3$P), etc.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Compounds of the Invention

In one aspect, the invention is a compound having Structural Formula I, or a pharmaceutically acceptable salt thereof:

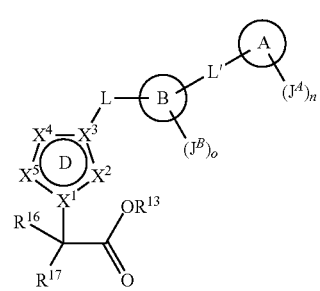

Formula I with the proviso that the compound having Formula I is not a compound selected from 5-[[6-methoxy-3-(4-methoxybenzoyl)-2-methyl-1H-pyrrolo[2,3-b]pyridin-1-yl]methyl]-α,α-dimethyl-2H-Tetrazole-2-acetic acid [CAS Registry No. 1097838-63-5], 5-[[5-(benzoylamino)-2-thiazolyl]thio]-2H-tetrazole-2-acetic acid [CAS Registry No. 1099441-56-1], 2-butyl-1-[[4-[(2-carboxybenzoyl)amino]phenyl]methyl]-5-chloro-1H-imidazole-4-acetic acid [CAS Registry No. 114798-40-2], and 2-butyl-1-[[4-[(2-carboxybenzoyl)amino]phenyl]methyl]-5-chloro-1H-imidazole-4-acetic acid [CAS Registry No. 114773-45-4], or a pharmaceutically acceptable salt thereof; wherein:

ring A is a monocyclic or bicyclic ring selected from a 6 to 10-membered aryl, a 5 to 10-membered heteroaryl, a $C_{3-10}$ cycloaliphatic and a 4 to 10-membered heterocycle; wherein said heteroaryl or heterocycle contains from 0 to 3 ring heteroatoms independently selected from N, O and S;

ring B is a monocyclic ring selected from a phenyl and a 5 to 6-membered heteroaryl, wherein said heteroaryl contains up to three ring heteroatoms independently selected from N, O and S;

ring D is a 5-membered heteroaryl; wherein
$x^1$ is selected from N and C;
$x^2$ is selected from N and C—R$^2$;
$x^3$ is selected from N and C;
$x^4$ is selected from N and C—R$^4$; and
$x^5$ is selected from N and C—R$^5$;
provided that at least one of $x^1$ or $x^3$ is N, but both are not simultaneously N;

R$^2$ is selected from —H, a halogen, —NO$_2$, —CN, a $C_{1-6}$ aliphatic radical, a $C_{1-6}$ alkoxy and a cyclopropyl ring, wherein R$^2$ is independently substituted with from 0 to 3 instances of R$^4$; wherein
each R$^4$ is independently selected from a halogen, —OH, a $C_{1-2}$ alkoxy and a $C_{1-2}$ haloalkoxy;

R$^4$ is selected from a halogen, —NO$_2$, —CN, —R$^6$, —OR$^6$, —C(O)R$^6$, —C(O)OR$^6$, —N(R$^6$)$_2$, —S(O)$_p$R$^6$, —S(O)$_2$N(R$^6$)$_2$, —NR$^6$S(O)$_2$R$^6$, —C(O)N(R$^6$)$_2$ and —NR$^6$C(O)R$^6$;

R$^5$ is selected from a halogen, —NO$_2$, —CN, —R$^6$, —OR$^6$, —C(O)R$^6$, —C(O)OR$^6$, —N(R$^6$)$_2$, —S(O)$_p$R$^6$, —S(O)$_2$N(R$^6$)$_2$, —NR$^6$S(O)$_2$R$^6$, —C(O)N(R$^6$)$_2$ and —NR$^6$C(O)R$^6$;

p is an integer selected from 0, 1 and 2;
each R$^6$ is independently selected from —H, a $C_{1-6}$ aliphatic radical, and a monocyclic or bicyclic ring; wherein the ring is selected from a 6 to 10-membered aryl, a 5 to 10-membered heteroaryl, a $C_{3-10}$ cycloaliphatic and a 4 to 10-membered heterocycle; wherein
when R$^6$ is a $C_{1-6}$ aliphatic radical, it is independently substituted with from 0 to 6 instances of R$^7$,
when R$^6$ is a non-aromatic ring or a heteroaryl, it is independently substituted with from 0 to 6 instances of R$^8$, and when $R^6$ is an aryl, it is independently substituted with from 0 to 6 instances of $R^{8'}$;

each $R^7$ is independently selected from a halogen, —CN, oxo, —$OR^9$, —$R^{10}$, —$C(O)R^9$, —$C(O)OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$;

each $R^8$ is independently selected from a halogen, —CN, —$NO_2$, oxo, a $C_{1-6}$ aliphatic radical, —$R^{10}$, —$C(O)R^9$, —$C(O)OR^9$, —$OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$;

each $R^{8'}$ is independently selected from a halogen, —CN, —$NO_2$, a $C_{1-6}$ aliphatic radical, —$R^{10}$, —$C(O)R^9$, —$C(O)OR^9$, —$OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$;

each $R^9$ is independently selected from hydrogen, a $C_{1-6}$ aliphatic radical and a monocyclic or bicyclic ring, wherein
the ring is selected from a 6 to 10-membered aryl, a 5 to 10-membered heteroaryl, a $C_{3-10}$ cycloaliphatic and a 4 to 10-membered heterocycle; wherein,
when $R^9$ is a $C_{1-6}$ aliphatic radical, it is independently substituted with from 0 to 6 instances of $R^{11}$, and
when $R^9$ is a ring, it is independently substituted with from 0 to 3 instances of $R^{12}$;

each $R^{10}$ is a monocyclic or bicyclic ring independently selected from a 6 to 10-membered aryl, a 5 to 10-membered heteroaryl, a $C_{3-10}$ cycloaliphatic and a 4 to 10-membered heterocycle; wherein
each $R^{10}$ is independently substituted with from 0 to 3 instances of $R^{12}$;

each $R^{11}$ is independently selected from a halogen, —CN, —OH, a $C_{1-4}$ alkoxy and a $C_{1-4}$ haloalkoxy;

each $R^{12}$ is independently selected from a halogen, —CN, —OH, a $C_{1-4}$ alkyl, a $C_{1-4}$ haloalkyl, a $C_{1-4}$ alkoxy and a $C_{1-4}$ haloalkoxy;

$R^{13}$ is selected from —H, a $C_{1-6}$ aliphatic radical, and a monocyclic or bicyclic ring; wherein the ring is selected from a 6 to 10-membered aryl, a 5 to 10-membered heteroaryl, a $C_{3-10}$ cycloaliphatic and a 4 to 10-membered heterocycle; wherein
when $R^{13}$ is a $C_{1-6}$ aliphatic radical, it is independently substituted with from 0 to 6 instances of $R^{14}$;
when $R^{13}$ is a non-aromatic ring or a heteroaryl, it is independently substituted with from 0 to 6 instances of $R^{15}$, and
when $R^{13}$ is an aryl, it is independently substituted with from 0 to 6 instances of $R^{15'}$;

each $R^{14}$ is independently selected from a halogen, —CN, oxo, —$OR^9$, —$R^{10}$, —$C(O)R^9$, —$C(O)OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$;

each $R^{15}$ is independently selected from a halogen, —CN, —$NO_2$, oxo, a $C_{1-6}$ aliphatic radical, —$R^{10}$, —$C(O)R^9$, —$C(O)OR^9$, —$OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$; and each $R^{15'}$ is independently selected from a halogen, —CN, —$NO_2$, a $C_{1-6}$ aliphatic radical, —$R^{10}$, —$C(O)R^9$, —$C(O)OR^9$, —$OR^9$, —$S(O)_mR^9$, —$N(R^9)_2$, —$S(O)_2N(R^9)_2$, —$NR^9S(O)_2R^9$, —$C(O)N(R^9)_2$ and —$NR^9C(O)R^9$;

$R^{16}$ and $R^{17}$ are each independently selected from —H, deuterium, a $C_{1-6}$ alkyl, a $C_{1-6}$ haloalkyl and a halogen, or
alternatively, $R^{16}$ and $R^{17}$ are independently selected from a $C_{1-6}$ alkyl and a $C_{1-6}$ haloalkyl, and $R^{16}$ and $R^{17}$ taken together with the atom to which they are attached form a cyclopropyl or halocyclopropyl ring;

L is a linker selected from a methylene, —C(O)—, —O—, —$S(O)_m$— and —$NR^1$—; wherein
when L is a methylene, it is independently substituted with from 0 to 2 instances of $R^{18}$;

m is 0, 1 or 2;

$R^1$ is selected from —H, a $C_{1-6}$ aliphatic radical, a $C_{3-6}$ cycloaliphatic, —$CO(C_{1-6}$ aliphatic), —$CO(C_{3-6}$ cycloaliphatic), —CO-(phenyl), a benzyl and —CO-(benzyl); wherein
when $R^1$ is selected from a $C_{1-6}$ aliphatic radical, —CO-(phenyl), a benzyl and —CO-(benzyl), it is independently substituted with from 0 to 3 instances of $R^B$; wherein
each $R^B$ is independently selected from a halogen, a $C_{1-2}$ alkyl and a $C_{1-2}$ alkoxy;

each $R^{18}$ is independently selected from a halogen, —CN, a $C_{1-6}$ aliphatic radical, a $C_{1-6}$ haloaliphatic radical, and a $C_{3-6}$ cycloaliphatic; or
alternatively, each $R^{18}$ is independently selected from a $C_{1-6}$ aliphatic radical and a $C_{1-6}$ haloaliphatic radical, and two $R^{18}$ groups, taken together with the atom to which they are attached form a cyclopropyl or a halocyclopropyl ring;

o is an integer selected from 0, 1 and 2;

each $J^B$ is independently selected from a halogen, —$NO_2$, —CN, —$R^{19}$, —C(O)H, —C(O)OH, —$C(O)NH_2$, —OH, —SH, —$NH_2$, —$C(O)R^{19}$, —$C(O)OR^{19}$, —$C(O)N(R^{20})R^{19}$, —$N(R^{20})C(O)R^{19}$, —$OR^{19}$, —$SR^{19}$ and —$NR^{19}R^{20}$; or
alternatively, two $J^B$ groups are attached to two vicinal ring B atoms and, together with said ring atoms, form a 5 to 6-membered heterocycle or a 5 to 6-membered heteroaryl, each of said rings independently substituted with from 0 to 2 instances of $R^E$, wherein each $R^E$ is independently selected from a halogen, a $C_{1-2}$ alkyl, a $C_{1-2}$ alkoxy, —CN and —OH;

each $R^{20}$ is independently selected from a —H and a $C_{1-6}$ aliphatic radical;

each $R^{19}$ is independently selected from a $C_{1-6}$ aliphatic radical, a $C_{3-6}$ cycloaliphatic, a phenyl, a benzyl, a 4 to 6-membered heterocycle and a 5 to 6-membered heteroaryl; wherein
when $R^{19}$ is a $C_{1-6}$ aliphatic radical, it is independently substituted with from 0 to 3 instances of $R^C$, wherein each $R^C$ is independently selected from a halogen, —CN, —OH, —$NH_2$, a $C_{3-4}$ cycloalkyl, a $C_{3-4}$ halocycloalkyl, a —$O(C_{1-4}$ alkyl), a —$O(C_{3-4}$ cycloalkyl), a —$O(C_{3-4}$ halocycloalkyl), a —$O(C_{1-4}$ haloalkyl), a —$NH(C_{1-4}$ alkyl), a —$N(C_{1-4}$ alkyl)$_2$, and —$NR^V$; wherein
—$NR^V$ is a 4 to 6-membered heterocycle containing a ring N atom linked to $J^B$, and wherein said heterocycle contains from 0 to 2 additional ring heteroatoms selected from O and N;

when $R^{19}$ is a heterocycle or a heteroaryl it contains from 1 to 3 ring heteroatoms independently selected from N, O and S;

when $R^{19}$ is a phenyl, it is independently substituted with from 0 to 3 instances of $R^D$, wherein each $R^D$ is independently selected from a halogen, a $C_{1-4}$ aliphatic radical, —CN, —OH, —$NH_2$, a —$O(C_{1-4}$ alkyl), a —$NH(C_{1-4}$ alkyl) and a —$N(C_{1-4}$ alkyl)$_2$; and when $R^{19}$ is a non-aromatic ring or a heteroaryl, it is independently substituted with from 0 to 3 instances of $R^{D'}$, wherein each $R^{D'}$ is independently selected from a halogen, oxo, a $C_{1-4}$ aliphatic radical, —CN, —OH, —$NH_2$, a —$O(C_{1-4}$ alkyl), a —$NH(C_{1-4}$ alkyl) and a —$N(C_{1-4}$ alkyl)$_2$;

L' is a linker selected from —Y—$SO_2$—, —$NR^{21}SO_2$—, —$SO_2NR^{21}$—, —$NR^{21}C(O)$— and —$C(O)NR^{21}$—; wherein
Y is selected from a single bond, a straight $C_{1-2}$ alkylene linker, and a branched $C_2$ alkylene linker, wherein the $C_{1-2}$ alkylene linker is independently substituted with from 0 to 3 a halogen atoms;

$R^{21}$ is selected from hydrogen, a $C_{1-6}$ alkyl, a $C_{1-6}$ haloalkyl and a $C_{3-6}$ cycloalkyl ring;

n is an integer selected from 0, 1, 2 and 3;

each $J^A$ is independently selected from a halogen, —NO$_2$, —CN, —R$^{22}$, —C(O)H, —C(O)OH, —C(O)NH$_2$, —OH, —SH and —NH$_2$, —C(O)R$^{22}$, —C(O)OR$^{22}$, —C(O)N(R$^{23}$)R$^{22}$, —N(R$^{23}$)C(O)R$^{22}$, —OR$^{22}$, —SR$^{22}$ and —NR$^{22}$R$^{23}$;

each R$^{23}$ is independently selected from a —H and a C$_{1-6}$ aliphatic radical;

each R$^{22}$ is independently selected from a C$_{1-6}$ aliphatic radical, a C$_{3-6}$ cycloaliphatic ring, a phenyl, a benzyl, a 4 to 6-membered heterocycle and a 5 to 6-membered heteroaryl; wherein when R$^{22}$ is a C$_{1-6}$ aliphatic radical, it is independently substituted with from 0 to 3 instances of R$^F$, wherein each R$^F$ is independently selected from a halogen, —CN, —OH, —NH$_2$, a C$_{3-4}$ cycloalkyl, a C$_{3-4}$ halocycloalkyl, a —O(C$_{1-4}$ alkyl), a —O(C$_{3-4}$ cycloalkyl), a —O(C$_{3-4}$ halocycloalkyl), a —O(C$_{1-4}$ haloalkyl), a —NH(C$_{1-4}$ alkyl), a —N(C$_{1-4}$ alkyl)$_2$ and —NR$^V$; wherein —NR$^V$ is a 4 to 6-membered heterocycle containing a ring N atom linked to J$^B$, and wherein the heterocycle contains from 0 to 2 additional ring heteroatoms selected from O and N;

when R$^{22}$ is a heterocycle or a heteroaryl, the ring contains from 1 to 3 ring heteroatoms independently selected from N, O and S;

when R$^{22}$ is a non-aromatic ring or a 5 to 6-membered heteroaryl, it is independently substituted with from 0 to 3 instances of R$^G$, wherein each R$^G$ is independently selected from a halogen, oxo, a C$_{1-4}$ aliphatic radical, —CN, —OH, —NH$_2$, a —O(C$_{1-4}$ alkyl), a —NH(C$_{1-4}$ alkyl) and a —N(C$_{1-4}$ alkyl)$_2$; and when R$^{22}$ is a phenyl 1, it is independently substituted with from 0 to 3 instances of R$^{G'}$, wherein each R$^{G'}$ is independently selected from a halogen, a C$_{1-4}$ aliphatic radical, —CN, —OH, —NH$_2$, —O(C$_{1-4}$ alkyl), —NH(C$_{1-4}$ alkyl) and —N(C$_{1-4}$ alkyl)$_2$.

In some embodiments, ring A is selected from a phenyl, a 5 to 6-membered heteroaryl, a C$_{3-6}$ cycloaliphatic or a 5 to 6-membered heterocycle, wherein said heteroaryl or heterocycle contains from 1 to 2 ring heteroatoms selected from N and O. In certain embodiments, ring A is selected from a phenyl or a 5 to 6-membered heterocyclic ring, wherein said heterocycle contains from 1 to 2 ring heteroatoms selected from O and N. In further embodiments, ring A is selected from a phenyl, a pyridine, a thiophene, a furan, a pyrimidine, a pyrazine, a piridazine, a piperidine, a piperazine, a morpholine or a pyrrolidine. In still further embodiments, ring A is selected from a phenyl, a morpholine or a pyrrolidine. In yet further embodiments, ring A is selected from a phenyl, an N-linked morpholine and an N-linked pyrrolidine.

In some embodiments, ring B is selected from a phenyl, a thiophene or a 6-membered heteroaryl. In other embodiments, ring B is selected from a phenyl, a thiophene or a pyridine. In certain embodiments, ring B is a phenyl.

In some embodiments, ring D is selected from a pyrrole, a pyrazole or an imidazole. In other embodiments, ring D is an imidazole, and x$^1$ and x$^3$ are N. In certain embodiments, ring D is a pyrazole, and x$^1$ and x$^2$ are N. In further embodiments, ring D is a pyrrole, and x$^1$ or x$^3$ is N, but both x$^1$ and x$^3$ are not simultaneously N. In still further embodiments, ring D is a pyrrole, and x$^1$ is N and x$^3$ is C.

In some embodiments, R$^2$ is selected from a halogen, —H, a cyclopropyl ring, a C$_{1-4}$ alkyl or a C$_{1-4}$ haloalkyl. In certain embodiments, R$^2$ is selected from a C$_{1-4}$ alkyl or —H. In further embodiments, R$^2$ is a methyl.

In some embodiments, R$^4$ is selected from a halogen, —NO$_2$, —R$^6$, —OR$^6$, —C(O)R$^6$, —C(O)OR$^6$, —N(R$^6$)$_2$, —S(O)$_p$R$^6$, —S(O)$_2$N(R$^6$)$_2$, —NR$^6$S(O)$_2$R$^6$, —C(O)N(R$^6$)$_2$ or —NR$^6$C(O)R$^6$. In other embodiments, R$^4$ is a —H, a halogen, —CN, a C$_{1-6}$ aliphatic radical, a C$_{3-6}$ cycloaliphatic ring radical, a C$_{1-6}$ haloaliphatic radical, a phenyl which is optionally substituted by R$^{8'}$ or a benzyl which is optionally substituted by R$^{8'}$. In certain embodiments, R$^4$ is selected from —H, a halogen, —CN, a C$_{1-4}$ alkyl, a C$_{1-4}$ haloalkyl, a C$_{3-6}$ cycloalkyl, a —O(C$_{1-4}$ alkyl), a —O(C$_{1-4}$ haloalkyl), a —O(C$_{3-6}$ cycloalkyl), a —O(phenyl), a —O(substituted phenyl), a —O(benzyl), a —O(substituted benzyl), a —C(O)(C$_{1-4}$ alkyl), a —C(O)(C$_{1-4}$ haloalkyl), a —C(O)(C$_{3-6}$ cycloalkyl), a —C(O)(phenyl), a —C(O)(substituted phenyl), a —C(O)(benzyl), —C(O)(substituted benzyl) or —C(O)H; wherein each of said substituted phenyl or benzyl rings, is substituted by from 0 to 4 instances of R$^{8'}$. In further embodiments, R$^4$ is selected from —H, a halogen, —CN, an ethyl, a methyl, a propyl, a trifluoroethyl, a trifluoromethyl, a cyclopropyl, a cyclopentyl, a cyclohexyl, a cyclopropyloxy, a cyclopentyloxy, a cyclohexyloxy, an ethoxy, a methoxy, a propyloxy, a trifluoromethoxy, a trifluoroethoxy, a benzoyl, a phenyl, a phenyloxy, a methylcarbonyl, an ethylcarbonyl, a trifluoromethylcarbonyl, a trifluoroethylcarbonyl or —C(O)H; wherein each of said benzoyl, phenyl or phenyloxy is independently substituted by from 0 to 4 instances of R$^{8'}$. In still further embodiments, R$^4$ is selected from a —H, a halogen, —CN, an ethyl, a methyl, a propyl, a trifluoroethyl, a trifluoromethyl, a cyclopropyl, a cyclopentyl, a cyclohexyl, phenyl, a benzoyl, a methylcarbonyl, an ethylcarbonyl, a trifluoromethylcarbonyl, a trifluoroethylcarbonyl or a —C(O)H; wherein each of said phenyl and benzoyl groups is independently substituted by from 0 to 4 instances of R$^{8'}$. In yet further embodiments, R$^4$ is selected from —H, iodo, —CN, methyl, 2,2,2-trifluoroethyl, benzoyl, methylcarbonyl, trifluoromethylcarbonyl, —C(O)H or phenyl; wherein said phenyl is independently substituted with from 0 to 2 instances of halogen. In yet further embodiments, R$^4$ is a phenyl substituted with from 0 to 2 instances of halogen. In yet further embodiments, R$^4$ is a phenyl substituted with from 0 to 2 instances of fluoro. In yet further embodiments, R$^4$ is selected from a —H, —CN, a methyl, 2,2,2-trifluoroethyl, a benzoyl, a methylcarbonyl, a trifluoromethylcarbonyl, —C(O)H, a phenyl or a fluorophenyl; wherein said fluorophenyl is substituted with from 0 to 2 instances of fluoro.

In some embodiments, R$^5$ is selected from a halogen, —CN, a C$_{1-6}$ aliphatic radical independently substituted with from 0 to 4 instances of R$^7$, a C$_{3-6}$ cycloaliphatic radical, a phenyl independently substituted with from 0 to 4 instances of R$^{8'}$ or a 6-membered heteroaryl independently substituted with from 0 to 4 instances of R$^{8'}$. In certain embodiments, R$^5$ is selected from a halogen, —CN, a C$_{1-6}$ alkyl independently substituted with from 0 to 4 instances of R$^7$, a C$_{3-6}$ cycloaliphatic, a phenyl independently substituted by from 0 to 4 instances of R$^{8'}$ or a 6-membered heteroaryl independently substituted by from 0 to 4 instances of R$^{8'}$. In further embodiments, R$^5$ is selected from a halogen, —CN; a C$_{1-6}$ alkyl substituted with from 0 to 2 instances of a substituent independently selected from halogen or —OH; a 3 to 6-membered cycloalkyl, a phenyl or a 6-membered heteroaryl; wherein each of said phenyl and 6-membered heteroaryl rings is substituted by from 0 to 3 instances of a substituent independently selected from a halogen, a C$_{1-4}$ alkyl, a C$_{1-4}$ haloalkyl, a C$_{1-4}$ alkoxy, a C$_{1-4}$ haloalkoxy and —CN. In still further embodiments, R$^5$ is selected from a halogen, —CN, an ethyl, a methyl, a propyl, a 3-6 membered cycloalkyl, a phenyl, a pyridinyl or a pyrimidinyl; wherein each said methyl, ethyl and propyl is substituted with from 0 to 4 instances of a halogen or —OH; and wherein each said phenyl, pyridinyl and pyrimidinyl is substituted with from 0 to 4 instances of a substituent selected from a halogen, a $C_{1-2}$ alkyl, a $C_{1-2}$ haloalkyl, a $C_{1-2}$ alkoxy or a $C_{1-2}$ haloalkoxy. In yet further embodiments, $R^5$ is selected from —CN, an ethyl, a methyl, a propyl, a cyclopropyl, a cyclopentyl, a cyclohexyl, a phenyl or a pyridinyl; wherein each said methyl, propyl and ethyl is independently substituted with from 0 to 2 instances of a halogen or —OH; wherein said phenyl is independently substituted by from 0 to 2 instances of a halogen or —CF$_3$; and wherein said pyridinyl is independently substituted by from 0 to 1 instances of a halogen, a $C_{1-2}$ alkoxy, a $C_{1-2}$ haloalkoxy or —CF$_3$. In even further embodiments, $R^5$ is selected from a —CN, a 2-hydroxyethyl, a methyl, a cyclopropyl, a cyclopentyl, a cyclohexyl, a phenyl or a pyridinyl; wherein said phenyl is independently substituted by from 0 to 2 instances of fluorine or —CF$_3$; and wherein said pyridinyl is independently substituted by from 0 to 1 instances of fluoro or chloro. In yet further embodiments, $R^5$ is selected from —CN, a methyl, a cyclopropyl, a cyclopentyl, a cyclohexyl, a phenyl, pyridinyl, a 3-chloro-4-pyridinyl or a 3-chloro-2-pyridinyl; wherein said phenyl is independently substituted by from 0 to 2 instances of fluorine or by from 0 to 1 instances of —CF$_3$.

In some embodiments, each of $R^{16}$ and $R^{17}$ is independently selected from —H or a methyl or, alternatively, $R^{16}$ and $R^{17}$, taken together with the carbon atom to which they are attached, form a cyclopropyl ring. In certain embodiments, $R^{16}$ and $R^{17}$ are both —H.

In some embodiments, L is selected from a methylene, —C(O)— or —S—. In certain embodiments, L is selected from a methylene or —S—.

In some embodiments, o is 0. In certain embodiments, o is 1 or 2 and $J^B$ is a halogen.

In some embodiments, L' is selected from —SO$_2$— or —CH$_2$SO$_2$—. In certain embodiments, L' is —SO$_2$—.

In some embodiments, $R^{13}$ is selected from a —H or a $C_{1-6}$ alkyl. In certain embodiments $R^{13}$ is —H.

Alternatively, the invention provides a compound having Structural Formula I, with the proviso that the compound having Formula I is not a compound selected from 5-[[6-methoxy-3-(4-methoxybenzoyl)-2-methyl-1H-pyrrolo[2,3-b]pyridin-1-yl]methyl]-α,α-dimethyl-2H-tetrazole-2-acetic acid [CAS Registry No. 1097838-63-5], a derivative of 5-[[6-methoxy-3-(4-methoxybenzoyl)-2-methyl-1H-pyrrolo[2,3-b]pyridin-1-yl]methyl]-α,α-dimethyl-2H-tetrazole-2-acetic acid in which a H atom is replaced with a methyl or ethyl group or a methyl group is replaced with a H atom, 5-[[5-(benzoylamino)-2-thiazolyl]thio]-2H-tetrazole-2-acetic acid [CAS Registry No. 1099441-56-1], a derivative of 5-[[5-(benzoylamino)-2-thiazolyl]thio]-2H-tetrazole-2-acetic acid in which a H atom is replaced with a methyl or ethyl group or a methyl group is replaced with a H atom, 2-butyl-1-[[4-[(2-carboxybenzoyl)amino]phenyl]methyl]-5-chloro-1H-imidazole-4-acetic acid [CAS Registry No. 114798-40-2], a derivative of 2-butyl-14-[[4-[(2-carboxybenzoyl)amino]phenyl]methyl]-5-chloro-1H-imidazole-4-acetic acid in which a H atom is replaced with a methyl or ethyl group or a methyl group is replaced with a H atom, 2-butyl-1-[[4-[(2-carboxybenzoyl)amino]phenyl]methyl]-5-chloro-1H-imidazole-4-acetic acid [CAS Registry No. 114773-45-4], and a derivative of 2-butyl-1-[[4-[(2-carboxybenzoyl)amino]phenyl]methyl]-5-chloro-1H-imidazole-4-acetic acid in which a H atom is replaced with a methyl or ethyl group or a methyl group is replaced with a H atom, or pharmaceutically acceptable salts thereof.

In a second aspect, the invention is directed to a compound described above with the further proviso that when ring D is a tetrazole and ring B is a thiazole, L is not —S—.

In a third aspect, the invention is directed to a compound described above, with the further proviso that when ring D is an imidazole such that $x^1$ is C, and x is C—$R^2$; ring B is a phenyl; and L is a methylene; then $R^2$ is not —H, a halogen, a $C_{1-6}$ aliphatic radical or a cyclopropyl ring.

In a fourth aspect, the invention is directed to a compound described above, with the further proviso that when D is a tetrazole and L is a methylene, two $J^B$ groups are not attached to two vicinal ring B atoms to form a 6-membered heterocycle or a 6-membered heteroaryl ring fused to ring D.

In a fifth aspect, the invention is directed to a compound having any one of structural formulae:

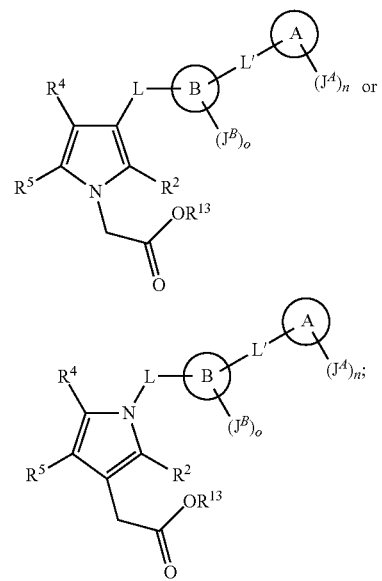

wherein each of the variables can be selected from those described in the embodiments above.

In another aspect, the invention is directed to a compound having any one of structural formulae:

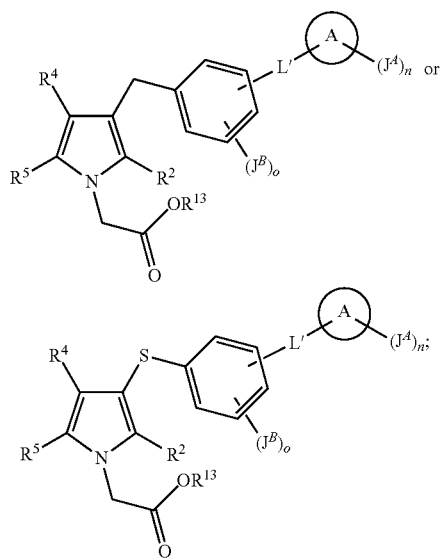

wherein each of the variables can be selected from those described in the embodiments above.

In another aspect, the invention is directed to a compound having any one of structural formulae:

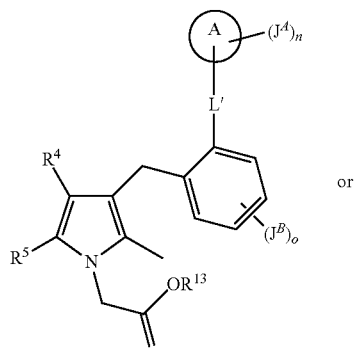

or

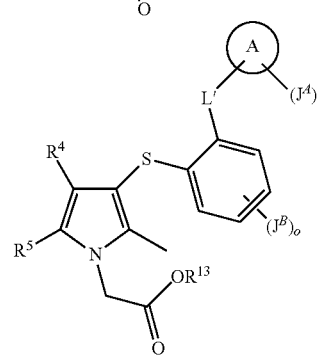

wherein each of the variables can be selected from those described in the embodiments above.

In another aspect, the invention is directed to a compound having any one of structural formulae:

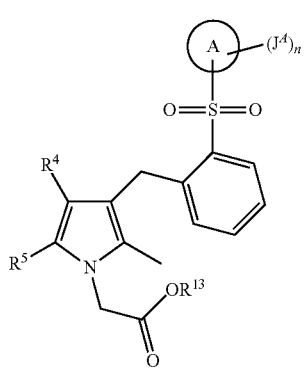

or

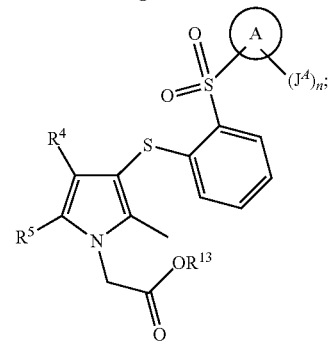

wherein each of the variables can be selected from those described in the embodiments above.

In another aspect, the invention is directed to a compound having any one of structural formulae:

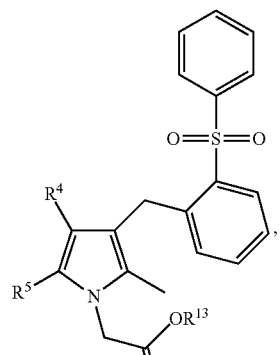

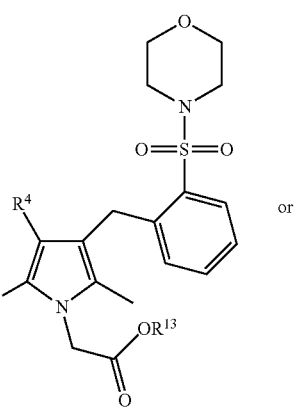

or

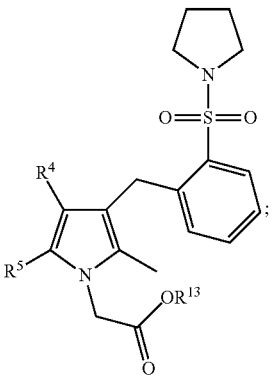

wherein each of the variables can be selected from those described in the embodiments above.

In another aspect, the invention is directed to a compound having any one of structural formulae:

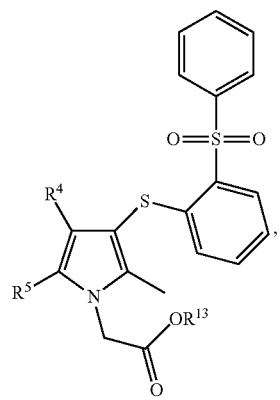

-continued
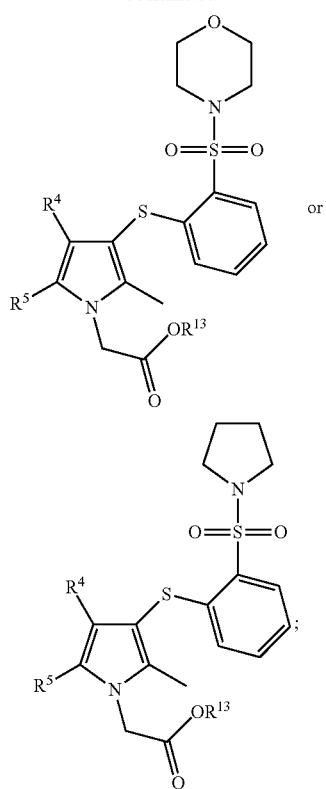
wherein each of the variables can be selected from those described in the embodiments above.
In another aspect, the invention is a compound selected from those depicted in Table I:
TABLE I
I-49
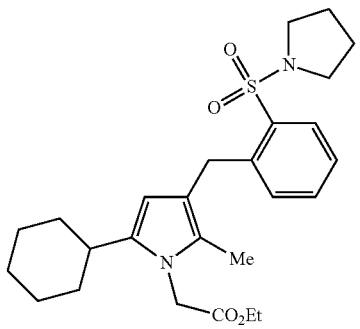 [SMILES: CCOC(=O)Cn1c(C2CCCCC2)cc(Cc2ccccc2S(=O)(=O)N2CCCC2)c1C]
I-58
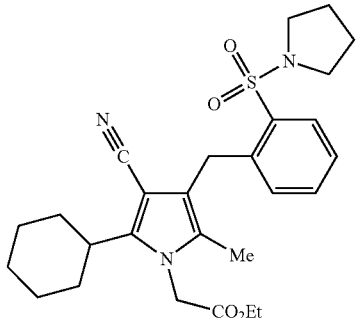
TABLE I-continued
I-14
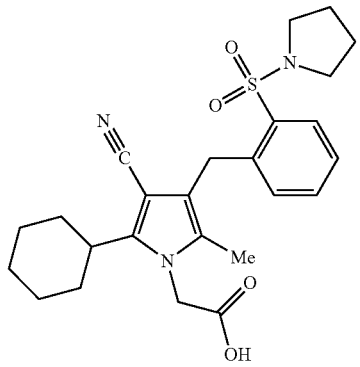 [SMILES: Cc1c(Cc2ccccc2S(=O)(=O)N2CCCC2)c(C#N)c(C2CCCCC2)n1CC(=O)O]
I-59
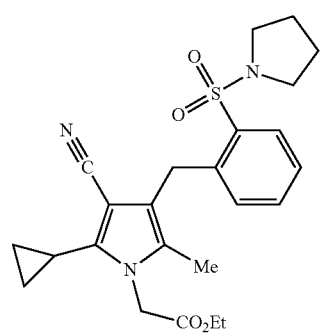 [SMILES: CCOC(=O)Cn1c(C)c(Cc2ccccc2S(=O)(=O)N2CCCC2)c(C#N)c1C1CC1]
I-16
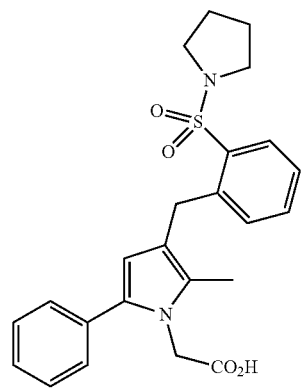 [SMILES: Cc1c(Cc2ccccc2S(=O)(=O)N2CCCC2)cc(-c2ccccc2)n1CC(=O)O]
I-33
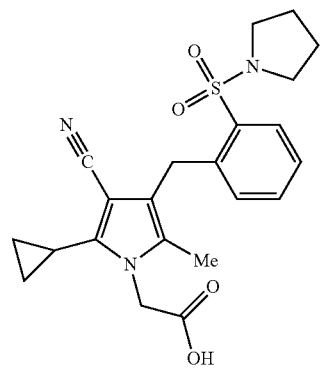 [SMILES: Cc1c(Cc2ccccc2S(=O)(=O)N2CCCC2)c(C#N)c(C2CC2)n1CC(=O)O]

TABLE I-continued
I-60
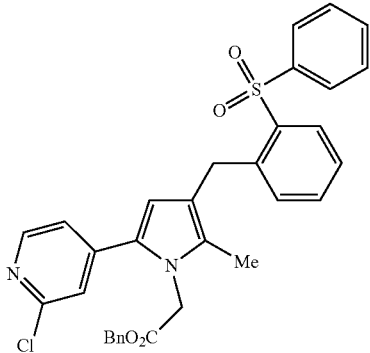
I-41
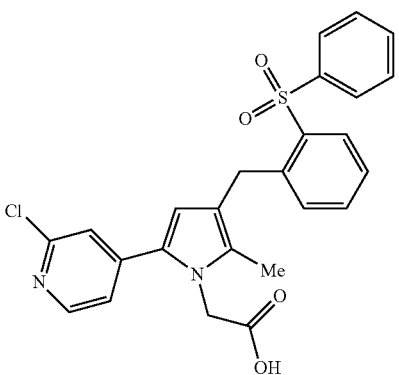 [SMILES: Cc1c(Cc2ccccc2S(=O)(=O)c2ccccc2)cc(-c2ccnc(Cl)c2)n1CC(=O)O]
I-44
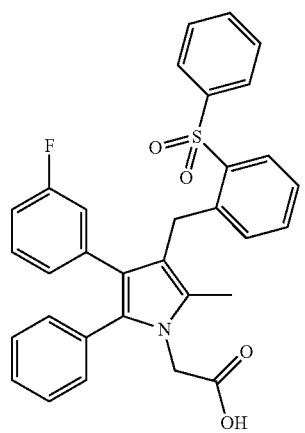 [SMILES: Cc1c(Cc2ccccc2S(=O)(=O)c2ccccc2)c(-c2cccc(F)c2)c(-c2ccccc2)n1CC(=O)O]
I-36
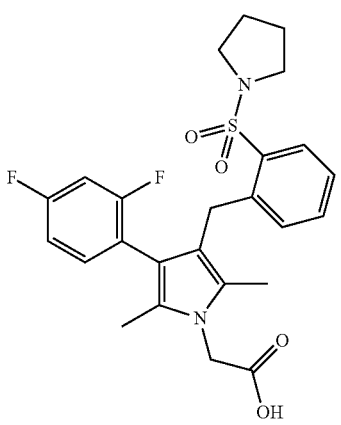 [SMILES: Cc1c(Cc2ccccc2S(=O)(=O)N2CCCC2)c(-c2ccc(F)cc2F)c(C)n1CC(=O)O]
TABLE I-continued
I-23
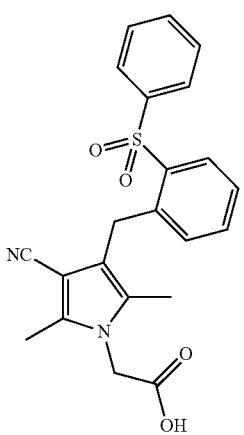 [SMILES: Cc1c(C#N)c(Cc2ccccc2S(=O)(=O)c2ccccc2)c(C)n1CC(=O)O]
I-9
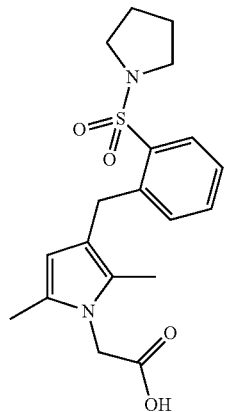 [SMILES: Cc1cc(Cc2ccccc2S(=O)(=O)N2CCCC2)c(C)n1CC(=O)O]
I-63
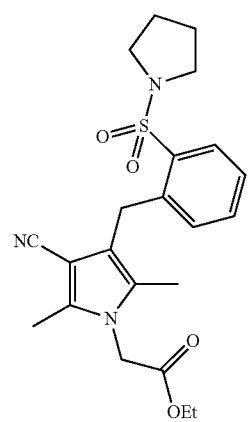 [SMILES: CCOC(=O)Cn1c(C)c(C#N)c(Cc2ccccc2S(=O)(=O)N2CCCC2)c1C]

TABLE I-continued
I-32
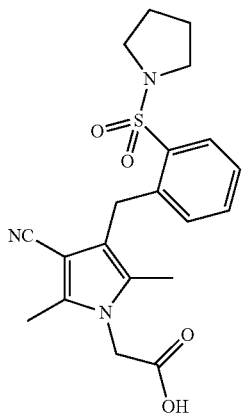 [SMILES: Cc1c(C#N)c(Cc2ccccc2S(=O)(=O)N2CCCC2)c(C)n1CC(=O)O]
I-46
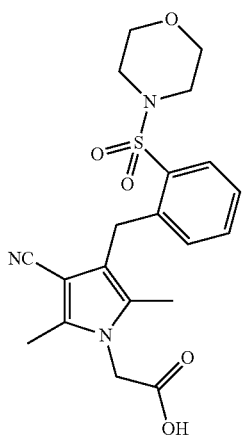 [SMILES: Cc1c(C#N)c(Cc2ccccc2S(=O)(=O)N2CCOCC2)c(C)n1CC(=O)O]
I-61
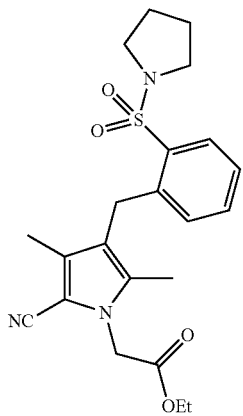 [SMILES: CCOC(=O)Cn1c(C)c(Cc2ccccc2S(=O)(=O)N2CCCC2)c(C)c1C#N]
I-62
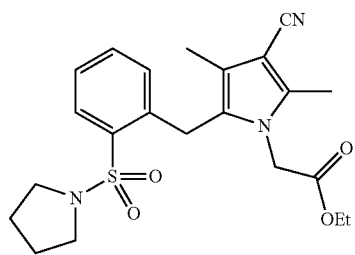 [SMILES: CCOC(=O)Cn1c(C)c(C#N)c(C)c1Cc1ccccc1S(=O)(=O)N1CCCC1]
TABLE I-continued
I-7
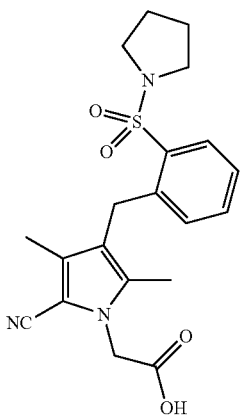 [SMILES: Cc1c(Cc2ccccc2S(=O)(=O)N2CCCC2)c(C)n(CC(=O)O)c1C#N]
I-64
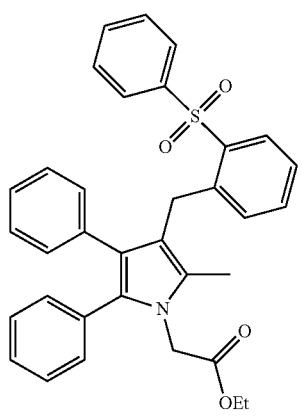 [SMILES: Cc1c(Cc2ccccc2S(=O)(=O)c2ccccc2)c(-c2ccccc2)c(-c2ccccc2)n1CC(=O)O]
I-12
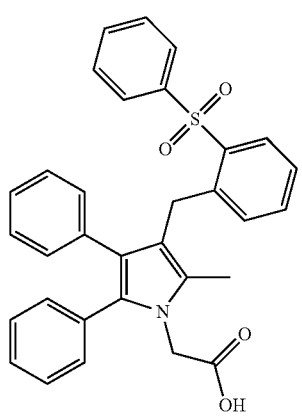
I-39
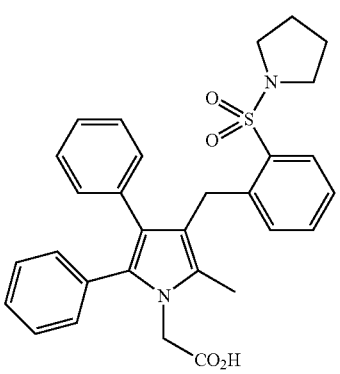 [SMILES: Cc1c(Cc2ccccc2S(=O)(=O)N2CCCC2)c(-c2ccccc2)c(-c2ccccc2)n1CC(=O)O]

TABLE I-continued
I-26
I-40
I-65
I-20
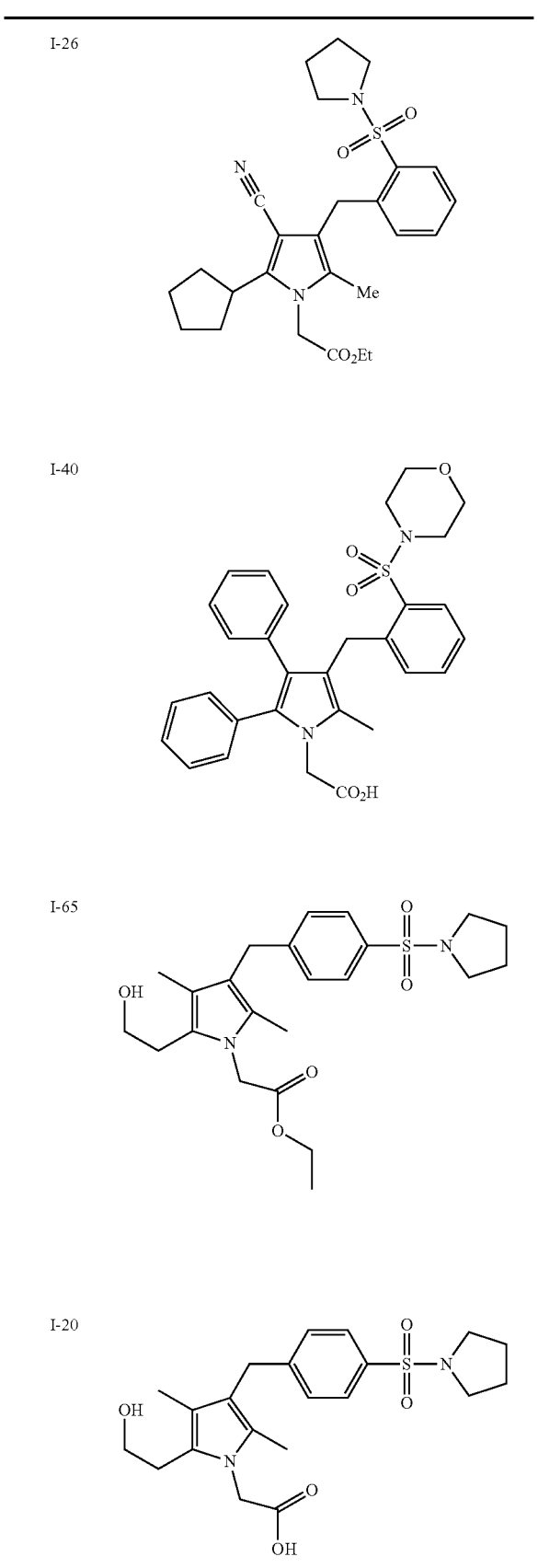
TABLE I-continued
I-66
I-37
I-67
I-38
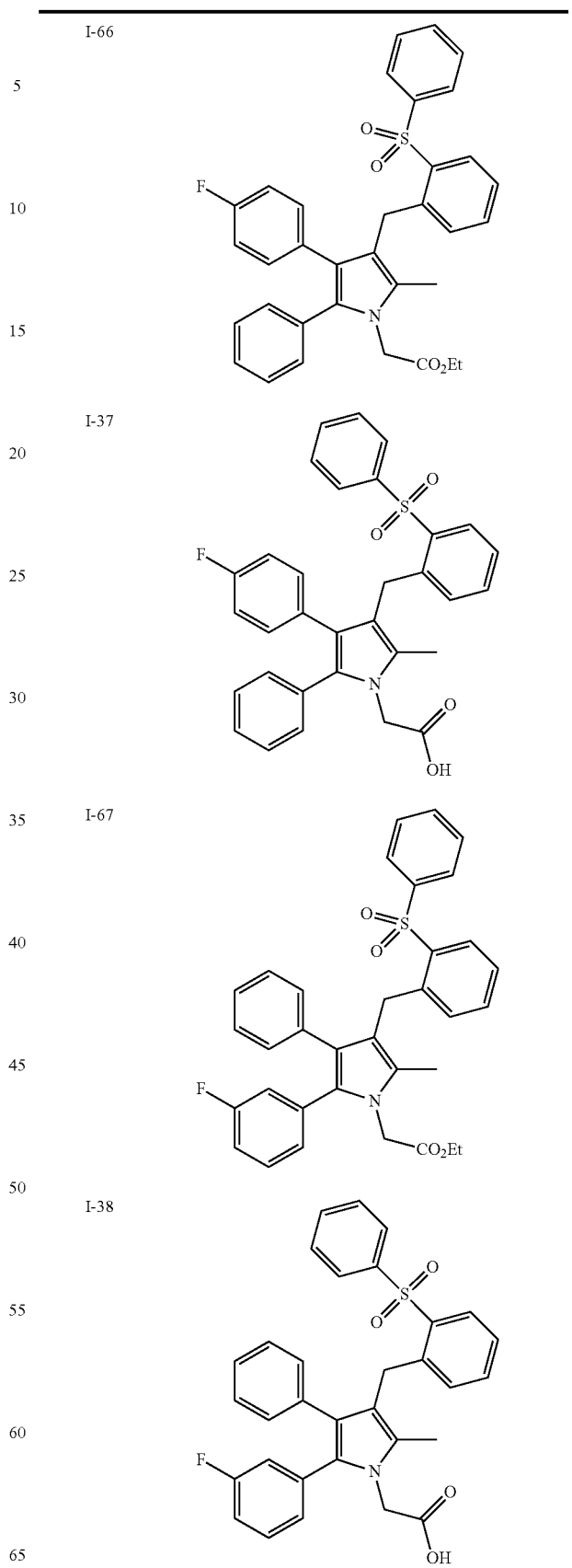

TABLE I-continued
I-6
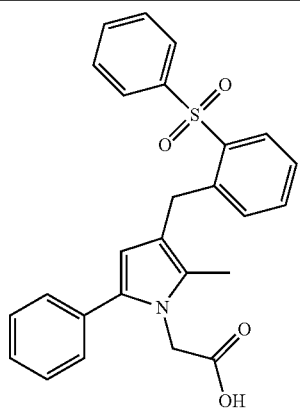
I-5
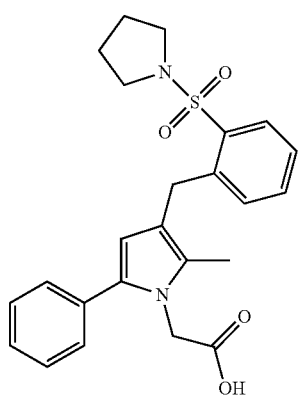 [SMILES: Cc1c(Cc2ccccc2S(=O)(=O)N2CCCC2)cc(-c2ccccc2)n1CC(=O)O]
I-13
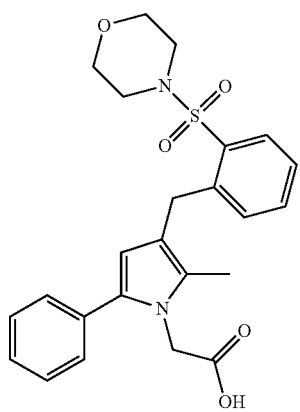 [SMILES: Cc1c(Cc2ccccc2S(=O)(=O)N2CCOCC2)cc(-c2ccccc2)n1CC(=O)O]
I-43
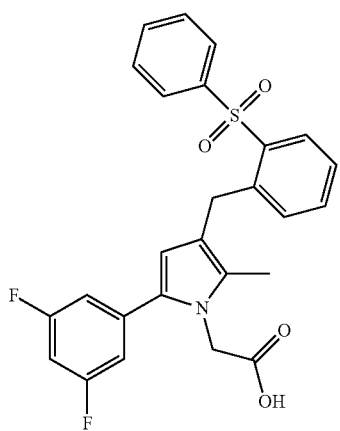 [SMILES: Cc1c(Cc2ccccc2S(=O)(=O)c2ccccc2)cc(-c2cc(F)cc(F)c2)n1CC(=O)O]
TABLE I-continued
I-4
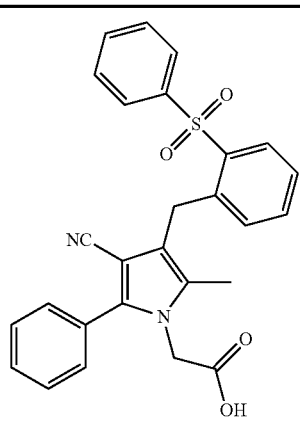
I-3
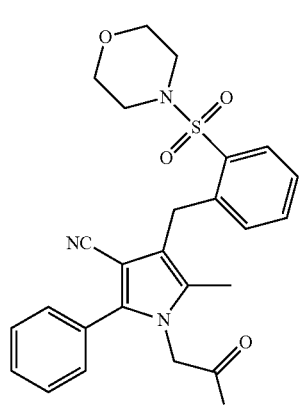
I-11
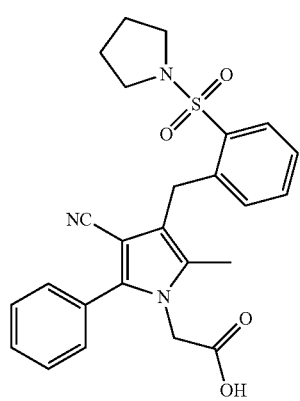 [SMILES: Cc1c(Cc2ccccc2S(=O)(=O)N2CCCC2)c(C#N)c(-c2ccccc2)n1CC(=O)O]
I-21
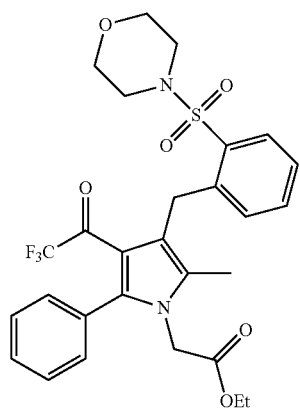

TABLE I-continued
I-50
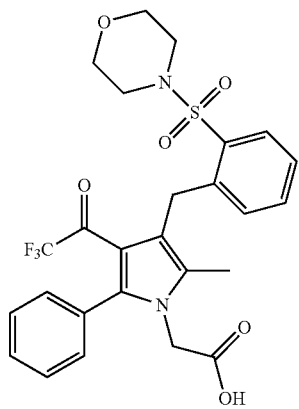 [SMILES: Cc1c(Cc2ccccc2S(=O)(=O)N2CCOCC2)c(C(=O)C(F)(F)F)c(-c2ccccc2)n1CC(=O)O]
I-45
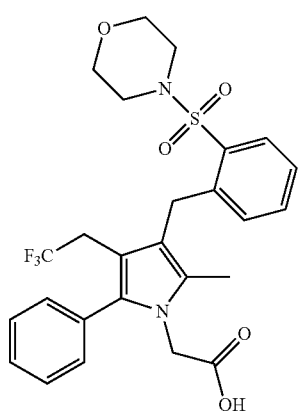 [SMILES: Cc1c(Cc2ccccc2S(=O)(=O)N2CCOCC2)c(CC(F)(F)F)c(-c2ccccc2)n1CC(=O)O]
I-52
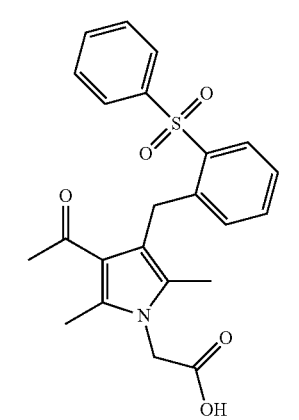 [SMILES: CC(=O)c1c(Cc2ccccc2S(=O)(=O)c2ccccc2)c(C)n(CC(=O)O)c1C]
I-53
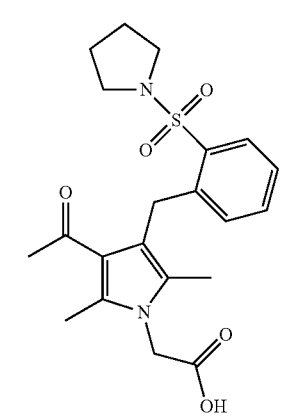 [SMILES: CC(=O)c1c(Cc2ccccc2S(=O)(=O)N2CCCC2)c(C)n(CC(=O)O)c1C]
TABLE I-continued
I-2
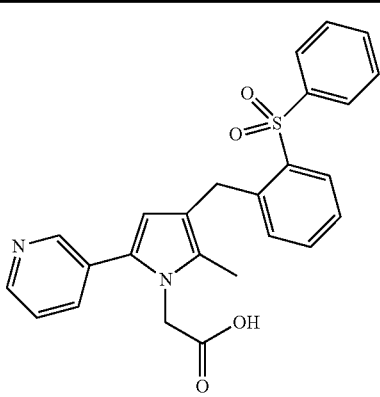
I-1
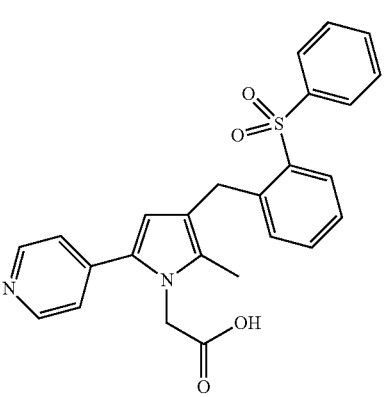 [SMILES: Cc1c(Cc2ccccc2S(=O)(=O)c2ccccc2)cc(-c2ccncc2)n1CC(=O)O]
I-17
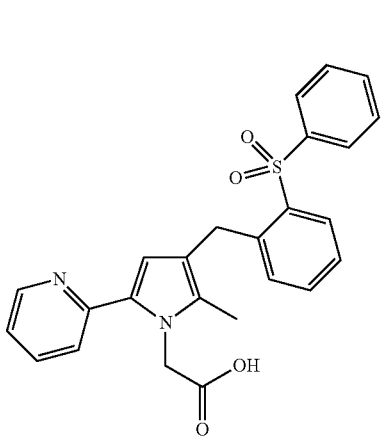 [SMILES: Cc1c(Cc2ccccc2S(=O)(=O)c2ccccc2)cc(-c2ccccn2)n1CC(=O)O]
I-68
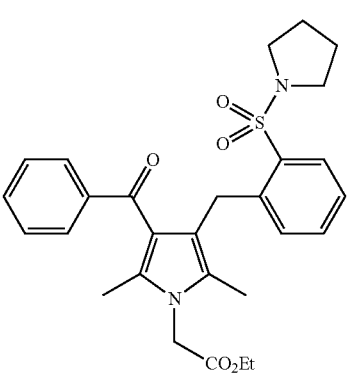 [SMILES: CCOC(=O)Cn1c(C)c(Cc2ccccc2S(=O)(=O)N2CCCC2)c(C(=O)c2ccccc2)c1C]

TABLE I-continued
I-55
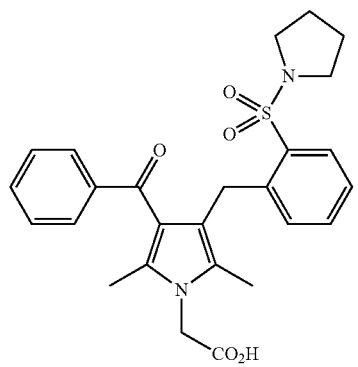 [SMILES: Cc1c(Cc2ccccc2S(=O)(=O)N2CCCC2)c(C(=O)c2ccccc2)c(C)n1CC(=O)O]
I-25
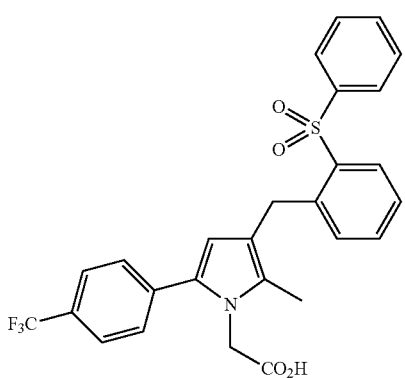 [SMILES: Cc1c(Cc2ccccc2S(=O)(=O)c2ccccc2)cc(-c2ccc(C(F)(F)F)cc2)n1CC(=O)O]
I-27
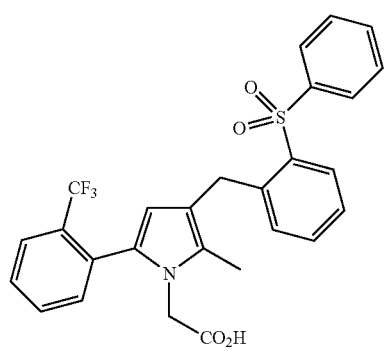 [SMILES: Cc1c(Cc2ccccc2S(=O)(=O)c2ccccc2)cc(-c2ccccc2C(F)(F)F)n1CC(=O)O]
I-18
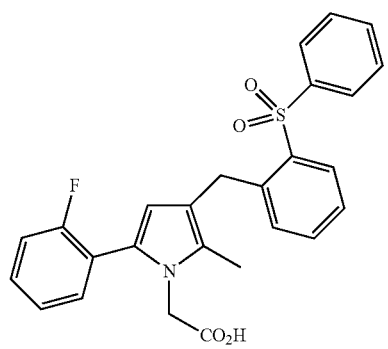 [SMILES: Cc1c(Cc2ccccc2S(=O)(=O)c2ccccc2)cc(-c2ccccc2F)n1CC(=O)O]
TABLE I-continued
I-8
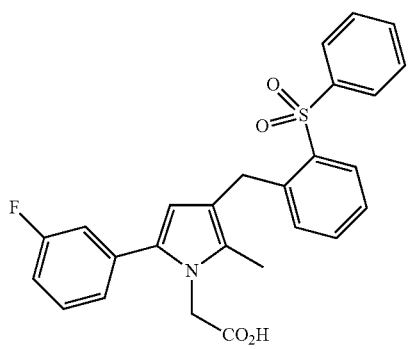 [SMILES: Cc1c(Cc2ccccc2S(=O)(=O)c2ccccc2)cc(-c2cccc(F)c2)n1CC(=O)O]
I-15
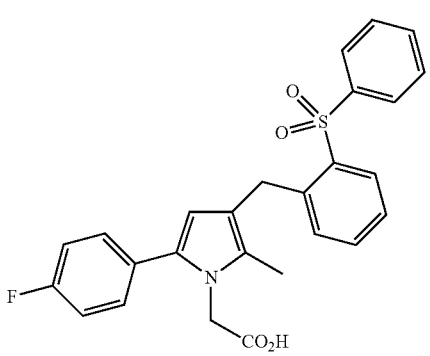 [SMILES: Cc1c(Cc2ccccc2S(=O)(=O)c2ccccc2)cc(-c2ccc(F)cc2)n1CC(=O)O]
I-69
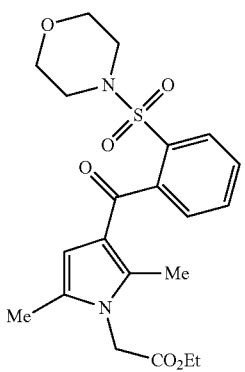 [SMILES: Cc1cc(C(=O)c2ccccc2S(=O)(=O)N2CCOCC2)c(C)n1CC(=O)O]
I-56
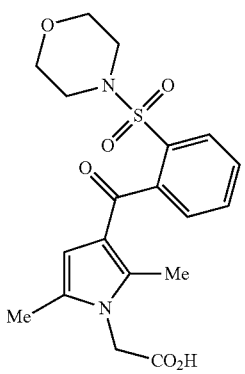

TABLE I-continued
I-70
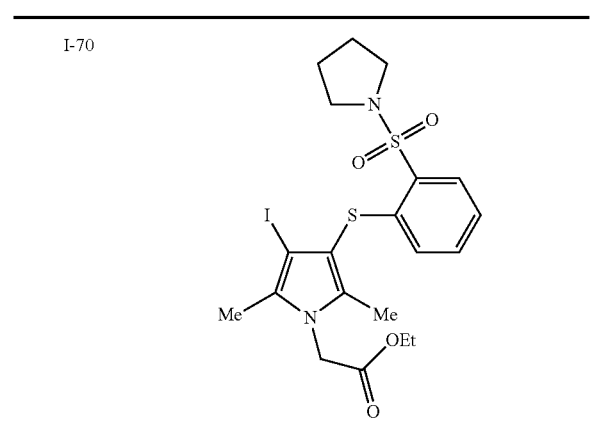
I-71
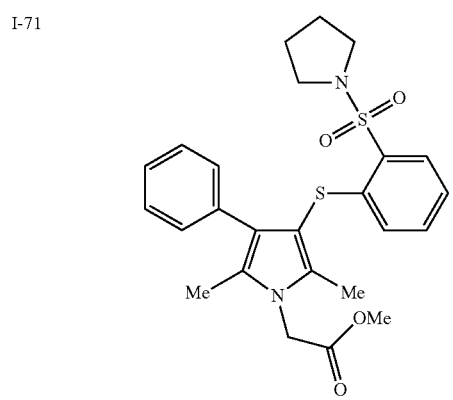
I-30
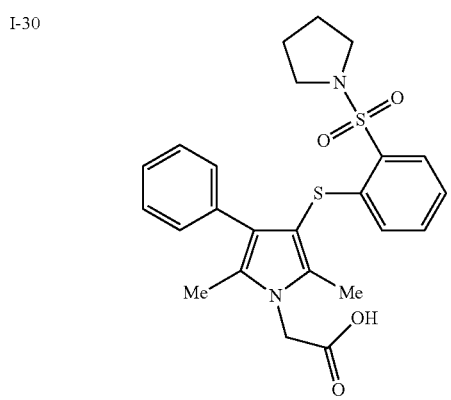
I-57
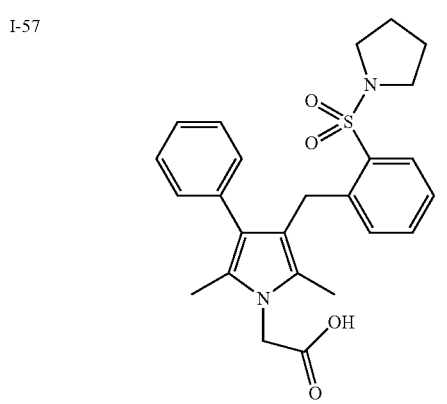
TABLE I-continued
I-72
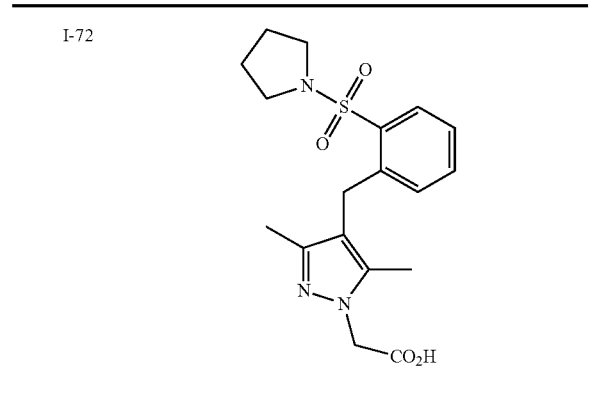
I-73
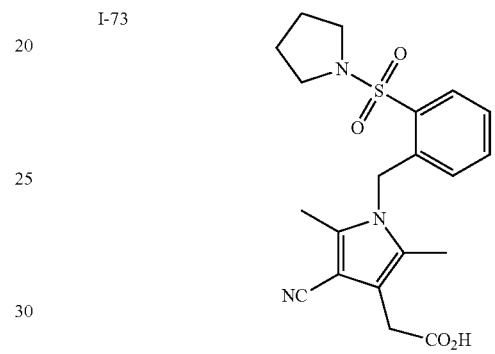
I-29
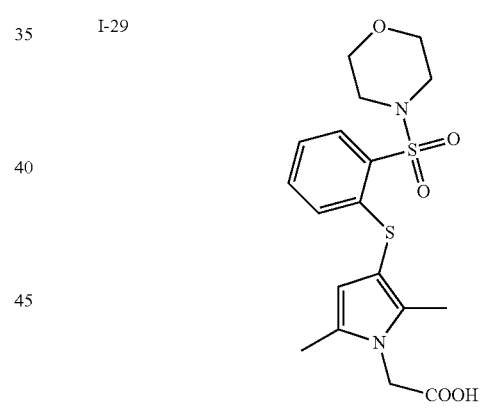
I-34
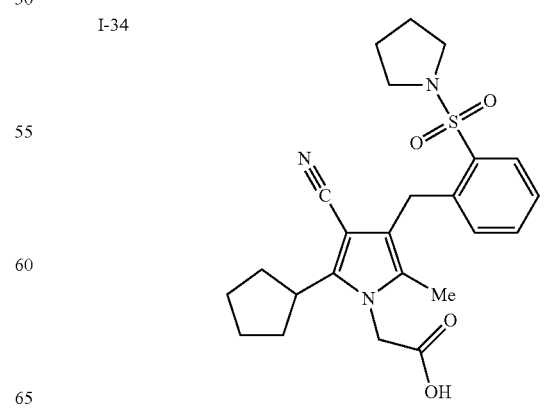

TABLE I-continued

I-74

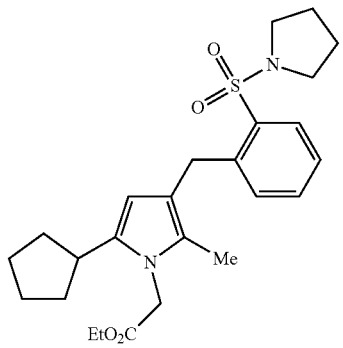 [SMILES: CCOC(=O)Cn1c(C2CCCC2)cc(Cc2ccccc2S(=O)(=O)N2CCCC2)c1C]

Pharmaceutically Acceptable Salts and Pro-Drugs.

The phrase "pharmaceutically acceptable salt," as used herein, refers to pharmaceutically acceptable organic or inorganic salts of a compound having Formula I. For use in medicine, the salts of the compounds having Formula I will be pharmaceutically acceptable salts. Other salts may, however, be useful in the preparation of the compounds having Formula I or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When the compound having Formula I is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N.sup.1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound having Formula I is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated herein by reference in its entirety.

In addition to the compounds described herein and their pharmaceutically acceptable salts, pharmaceutically acceptable solvates (e.g., hydrates) and co-crystals of these compounds and salts may also be employed in compositions to treat or prevent the herein identified disorders.

As used herein, the term "pharmaceutically acceptable solvate," is a solvate formed from the association of one or more pharmaceutically acceptable solvent molecules to one of the compounds described herein. As used herein, the term "hydrate" means a compound described herein or a salt thereof that further includes a stoichiometric or non-stoichiometric amount of water bound by non-covalent intermolecular forces. The term solvate includes hydrates (e.g., hemihydrate, monohydrate, dihydrate, trihydrate, tetrahydrate, and the like).

"Pharmaceutically acceptable co-crystals" result when a pharmaceutically active compound crystallizes with another material (e.g. a carboxylic acid, a 4,4'-bipyridine or an excipient) that is also a solid at room temperature. Some pharmaceutically acceptable excipients are described in the next section. Other pharmaceutically acceptable substances that can be used to form co-crystals are exemplified by the GRAS (Generally regarded as safe) list of the US FDA.

In addition to the compounds described herein, pharmaceutically acceptable pro-drugs of these compounds may also be employed in compositions to treat or prevent the herein identified disorders.

A "pharmaceutically acceptable pro-drug" includes any pharmaceutically acceptable ester, salt of an ester or other derivative or salt thereof of a compound described herein which, upon administration to a recipient, is capable of providing, either directly or indirectly, a compound described herein. Particularly favored pro-drugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species. The term "pro-drug" encompasses a derivative of a compound that can hydrolyze, oxidize, or otherwise react under biological conditions (in vitro or in vivo) to provide a compound described herein. Examples of pro-drugs include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of pro-drugs include derivatives of compounds that comprise —NO, —NO$_2$, —ONO, or —ONO$_2$ moieties. Pro-drugs can typically be prepared using well-known methods, such as those described by BURGER'S MEDICINAL CHEMISTRY AND DRUG DISCOVERY (1995) 172-178, 949-982 (Manfred E. Wolff ed., 5th Ed).

Pharmaceutical Compositions and Methods of Administration

Compositions of the Invention

In another aspect, the invention is a composition comprising a pharmaceutically acceptable carrier and a compound according described above.

The compounds herein disclosed, and their pharmaceutically acceptable salts, solvates, co-crystals and pro-drugs thereof may be formulated as pharmaceutical compositions or "formulations".

A typical formulation is prepared by mixing a compound having Formula I, or a pharmaceutically acceptable salt, solvate, co-crystal or pro-drug thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound having Formula I is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound having Formula I or pharmaceutical composition thereof) or aid in the manufacturing of the pharmaceutical product (i.e., medicament).

The formulations may be prepared using conventional dissolution and mixing procedures. For example, the bulk drug substance (i.e., compound having Formula I, a pharmaceutically acceptable salt, solvate, co-crystal or pro-drug thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound having Formula I or a pharmaceutically acceptable salt, solvate, co-crystal or pro-drug thereof is typically formulated into pharmaceutical dosage forms to provide an easily controllable dosage of the drug and to enable patient compliance with the prescribed regimen. Pharmaceutical formulations of compounds having Formula I, or a pharmaceutically acceptable salt, solvate, co-crystal or pro-drug thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount" of the compound to be administered will be governed by such considerations, and is the minimum amount necessary to ameliorate, cure or treat the disease or disorder or one or more of its symptoms.

The pharmaceutical compositions having Formula I will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder or one or more of its symptoms before it is acquired or before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, $21^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(−)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent disaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGITO, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g. methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water-permeable, non-dissolving and non-eroding coating surrounding the core which controls the influx of water into the core from an aqueous environment of use so as to cause drug release by extrusion of some or the entire core to the environment of use. In certain embodiments, the coating is polymeric, aqueous-permeable, and has at least one delivery port. The core of the osmotic device optionally includes an osmotic agent which acts to imbibe water from the surrounding environment via such a semi-permeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non-limiting examples of osmotic control devices are disclosed in U.S. patent application Ser. No. 09/495,061.

The amount of water-swellable hydrophilic polymers present in the core may range from about 5 to about 80 wt % (including for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly (acrylic) acid, poly (methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolate. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non-limiting examples of standard disintegrants include materials such as sodium starch glycolate (e.g., Explotab™ CLV), microcrystalline cellulose (e.g., Avicel™), microcrystalline silicified cellulose (e.g., ProSolv™) and croscarmellose sodium (e.g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multi-layered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. Nos. 6,419,952, 6,342,249, 5,324,280, 4,672,850, 4,627,850, 4,203,440, and 3,995,631.

As further noted above, the agents described herein may be provided in the form of microparticulates, generally ranging in size from about 10 μm to about 2 mm (including, for example, from about 100 μm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono-di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto 2005 Molecule 10:65-80). Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, ultrafine particles (sized around 0.1 μm) can be designed using polymers able to be degraded in vivo (e.g. biodegradable polyalkyl-cyanoacrylate nanoparticles). Such particles are described in the prior art (Couvreur et al, 1980; 1988; zur Muhlen et al., 1998; Zambaux et al. 1998; Pinto-Alphandry et al., 1995 and U.S. Pat. No. 5,145,684).

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula I that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending the compound of Formula I in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of compounds of Formula I contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection.

This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using compounds having Formula I may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of compounds having Formula I include Tween™-60, Span™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound having Formula I or a pharmaceutically acceptable salt thereof, co-crystal, solvate or pro-drug thereof may be formulated in a veterinary composition comprising a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Methods of Use

In another aspect, the present invention also provides a method for preventing or lessening the severity of or treating a patient suffering from a disease or disorder involving the CRTH2 receptor in a patient comprising administering to said patient a therapeutically effective amount of a compound of the invention.

In one embodiment of this aspect, the disease or disorder being treated is asthma, atopic dermatitis, allergic rhinitis, allergy, Grave's Disease, acute rhinitis, atrophic rhinitis or chronic rhinitis, rhinitis caseosa, hypertrophic rhinitis, rhinitis purulenta, rhinitis sicca, rhinitis medicamentosa, membranous rhinitis, croupous rhinitis, fibrinous rhinitis, pseudomembranous rhinitis, scrofulous rhinitis, perennial allergic rhinitis, seasonal rhinitis, rhinitis nervosa, vasomotor rhinitis, antitussive activity, bronchial asthma, allergic asthma, intrinsic asthma, extrinsic asthma, dust asthma, chronic asthma, inveterate asthma, late asthma, airway hyper-responsiveness, bronchitis, chronic bronchitis, eosinophilic bronchitis, chronic inflammatory diseases of the lung which result in interstitial fibrosis, interstitial lung diseases (ILD), idiopathic pulmonary fibrosis, ILD associated with rheumatoid arthritis, scleroderma lung disease, chronic obstructive pulmonary disease (COPD), chronic sinusitis, conjunctivitis, allergic conjunctivitis, cystic fibrosis, fanner's lung, fibroid lung, hypersensitivity lung disease, hypersensitivity pneumonitis, idiopathic interstitial pneumonia, nasal congestion, nasal polyposis, otitis media, chronic cough associated with inflammation, systemic anaphylaxis, hypersensitivity responses, drug allergies, insect sting allergies, food related allergies, food-related allergies with symptoms of migraine, rhinitis or eczema, arthritis, rheumatic arthritis, infectious arthritis, autoimmune arthritis, seronegative arthritis, spondyloarthropathy, ankylosing spondylitis, psoriatic arthritis, Reiter's disease, osteoarthritis, systemic sclerosis, psoriasis, atopical dermatitis, contact dermatitis, seborrheic dermatitis, cutaneous eosinophilias, chronic skin ulcers, cutaneous lupus erythematosus, contact hypersensitivity, allergic contact dermatitis, eosinophilic folliculitis, Celiac disease, cholecystitis, Crohn's disease, enteritis, eosinophilic gastroenteritis, eosinophilic esophagitis, enteropathy associated with seronegative arthropathies, gastritis, inflammatory bowel disease, irritable bowel disease, acute and chronic allograft rejection following solid organ transplant, chronic graft versus host disease, skin graft rejection, bone marrow transplant rejection, inflammation, hyperalgesia, allodynia, neuropathic pain, lupus erythematosus; systemic lupus, erythematosus; Hashimoto's thyroiditis, Grave's disease, type I diabetes, eosinophilia fasciitis, hyper IgE syndrome, idiopathic thrombocytopenia purpura; post-operative adhesions, ischemic/reperfusion injury in the heart, brain, peripheral limb hepatitis, mastocytosis, mastitis, vaginitis, vasculitis, myositis, basophilic leukemia, basophilic leukocytosis, or Churg-Strauss syndrome. More preferably the disease or disorder being treated with a composition of the invention is asthma or preventing an asthma attack. The disease or disorder being treated with a composition of the invention is may also be allergic rhinitis. The disease or disorder being treated may also be Chronic Obstructive Pulmonary Disease. The disease or disorder being treated may also be neuropathic pain. The disease or disorder being treated may also be atopic dermatitis. The disease or disorder being treated may also be allergic conjunctivitis. The disease or disorder being treated may also be gastrointestinal tract related diseases and disorders selected from Crohn's disease, eosinophilic gastroenteritis, eosinophilic esophagitis, inflammatory bowel disease or irritable bowel disease.

In another aspect, the compounds of the invention are CRTH2 antagonists that can be used, for example, to prevent and/or treat conditions or disorders in which it is considered desirable to reduce or eliminate CRTH2 activity. CRTH2 antagonists may be used to aid in preventing and/or treating a disease or disorder mediated, regulated or influenced by, for example, Th2 cells, eosinophils, basophils, platelets, Langerhans cells, dendritic cells or mast cells. They also may be used to aid in the prevention or treatment of a disease or disorder mediated, regulated or influenced by $PGD_2$ and metabolites thereof, such as 13,14-dihydro-15-keto-$PGD_2$ and 15-deoxy-A1 2,1'-$PGD_2$.

Definitions

The terms, "disease", "disorder", and "condition" may be used interchangeably here to refer to a CRTH2 receptor mediated medical or pathological condition.

As used herein, the terms "subject" and "patient" are used interchangeably. The terms "subject" and "patient" refer to an animal (e.g., a bird such as a chicken, quail or turkey, or a mammal). A "mammal" includes a non-primate (e.g., a cow, pig, horse, sheep, rabbit, guinea pig, rat, cat, dog, and mouse) and a primate (e.g., a monkey, chimpanzee and a human), and in particular a human. In one embodiment, the subject is a non-human animal such as a farm animal (e.g., a horse, cow, pig or sheep), or a pet (e.g., a dog, cat, guinea pig or rabbit). In another embodiment, the subject is a human.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of a CRTH2 receptor mediated condition, or the amelioration of one or more symptoms (preferably, one or more discernible symptoms) of said condition, resulting from the administration of one or more therapies (e.g., one or more therapeutic agents such as a compound or composition of the invention). In specific embodiments, the terms "treat", "treatment" and "treating" refer to the amelioration of at least one measurable physical parameter of a CRTH2 receptor mediated condition. In other embodiments the terms "treat", "treatment" and "treating" refer to the inhibition of the progression of a CRTH2 receptor mediated condition, either physically by, e.g., stabilization of a discernible symptom, physiologically by, e.g., stabilization of a physical parameter, or both.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended. For example, in the Physician's Desk Reference, a standard text in the field, the term "prevent" occurs hundreds of times. As used herein, the terms "prevent", "preventing" and "prevention" with regard to a disorder or disease refer to averting the cause and/or effects of a disease or disorder prior to the disease or disorder manifesting itself. The terms "prophylaxis" or "prophylactic use", as used herein, refer to any medical or public health procedure whose purpose is to prevent, rather than treat or cure a disease. As used herein, the terms "prevent", "prevention" and "preventing" also refer to the reduction in the risk of acquiring or developing a given condition, or the reduction or inhibition of the recurrence or said condition in a subject who is not ill, but who has been or may be near a person with the disease.

In one embodiment, the methods of the invention are a preventative or "preemptive" measure to a patient, preferably a human; having a predisposition to developing a CRTH2 receptor related disease or symptom. For example, the compounds described herein may be used to prevent the onset or re-occurrence of an asthma attack or allergic rhinitis, or prevent the onset or re-occurrence of atopic dermatitis.

The compounds and pharmaceutical compositions described herein can be used alone or in combination therapy for the treatment or prevention of a disease or disorder mediated, regulated or influenced by, for example, Th2 cells, eosinophils, basophils, platelets, Langerhans cells, dendritic cells or mast cells. They also may be used to aid in the prevention or treatment of a disease or disorder mediated, regulated or influenced by $PGD_2$ and metabolites thereof, such as 13,14-dihydro-15-keto-$PGD_2$ and 15-deoxy-A1 2,1'-$PGD_2$.

CRTH2 antagonists may be useful in the prevention and/or treatment of disease and disorders characterized by undesirable activation of Th2 cells, eosinophils, and basophils e.g., asthma, atopic dermatitis, allergic rhinitis, allergies (e.g., food allergies, dust allergies, pollen allergies, mold allergies), and Grave's Disease. CRTH2 antagonists or agonists may be used to aid in preventing and/or treating the following types of diseases, conditions and disorders:

(1) respiratory tract/obstructive airways diseases and disorders including: acute-, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofulous rhinitis, perennial allergic rhinitis, seasonal rhinitis (including rhinitis nervosa (hay fever) and vasomotor rhinitis), antitussive activity, asthma (such as bronchial, allergic, intrinsic, extrinsic and dust asthma particularly chronic or inveterate asthma (e.g. late asthma and airways hyper-responsiveness)), bronchitis (including chronic and eosinophilic bronchitis), chronic inflammatory diseases of the lung which result in interstitial fibrosis, such as interstitial lung diseases (ILD) (e.g., idiopathic pulmonary fibrosis, or ILD associated with rheumatoid arthritis, scleroderma lung disease, or other autoimmune conditions), chronic obstructive pulmonary disease (COPD) (such as irreversible COPD), chronic sinusitis, conjunctivitis (e.g. allergic conjunctivitis), cystic fibrosis, fanner's lung and related diseases, fibroid lung, hypersensitivity lung diseases, hypersensitivity pneumonitis, idiopathic interstitial pneumonia, nasal congestion, nasal polyposis, otitis media, and chronic cough associated with inflammation or iatrogenic induced;

(2) systemic anaphylaxis or hypersensitivity responses, drug allergies (e.g., to penicillin, cephalosporins), insect sting allergies, and food related allergies which may have effects remote from the gut (such as migraine, rhinitis and eczema);

(3) bone and joint related diseases and disorders including: arthritis including rheumatic, infectious, autoimmune, seronegative, spondyloarthropathies (such as ankylosing spondylitis, psoriatic arthritis and Reiter's disease), osteoarthritis, and systemic sclerosis;

(4) skin and eye related diseases and disorders including: psoriasis, atopical dermatitis, contact dermatitis, other eczematous, dermitides, seborrheic dermatitis, cutaneous eosinophilias, chronic skin ulcers, cutaneous lupus erythematosus, contact hypersensitivity/allergic contact dermatitis (including sensitivity to poison ivy, sumac, or oak), and eosinophilic folliculitis (Ofuji's disease);

(5) gastrointestinal tract related diseases and disorders including: Celiac disease, cholecystitis, Crohn's disease, enteritis (including eosinophilic gastroenteritis), eosinophilic esophagitis, enteropathy associated with seronegative arthropathies, gastritis, inflammatory bowel disease and irritable bowel disease;

(6) transplant rejection related conditions including: acute and chronic allograft rejection following solid organ transplant, for example, transplantation of kidney, heart, liver, lung, and cornea, chronic graft versus host disease, skin graft rejection, and bone marrow transplant rejection;

(7) inflammation;

(8) hyperalgesia, allodynia and neuropathic pain; and (8) other diseases and disorders including: lupus erythematosus; systemic lupus, erythematosus; Hashimoto's thyroiditis, Grave's disease, type I diabetes, eosinophilia fasciitis, hyper IgE syndrome, idiopathic thrombocytopenia purpura; post-operative adhesions, ischemic/reperfusion injury in the heart, brain, peripheral limbs hepatitis (alcoholic, steatohepatitis and chronic viral), mastocytosis (cutaneous and systemic), mastitis (mammary gland), vaginitis, vasculitis (e.g., necrotizing, cutaneous, and hypersensitivity vasculitis), myositis (including polyinyositis, derinatomyositis), basophile related diseases including basophilic leukemia and basophilic leukocytosis, and eosinophil related diseases such as Churg-Strauss syndrome.

Compounds and compositions of the invention are also useful for veterinary treatment of companion animals, exotic animals and farm animals, including, without limitation, dogs, cats, mice, rats, hamsters, gerbils, guinea pigs, rabbits, horses, pigs and cattle.

In another embodiment, the invention provides a method of reducing CRTH2 receptor activity in a biological sample, comprising contacting said biological sample with a compound or composition of the invention. Use of a CRTH2 receptor antagonist in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound having Formula I or a pharmaceutically acceptable salt, solvate (e.g., hydrate), co-crystal or pro-drug thereof and a second amount of an additional suitable therapeutic agent (e.g. an agent to treat pain).

In one embodiment of this invention, the compound having Formula I and the additional therapeutic agent are each administered in an effective amount (i.e., each in an amount which would be therapeutically effective if administered alone). In another embodiment, the compound having Structural Formula I and the additional therapeutic agent are each administered in an amount which alone does not provide a therapeutic effect (a sub-therapeutic dose). In yet another embodiment, the compound having Structural Formula I can be administered in an effective amount, while the additional therapeutic agent is administered in a sub-therapeutic dose. In still another embodiment, the compound having Structural Formula I can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order. When co-administration involves the separate administration of the first amount of a compound having Structural Formulae I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound having Formula I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of the invention, either administered separately or in the same pharmaceutical compositions, include, but are not limited to:

(1) inactivating antibodies (e.g., monoclonal or polyclonal) to interleukins (e.g., IL-4 and IL-5 (for example see Leckie et al. 2000 *Lancet* 356:2144));

(2) soluble chemokine receptors (e.g. recombinant soluble IL-4 receptor (Steinke and Borish 2001 *Respiratory Research* 2:66));

(3) chemokine receptor modulators including but not limited to antagonists of CCR1 (e.g., CP-481,715 (Gladue et al. *J Biol Chem* 278:40473)), CCR3 (e.g., UCB35625 (Sabroe et al. *J Biol Chem* 2000 275:25985), CCR5 and those described in: WO0039125A1, WO02070523A1, WO03035627A1, WO03084954A1, WO04011443A1, WO04014875A1, WO04018425A1, WO04018435A1, WO04026835A1, WO04026880A1, WO04039376A1, WO04039377A1, WO04039787A1, WO04056773A1, WO04056808A1, and WO04056809A1;

(4) histamine HI receptor antagonists/antihistamines (i.e. any compound that is capable of blocking, inhibiting, reducing or otherwise interrupting the interaction between histamine and its receptor) including but not limited to: -4 asternizole, acrivastine, antazoline, asternizole, azatadine, azelastine, bromopheniramine, carbinoxamine, carebastine, cetirizine, chlorpheniramine, clemastine, cyclizine, cyproheptadine, descarboethoxyloratadine, dexchlorpheniramine, dimethindene, diphenhydramine, diphenylpyraline, doxylarnine, ebastine, efletirizine, epinastine, fexofenadine, hydroxyzine, hydroxyzine, ketotifen, levocabastine, levocetirizine, levocetirizine, loratadine, meclizine, mequitazine, methdilazine, mianserin, mizolastine, noberastine, norasternizole, noraztemizole, pheniramine, picumast, promethazine, pyrilamine, temelastine, terfenadine, trimeprazine, tripelenamine, and triprolidin; leukotriene D4 receptor antagonists/leukotriene antagonists/LTD4 antagonists (i.e., any compound that is capable of blocking, inhibiting, reducing or otherwise interrupting the interaction between leukotrienes and the Cys LTI receptor) including but not limited to: zafirlukast, montelukast, montelukast sodium (Singulair®), pranlukast, iralukast, pobilukast, SKB-106,203 and compounds described as having LTD4 antagonizing activity described in U.S. Pat. No. 5,565,473;

(5) PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, WO0178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

(6) VLA-4 antagonists;

(7) corticosteroids, such as beclomethasone, methylprednisolone, betamethasone, prednisone, prenisolone, triamcinolone, dexamethasone, fluticasone, flunisolide and hydrocortisone, and corticosteroid analogs such as budesonide;

(8) immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);

(9) non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005);

(10) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);

(11) cyclooxygenase-2 (COX-2) inhibitors such as celecoxib (Celebrex®), rofecoxib (Vioxx®), valdecoxib, etoricoxib, parecoxib and lumiracoxib;

(12) inhibitors of phosphodiesterase type IV (PDE-IV);

(13) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine;

(14) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat);

(15) anti-diabetic agents such as insulin and insulin mimetics, sulfonylureas (e.g., glyburide, meglinatide), biguanides, e.g., metformin (Glucophage®), α-glucosidase inhibitors (acarbose), thiazolidinone compounds, e.g., rosiglitazone (Avandia®), troglitazone (Rezulin®), ciglitazone, pioglitazone (Actos®) and englitazone;

(16) preparations of interferon beta (interferon β-I α, interferon β-I β);

(17) gold compounds such as auranofin and aurothioglucose;

(18) TNF inhibitors, e.g., etanercept (Enbrel®), antibody therapies such as orthoclone (OKT3), daclizumab (Zenapax®), basiliximab (Simulec®)), infliximab (Remicade®) and D2E6 TNF antibody;

(19) lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin;

(20) multiple sclerosis therapeutic agents such as interferon β-I β (Betaseron®), interferon β-I α (Avonex®), azathioprine (Imurek®, Imuran®), glatiramer acetate (Capoxone®), a glucocorticoid (e.g., prednisolone) and cyclophosphamide; and

(21) other compounds such as 5-aminosalicylic acid and prodrugs thereof, DNA-alkylating agents (e.g., cyclophosphamide, ifosfamide), antimetabolites (e.g., azathioprine, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, hormone therapy (e.g., tamoxifen, and flutamide), and cytostatic agents, e.g., imatinib (STI571, Gleevec®) and rituximab (Rituxan®).

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for cotherapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of other one or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Methods of Preparing the Compounds

The compounds having Formula I may be prepared according to the schemes and examples depicted and described below. Unless otherwise specified, the starting materials and various intermediates may be obtained from commercial sources, prepared from commercially available compounds or prepared using well-known synthetic methods.

Syntheses

General synthetic procedures for the compounds of this invention are described below. The synthetic schemes are presented as examples and do not limit the scope of the invention in any way.

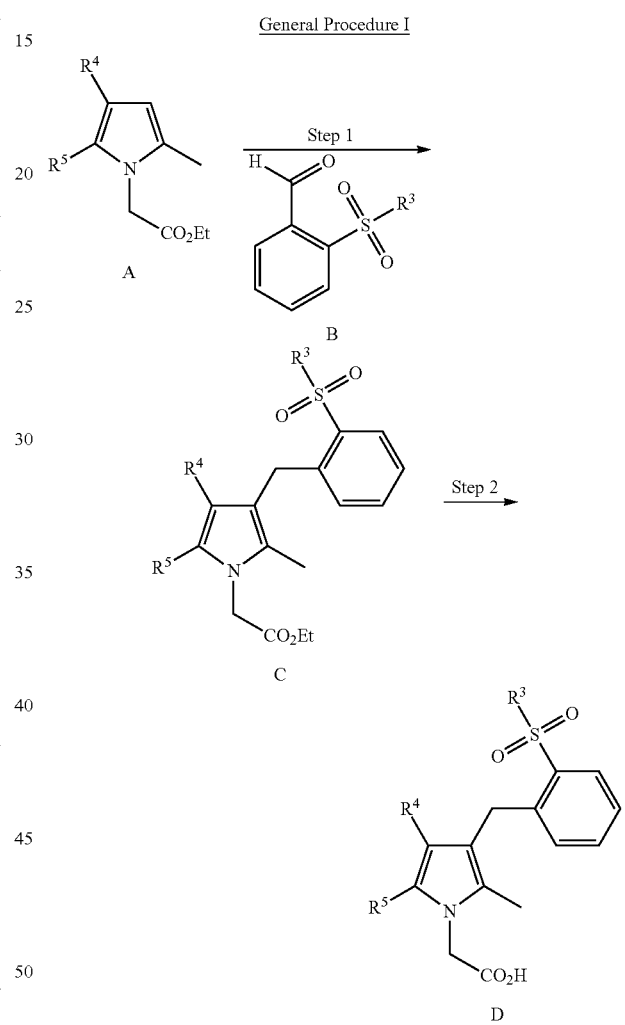

Step 1

To a −78° C. solution of the pyrrole A (1.0 equiv.) in dichloromethane (volume to 0.4M) was added triethylsilane (3.0 equiv.) followed by trimethylsilyl trifluoromethanesulfonate (2.0 equiv.). The reaction was stirred for 10 minutes at −78° C., after which a 0.4M solution of the aldehyde B (1.0 equiv.) in dichloromethane was added slowly over five minutes. The reaction was stirred at −78° C. for 1 hour after which it was slowly allowed to warm to room temperature. After one hour at room temperature, the reaction was poured into a separatory funnel containing saturated aqueous sodium bicarbonate solution and the dichloromethane separated, dried (sodium sulfate), filtered, and concentrated to a yellow residue. Purification of C was achieved by silica gel chromatography using either an ethyl acetate in hexanes gradient or 1 to 8% of 7:1 acetonitrile/methanol in dichloromethane gradient as the eluent.

Step 2 when $R^4$=CN

To a room temperature solution of the cyanoester C (1.0 equiv) in THF:water:methanol (3:1:1, concentration of 0.1M) was added solid lithium hydroxide hydrate (2.0 equiv.). The reaction was stirred at room temperature for 30 minutes, after which the reaction was concentrated to a residue and slurried in water. Neutralization with 3M aqueous HCl solution (2.0 equiv) followed by extraction with dichloromethane, drying (sodium sulfate), filtering and concentration under vacuum afforded the acid D as a solid*.

Step 2 when $R^4$=Anything Else

To a room temperature solution of the ester C (1.0 equiv) in THF:water (1:1, concentration of 0.1M) was added a solution of aqueous sodium hydroxide (2.0 equiv.). The reaction mixture was stirred at room temperature for 30 minutes, after which the reaction was concentrated to a residue and slurried in water. Neutralization with 3M aqueous HCl solution (2.0 equiv) followed by extraction with dichloromethane, drying (sodium sulfate), filtering and concentration afforded the acid D as a solid*.

*For scales larger than 50 mg of starting ester C the product acid D was precipitated out after neutralization with HCl instead of extracting the product with dichloromethane.

General Procedure II

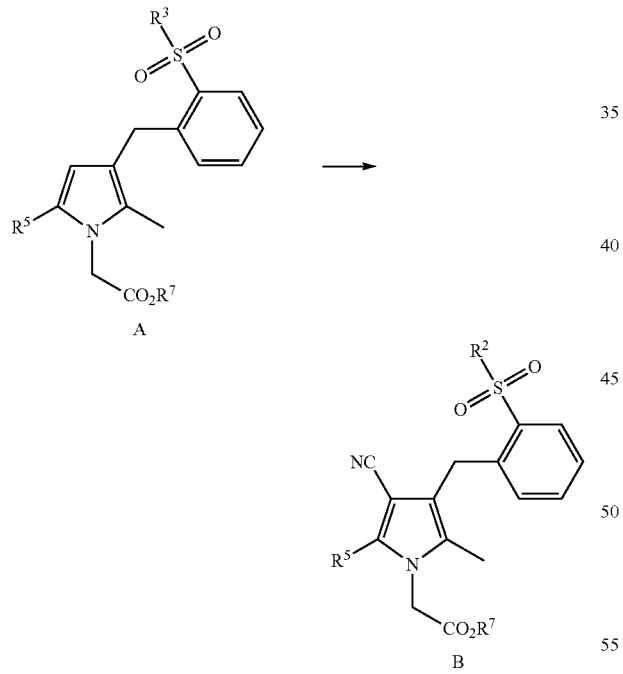

In an appropriate reaction vessel under a positive nitrogen atmosphere, at room temperature, pyrrole compound A (1 eq) was dissolved in acetonitrile (0.05 M) and then, the vessel additionally charged with chlorosulfonyl isocyanate (1.25 eq).

The reaction was monitored by LC/MS. After ~30 minutes, DMF (20 equiv) was added and the resulting reaction was stirred for 15 minutes, then quenched with water and extracted 3 times with dichloromethane. The organic portions were combined, dried ($Na_2SO_4$), filtered, and concentrated under vacuum. The crude material B was then purified via silica gel based chromatography using an appropriate gradient of solvents to deliver the desired material.

EXAMPLES

All references provided in the Examples are herein incorporated by reference. As used herein, all abbreviations, symbols and conventions are consistent t with those used in the contemporary scientific literature. See, e.g. Janet S. Dodd, ed., The ACS Style Guide: A Manual for Authors and Editors, $2^{nd}$ Ed., Washington, D.C.: American Chemical Society, 1997, herein incorporated in its entirety by reference.

Example 1

Synthesis of 2-(3-cyano-2-cyclohexyl-5-methyl-4-(2-(pyrrolidin-1-ylsulfonyl)benzyl)-1H-pyrrol-1-yl) acetic acid General synthetic scheme:

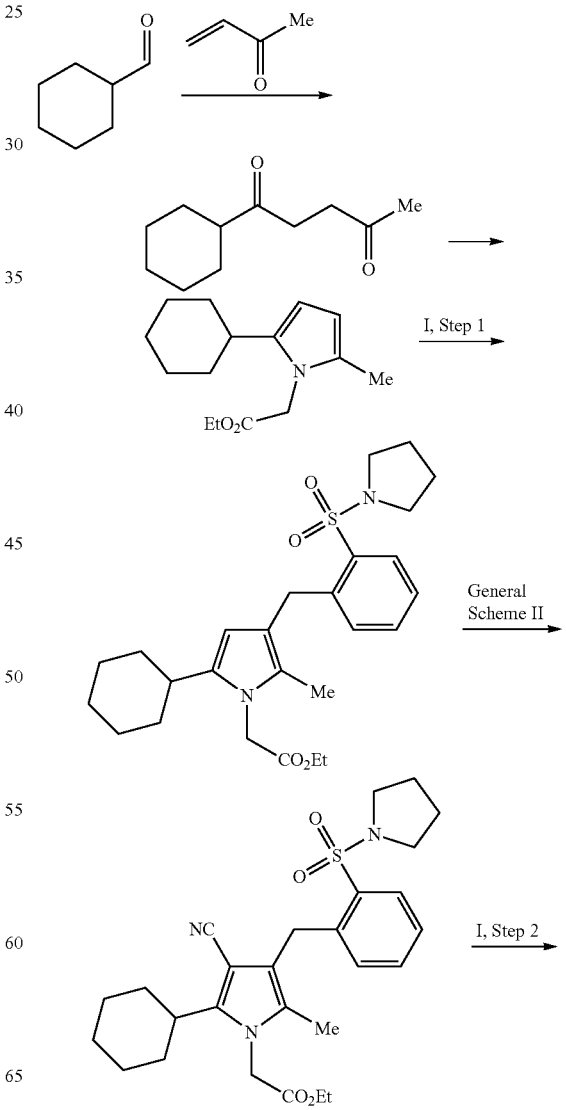

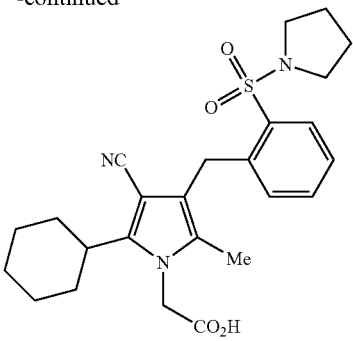

Preparation of 1-cyclohexylpentane-1,4-dione

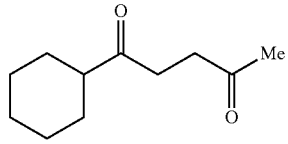 [SMILES: CC(=O)CCC(=O)C1CCCCC1]

To a solution of cyclohexanecarbaldehyde (3.22 mL, 26.7 mmol) in ethanol (9.5 mL) was added triethylamine (7.46 mL, 53.5 mmol), but-3-en-2-one (2.22 mL, 26.7 mmol), and 3-ethyl-5-(2-hydroxyethyl)-4-methylthiazol-3-ium bromide (1.35 g, 5.35 mmol). The reaction mixture was heated at 85° C. for 18.5 hours. The reaction was then concentrated under vacuum and the resulting residue was extracted with ethyl acetate (3×50 mL). The organic layer was dried (sodium sulfate), filtered and concentrated to an orange residue which was purified on silica gel using an automated system (ISCO 120 g, 20 mL/min) and 0 to 45% ethyl acetate in hexanes over 60 minutes as the eluent. The product was isolated as a yellow oil (1.32 g, 7.24 mmol, 27% yield). 1H NMR (400 MHz, CDCl3) δ (ppm) 2.68-2.73 (m, 4H), 2.35-2.42 (m, 1H), 2.19 (s, 3H), 1.85-1.89 (m, 2H), 1.76-1.79 (m, 2H), 1.65-1.69 (m, 1H), 1.17-1.39 (m, 5H).

Preparation of ethyl 2-(2-cyclohexyl-5-methyl-1H-pyrrol-1-yl)acetate

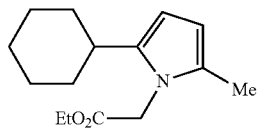

To a solution of 1-cyclohexylpentane-1,4-dione (1.32 g, 7.24 mmol) in dichloromethane (10 mL) was added ethyl 2-aminoacetate hydrochloride (1.01 g, 7.24 mmol) and solid sodium bicarbonate (1.52 g, 18.1 mmol). The reaction was heated at 55° C. for 6 hours, then stirred at 40° C. for an additional 14 hours, after which the reaction was nearly complete by LCMS analysis. The reaction mixture was cooled to room temperature, extracted with dichloromethane (3×50 mL), dried (sodium sulfate), filtered, and concentrated to a brown residue. Purification by silica gel column chromatography (Luknova 80 g, 20 mL/min) using 0 to 35% ethyl acetate in hexanes over 50 minutes afforded the product as a clear, colorless oil (1.45 g, 5.82 mmol, 80% yield). 1H NMR (400 MHz, CDCl3): δ (ppm) 5.86 (dd, 1H), 5.83 (d, 1H), 4.53 (s, 2H), 4.24 (q, 2H), 2.33 (m, 1H), 2.17 (d, 3H), 1.71-1.89 (m, 5H), 1.32-1.42 (m, 5H), 1.29 (t, 3H).

Preparation of ethyl 2-(5-cyclohexyl-2-methyl-3-(2-(pyrrolidin-1-ylsulfonyl)benzyl)-1H-pyrrol-1-yl) acetate (compound I-49)

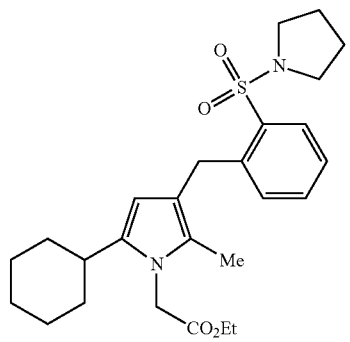 [SMILES: CCOC(=O)Cn1c(C2CCCCC2)cc(Cc2ccccc2S(=O)(=O)N2CCCC2)c1C]

General procedure I (step 1) was followed using ethyl 2-(2-cyclohexyl-5-methyl-1H-pyrrol-1-yl)acetate (1.00 g, 4.01 mmol), triethylsilane (1.92 mL, 12.0 mmol), trimethylsilyl trifluoromethanesulfonate (1.45 mL, 8.02 mmol) and 2-(pyrrolidin-1-ylsulfonyl)benzaldehyde (0.960 g, 4.01 mmol) to afford ethyl 2-(5-cyclohexyl-2-methyl-3-(2-(pyrrolidin-1-ylsulfonyl)benzyl)-1H-pyrrol-1-yl)acetate (642 mg, 1.36 mmol, 34% yield).

Preparation of ethyl 2-(3-cyano-2-cyclohexyl-5-methyl-4-(2-(pyrrolidin-1-ylsulfonyl)benzyl)-1H-pyrrol-1-yl)acetate (compound I-58)

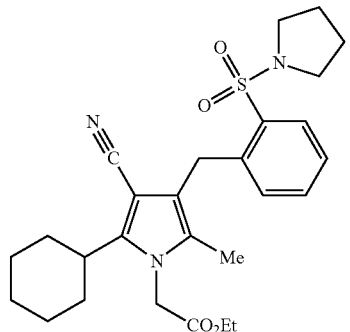

General procedure II was followed using ethyl 2-(5-cyclohexyl-2-methyl-3-(2-(pyrrolidin-1-ylsulfonyl)benzyl)-1H-pyrrol-1-yl)acetate (642 mg, 1.36 mmol), chlorosulfonyl isocyanate (0.147 mL, 1.70 mmol) and N,N-dimethylformamide (0.105 mL, 1.36 mmol) to afford ethyl 2-(3-cyano-2-cyclohexyl-5-methyl-4-(2-(pyrrolidin-1-ylsulfonyl)benzyl)-1H-pyrrol-1-yl)acetate (485 mg, 0.975 mmol, 72% yield) as a white sticky foam.

1D-NOESY experiment was performed to confirm the drawn regioisomer (irradiation of methyl group and 1-2% interaction with both methylene groups).

Synthesis of 2-(3-cyano-2-cyclohexyl-5-methyl-4-(2-(pyrrolidin-1-ylsulfonyl)benzyl)-1H-pyrrol-1-yl) acetic acid (compound I-14)

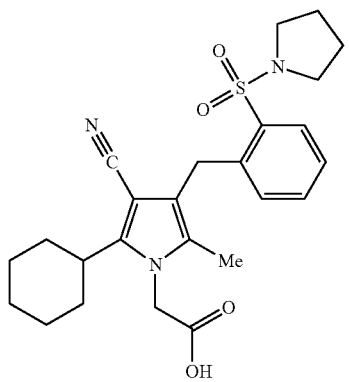 [SMILES: Cc1c(Cc2ccccc2S(=O)(=O)N2CCCC2)c(C#N)c(C2CCCCC2)n1CC(=O)O]

To a solution of ethyl 2-(3-cyano-2-cyclohexyl-5-methyl-4-(2-(pyrrolidin-1-ylsulfonyl)benzyl)-1H-pyrrol-1-yl)acetate (485 mg, 0.975 mmol) in tetrahydrofuran (2.9 mL), and water (0.98 mL), was added solid lithium hydroxide monohydrate (40.9 mg, 0.975 mmol). The reaction was stirred at room temperature for 45 minutes, after which analysis by LCMS indicated that the reaction was not complete. After 20 more minutes, an additional equivalent of lithium hydroxide monohydrate (40.9 mg) was added, and the reaction was stirred at room temperature for an additional 20 minutes, after which it was determined to be complete by LCMS analysis. Concentration of the reaction mixture, followed by acidification with aqueous 3M hydrochloric acid solution (0.65 mL), extraction with dichloromethane (1×50 mL), then ethyl acetate (2×50 mL), drying (sodium sulfate), filtering and concentration afforded 2-(3-cyano-2-cyclohexyl-5-methyl-4-(2-(pyrrolidin-1-ylsulfonyl)benzyl)-1H-pyrrol-1-yl)acetic acid (442 mg, 0.941 mmol, 97% yield). 1H NMR (400 MHz, CDCl3) δ (ppm) 7.96 (d, 1H), 7.43 (app. t, 1H), 7.32 (dd, 1H), 7.04 (d, 1H), 4.57 (s, 2H), 4.29 (s, 2H), 3.33-3.36 (m, 4H), 2.50 (m, 1H), 1.93-1.96 (m, 7H), 1.70-1.88 (m, 8H), 1.28-1.32 (m, 2H).

Preparation of 1-cyclopentylpentane-1,4-dione

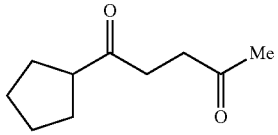 [SMILES: CC(=O)CCC(=O)C1CCCC1]

To a solution of cyclopentanecarbaldehyde (2.00 g, 20.38 mmol) in ethanol (7.2 mL) was added triethylamine (5.68 mL, 40.8 mmol), but-3-en-2-one (1.69 mL, 26.7 mmol), and 3-ethyl-5-(2-hydroxyethyl)-4-methylthiazol-3-ium bromide (1.03 g, 4.08 mmol). The reaction mixture was heated at 85° C. for 72 hours after which it was concentrated. The resulting residue was extracted with ethyl acetate (3×50 mL) and the organic layers were dried (sodium sulfate), filtered and concentrated to an orange residue which was used in the next step without further purification. The crude product, 1-cyclohexylpentane-1,4-dione (3.68 g, 21.9 mmol) was isolated as an orange oil. $^1$H NMR (400 MHz, CDCl$_3$) δ (ppm): 2.91 (m, 1H), 2.68-2.78 (m, 4H), 2.19 (s, 3H), 1.70-1.87 (m, 4H), 1.54-1.69 (m, 4H).

Preparation of ethyl 2-(2-cyclopentyl-5-methyl-1H-pyrrol-1-yl)acetate

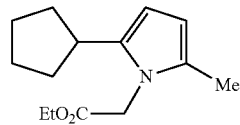

A slurry of ethyl 2-aminoacetate hydrochloride (2.93 g, 21.0 mmol), 1-cyclopentylpentane-1,4-dione (3.43 g, 20.4 mmol), and sodium bicarbonate (4.28 g, 51.0 mmol) in dichloromethane (20.4 mL) was heated at 50° C. for 72 hours, after which the reaction was diluted in water and extracted with dichloromethane (3×30 mL), dried (sodium sulfate), filtered and concentrated to a gold residue. Purification by silica gel chromatography (ISCO 120 g, 20 mL/min) using 0 to 35% ethyl acetate in hexanes afforded ethyl 2-(2-cyclopentyl-5-methyl-1H-pyrrol-1-yl)acetate (3.49 g, 14.8 mmol, 73% yield) as a clear colorless liquid. $^1$H NMR (400 MHz, CDCl$_3$) δ (ppm): 5.84 (s, 2H, two shifts isochronous), 4.54 (s, 2H), 4.23 (q, 2H), 2.83 (m, 1H), 2.19 (s, 3H), 1.91-1.98 (m, 2H), 1.73-1.79 (m, 2H), 1.58-1.64 (m, 4H), 1.27 (t, 3H).

Preparation of ethyl 2-(5-cyclopentyl-2-methyl-3-(2-(pyrrolidin-1-ylsulfonyl)benzyl)-1H-pyrrol-1-yl) acetate (compound I-74)

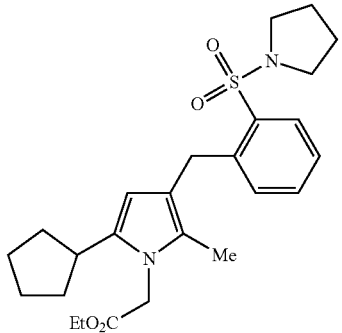 [SMILES: CCOC(=O)Cn1c(C2CCCC2)cc(Cc2ccccc2S(=O)(=O)N2CCCC2)c1C]

The general procedure was followed using ethyl 2-(2-cyclopentyl-5-methyl-1H-pyrrol-1-yl)acetate (3.49 g, 14.8 mmol), triethylsilane (7.11 mL, 44.5 mmol), trimethylsilyl trifluoromethanesulfonate (5.36 mL, 29.7 mmol), and 2-(pyrrolidin-1-ylsulfonyl)benzaldehyde (3.55 g, 14.8 mmol) in dichloromethane of (total volume: 170 ml). Purification on silica gel (Luknova 330 g, 20 mL/min) using 1 to 7% of a 7:1 acetonitrile/methanol solution in dichloromethane over 70 minutes afforded ethyl 2-(5-cyclopentyl-2-methyl-3-(2-(pyrrolidin-1-ylsulfonyl)benzyl)-1H-pyrrol-1-yl)acetate (2.54 g, 5.54 mmol, 37% yield) as a viscous gold residue that was approximately 90% pure by ¹H-NMR analysis, with the impurity being ethyl 2-(2-cyclopentyl-5-methyl-3-(2-(pyrrolidin-1-ylsulfonyl)benzyl)-1H-pyrrol-1-yl)acetate. ¹H NMR (400 MHz, CDCl₃) δ (ppm): 7.96 (dd, 1H), 7.40 (ddd, 1H), 7.22-7.28 (m, 2H, composite of two shifts), 4.56 (s, 2H), 4.23 (s, 2H), 4.18 (q, 2H), 3.28-3.31 (m, 4H), 2.83 (m, 1H), 2.03 (s, 3H), 1.89-1.99 (m, 3H), 1.84-1.88 (m, 4H), 1.49-1.74 (m, 5H, composite of multiple shifts), 1.29 (t, 3H).

Preparation of ethyl 2-(3-cyano-2-cyclopentyl-5-methyl-4-(2-(pyrrolidin-1-ylsulfonyl)benzyl)-1H-pyrrol-1-yl)acetate (compound I-26)

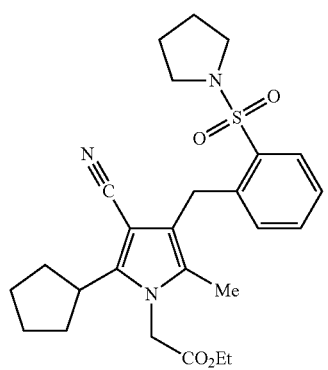 [SMILES: CCOC(=O)Cn1c(C)c(Cc2ccccc2S(=O)(=O)N2CCCC2)c(C#N)c1C1CCCC1]

To a solution of ethyl 2-(5-cyclopentyl-2-methyl-3-(2-(pyrrolidin-1-ylsulfonyl)benzyl)-1H-pyrrol-1-yl)acetate (2.54 g, 5.54 mmol) in acetonitrile (28 mL) was added chlorosulfonyl isocyanate (0.818 ml, 9.42 mmol). The reaction was stirred at room temperature for 30 minutes, after which the starting pyrrole had still not been consumed. The reaction was then heated to 55° C. for 30 minutes after which the starting pyrrole was consumed (by LCMS analysis). To the reaction mixture at 55° C. was added N,N-dimethylformamide (0.729 ml, 9.42 mmol). The reaction was stirred at 55° C. for 30 minutes after which analysis of the reaction (by LCMS) indicated that the reaction to afford the desired product was complete. The reaction was quenched by the addition of water, and extracted with dichloromethane (3×50 mL), dried (sodium sulfate), filtered and concentrated to a deep maroon residue. Purification was achieved by silica gel chromatography (Luknova 240 g, 20 mL/min) using 1 to 7% of a 7:1 acetonitrile/methanol solution in dichloromethane over 70 minutes. The product ethyl 2-(3-cyano-2-cyclopentyl-5-methyl-4-(2-(pyrrolidin-1-ylsulfonyl)benzyl)-1H-pyrrol-1-yl)acetate (747 mg, 1.55 mmol, 28% yield) was isolated as a white foam. ¹H NMR (400 MHz, CDCl₃) δ (ppm): 8.01 (d, 1H), 7.40 (dd, 1H), 7.30 (ddd, 1H), 6.99 (d, 1H), 4.59 (s, 2H), 4.30 (s, 2H), 4.27 (q, 2H), 3.32-3.36 (m, 4H), 2.96 (m, 1H), 1.84-2.09 (m, 13H, composite of multiple shifts), 1.63-1.71 (m, 2H).

¹D-NOESY analysis of ethyl 2-(3-cyano-2-cyclopentyl-5-methyl-4-(2-(pyrrolidin-1-ylsulfonyl)benzyl)-1H-pyrrol-1-yl)acetate (irradiation of the 3-position methylene protons) showed a ~2% correlation between the 5-methyl group, the ortho position of the phenyl ring and the sulfonyl pyrrolidine protons adjacent to the nitrogen. This analysis confirms the drawn regioisomer.

2-(3-cyano-2-cyclohexyl-5-methyl-4-(2-(pyrrolidin-1-ylsulfonyl)benzyl)-1H-pyrrol-1-yl)acetic acid (compound I-34)

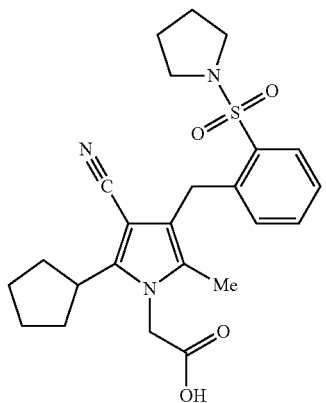 [SMILES: Cc1c(Cc2ccccc2S(=O)(=O)N2CCCC2)c(C#N)c(C2CCCC2)n1CC(=O)O]

General procedure I was followed using ethyl 2-(3-cyano-2-cyclopentyl-5-methyl-4-(2-(pyrrolidin-1-ylsulfonyl)benzyl)-1H-pyrrol-1-yl)acetate (747 mg, 1.55 mmol) and lithium hydroxide monohydrate (130 mg, 3.09 mmol) in tetrahydrofuran (9.3 mL), methanol (3.1 mL), and water (3.1 mL). The product 2-(3-cyano-2-cyclopentyl-5-methyl-4-(2-(pyrrolidin-1-ylsulfonyl)benzyl)-1H-pyrrol-1-yl)acetic acid (685 mg, 1.50 mmol, 97% yield) was isolated as a tan solid. ¹H NMR (400 MHz, CDCl₃) δ (ppm): 7.99 (dd, 1H), 7.42 (ddd, 1H), 7.31 (dd, 1H), 7.00 (d, 1H), 4.65 (s, 2H), 4.30 (s, 2H), 3.32-3.36 (m, 4H), 2.94 (m, 1H), 1.87-2.04 (m, 13H, composite of multiple shifts), 1.59-1.70 (m, 2H).

Example 2

Synthesis of 2-(3-cyano-2-cyclopropyl-5-methyl-4-(2-(pyrrolidin-1-ylsulfonyl)benzyl)-1H-pyrrol-1-yl) acetic acid General Synthetic Scheme:

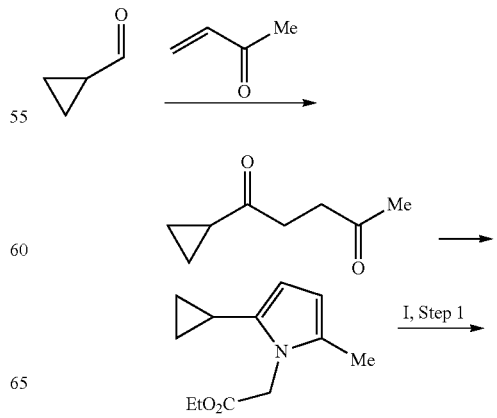

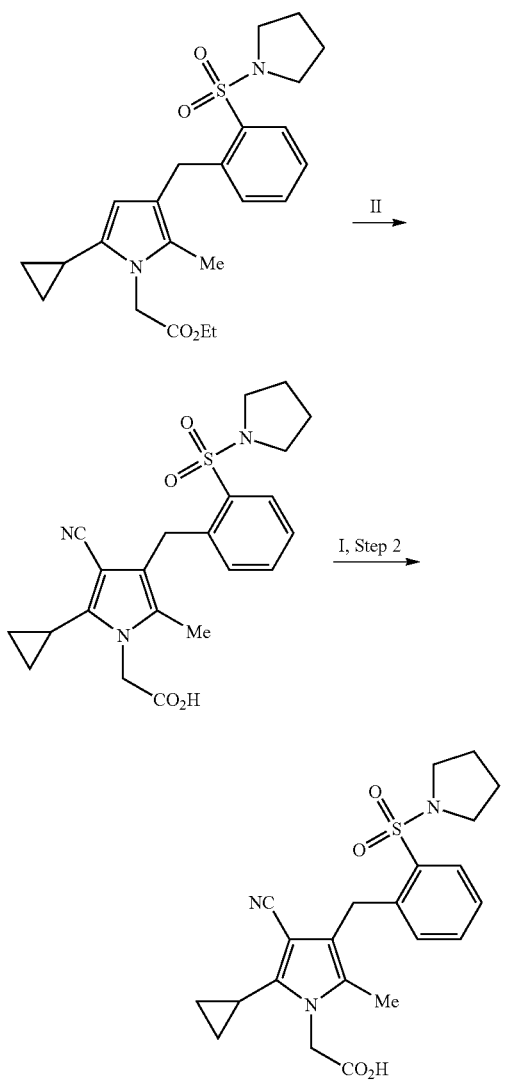

Preparation of 1-cyclopropylpentane-1,4-dione

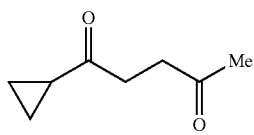

To a solution of cyclopropanecarbaldehyde (3.20 ml, 42.8 mmol) in ethanol (15.3 mL) was added triethylamine (11.9 mL, 86.0 mmol), but-3-en-2-one (3.54 mL, 42.8 mmol), and 3-ethyl-5-(2-hydroxyethyl)-4-methylthiazol-3-ium bromide (2.16 g, 8.56 mmol). The reaction mixture was heated at 85° C. for 18.5 h. The reaction was then concentrated and the resulting residue was extracted with ethyl acetate (3×50 mL). The organic layer was dried (sodium sulfate), filtered and concentrated to an orange residue which was purified on silica gel on an automated system (ISCO 120 g, 20 mL/min) using 0 to 75% ethyl acetate in hexanes over 60 minutes. The product, 1-cyclopropylpentane-1,4-dione, was isolated as a yellow oil (2.21 g, 15.8 mmol, 37% yield). 1H NMR (400 MHz, CDCl3) δ (ppm) 2.86 (t, 2H), 2.72 (t, 2H), 2.19 (s, 3H), 1.90-1.99 (m, 1H), 1.01 (m, 2H), 0.88 (m, 2H).

Preparation of ethyl 2-(2-cyclopropyl-5-methyl-1H-pyrrol-1-yl)acetate

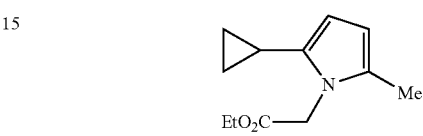

A slurry of ethyl 2-aminoacetate hydrochloride (2.20 g, 15.8 mmol), and solid sodium bicarbonate (3.31 g, 39.4 mmol) in dichloromethane (19.7 mL) was heated at 50° C. for 72 hours, after which the reaction was diluted in water and extracted with dichloromethane (3×30 mL), dried (sodium sulfate), filtered and concentrated to a gold residue. Purification by silica gel chromatography using an automated system (ISCO 120 g, 20 mL/min) and 5 to 75% ethyl acetate in hexanes afforded ethyl 2-(2-cyclopropyl-5-methyl-1H-pyrrol-1-yl)acetate as a clear colorless liquid (2.16 g, 10.4 mmol, 66% yield). 1H NMR (400 MHz, CDCl3): δ (ppm) 5.79 (dd, 1H), 5.76 (dd, 1H), 4.68 (s, 2H), 4.24 (q, 2H), 2.17 (s, 3H), 1.29 (t, 3H), 0.76-0.81 (m, 2H), 0.54-0.59 (m, 2H).

Preparation of ethyl 2-(5-cyclopropyl-2-methyl-3-(2-(pyrrolidin-1-ylsulfonyl)benzyl)-1H-pyrrol-1-yl)acetate

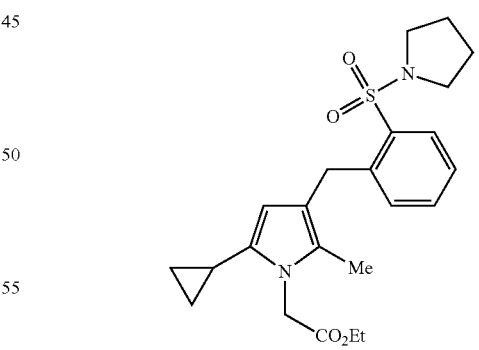

General procedure I (step 1) was followed using 2-(2-cyclopropyl-5-methyl-1H-pyrrol-1-yl)acetate (1.25 g, 6.03 mmol), triethylsilane (2.89 mL, 18.1 mmol), trimethylsilyl trifluoromethanesulfonate (2.18 mL, 12.1 mmol) and 2-(pyrrolidin-1-ylsulfonyl)benzaldehyde (1.44 g, 6.03 mmol) to afford ethyl 2-(5-cyclopropyl-2-methyl-3-(2-(pyrrolidin-1-ylsulfonyl)benzyl)-1H-pyrrol-1-yl)acetate (642 mg, 1.49 mmol, 25% yield) as an oil.

Synthesis of ethyl 2-(3-cyano-2-cyclopropyl-5-methyl-4-(2-(pyrrolidin-1-ylsulfonyl)benzyl)-1H-pyrrol-1-yl)acetate (compound I-59)

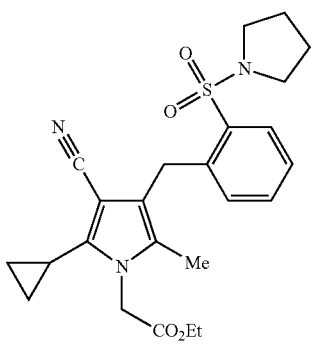 [SMILES: CCOC(=O)Cn1c(C)c(Cc2ccccc2S(=O)(=O)N2CCCC2)c(C#N)c1C1CC1]

General procedure II was followed using ethyl 2-(5-cyclopropyl-2-methyl-3-(2-(pyrrolidin-1-ylsulfonyl)benzyl)-1H-pyrrol-1-yl)acetate (1.09 g, 2.53 mmol), chlorosulfonyl isocyanate (0.275 mL, 3.16 mmol) and N,N-dimethylformamide (0.196 mL, 2.53 mmol) to afford ethyl 2-(3-cyano-2-cyclopropyl-5-methyl-4-(2-(pyrrolidin-1-ylsulfonyl)benzyl)-1H-pyrrol-1-yl)acetate (58.0 mg, 0.127 mmol, 5% yield) as a viscous oil. 1D-NOESY experiment was performed to confirm the drawn regioisomer (irradiation of methyl group and 1-2% interaction with both methylene groups).

Synthesis of 2-(3-cyano-2-cyclopropyl-5-methyl-4-(2-(pyrrolidin-1-ylsulfonyl)benzyl)-1H-pyrrol-1-yl)acetic acid (compound I-33)

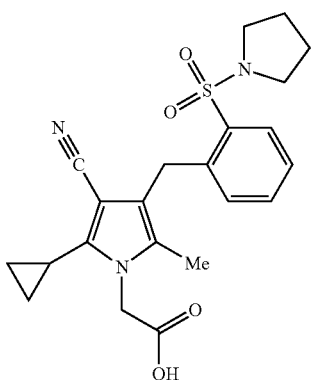 [SMILES: Cc1c(Cc2ccccc2S(=O)(=O)N2CCCC2)c(C#N)c(C2CC2)n1CC(=O)O]

General procedure I (step 2) was followed using ethyl 2-(3-cyano-2-cyclopropyl-5-methyl-4-(2-(pyrrolidin-1-ylsulfonyl)benzyl)-1H-pyrrol-1-yl)acetate (65.4 mg, 0.144 mmol) and lithium hydroxide hydrate (12.05 mg, 0.287 mmol) to afford 2-(3-cyano-2-cyclopropyl-5-methyl-4-(2-(pyrrolidin-1-ylsulfonyl)benzyl)-1H-pyrrol-1-yl)acetic acid as a white solid (58.5 mg, 0.137 mmol, 95% yield). 1H NMR (400 MHz, CDCl3) δ (ppm) 7.94 (d, 1H), 7.43 (dd, 1H), 7.32 (dd, 1H), 7.08 (d, 1H), 4.69 (s, 2H), 4.26 (s, 2H), 3.31-3.35 (m, 4H), 1.90-1.95 (m, 7H), 1.65 (m, 1H), 0.86-0.97 (m, 4H).

Example 3

Synthesis of 2-(5-(2-chloropyridin-4-yl)-2-methyl-3-(2-(phenylsulfonyl)benzyl)-1H-pyrrol-1-yl)acetic acid General Synthetic Scheme

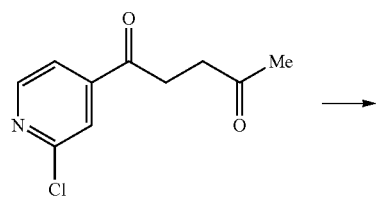

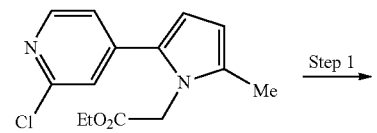

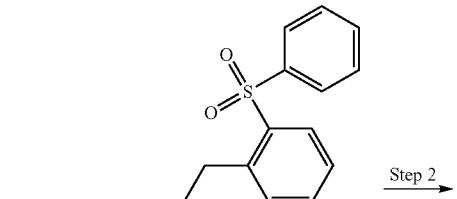

Step 1

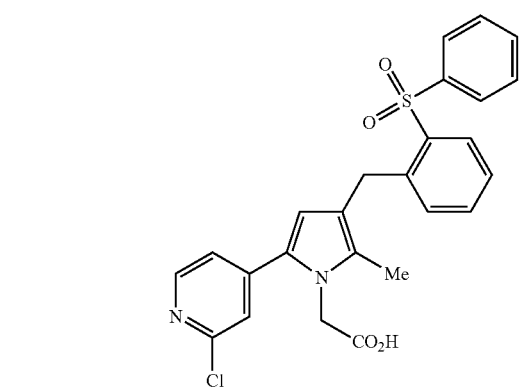

Step 2

Preparation of 1-(2-chloropyridin-4-yl)pentane-1,4-dione

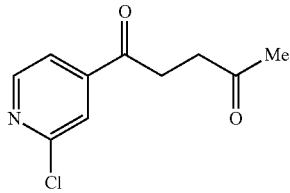 [SMILES: CC(=O)CCC(=O)c1ccnc(Cl)c1]

To a solution of 2-chloroisonicotinaldehyde (1.50 g, 10.6 mmol) in ethanol (3.8 mL) was added triethylamine (2.95 mL, 21.2 mmol), but-3-en-2-one (0.877 mL, 10.6 mmol), and 3-ethyl-5-(2-hydroxyethyl)-4-methylthiazol-3-ium bromide (0.534 g, 2.12 mmol). The reaction mixture was heated at 85° C. for 18.5 hours. The reaction was then concentrated and the organic layer was extracted with ethyl acetate (3×50 mL), dried (sodium sulfate), filtered and concentrated to an orange residue. Purification by silica gel chromatography with an automated system (ISCO 120 g, 20 mL/min) and using 0 to 75% ethyl acetate in hexanes over 60 minutes afforded 1-(2-chloropyridin-4-yl)pentane-1,4-dione as a gold/tan solid (0.986 g, 4.66 mmol, 44% yield). 1H NMR (400 MHz, CDCl3): δ (ppm) 8.58 (d, 1H), 7.80 (s, 1H), 7.69 (dd, 1H), 3.19-3.22 (m, 2H), 2.92-2.95 (m, 2H), 2.27 (s, 3H).

Preparation of benzyl 2-(2-(2-chloropyridin-4-yl)-5-methyl-1H-pyrrol-1-yl)acetate

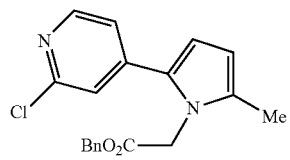

A slurry of benzyl 2-aminoacetate hydrochloride (922 mg, 4.57 mmol), 1-(2-chloropyridin-4-yl)pentane-1,4-dione (968 mg, 4.57 mmol), and solid sodium bicarbonate (961 mg, 11.4 mmol) in dichloromethane (15.2 mL) was heated to 45° C. for 14 hours. A significant amount of starting material was observed after 14 hours by LC/MS, so the reaction was heated to 65° C. The reaction was allowed to stir (with occasional monitoring by LCMS) at this temperature for 11 days. The reaction was then allowed to cool down to room temperature and poured onto water and extracted with dichloromethane (3×50 mL), dried (sodium sulfate), filtered, and concentrated to a dark orange residue. Purification was achieved by column chromatography (Luknova 80 g, 20 mL/min) using 5 to 45% ethyl acetate in hexanes over 60 minutes. The product, benzyl 2-(2-(2-chloropyridin-4-yl)-5-methyl-1H-pyrrol-1-yl)acetate was isolated as a light orange oil (890 mg, 2.61 mmol, 57% yield). $^1$H NMR (400 MHz, CDCl$_3$): δ (ppm) 8.23 (d, 1H), 7.36-7.40 (m, 5H), 7.21 (m, 1H), 7.02 (dd, 1H), 6.37 (d, 1H), 6.07 (d, 1H), 5.25 (s, 2H), 4.64 (s, 2H), 2.22 (s, 3H).

Synthesis of benzyl 2-(5-(2-chloropyridin-4-yl)-2-methyl-3-(2-(phenylsulfonyl)benzyl)-1H-pyrrol-1-yl)acetate (compound I-60)

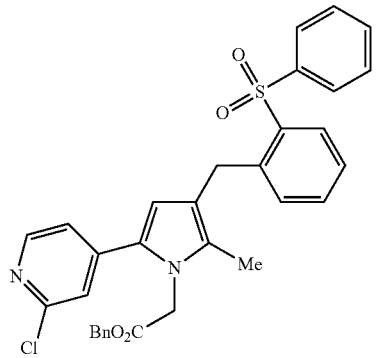

General procedure I (step 1) was followed using benzyl 2-(2-(2-chloropyridin-4-yl)-5-methyl-1H-pyrrol-1-yl)acetate (0.900 g, 2.64 mmol), triethylsilane (1.27 ml, 7.92 mmol), trimethylsilyl trifluoromethanesulfonate (0.954 ml, 5.28 mmol) and 2-(phenylsulfonyl)benzaldehyde (0.650 g, 2.64 mmol) to afford benzyl 2-(5-(2-chloropyridin-4-yl)-2-methyl-3-(2-(phenylsulfonyl)benzyl)-1H-pyrrol-1-yl)acetate (514 mg, 0.450 mmol, 17% yield). 1D-NOESY experiment was performed to confirm the drawn regioisomer (irradiation of methyl group and 1-2% interaction with both methylene groups).

2-(5-(2-chloropyridin-4-yl)-2-methyl-3-(2-(phenylsulfonyl)benzyl)-1H-pyrrol-1-yl)acetic acid (compound I-41)

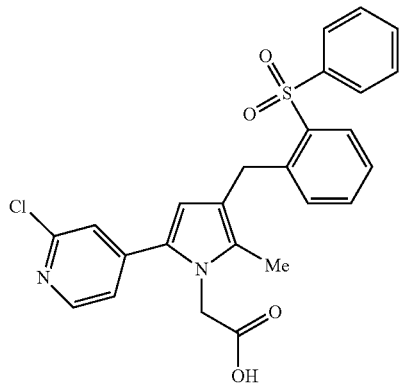 [SMILES: Cc1c(Cc2ccccc2S(=O)(=O)c2ccccc2)cc(-c2ccnc(Cl)c2)n1CC(=O)O]

To a solution of crude benzyl 2-(5-(2-chloropyridin-4-yl)-2-methyl-3-(2-(phenylsulfonyl)benzyl)-1H-pyrrol-1-yl)acetate (514 mg, 0.360 mmol, contaminated with ~60% 2-(phenylsulfonyl)phenyl)methanol) in tetrahydrofuran (4 mL) and water (4 mL) was added a 3M solution of aqueous sodium hydroxide (28.8 mg, 0.720 mmol). The reaction turned yellow upon addition of the base solution, and the reaction was stirred at room temperature for 20 minutes after which LCMS analysis indicated that the saponification was complete. The reaction was concentrated to remove the THF, and then diluted in water and washed with dichloromethane (2×50 mL) and ethyl acetate (1×50 mL). The water layer was acidified to pH=4 with 3M aqueous hydrochloric acid solution. The product was extracted with ethyl acetate and washed with a brined aqueous layer (3×50 mL), dried (sodium sulfate), filtered and concentrated to a yellow solid. A significant loss of product was observed. In order to recover additional product, the aqueous layer prior to the final extraction was further acidified and re-extracted with ethyl acetate (3×50 mL), dried (sodium sulfate), filtered and concentrated. The batches were combined to afford 2-(5-(2-chloropyridin-4-yl)-2-methyl-3-(2-(phenylsulfonyl)benzyl)-1H-pyrrol-1-yl)acetic acid as a yellow solid (99.5 mg, 0.207 mmol, 58% yield). $^1$H NMR (400 MHz, CDCl$_3$): δ (ppm) 8.31 (d, 1H), 8.27 (d, 1H), 7.85 (m, 2H), 7.40-7.56 (m, 5H), 7.13-7.16 (m, 2H), 7.04 (d, 1H), 5.85 (s, 1H), 4.64 (s, 2H), 4.05 (s, 2H), 2.00 (s, 3H).

Example 4

Synthesis of 2-(3-(3-fluorophenyl)-5-methyl-2-phenyl-4-(2-(phenylsulfonyl)benzyl)-1H-pyrrol-1-yl)acetic acid General Synthetic Scheme

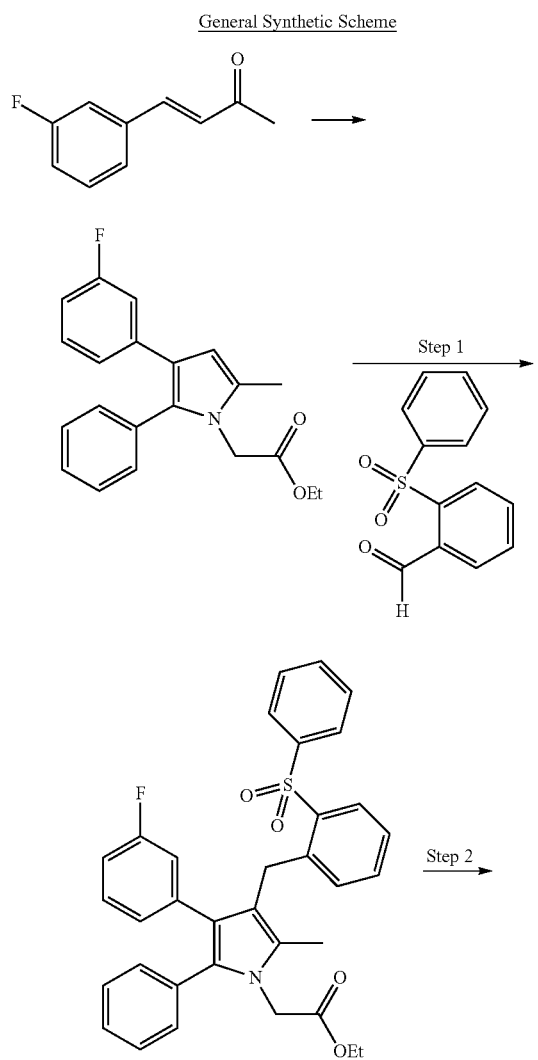

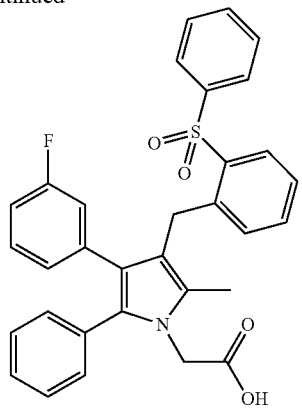

Preparation of (E)-4-(3-fluorophenyl)but-3-en-2-one

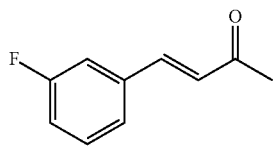

To a mixture of 3-fluorobenzaldehyde (4.0 ml, 37.7 mmol) and acetone (8.86 ml, 121 mmol) in water (10 ml), was added 0.25 M sodium hydroxide (15.08 ml, 3.77 mmol). The reaction mixture was heated at 65° C. for 2 h. The mixture was poured into ice water and extracted with ethyl acetate (200 ml). The organic layer was dried, filtered, and evaporated to give (E)-4-(3-fluorophenyl)but-3-en-2-one as yellow oil. It was used for the next reaction without purification (6.92 g, 42.1 mmol, 112% yield). 1H NMR (CDCl3/400 MHz): δ (ppm) 7.46 (d, 1H), 7.40-7.34 (m, 1H), 7.33-7.29 (m, 1H), 7.26-7.21 (m, 1H), 7.12-7.06 (m, 1H), 6.70 (d, 1H), 2.38 (s, 3H).

Preparation of ethyl 2-(3-(3-fluorophenyl)-5-methyl-2-phenyl-1H-pyrrol-1-yl)acetate

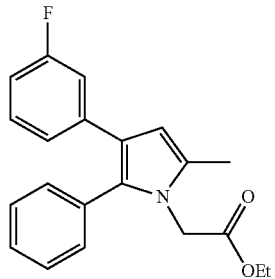 [SMILES: CCOC(=O)Cn1c(C)cc(-c2cccc(F)c2)c1-c1ccccc1]

A 250 ml round bottom flask equipped with a stir bar and an addition funnel was charged with sodium cyanide (1.386 g, 28.3 mmol) and DMF (20 ml). The flask was placed in an oil bath at 35° C. To this suspension at 35° C., was added over the course of 30 minutes, solution of benzaldehyde (5.55 ml, 54.8 mmol) in DMF (20.00 ml). The mixture was stirred at 35° C. for an additional 1.5 h. To this mixture, was added over the course of 2 hours, a solution of (E)-4-(3-fluorophenyl)but-3-en-2-one (6.92 g, 42.1 mmol) in DMF (20 ml). The mixture was stirred at 35° C. overnight. The mixture was quenched with water (100 ml×2) and extracted with ethyl acetate (200 ml). The organic layer was washed with water (100 ml×3) and brine (100 ml). The combined organic layers were dried, filtered, and evaporated to give an oil. The oil was combined with ethyl 2-aminoacetate hydrochloride (4.03 g, 28.9 mmol), triethylamine (6.03 ml, 43.3 mmol) and EtOH (26.2 ml) and the resulting mixture was heated at 100° C. for 18 hours. It was then allowed to cool to room temperature and ethanol was removed. The residue was taken up in ethyl acetate (200 ml) and water (50 ml) and the organic layer was washed with water (100 ml×4). The organic layer was dried, filtered, and evaporated to give an oil which was further purified by column chromatography on silica gel (0 to 40% ethyl acetate in hexanes) to give ethyl 2-(3-(3-fluorophenyl)-5-methyl-2-phenyl-1H-pyrrol-1-yl)acetate (1.74 g, 5.16 mmol, 17.87% yield). 1H NMR (CDCl3/400 MHz): δ (ppm) 7.61-7.51 (m, 2H), 7.49-7.40 (m, 3H), 7.40-7.35 (m, 3H), 7.34-7.31 (m, 1H), 6.23 (d, 1H), 4.41 (s, 2H), 4.20 (q, 2H), 2.26 (d, 3H), 1.25 (t, 2H). MS m/z: 338.2 (M+1).

Synthesis of 2-(3-(3-fluorophenyl)-5-methyl-2-phenyl-4-(2-(phenylsulfonyl)benzyl)-1H-pyrrol-1-yl)acetic acid (compound I-44)

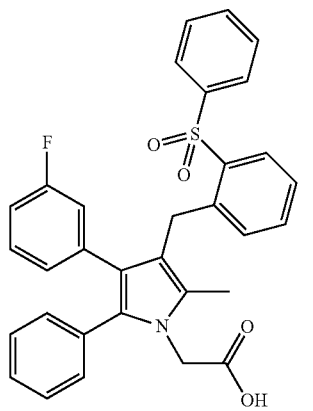 [SMILES: Cc1c(Cc2ccccc2S(=O)(=O)c2ccccc2)c(-c2cccc(F)c2)c(-c2ccccc2)n1CC(=O)O]

General procedure I (step 1 and 2) were followed for the remainder of the synthesis.

1H NMR (CDCl3/400 MHz) δ (ppm) 9.11 (bs, 1H), 8.35-8.29 (m, 1H), 7.85-7.79 (m, 1H), 7.55-7.44 (m, 4H), 7.44-7.35 (m, 3H), 7.29-7.25 (m, 3H), 7.24-7.19 (m, 1H), 7.16-7.09 (m, 1H), 6.85-6.78 (m, 1H), 6.65-6.59 (m, 1H), 6.49-6.44 (m, 1H), 6.37-6.32 (m, 1H), 4.57 (s, 2H), 4.00 (s, 2H), 1.88 (s, 3H). MS m/z: 540.3 (M+1).

Example 5

Synthesis of 2-(3-(2,4-difluorophenyl)-2,5-dimethyl-4-(2-(pyrrolidin-1-ylsulfonyl)benzyl)-1H-pyrrol-1-yl)acetic acid General Synthetic Scheme

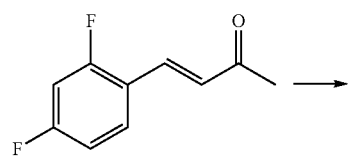

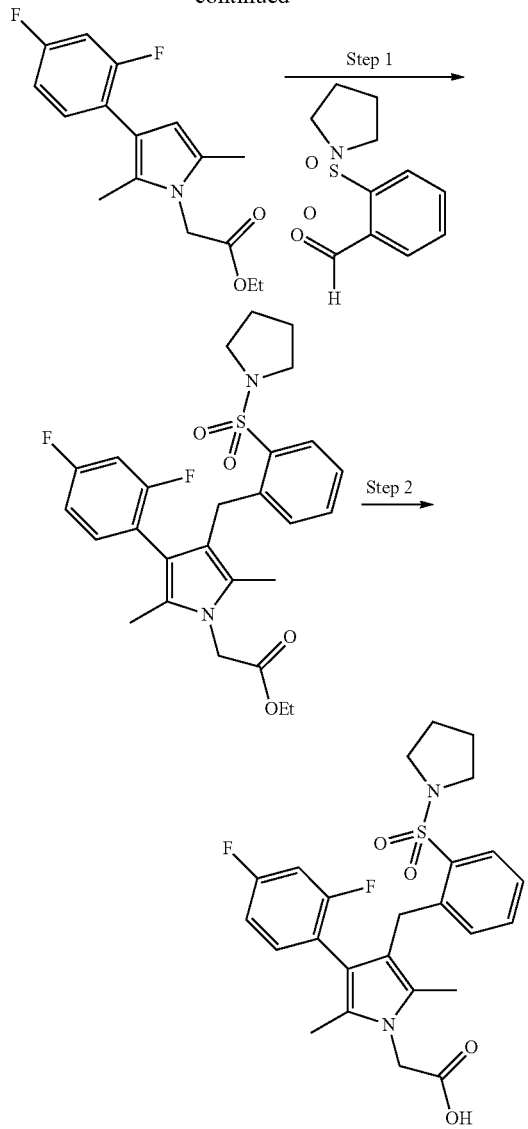

Preparation of (E)-4-(2,4-difluorophenyl)but-3-en-2-one

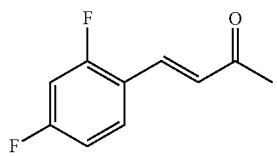

To a mixture of 2,4-difluorobenzaldehyde (5.0 ml, 45.7 mmol) and acetone (10.75 ml, 146 mmol) in Water (10 ml), was added 0.25M sodium hydroxide (18.30 ml, 4.57 mmol). The reaction mixture was heated to for 2 h. The mixture was poured into ice water. It was extracted with ethyl acetate (200 ml). The organic layer was dried, filtered, and evaporated to give (E)-4-(2,4-difluorophenyl)but-3-en-2-one as yellow oil. It was used for the next reaction without purification. 1H NMR (CDCl3/400 MHz): δ (ppm) 7.60 (d, 1H), 7.60-7.53 (m, 1H), 6.96-6.86 (m, 2H), 6.73 (d, 1H), 2.39 (s, 3H).

Preparation of ethyl 2-(3-(2,4-difluorophenyl)-2,5-dimethyl-1H-pyrrol-1-yl)acetate

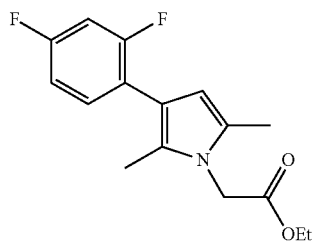 [SMILES: CCOC(=O)Cn1c(C)cc(-c2ccc(F)cc2F)c1C]

To solution of (E)-4-(2,4-difluorophenyl)but-3-en-2-one, acetic anhydride, and magnesium in DMF (100 ml), was added TMS-Cl. The mixture was placed in an ice bath and stirred for 18 hours. The reaction mixture was poured into mixture of ice and sodium bicarbonate and the pH was adjusted to ~10, the mixture diluted with water and extracted with ethyl acetate (200 ml). The organic layer was washed with water (100 ml×5), dried, filtered, and evaporated to give an oil. This material was directly taken on to the next step without further purification. The oil was combined with ethyl 2-aminoacetate hydrochloride (2.78 g, 19.89 mmol), triethylamine (5.55 ml, 39.8 mmol), and EtOH (18.08 ml) and the resulting mixture was heated at 100° C. for 16 hours. The mixture was allowed to cool down to room temperature and concentrated under vacuum. The remaining residue was dissolved in dichloromethane (100 ml) and washed with water (50 ml). The organic layer was dried, filtered, and evaporated to give a crude oil which was purified by column chromatography (0 to 20% ethyl acetate in hexanes) to give ethyl 2-(3-(2,4-difluorophenyl)-2,5-dimethyl-1H-pyrrol-1-yl) acetate (1.86 g, 6.34 mmol, 31.9% yield). 1H NMR (CDCl3/400 MHz) δ (ppm) 7.30-7.21 (m, 2H), 6.90-6.81 (m, 1H), 5.99-5.91 (m, 1H), 4.54 (s, 2H), 4.28 (q, 2H), 2.22 (s, 3H), 2.14 (d, 3H), 1.30 (t, 3H).

Preparation of 2-(3-(2,4-difluorophenyl)-2,5-dimethyl-4-(2-(pyrrolidin-1-ylsulfonyl)benzyl)-1H-pyrrol-1-yl)acetic acid (compound I-36)

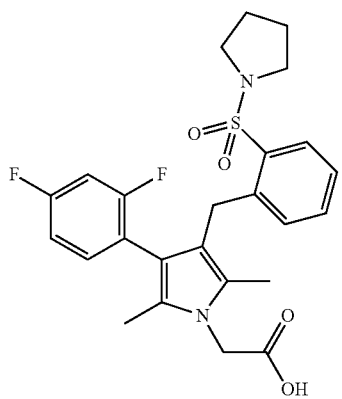 [SMILES: Cc1c(Cc2ccccc2S(=O)(=O)N2CCCC2)c(-c2ccc(F)cc2F)c(C)n1CC(=O)O]

General procedure I (step 1 and 2) were followed for the remainder of the synthesis to provide 2-(3-(2,4-difluorophenyl)-2,5-dimethyl-4-(2-(pyrrolidin-1-ylsulfonyl)benzyl)-1H-pyrrol-1-yl)acetic acid. $^1$H NMR (CDCl$_3$/400 MHz) δ (ppm) 7.92-7.88 (m, 1H), 7.40-7.35 (m, 1H), 7.27-7.21 (m, 1H), 7.14-7.09 (m, 1H), 7.02-6.94 (m, 1H), 6.79-6.68 (m, 2H), 6.80 (bs, 1H), 4.66 (s, 2H), 4.09 (s, 2H), 3.19-3.13 (m, 4H), 2.09 (s, 3H), 2.03 (s, 3H), 1.80-1.74 (m, 4H). MS m/z: 489.3 (M+1).

Example 6

Synthesis of 2-(3-cyano-2,5-dimethyl-4-(2-(phenylsulfonyl)benzyl)-1H-pyrrol-1-yl)acetic acid General Synthetic Scheme

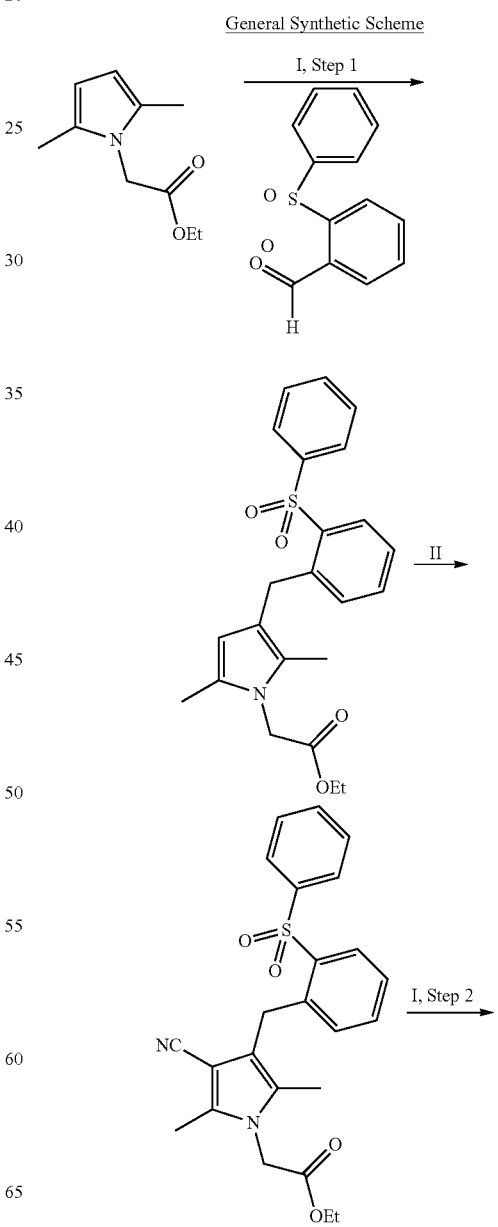

85
-continued

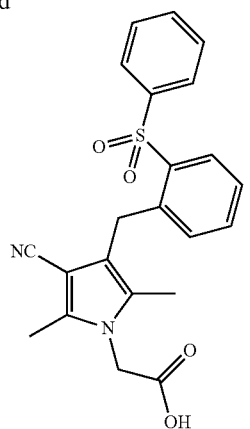

Preparation of ethyl
2-(2,5-dimethyl-1H-pyrrol-1-yl)acetate

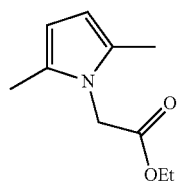

Glycine ethyl ester HCl (22 g, 158 mmol) was added to a stirring mixture of hexane-2,5-dione (18 g, 158 mmol) in dichloromethane (100 mL) in an Erlenmeyer flask. To the stirring heterogeneous mixture was slowly added triethylamine (66 mL, 473 mmol). After 30 minutes, dichloromethane (50 mL) and NaHCO3 (sat. aq. 100 mL) were added and the mixture continued to stir for 20 minutes. The dichloromethane layer was injected directly onto a 330 g silica gel column and the product was eluted with 0-100% ethyl acetate in hexanes. Pertinent fractions were combined and concentrated to afford ethyl 2-(2,5-dimethyl-1H-pyrrol-1-yl)acetate as a white solid (16 g, 56%). 1H NMR (CDCl3/400 MHz) δ (ppm) 5.8 (s, 2H), 4.85 (s, 2H), 4.22 (q, 2H), 2.17 (s, 6H), 1.28 (t, 3H)

Preparation of 2-(3-cyano-2,5-dimethyl-4-(2-(phenylsulfonyl)benzyl)-1H-pyrrol-1-yl)acetic acid (compound I-23)

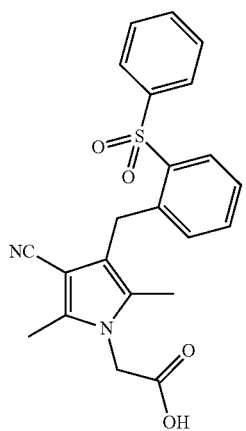 [SMILES: Cc1c(C#N)c(Cc2ccccc2S(=O)(=O)c2ccccc2)c(C)n1CC(=O)O]

General procedure I (step 1 and 2) and general procedure II were followed for the remainder of the synthesis to give

86

2-(3-cyano-2,5-dimethyl-4-(2-(phenylsulfonyl)benzyl)-1H-pyrrol-1-yl)acetic acid. 1H NMR (CDCl3/400 MHz): δ (ppm) 8.25-8.17 (m, 1H), 7.88-7.81 (m, 1H), 7.61-7.34 (m, 5H), 7.27-7.23 (m, 1H), 7.02-6.96 (m, 1H), 4.47 (s, 2H), 4.02 (s, 2H), 2.22 (s, 3H), 2.17 (s, 3H). MS m/z: 409.5 (M+1).

Example 7

Synthesis of 2-(2,5-dimethyl-3-(2-(pyrrolidin-1-ylsulfonyl)benzyl)-1H-pyrrol-1-yl)acetic acid and 2-(3-cyano-2,5-dimethyl-4-(2-(pyrrolidin-1-ylsulfonyl)benzyl)-1H-pyrrol-1-yl)acetic acid General Synthetic Scheme:

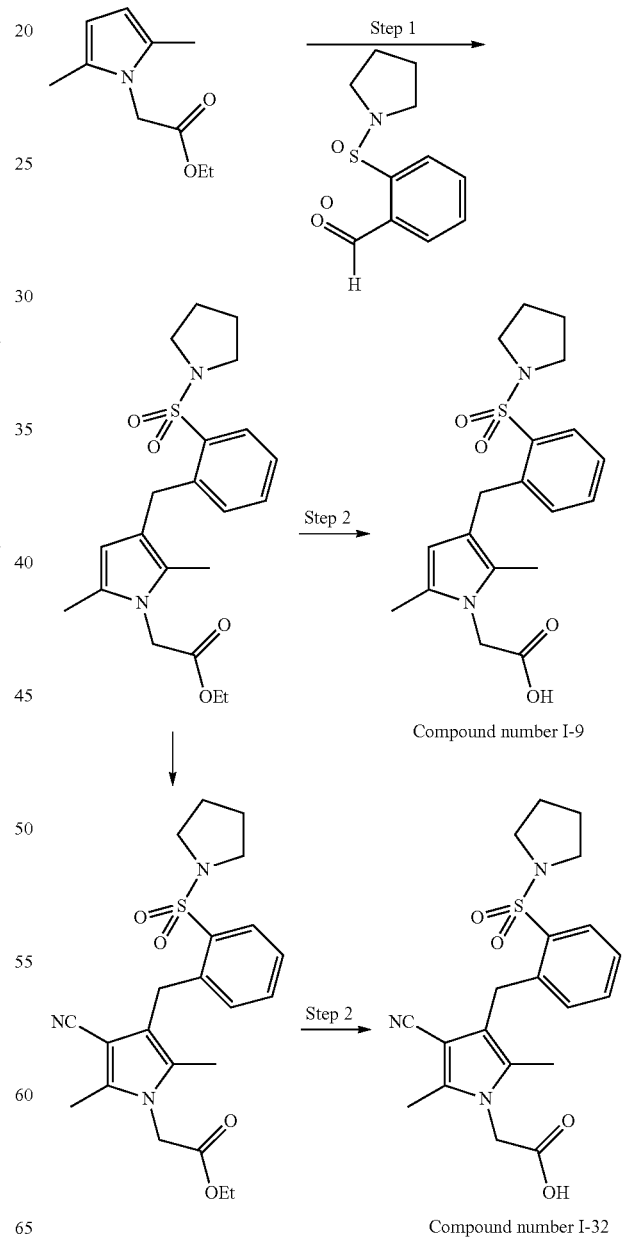

87

Synthesis of 2-(2,5-dimethyl-3-(2-(pyrrolidin-1-yl-sulfonyl)benzyl)-1H-pyrrol-1-yl)acetic acid (compound I-9)

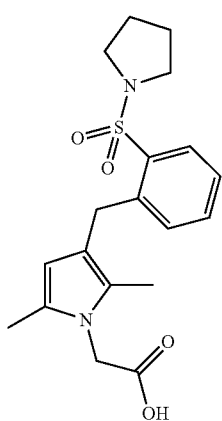 [SMILES: Cc1cc(Cc2ccccc2S(=O)(=O)N2CCCC2)c(C)n1CC(=O)O]

General procedure I (step 1 and 2) were followed for this synthesis to give 2-(2,5-dimethyl-3-(2-(pyrrolidin-1-ylsulfonyl)benzyl)-1H-pyrrol-1-yl)acetic acid. 1H NMR (CDCl3/400 MHz) δ (ppm) 7.35 (dd, 1H), 7.43-7.38 (m, 1H), 7.28-7.22 (m, 2H), 5.65 (s, 1H), 4.56 (s, 2H), 4.17 (s, 2H), 3.30 (t, 4H), 2.19 (s, 3H), 2.09 (s, 3H), 1.84 (t, 4H). MS m/z=377.3 (M+1).

Synthesis of Ethyl 2-(3-cyano-2,5-dimethyl-4-(2-(pyrrolidin-1-ylsulfonyl)benzyl)-1H-pyrrol-1-yl)acetate (compound I-63)

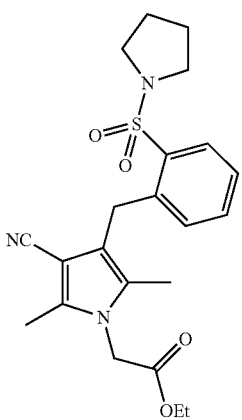

General procedure I (step 1) and II were followed for this synthesis. Ethyl 2-(3-cyano-2,5-dimethyl-4-(2-(pyrrolidin-1-ylsulfonyl)benzyl)-1H-pyrrol-1-yl)acetate: 1HNMR (CDCl3/400 MHz) δ (ppm) 8.00 (d, 1H), 7.41 (t, 1H), 7.30 (t, 1H), 7.01 (d, 1H), 4.54 (s, 2H), 4.29 (s, 2H), 4.25 (t, 2H), 3.35 (t, 4H), 2.34 (s, 3H), 2.01 (s, 3H), 1.95-1.92 (m, 4H), 1.31 (t, 3H).

88

Preparation of 2-(3-cyano-2,5-dimethyl-4-(2-(pyrrolidin-1-ylsulfonyl)benzyl)-1H-pyrrol-1-yl)acetic acid (compound I-32)

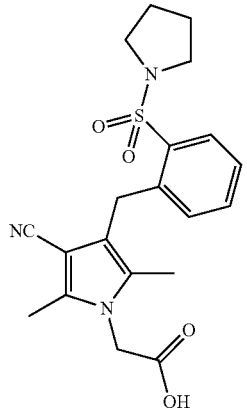 [SMILES: Cc1c(C#N)c(Cc2ccccc2S(=O)(=O)N2CCCC2)c(C)n1CC(=O)O]

General procedure I (step 2) was followed for this synthesis. 2-(3-cyano-2,5-dimethyl-4-(2-(pyrrolidin-1-ylsulfonyl)benzyl)-1H-pyrrol-1-yl)acetic acid 1H NMR (400 MHz, CDCl3) δ (ppm) 8.76 (bs, 1H), 7.98 (dd, 1H), 7.40 (ddd, 1H), 7.30 (ddd, 1H), 7.00 (dd, 1H), 4.60 (s, 2H), 4.28 (s, 2H), 3.36-3.32 (m, 4H), 2.34 (s, 3H), 2.02 (s, 3H), 1.95-1.91 (m, 4H) ppm.

Example 8

Synthesis of 2-(3-cyano-2,5-dimethyl-4-(2-(morpholinosulfonyl)benzyl)-1H-pyrrol-1-yl)acetic acid (compound I-46)

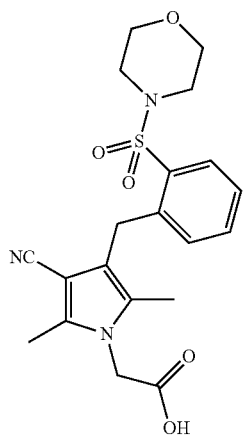 [SMILES: Cc1c(C#N)c(Cc2ccccc2S(=O)(=O)N2CCOCC2)c(C)n1CC(=O)O]

2-(3-cyano-2,5-dmethyl-4-(2-(morpholinosulfonyl)benzyl)-1H-pyrrol-1-yl)acetic acid was synthesized in the same manner as 2-(3-cyano-2,5-dimethyl-4-(2-(pyrrolidin-1-ylsulfonyl)benzyl)-1H-pyrrol-1-yl)acetic acid except 2-(morpholinosulfonyl)benzaldehyde was used in step 1 of general procedure I. 1H NMR (CD3OD/400 MHz) δ (ppm) 8.02-7.94 (m, 1H), 7.58-7.52 (m, 1H), 7.48-7.40 (m, 1H), 7.21-7.15 (m, 1H), 4.54 (s, 2H), 4.29 (s, 2H), 3.79-3.73 (m, 4H), 3.24-3.17 (m, 4H), 2.36 (s, 3H), 2.07 (s, 3H). MS m/z: 418.3 (M+1).

Example 9

Synthesis of 2-(2-cyano-3,5-dimethyl-4-(2-(pyrrolidin-1-ylsulfonyl)benzyl)-1H-pyrrol-1-yl)acetic acid and 2-(3-cyano-2,4-dimethyl-5-(2-(pyrrolidin-1-ylsulfonyl)benzyl)-1H-pyrrol-1-yl)acetic acid General Synthetic Scheme

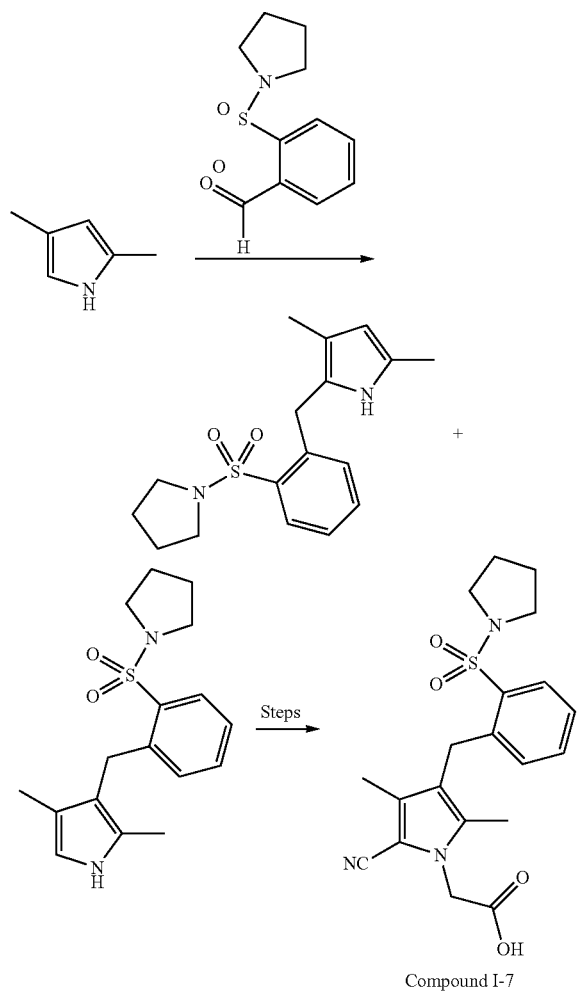

Preparation of 2,4-dimethyl-3-(2-(pyrrolidin-1-ylsulfonyl)benzyl)-1H-pyrrole and 3,5-dimethyl-2-(2-(pyrrolidin-1-ylsulfonyl)benzyl)-1H-pyrrole

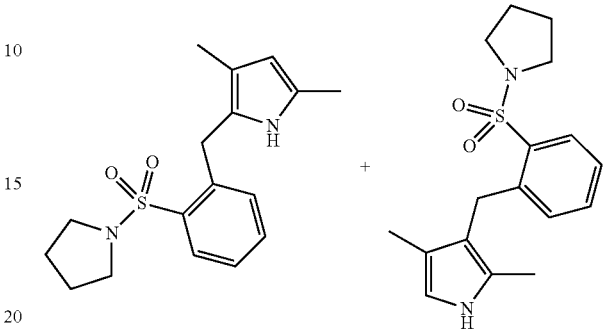

A mixture of 2,4-dimethyl-1H-pyrrole (2.0 ml, 19.42 mmol) and 2-(pyrrolidin-1-ylsulfonyl)benzaldehyde (4.65 g, 19.42 mmol) in trifluoroethanol (48.6 ml) and 12.5 sodium hydroxide (1.554 ml, 19.42 mmol) was heated at 50° C. for 1 h. The mixture was poured into ice and the resulting murky solution was decanted. The remaining residue was taken up in benzene and concentrated under vacuum. This residue was diluted in DCM (48.6 ml) and cooled to 0° C. To this solution, were added TFA (7.48 ml, 97 mmol) and triethylsilane (31.0 ml, 194 mmol). This mixture was heated at reflux (50° C.) for 15 min and poured into a mixture of ice and saturated solution of sodium bicarbonate. The mixture was extracted with dichloromethane (100 ml×2). The organic layers were combined, washed with brine (50 ml), dried, filtered, and concentrated to give an oil. Purification of the oil by column chromatography (0 to 20% ethyl acetate in hexanes) gave 2,4-dimethyl-3-(2-(pyrrolidin-1-ylsulfonyl)benzyl)-1H-pyrrole (380.0 mg, 1.193 mmol, 6.14% yield,) [Rf=0.73 (20% ethyl acetate in hexanes)] and 3,5-dimethyl-2-(2-(pyrrolidin-1-ylsulfonyl)benzyl)-1H-pyrrole (1.07 g, 3.36 mmol, 17.30% yield) [Rf=0.63 (20% ethyl acetate in hexanes)].

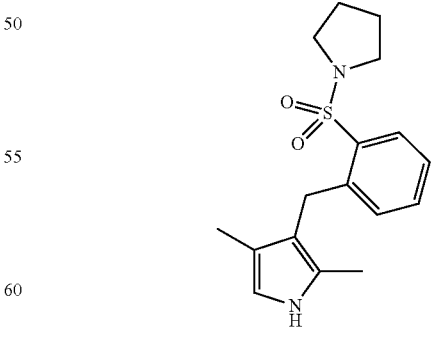

1H NMR (CDCl3/400 MHz) δ (ppm) 8.42 (bs, 1H), 7.91-7.82 (m, 2H), 7.57-7.50 (m, 1H), 7.48-7.41 (m, 1H), 5.64-5.62 (m, 1H), 4.20 (s, 2H), 3.38-3.32 (m, 4H), 2.15 (s, 3H), 2.14-2.13 (m, 3H), 1.97-1.90 (m, 4H).

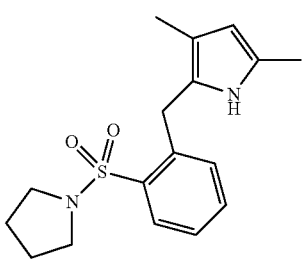 [SMILES: Cc1cc(C)c(Cc2ccccc2S(=O)(=O)N2CCCC2)[nH]1]

1H NMR (CDCl3/400 MHz) δ (ppm) 7.98-7.94 (m, 1H), 7.66 (bs, 1H), 7.41-7.35 (m, 1H), 7.30-7.24 (m, 1H), 7.06-7.02 (m, 1H), 6.50-6.47 (m, 1H), 4.17 (s, 2H), 3.41-3.34 (m, 4H), 2.12-2.10 (m, 3H), 1.96-1.91 (m, 4H), 1.86-1.84 (m, 3H).

Preparation of 3,5-dimethyl-4-(2-(pyrrolidin-1-ylsulfonyl)benzyl)-1H-pyrrole-2-carbonitrile

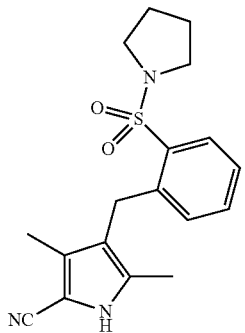 [SMILES: Cc1[nH]c(C#N)c(C)c1Cc1ccccc1S(=O)(=O)N1CCCC1]

A mixture of 2,4-dimethyl-3-(2-(pyrrolidin-1-ylsulfonyl)benzyl)-1H-pyrrole (128.0 mg, 0.402 mmol) and N-chlorosulfonylisocyanide (43.7 μl, 0.502 mmol) in acetonitrile (2.0 ml) was stirred at 25° C. for 1 hour. DMF (31.1 μl, 0.402 mmol) was then added and the resulting mixture was stirred for an additional 16 h at room temperature. The reaction was quenched with water (100 ml) and extracted with dichloromethane (100 ml×2). The organic layers were combined, filtered, and evaporated to give an oil. The oil was purified by column chromatography (0 to 50% ethyl acetate in hexanes) to give 3,5-dimethyl-4-(2-(pyrrolidin-1-ylsulfonyl)benzyl)-1H-pyrrole-2-carbonitrile (49.6 mg, 0.144 mmol, 35.9% yield).

1H NMR (CDCl3/400 MHz) δ (ppm) 8.45 (bs, 1H), 7.95-7.91 (m, 1H), 7.43-7.37 (m, 1H), 7.34-7.28 (m, 1H), 6.93-6.88 (m, 1H), 4.17 (s, 2H), 3.43-3.34 (m, 4H), 2.13 (s, 3H), 2.05 (s, 3H), 1.99-1.93 (m, 4H). MS m/z: 344.3 (M+1).

Preparation of 2,4-dimethyl-5-(2-(pyrrolidin-1-ylsulfonyl)benzyl)-1H-pyrrole-3-carbonitrile

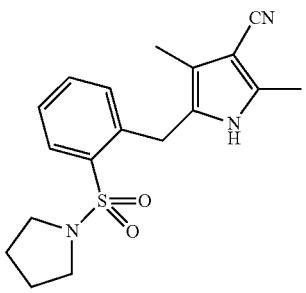 [SMILES: Cc1[nH]c(Cc2ccccc2S(=O)(=O)N2CCCC2)c(C)c1C#N]

A mixture of 3,5-dimethyl-2-(2-(pyrrolidin-1-ylsulfonyl)benzyl)-1H-pyrrole (576.0 mg, 1.809 mmol) and N-chlorosulfonylisocyanide (197 μl, 2.261 mmol) in acetonitrile (9.0 ml) was stirred at 25° C. for 1 hour. DMF (140 μl, 1.809 mmol) was then added and the resulting mixture was stirred for an additional 16 hours. It was quenched with water (100 ml) and extracted with dichloromethane (100 ml×2). The organic layers were combined, filtered, and evaporated to give an oil. The oil was purified by column chromatography (0 to 70% ethyl acetate in hexanes) to give 2,4-dimethyl-5-(2-(pyrrolidin-1-ylsulfonyl)benzyl)-1H-pyrrole-3-carbonitrile (513.6 mg, 1.495 mmol, 83% yield) as brown oil. 1H NMR (CDCl3/400 MHz) δ (ppm) 9.10 (bs, 1H), 7.82-7.77 (m, 1H), 7.46-7.40 (m, 1H), 7.30-7.23 (m, 2H), 4.10 (s, 2H), 3.33-3.27 (m, 4H), 2.20 (s, 3H), 2.18 (s, 3H), 1.92-1.88 (m, 4H). MS m/z: 344.3 (M+1).

Synthesis of ethyl 2-(2-cyano-3,5-dimethyl-4-(2-(pyrrolidin-1-ylsulfonyl)benzyl)-1H-pyrrol-1-yl)acetate (compound I-61)

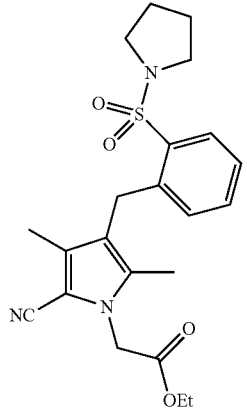

To a mixture of 3,5-dimethyl-4-(2-(pyrrolidin-1-ylsulfonyl)benzyl)-1H-pyrrole-2-carbonitrile (29.1 mg, 0.085 mmol), cesium carbonate (110 mg, 0.339 mmol), and TBAI (3.13 mg, 8.47 μmol) in DMF (424 μl), was added ethyl bromoacetate (14.15 μl, 0.127 mmol). The mixture was heated at 60° C. for 5 hours and then allowed to cool down to room temperature and diluted with ethyl acetate (100 ml). The resulting mixture was washed with water (50 ml×3), dried, filtered, and evaporated to give an oil. This crude oil was purified by column chromatography (0 to 50% ethyl acetate in hexanes) to give ethyl 2-(2-cyano-3,5-dimethyl-4-(2-(pyrrolidin-1-ylsulfonyl)benzyl)-1H-pyrrol-1-yl)acetate (40.0 mg, 0.093 mmol, 110% yield).

1H NMR (CDCl3/400 MHz) δ (ppm) 7.94-7.90 (m, 1H), 7.42-7.37 (m, 1H), 7.32-7.27 (m, 1H), 6.92-6.89 (m, 1H), 4.69 (s, 2H), 4.18 (s, 2H), 4.25 (q, 2H), 3.40-3.34 (m, 4H), 2.04 (s, 3H), 2.03 (s, 3H), 1.98-1.93 (m, 4H), 1.30 (q, 3H).

Preparation of ethyl 2-(3-cyano-2,4-dimethyl-5-(2-(pyrrolidin-1-ylsulfonyl)benzyl)-1H-pyrrol-1-yl)acetate

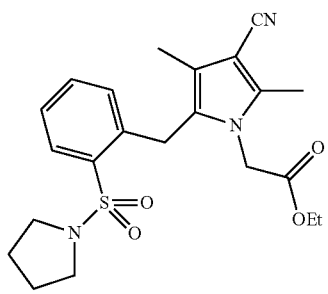 [SMILES: CCOC(=O)Cn1c(C)c(C#N)c(C)c1Cc1ccccc1S(=O)(=O)N1CCCC1]

A mixture of 2,4-dimethyl-5-(2-(pyrrolidin-1-ylsulfonyl)benzyl)-1H-pyrrole-3-carbonitrile (513.6 mg, 1.495 mmol), TBAI (55.2 mg, 0.150 mmol), cesium carbonate (1462 mg, 4.49 mmol), and ethyl bromoacetate (250 µl, 2.243 mmol) in DMF (7.5 ml) was heated at 60° C. for 4 hours. The mixture was diluted in ethyl acetate (100 ml) and washed with water (50 ml×3). The organic layer was dried, filtered, and evaporated to give an oil. This oil was purified by column chromatography (0 to 40% ethyl acetate in hexanes) to give ethyl 2-(3-cyano-2,4-dimethyl-5-(2-(pyrrolidin-1-ylsulfonyl)benzyl)-1H-pyrrol-1-yl)acetate (286.9 mg, 0.668 mmol, 44.7% yield). 1H NMR (CDCl3/400 MHz) δ (ppm) 7.92-7.88 (m, 1H), 7.44-7.38 (m, 1H), 7.35-7.29 (m, 1H), 6.96-6.92 (m, 1H), 4.36 (s, 2H), 4.28 (s, 2H), 3.94 (q, 2H), 3.38-3.30 (m, 4H), 2.27 (s, 3H), 2.13 (s, 3H), 1.98-1.92 (m, 4H), 1.11 (t, 3H). MS m/z: 430.3 (M+1).

Preparation of 2-(2-cyano-3,5-dimethyl-4-(2-(pyrrolidin-1-ylsulfonyl)benzyl)-1H-pyrrol-1-yl)acetic acid (compound I-7)

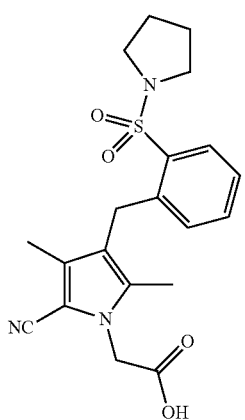 [SMILES: Cc1c(Cc2ccccc2S(=O)(=O)N2CCCC2)c(C)n(CC(=O)O)c1C#N]

To a solution of ethyl 2-(2-cyano-3,5-dimethyl-4-(2-(pyrrolidin-1-ylsulfonyl)benzyl)-1H-pyrrol-1-yl)acetate (40.0 mg, 0.093 mmol) in THF (1.1 ml), MeOH (372 µl), and Water (372 µl) at 0° C., was added lithium hydroxide (5.2 mg, 0.217 mmol). The mixture was stirred for 1 hour. This mixture was left standing over the course of 2 days at room temperature. To this mixture, was added HCl (214 µl, 0.214 mmol), then, the mixture was concentrated under vacuum, diluted in dichloromethane (50 ml) and washed with water (20 ml×3). The organic layer was dried, filtered, and evaporated to give 2-(2-cyano-3,5-dimethyl-4-(2-(pyrrolidin-1-ylsulfonyl)benzyl)-1H-pyrrol-1-yl)acetic acid as a solid. 1H NMR (CDCl3/400 MHz) δ (ppm) 7.95-7.90 (m, 1H), 7.43-7.37 (m, 1H), 7.34-7.28 (m, 1H), 6.92-6.86 (m, 1H), 4.77 (s, 2H), 4.19 (s, 2H), 3.44-3.33 (m, 4H), 2.07 (s, 3H), 2.02 (s, 3H), 1.98-1.93 (m, 4H). MS m/z: 402.3 (M+1).

Preparation of 2-(3-cyano-2,4-dimethyl-5-(2-(pyrrolidin-1-ylsulfonyl)benzyl)-1H-pyrrol-1-yl)acetic acid

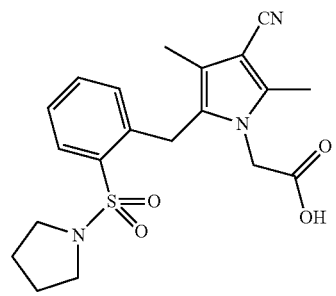 [SMILES: Cc1c(C#N)c(C)n(CC(=O)O)c1Cc1ccccc1S(=O)(=O)N1CCCC1]

To a solution of ethyl 2-(3-cyano-2,4-dimethyl-5-(2-(pyrrolidin-1-ylsulfonyl)benzyl)-1H-pyrrol-1-yl)acetate (286.9 mg, 0.668 mmol) in THF (8.0 ml), MeOH (2.7 ml), and water (2.7 ml) at 0° C., was added lithium hydroxide (32.0 mg, 1.336 mmol). The mixture was stirred for 1 hour. To this mixture, was then added HCl (1336 µl, 1.336 mmol) and the resulting mixture concentrated under vacuum, diluted in dichloromethane (50 ml) and washed with water (20 ml×3). The organic layer was dried, filtered, and evaporated to give 2-(3-cyano-2,4-dimethyl-5-(2-(pyrrolidin-1-ylsulfonyl)benzyl)-1H-pyrrol-1-yl)acetic acid (290.0 mg, 0.722 mmol, 108% yield) as a solid. 1H NMR (CDCl3/400 MHz) δ (ppm) 9.52 (bs, 1H), 7.87-7.82 (m, 1H), 7.42-7.35 (m, 1H), 7.34-7.28 (m, 1H), 6.92-6.86 (m, 1H), 4.33 (s, 2H), 4.25 (s, 2H), 3.40-3.28 (m, 4H), 2.25 (s, 3H), 2.10 (s, 3H), 1.97-1.91 (m, 4H). MS m/z: 402.3 (M+1).

Example 10

Synthesis of 2-(2-methyl-4,5-diphenyl-3-(2-(phenylsulfonyl)benzyl)-1H-pyrrol-1-yl)acetic acid General Synthetic Scheme

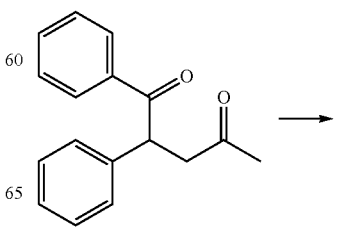

95

-continued

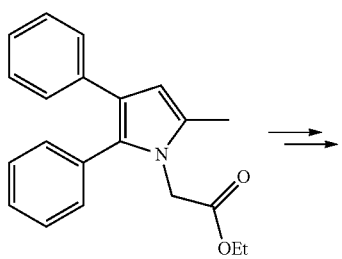

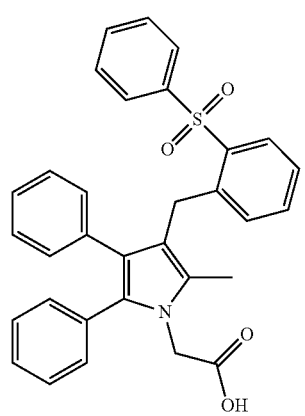

Preparation of 1,2-diphenylpentane-1,4-dione

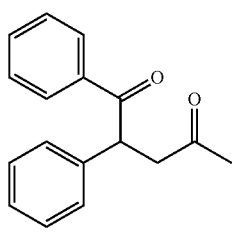 [SMILES: CC(=O)CC(C(=O)c1ccccc1)c1ccccc1]

A solution of benzaldehyde (10.10 ml, 100 mmol) in DMF (50 ml) was added dropwise in the course of ½ hour to a mixture of sodium cyanide (2.450 g, 50 mmol) in DMF (50 ml) at 35° C. Stirring was continued for 1.5 hours at 35° C. A solution of (E)-4-phenylbut-3-en-2-one (10.9 g, 74.6 mmol) in DMF (50 ml) was slowly added dropwise over the course of 1.5 hours at 35° C. Stirring was continued for 3.5 hours at the same temperature. The reaction was quenched with twice its quantity of water and extracted with DCM, combined extracts were washed with water and brine, dried over Na2SO4, filtered and concentrated to give a liquid residue. This was purified by chromatography on silica gel using an automated Biotage system and EtOAc/Hexanes, 0-50%, to give 1,2-diphenylpentane-1,4-dione (7.3 g, 28.9 mmol, 38.8% yield). 1H NMR (400 MHz, CDCl3) δ (ppm) 7.97-7.94 (m, 2H), 7.49-7.49 (m, 1H), 7.39-7.35 (m, 2H), 7.29-7.20 (m, 5H), 5.10 (dd, 1H), 3.61 (dd, 1H), 2.75 (dd, 1H), 2.19 (s, 3H).

96

Preparation of ethyl 2-(5-methyl-2,3-diphenyl-1H-pyrrol-1-yl)acetate

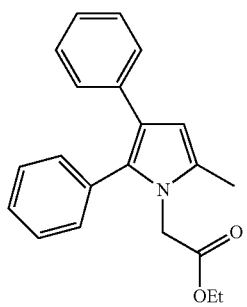 [SMILES: CCOC(=O)Cn1c(C)cc(-c2ccccc2)c1-c1ccccc1]

Ethyl 2-aminoacetate hydrochloride (0.548 g, 3.92 mmol) was diluted with Ethanol (10 ml) then charged with triethylamine (0.746 ml, 5.35 mmol) and 1,2-diphenylpentane-1,4-dione (0.900 g, 3.57 mmol), added as a solution in DCM. The reaction was heated at 100° C. overnight, after which TLC showed a new spot (less polar, Rf~0.9 in 20% EtOAc/hexanes). The reaction was diluted with 10 mL DCM and washed with water (10 mL). The aqueous layer was back-extracted with DCM (10 mL×2). The organics were combined, dried, filtered, and concentrated to yield a crude orange oil. This oil was loaded on a SiO2 column and purified using a 0-20% gradient of EtOAc in hexanes, affording ethyl 2-(5-methyl-2,3-diphenyl-1H-pyrrol-1-yl)acetate (0.780 g, 2.442 mmol, 68.5% yield). 1H NMR (400 MHz, CDCl3) δ (ppm) 7.37-7.33 (m, 3H), 7.27-7.24 (m, 2H), 7.16-7.11 (m, 4H), 7.07-7.04 (m, 1H), 6.24 (b, 1H), 4.42 (s, 2H), 4.21 (q, 2H), 2.27 (s, 3H), 1.25 (t, 3H).

Preparation of Ethyl 2-(2-methyl-4,5-diphenyl-3-(2-(phenylsulfonyl)benzyl)-1H-pyrrol-1-yl)acetate (compound I-64)

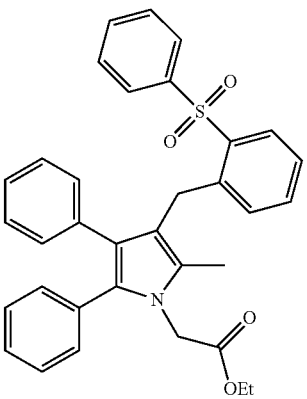

In a scintillation vial, ethyl 2-(5-methyl-2,3-diphenyl-1H-pyrrol-1-yl)acetate (0.3 g, 0.939 mmol) was dissolved in 10 mL of DCM and the mixture cooled to −78° C. Trimethylsilyl trifluoromethanesulfonate (0.382 ml, 2.113 mmol) was then added followed by triethylsilane (0.450 ml, 2.82 mmol). The resulting mixture was stirred at −78° C. for 30 minutes. At this time, 2-(phenylsulfonyl)benzaldehyde (0.231 g, 0.939 mmol) was added portionwise as a solution in 2.0 mL of DCM and the reaction evolution was monitored by LC/MS. Following addition of the aldehyde, the cold bath was removed and the reaction was stirred overnight (gradually warming to room temp). The reaction was quenched with a sodium bircarbonate solution and moved to a separatory funnel. Layers were separated and the aqueous portion was extracted 2 additional times with DCM. The organics were combined, dried, filtered, and concentrated. The crude oil was purified by column chromatography (SiO2) using a 0-40% EtOAc/hexane gradient to give ethyl 2-(2-methyl-4,5-diphenyl-3-(2-(phenylsulfonyl)benzyl)-1H-pyrrol-1-yl)acetate (294 mg, 0.535 mmol, 56.9% yield). 1H NMR (400 MHz, CDCl3) δ (ppm) 8.31-8.29 (m, 1H), 7.84-7.82 (m, 2H), 7.52-7.48 (m, 2H), 7.42-7.38 (m, 3H), 7.28-7.21 (m, 4H), 7.15-7.13 (m, 2H), 6.93-6.86 (m, 3H), 6.75-6.73 (m, 2H), 4.51 (s, 2H), 4.21 (q, 2H), 4.04 (s, 2H), 1.79 (s, 3H), 1.25 (t, 3H).

Preparation of 2-(2-methyl-4,5-diphenyl-3-(2-(phenylsulfonyl)benzyl)-1H-pyrrol-1-yl)acetic acid (compound I-12)

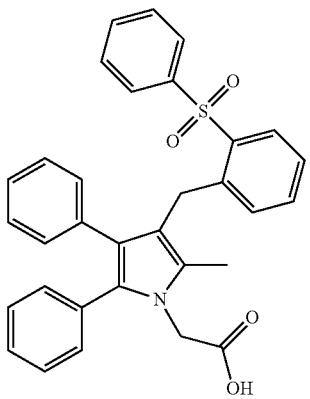 [SMILES: Cc1c(Cc2ccccc2S(=O)(=O)c2ccccc2)c(-c2ccccc2)c(-c2ccccc2)n1CC(=O)O]

Ethyl 2-(2-methyl-4,5-diphenyl-3-(2-(phenylsulfonyl)benzyl)-1H-pyrrol-1-yl)acetate (0.300 g, 0.546 mmol) was dissolved in a 3:1:1 mixture of THF/MeOH/water (10 ml) and charged with lithium hydroxide (0.065 g, 2.73 mmol). The reaction was stirred at rt for 1 h, at which time LC/MS suggested the reaction was complete. The reaction was acidified with 3 N HCl, and the resulting mixture concentrated to almost dryness (water left), diluted with 3 mL brine solution and extracted 3 times with DCM. The organic layers were combined, dried, filtered, and concentrated under vacuum to yield 2-(2-methyl-4,5-diphenyl-3-(2-(phenylsulfonyl)benzyl)-1H-pyrrol-1-yl)acetic acid (285 mg, 0.546 mmol, 100% yield).

1H NMR (400 MHz, CDCl3) δ (ppm) 8.30-8.28 (m, 1H), 7.82-7.80 (m, 2H), 7.51-7.47 (m, 2H), 7.41-7.37 (m, 3H), 7.24-7.21 (m, 4H), 7.13-7.11 (m, 2H), 6.93-6.85 (m, 3H), 6.71-6.69 (m, 2H), 4.57 (s, 2H), 4.01 (s, 2H), 1.82 (s, 3H).

Example 11

Synthesis of 2-(2-methyl-4,5-diphenyl-3-(2-(pyrrolidin-1-ylsulfonyl)benzyl)-1H-pyrrol-1-yl)acetic acid (Compound I-39)

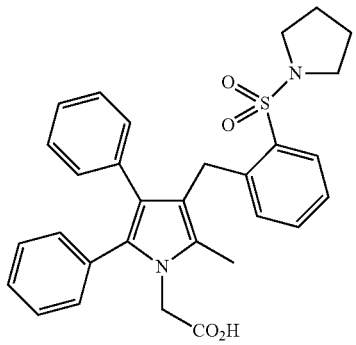 [SMILES: Cc1c(Cc2ccccc2S(=O)(=O)N2CCCC2)c(-c2ccccc2)c(-c2ccccc2)n1CC(=O)O]

2-(2-methyl-4,5-diphenyl-3-(2-(pyrrolidin-1-ylsulfonyl)benzyl)-1H-pyrrol-1-yl)acetic acid was synthesized according to 2-(2-methyl-4,5-diphenyl-3-(2-(phenylsulfonyl)benzyl)-1H-pyrrol-1-yl)acetic acid using 2-(pyrrolidin-1-ylsulfonyl)benzaldehyde in the general procedure I (step 1). 1H NMR (CDCl3/400 MHz) δ (ppm) 8.00 (d, 1H), 7.50-7.45 (m, 1H), 7.34-7.24 (m, 5H), 7.19-7.16 (m, 2H), 7.05-7.00 (m, 3H), 6.92-6.88 (m, 2H), 4.65 (s, 2H), 4.21 (s, 2H), 3.15 (t, 4H), 2.10 (s, 3H), 1.69-1.65 (m, 4H). MS m/z: 515.34 (M+1).

Example 12

Synthesis of 2-(2-methyl-3-(2-(morpholinosulfonyl)benzyl)-4,5-diphenyl-1H-pyrrol-1-yl)acetic acid (compound I-40)

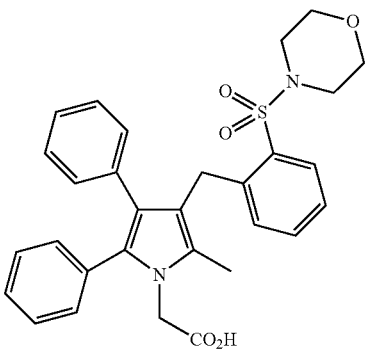 [SMILES: Cc1c(Cc2ccccc2S(=O)(=O)N2CCOCC2)c(-c2ccccc2)c(-c2ccccc2)n1CC(=O)O]

2-(2-methyl-3-(2-(morpholinosulfonyl)benzyl)-4,5-diphenyl-1H-pyrrol-1-yl)acetic acid was synthesized according to 2-(2-methyl-4,5-diphenyl-3-(2-(phenylsulfonyl)benzyl)-1H-pyrrol-1-yl)acetic acid using 2-(morpholinosulfonyl)benzaldehyde in the general procedure X (step 1). 1H NMR (CDCl3/400 MHz) δ (ppm) 7.95 (d, 1H), 7.52 (t, 1H), 7.37-7.24 (m, 5H), 7.19-7.15 (m, 2H), 7.08-7.04 (m, 3H), 6.95-6.91 (m, 2H), 4.65 (s, 2H), 4.23 (s, 2H), 3.52 (t, 4H), 3.02 (t, 4H), 2.09 (s, 3H). MS m/z: 531.35 (M+1).

Example 13

Synthesis of 2-(2-(2-hydroxyethyl)-3,5-dimethyl-4-(4-(pyrrolidin-1-ylsulfonyl)benzyl)-1H-pyrrol-1-yl)acetic acid General Synthetic Scheme

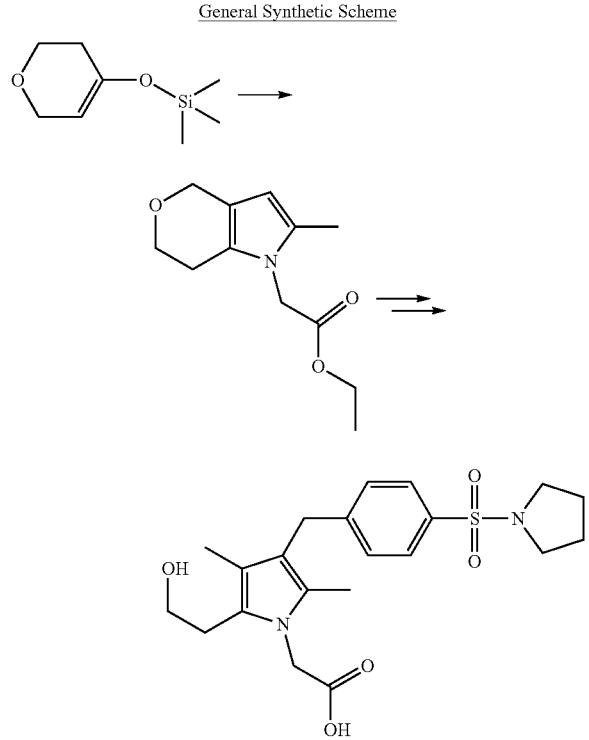

Preparation of (3,6-dihydro-2H-pyran-4-yloxy)trimethylsilane

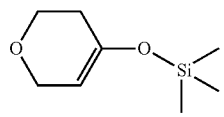

To a flame-dried sealed tube was added DMF (3 ml) and triethylamine (3.34 ml, 23.97 mmol), followed by tetrahydro-4H-pyran-4-one (0.923 ml, 9.99 mmol) and TMS-Cl (1.532 ml, 11.99 mmol). The mixture was heated at 140° C. for 16 hours, allowed to cool to room temperature, diluted with pentane and decanted into ice cooled saturated sodium bicarbonate and extracted with pentane (50 ml×3). The combined pentane layers were washed with brine and dried over sodium sulfate, filtered and concentrated to give 1.0 g of the product as a liquid (5.80 mmol, yield 58.1%). 1H NMR (400 MHz, CDCl3) δ (ppm) 4.63-4.61 (m, 1H), 3.95-3.93 (m, 2H), 3.60-3.58 (m, 2H), 1.94-1.90 (m, 2H), 0.01 (b, 9H).

Preparation of 3-(2-oxopropyl)dihydro-2H-pyran-4(3H)-one

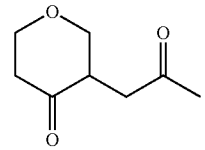

(3,6-dihydro-2H-pyran-4-yloxy)trimethylsilane (1.0 g, 5.80 mmol) and trimethyl(prop-1-en-2-yloxy)silane (7.56 g, 58.0 mmol) were added dropwise to a vigorously stirred suspension of ceric ammonium nitrate (6.36 g, 11.61 mmol) and sodium bicarbonate (1.950 g, 23.22 mmol) in dry acetonitrile (40 ml). The resulting mixture was stirred until the orange color disappeared and a thick white precipitate formed. The reaction mixture was then poured into water and extracted with EtOAc. The combined extracts were washed by brine, and dried over Na2SO4, filtered and concentrated under vacuum. The residue was purified by column chromatography on silica gel, using EtOAc/Hex 10-50% to give the product (0.42 g, 46.3% yield). 1H NMR (400 MHz, CDCl3) δ (ppm) 4.30-4.25 (m, 1H), 4.21-4.16 (m, 1H), 3.68-3.62 (m, 1H), 3.37-3.31 (m, 1H), 3.19-3.15 (m, 1H), 2.91-2.85 (m, 1H), 2.75-2.66 (m, 1H), 2.39-2.34 (m, 1H), 2.21-2.15 (m, 4H).

Preparation of ethyl 2-(2-methyl-6,7-dihydropyrano[4,3-b]pyrrol-1(4H)-yl)acetate

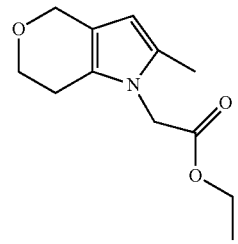 [SMILES: CCOC(=O)Cn1c(C)cc2c1CCOC2]

3-(2-oxopropyl)dihydro-2H-pyran-4(3H)-one (0.41 g, 2.63 mmol) in dichloromethane (3 ml) was stirred at room temperature, and ethyl 2-aminoacetate hydrochloride (0.366 g, 2.63 mmol) was added, followed by sodium bicarbonate (0.441 g, 5.25 mmol). The resulting mixture was stirred at 25° C. for 15 hours, after which TLC showed that the reaction was complete. DCM was added, the organic layer was separated, washed with water, brine, dried over Na2SO4, filtered and concentrated. The residue was chromatographed on silica gel using an automated Biotage system, EtOAc/Hexane 5-30%, to give the desired product (0.41 g, yield 70%). 1H NMR (400

MHz, CDCl3) δ (ppm) 5.69 (s, 1H), 4.62 (s, 2H), 4.44 (s, 2H), 4.21 (q, 2H), 3.95-3.94 (m, 2H), 2.58-2.55 (m, 2H), 2.18 (s, 3H), 1.28 (t, 2H).

Ethyl 2-(2-(2-hydroxyethyl)-3,5-dimethyl-4-(4-(pyrrolidin-1-ylsulfonyl)benzyl)-1H-pyrrol-1-yl)acetate (compound I-65)

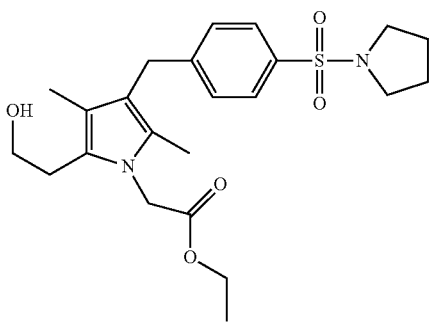 [SMILES: CCOC(=O)Cn1c(C)c(Cc2ccc(S(=O)(=O)N3CCCC3)cc2)c(C)c1CCO]

To a flame-dried vial was charged with DCM (2 ml) and trimethylsilyl trifluoromethanesulfonate (0.081 ml, 0.448 mmol) was added at 0° C., followed by a solution of ethyl 2-(2-methyl-6,7-dihydropyrano[4,3-b]pyrrol-1(4H)-yl)acetate (50 mg, 0.224 mmol) and 4-(pyrrolidin-1-ylsulfonyl) benzaldehyde (53.6 mg, 0.224 mmol) in CH2Cl2 (5 ml) (cannulated), the mix was stirred at 0° C. for 15 min, neat triethylsilane (0.143 ml, 0.896 mmol) was added slowly, stirred for 30 min at 0° C., then slowly warmed to r.t. TLC confirmed that reaction was done. Therefore, it was quenched with sat. NaHCO3, extracted with DCM. Combined DCM was dried with Na2SO4, filtered and concentrated under vacuum. The residue was chromatographed on silica using a Biotage automated system (5-30-50% ethyl acetate/hexanes) to give ethyl 2-(2-(2-hydroxyethyl)-3,5-dimethyl-4-(4-(pyrrolidin-1-ylsulfonyl)benzyl)-1H-pyrrol-1-yl)acetate (34 mg, 0.076 mmol, 33.8% yield).

1H NMR (400 MHz, CDCl3) δ (ppm) 7.62 (d, 2H), 7.18 (d, 2H), 4.52 (s, 2H), 4.16 (q, 2H), 3.75 (s, 2H), 3.60 (t, 2H), 3.19-3.14 (m, 4H), 2.71 (t, 2H), 2.00 (s, 3H), 1.78 (s, 3H), 1.70-1.60 (m, 4H), 1.23 (t, 3H).

2-(2-(2-hydroxyethyl)-3,5-dimethyl-4-(4-(pyrrolidin-1-ylsulfonyl)benzyl)-1H-pyrrol-1-yl)acetic acid (compound I-20)

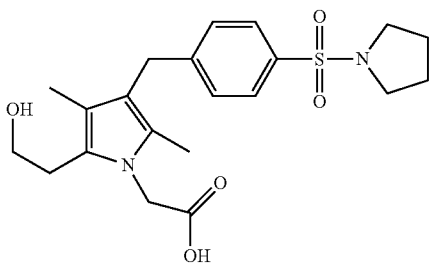 [SMILES: Cc1c(Cc2ccc(S(=O)(=O)N3CCCC3)cc2)c(C)n(CC(=O)O)c1CCO]

Ethyl 2-(2-(2-hydroxyethyl)-3,5-dimethyl-4-(4-(pyrrolidin-1-ylsulfonyl)benzyl)-1H-pyrrol-1-yl)acetate (20 mg, 0.045 mmol) in THF (2.0 ml), MeOH (0.500 ml) and water (0.50 ml) was stirred and LiOH (4.27 mg, 0.178 mmol) was added. The resulting mixture was stirred at 25° C. for two hours. The solvent was then removed and water was added, followed by 1 N HCl. The solvent was again removed, MeOH was added, and the resulting solution purified by preparative HPLC to give 12 mg of a light blue solid (12 mg, 0.029 mmol, 64.0% yield). 1H NMR (400 MHz, CDCl3) δ (ppm) 7.63 (d, 2H), 7.19 (d, 2H), 4.57 (s, 2H), 3.76 (s, 2H), 3.66 (t, 2H), 3.18-3.15 (m, 4H), 2.76-2.73 (m, 4H), 2.03 (s, 3H), 1.78 (s, 3H), 1.70-1.66 (m, 4H).

Example 14

Synthesis of 2-(3-(4-fluorophenyl)-5-methyl-2-phenyl-4-(2-(phenylsulfonyl)benzyl)-1H-pyrrol-1-yl) acetic acid General Synthetic Scheme

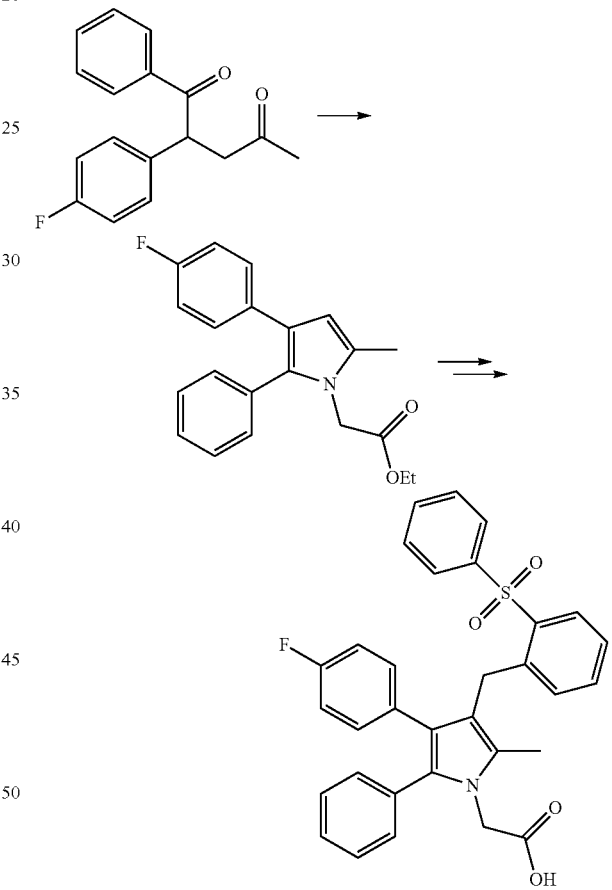

Preparation of (E)-4-(4-fluorophenyl)but-3-en-2-one

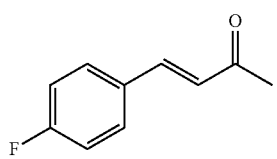

To a mixture of 4-fluorobenzaldehyde (5 mL, 45.2 mmol), propan-2-one (9.13 mL, 124 mmol), and water (9.5 mL) was added 12 mL of a 1% solution of NaOH in water. The reaction mixture was heated at 65° C. for 2 h. The mixture was then partitioned between EtOAc and ice water, the organic layer separated and the aqueous layer was extracted twice with EtOAc. The combined organic layers were dried with MgSO4 and concentrated under vacuum. The product was obtained as a yellow oil and was used in the next step without further purification (7.93 g, 48.3 mmol, 100% yield). 1H NMR (400 MHz, CDCl3) δ (ppm) 7.54-7.51 (m, 2H), 7.47 (d, 1H), 7.08 (t, 2H), 6.64 (d, 1H), 2.37 (s, 3H).

Preparation of 2-(4-fluorophenyl)-1-phenylpentane-1,4-dione

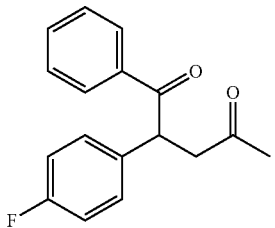 [SMILES: CC(=O)CC(C(=O)c1ccccc1)c1ccc(F)cc1]

A solution of benzaldehyde (1.650 ml, 16.32 mmol) in DMF (5 ml) was added dropwise over the course of ½ hour to a mixture of sodium cyanide (0.401 g, 8.17 mmol) in DMF (20 ml) at 35° C. Stirring was then continued for 1.5 hours at 35° C. A solution of (E)-4-(4-fluorophenyl)but-3-en-2-one (2.0 g, 12.18 mmol) and DMF (10 ml) was then slowly added dropwise over the course of 3.5 hours at 35° C. Stirring was then continued for 3.5 hours at the same temperature. The reaction mixture was treated with twice its volume of water and extracted with DCM. The combined extracts were washed with water and brine, dried with Na2SO4, filtered and concentrated to give a liquid, which was further purified by chromatography on silica gel using an automated Biotage system and EtOAc/Hex (0-50%) to give 2-(4-fluorophenyl)-1-phenylpentane-1,4-dione (1.5 g, 5.55 mmol, 45.6% yield). 1H NMR (400 MHz, CDCl3) δ (ppm) 7.95-7.93 (m, 2H), 7.50-7.46 (m, 1H), 7.40-7.32 (m, 3H), 7.26-7.21 (m, 3H), 5.11 (dd, 1H), 3.59 (dd, 1H), 2.76 (dd, 1H), 2.19 (s, 3H).

Preparation of ethyl 2-(3-(4-fluorophenyl)-5-methyl-2-phenyl-1H-pyrrol-1-yl)acetate

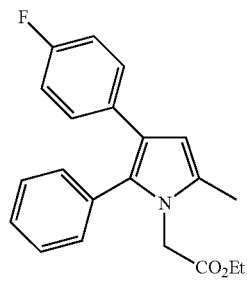 [SMILES: CCOC(=O)Cn1c(C)cc(-c2ccc(F)cc2)c1-c1ccccc1]

Ethyl 2-aminoacetate hydrochloride (0.775 g, 5.55 mmol) was diluted with ethanol (5 ml) then triethylamine was added (1.160 ml, 8.32 mmol), followed by 2-(4-fluorophenyl)-1-phenylpentane-1,4-dione (1.5 g, 5.55 mmol), added as a solution in DCM. The reaction was heated at 100° C. overnight, after which TLC showed a new spot (less polar, Rf~0.9 in 20% EtOAc/hexanes). The reaction was diluted with 10 mL DCM and washed with water (10 mL) and the aqueous layer was back-extracted with DCM (10 mL×2). The organics were combined, dried, filtered, and concentrated under vacuum to yield a crude orange oil. This oil was loaded onto a SiO2 column and purified using a 0-20% gradient of EtOAc in hexanes, affording the desired product ethyl 2-(3-(4-fluorophenyl)-5-methyl-2-phenyl-1H-pyrrol-1-yl)acetate (0.804 g, 2.383 mmol, 42.9% yield). 1H NMR (400 MHz, CDCl3) δ (ppm) 7.36-7.34 (m, 3H), 7.26-7.22 (m, 2H), 7.11-7.07 (m, 2H), 6.85-6.81 (m, 2H), 6.20 (b, 1H), 4.42 (s, 2H), 4.21 (q, 2H), 2.26 (s, 3H), 1.25 (t, 3H).

Synthesis of ethyl 2-(3-(4-fluorophenyl)-5-methyl-2-phenyl-4-(2-(phenylsulfonyl)benzyl)-1H-pyrrol-1-yl)acetate (compound I-66)

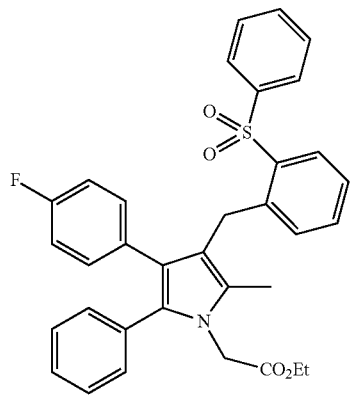 [SMILES: CCOC(=O)Cn1c(C)c(Cc2ccccc2S(=O)(=O)c2ccccc2)c(-c2ccc(F)cc2)c1-c1ccccc1]

Ethyl 2-(3-(4-fluorophenyl)-5-ethyl-2-phenyl-1H-pyrrol-1-yl)acetate (0.8 g, 2.371 mmol) was dissolved in 10 mL DCM and cooled to −78° C. Trimethylsilyl trifluoromethylsulfonate (0.964 ml, 5.34 mmol) was then added, followed by triethylsilane (1.136 ml, 7.11 mmol). The reaction mixture was stirred at −78° C. for 30 minutes. At this time, 2-(phenylsulfonyl)benzaldehyde (0.876 g, 3.56 mmol) was added portion-wise as a solution in 2.0 mL DCM. The reaction was monitored by LC/MS. Following addition of the aldehyde, the cold bath was removed and the mixture was stirred overnight (gradually warming to room temp). The reaction was quenched with sodium bircarbonate and moved to a separatory funnel. Layers were separated and the aqueous portion was extracted two additional times with DCM. The organics were combined, dried, filtered, and concentrated. The resulting crude oil was purified via column chromatography (SiO2) using a 0-40% EtOAc/hexane gradient to give ethyl 2-(3-(4-fluorophenyl)-5-methyl-2-phenyl-4-(2-(phenylsulfonyl)benzyl)-1H-pyrrol-1-yl)acetate (1.0 g, 1.762 mmol, 74.3% yield). 1H NMR (400 MHz, CDCl3) δ (ppm) 8.31-8.29 (m, 1H), 7.80-7.78 (m, 2H), 7.53-7.49 (m, 2H), 7.43-7.36 (m, 3H), 7.25-7.21 (m, 4H), 7.10-7.07 (m, 2H), 6.60-6.56 (m, 2H), 6.52-6.48 (m, 2H), 4.49 (s, 2H), 4.21 (q, 2H), 3.97 (s, 2H), 1.86 (s, 3H), 1.26 (t, 3H).

2-(3-(4-fluorophenyl)-5-methyl-2-phenyl-4-(2-(phenylsulfonyl)benzyl)-1H-pyrrol-1-yl)acetic acid (compound I-37)

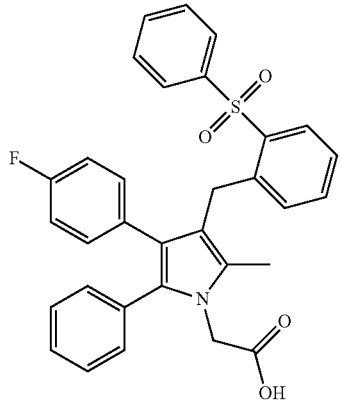 [SMILES: Cc1c(Cc2ccccc2S(=O)(=O)c2ccccc2)c(-c2ccc(F)cc2)c(-c2ccccc2)n1CC(=O)O]

Ethyl 2-(3-(4-fluorophenyl)-5-methyl-2-phenyl-4-(2-(phenylsulfonyl)benzyl)-1H-pyrrol-1-yl)acetate (0.91 g, 1.603 mmol) was dissolved in a 3:1:1 mixture of THF/MeOH/water (17 ml) and charged with lithium hydroxide (0.192 g, 8.02 mmol). The reaction mixture was stirred at rt for 2 h, at which time LC/MS suggested the reaction was complete. The mixture was concentrated to almost dryness (water left) and diluted with 10 mL water. This aqueous mixture was then extracted with ether, the water layer was acidified with 6N HCl at 0 OC and the resulting precipitate was filtered and dried, to give 24344-fluorophenyl)-5-methyl-2-phenyl-4-(2-(phenylsulfonyl)benzyl)-1H-pyrrol-1-yl)acetic acid (0.755 g, 1.399 mmol, 87% yield). 1H NMR (400 MHz, CDCl3) δ (ppm) 8.32-8.30 (m, 1H), 7.80-7.78 (m, 2H), 7.53-7.49 (m, 2H), 7.43-7.36 (m, 3H), 7.28-7.25 (m, 3H), 7.21-7.19 (m, 1H), 7.11-7.08 (m, 2H), 6.60-6.56 (m, 2H), 6.52-6.48 (m, 2H), 4.59 (s, 2H), 3.97 (s, 2H), 1.90 (s, 3H).

Example 15

Synthesis of 2-(2-(3-fluorophenyl)-5-methyl-3-phenyl-4-(2-(phenylsulfonyl)benzyl)-1H-pyrrol-1-yl)acetic acid General Synthetic Scheme

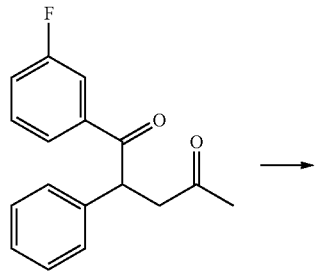

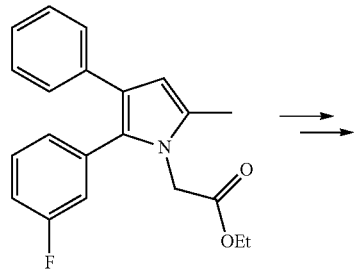

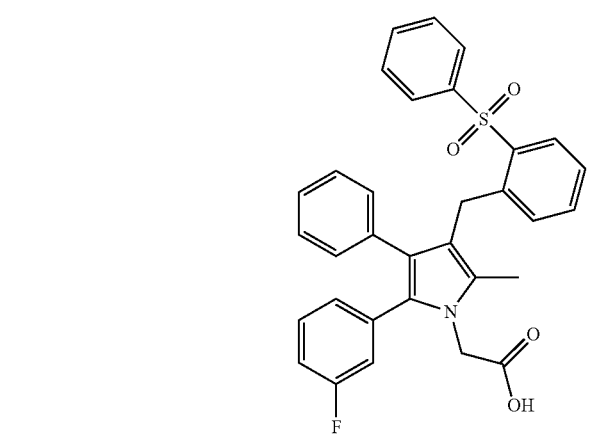

Preparation of 1-(3-fluorophenyl)-2-phenylpentane-1,4-dione

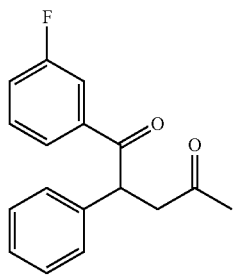 [SMILES: CC(=O)CC(C(=O)c1cccc(F)c1)c1ccccc1]

A solution of 3-fluorobenzaldehyde (2.005 ml, 18.33 mmol) in DMF (5 ml) was added dropwise over the course of 0.5 hours to a mixture of sodium cyanide (0.450 g, 9.18 mmol) in DMF (20 ml) at 35° C. Stirring was then continued for 1.5 hours at 35° C. A solution of (E)-4-phenylbut-3-en-2-one (2.0 g, 13.68 mmol) in DMF (5 ml) was then slowly added dropwise over the course of 0.5 hours at 35° C. Stirring was continued for 3.5 hours at the same temperature. The reaction mixture was treated with twice its volume of water and extracted with DCM. The combined extracts were washed with water and brine, dried with Na2SO4, filtered and concentrated to give a liquid, purified by chromatography on silica gel using an automated Biotage system (EtOAc/Hex, 0-50%) to give 1-(3-fluorophenyl)-2-phenylpentane-1,4-dione (2.1 g, 7.77 mmol, 56.8% yield). 1H NMR (400 MHz, CDCl3) δ (ppm) 7.75-7.73 (m, 1H), 7.64-7.61 (m, 1H), 7.37-7.12 (m, 7H), 5.03 (dd, 1H), 3.61 (dd, 1H), 2.76 (dd, 1H), 2.19 (s, 3H).

Preparation of ethyl 2-(2-(3-fluorophenyl)-5-methyl-3-phenyl-1H-pyrrol-1-yl)acetate

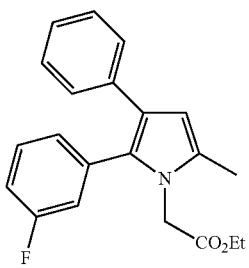 [SMILES: CCOC(=O)Cn1c(C)cc(-c2ccccc2)c1-c1cccc(F)c1]

The same procedure as the synthesis of Ethyl 2-(3-(4-fluorophenyl)-5-methyl-2-phenyl-1H-pyrrol-1-yl)acetate was used, giving a yield of 53.4%.

1H NMR (400 MHz, CDCl3) δ (ppm) 7.34-7.29 (m, 1H), 7.19-7.14 (m, 4H), 7.11-6.97 (m, 4H), 6.24 (b, 1H), 4.43 (s, 2H), 4.23 (q, 2H), 2.27 (s, 3H), 1.27 (t, 3H).

Preparation of ethyl 2-(2-(3-fluorophenyl)-5-methyl-3-phenyl-4-(2-(phenylsulfonyl)benzyl)-1H-pyrrol-1-yl)acetate (compound I-67)

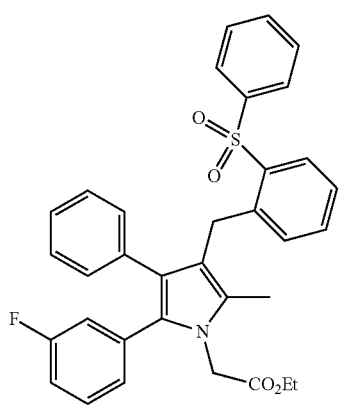 [SMILES: CCOC(=O)Cn1c(C)c(Cc2ccccc2S(=O)(=O)c2ccccc2)c(-c2ccccc2)c1-c1cccc(F)c1]

The preparation followed the same procedure as used in the synthesis of ethyl 2-(3-(4-fluorophenyl)-5-methyl-2-phenyl-4-(2-(phenylsulfonyl)benzyl)-1H-pyrrol-1-yl)acetate. (yield 82%). 1H NMR (400 MHz, CDCl3) δ (ppm) 8.29-8.27 (m, 1H), 7.82-7.80 (m, 2H), 7.51-7.47 (m, 2H), 7.41-7.38 (m, 3H), 7.24-7.17 (m, 2H), 6.95-6.81 (m, 6H), 6.71-6.69 (m, 2H), 4.48 (s, 2H), 4.21 (q, 2H), 3.99 (s, 2H), 1.78 (s, 3H), 1.26 (t, 3H).

Preparation of 2-(2-(3-fluorophenyl)-5-methyl-3-phenyl-4-(2-(phenylsulfonyl)benzyl)-1H-pyrrol-1-yl)acetic acid (compound I-38)

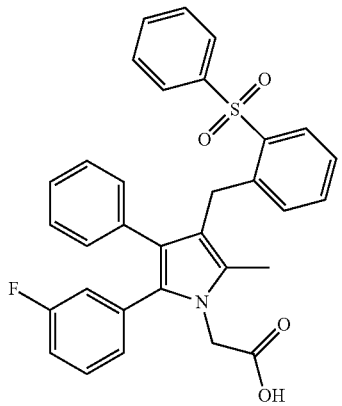 [SMILES: Cc1c(Cc2ccccc2S(=O)(=O)c2ccccc2)c(-c2ccccc2)c(-c2cccc(F)c2)n1CC(=O)O]

The preparation followed the same procedure as the synthesis of 2-(3-(4-fluorophenyl)-5-methyl-2-phenyl-4-(2-(phenylsulfonyl)benzyl)-1H-pyrrol-1-yl)acetic acid (yield 85%). 1H NMR (400 MHz, CDCl3) δ (ppm) 8.29-8.27 (m, 1H), 7.81-7.79 (m, 2H), 7.53-7.46 (m, 2H), 7.41-7.37 (m, 3H), 7.25-7.17 (m, 2H), 6.98-6.88 (m, 5H), 6.84-6.81 (m, 1H), 6.71-6.69 (m, 2H), 4.58 (s, 2H), 3.99 (s, 2H), 1.82 (s, 3H).

Example 16

Synthesis of 2-(2-methyl-5-phenyl-3-(2-(phenylsulfonyl)benzyl)-1H-pyrrol-1-yl)acetic acid and 2-(5-methyl-2-phenyl-3-(2-(phenylsulfonyl)benzyl)-1H-pyrrol-1-yl)acetic acid General Synthetic Scheme

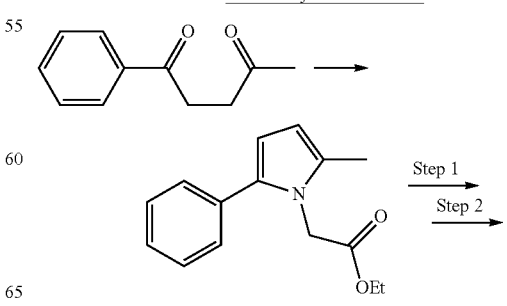

-continued

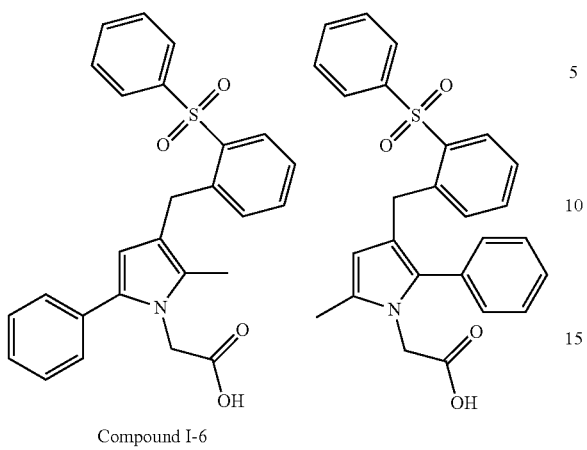

Compound I-6

Preparation of ethyl 2-(2-methyl-5-phenyl-1H-pyrrol-1-yl)acetate

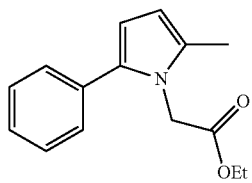 [SMILES: CCOC(=O)Cn1c(C)ccc1-c1ccccc1]

Ethyl 2-aminoacetate hydrochloride (1.378 g, 9.87 mmol) was diluted with ethanol (50 ml) then charged with TEA (8 ml, 57.4 mmol). 1-Phenylpentane-1,4-dione (1.74 g, 9.87 mmol) was then added and reaction was heated at 70° C. overnight. The reaction mixture was then diluted with 100 mL DCM and washed with water (100 mL). The aqueous was back-extracted with DCM (50 mL×2), the organics were combined, dried (Na2SO4), filtered, and concentrated to yield a crude orange oil. This oil was loaded onto a SiO2 column and purified using a 0-20% gradient of EtOAc in hexanes, affording 1.74 g (72.4% yield) of the desired ethyl 2-(2-methyl-5-phenyl-1H-pyrrol-1-yl)acetate.

Synthesis of Compound I-6

General procedure I (step 1 and 2) was carried out for the remainder of the synthesis. Following the general reductive alkylation conditions (step 1) employing 2-(phenylsulfonyl) benzaldehyde followed by general saponification conditions (step 2), Compound I-6 and its side product were generated as a separable 3:1 mixture (respectively) in a combined 57% yield.

2-(2-methyl-5-phenyl-3-(2-(phenylsulfonyl)benzyl)-1H-pyrrol-1-yl)acetic acid (compound number I-6)

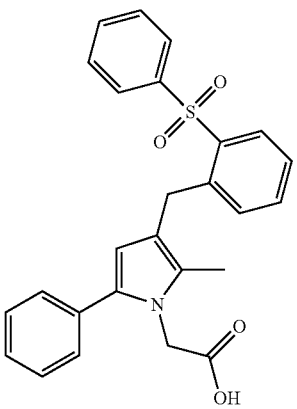 [SMILES: Cc1c(Cc2ccccc2S(=O)(=O)c2ccccc2)cc(-c2ccccc2)n1CC(=O)O]

1H NMR (400 MHz, CDCl3) δ (ppm) 8.27 (dd, 1H), 7.86 (dd, 2H), 7.55-7.21 (m, 11H), 5.71 (s, 1H), 4.60 (s, 2H), 4.03 (s, 2H), 1.94 (s, 3H).

2-(5-methyl-2-phenyl-3-(2-(phenylsulfonyl)benzyl)-1H-pyrrol-1-yl)acetic acid

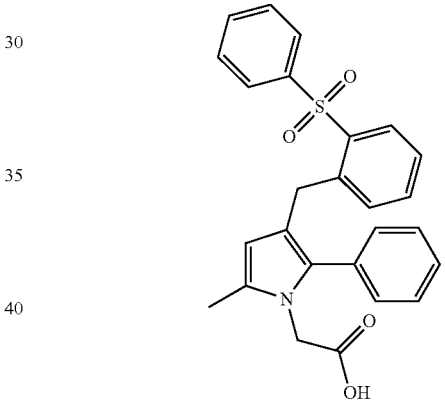

1H NMR (400 MHz, CDCl3) δ (ppm) 8.22 (dd, 1H), 7.76-7.74 (m, 2H), 7.55-7.21 (m, 11H), 5.49 (s, 1H), 4.49 (s, 2H), 3.92 (s, 2H), 2.15 (s, 3H) ppm.

Example 17

Synthesis of 2-(2-methyl-5-phenyl-3-(2-(pyrrolidin-1-ylsulfonyl)benzyl)-1H-pyrrol-1-yl)acetic acid and 2-(5-methyl-2-phenyl-3-(2-(pyrrolidin-1-ylsulfonyl)benzyl)-1H-pyrrol-1-yl)acetic acid General Synthetic Scheme

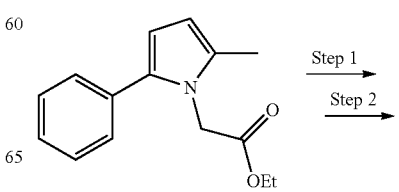

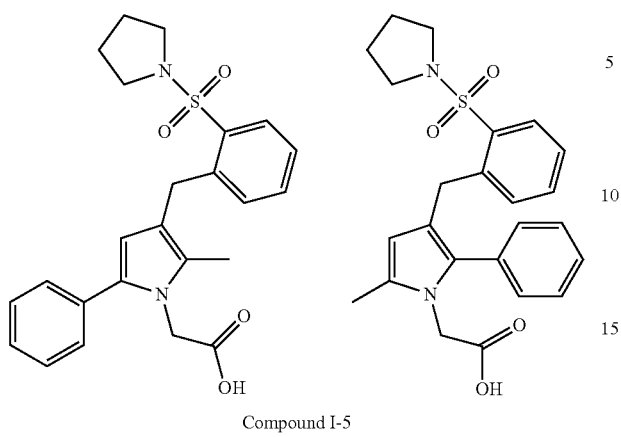

Compound I-5

Preparation of Compound I-5

General procedure I (step 1 and 2) was carried out for the remainder of the synthesis. Following general reductive alkylation conditions (step 1) employing 2-(pyrrolidin-1-ylsulfonyl)benzaldehyde followed by general saponification conditions, Compound I-5 and its side product were generated as a separable 2:1 mixture (respectively) in a combined 57% yield.

2-(2-methyl-5-phenyl-3-(2-(pyrrolidin-1-ylsulfonyl)benzyl)-1H-pyrrol-1-yl)acetic acid (compound I-5): 1H NMR (400 MHz, CDCl3) δ 9.70 (bs, 1H), 7.97 (dd, 1H), 7.47-7.26 (m, 8H), 5.94 (s, 1H), 4.67 (s, 2H), 4.27 (s, 2H), 3.31-3.27 (m, 4H), 2.17 (s, 3H), 1.86-1.82 (m, 4H) ppm.

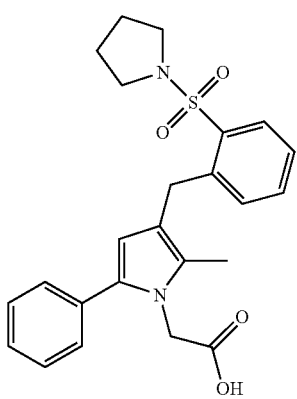 [SMILES: Cc1c(Cc2ccccc2S(=O)(=O)N2CCCC2)cc(-c2ccccc2)n1CC(=O)O]

2-(5-methyl-2-phenyl-3-(2-(pyrrolidin-1-ylsulfonyl)benzyl)-1H-pyrrol-1-yl)acetic acid: 1H NMR (400 MHz, CDCl3) δ7.94 (dd, 1H), 7.44-7.19 (m, 8H), 5.80 (s, 1H), 4.53 (s, 2H), 4.13 (s, 2H), 3.17-3.14 (m, 4H), 2.23 (s, 3H), 1.74-1.71 (m, 4H).

Example 18

Synthesis of 2-(2-methyl-3-(2-(morpholinosulfonyl)benzyl)-5-phenyl-1H-pyrrol-1-yl)acetic acid (compound I-13)

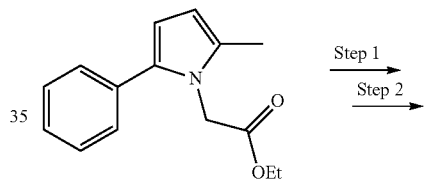

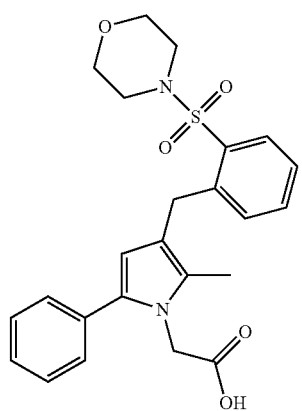

General procedure I (step 1 and 2) were carried out for the remainder of the synthesis.

Following general reductive alkylation conditions (step 1) employing 2-(morpholinosulfonyl)benzaldehyde and then general saponification conditions. 2-(2-methyl-3-(2-(morpholinosulfonyl)benzyl)-5-phenyl-1H-pyrrol-1-yl)acetic acid was generated in an overall 30% yield. 1H NMR (400 MHz, CDCl3) δ 10.42 (bs, 1H), 7.95 (dd, 1H), 7.49 (ddd, 1H), 7.39-7.26 (m, 7H), 5.92 (s, 1H), 4.66 (s, 2H), 4.26 (s, 2H), 3.66 (t, 4H), 3.13 (t, 4H), 2.18 (s, 3H) ppm.

Example 19

Synthesis of 2-(5-(3,5-difluorophenyl)-2-methyl-3-(2-(phenylsulfonyl)benzyl)-1H-pyrrol-1-yl)acetic acid General Synthetic Scheme

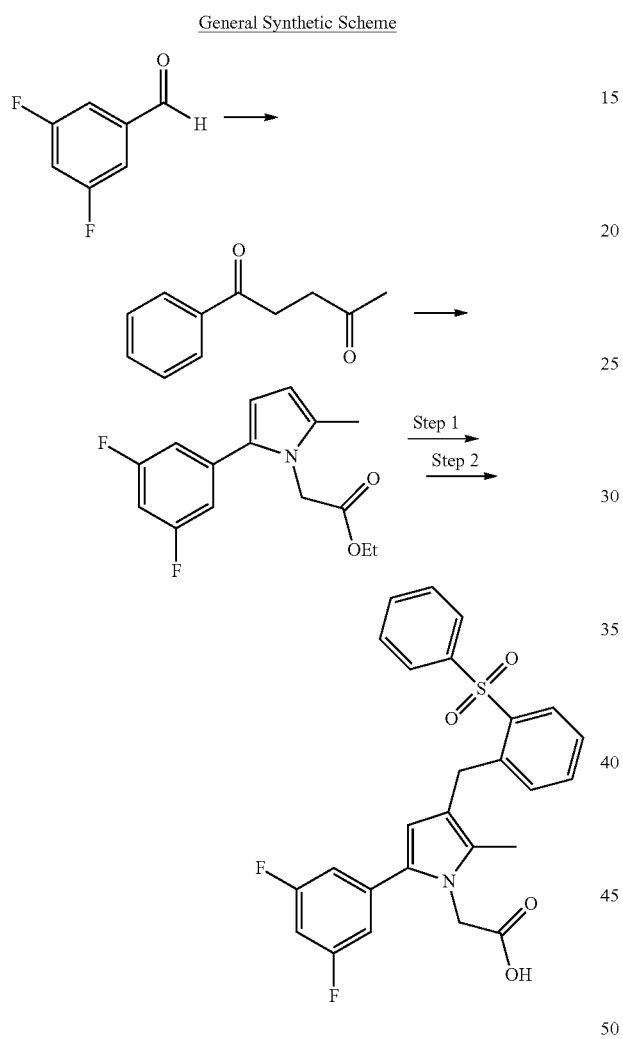

Preparation of 1-phenylpentane-1,4-dione

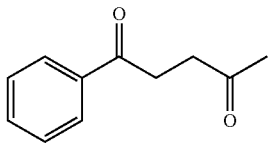

To a vial charged with 3,5-difluorobenzaldehyde (5.0 g, 35.2 mmol) in 10 mL EtOH was added triethylamine (6.32 mL, 45.3 mmol), but-3-en-2-one (2.93 ml, 35.2 mmol) and 3-ethyl-5-(2-hydroxyethyl)-4-methylthiazol-3-ium bromide (1.775 g, 7.04 mmol). The reaction mixture became deep green and was heated at 90° C. for 15 h. 1-phenylpentane-1,4-dione was taken crude on to the next step.

Preparation of ethyl 2-(2-(3,5-difluorophenyl)-5-methyl-1H-pyrrol-1-yl)acetate

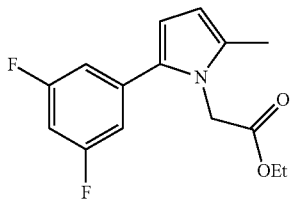 [SMILES: CCOC(=O)Cn1c(C)ccc1-c1cc(F)cc(F)c1]

The crude solution of dione from the above step was diluted with 40 mL of EtOH to bring the total volume of EtOH to 50 mL. An additional amount of triethylamine (14.72 ml, 106 mmol) was added, followed by ethyl 2-aminoacetate hydrochloride (9.83 g, 70.4 mmol), and the resulting mixture was stirred at 70° C. for 6 hours. At this time, the reaction was concentrated to 20% of its original volume and diluted with 100 mL DCM. This organic mixture was extracted with NH4Cl (100 mL). The layers were separated, and the organic portion was dried, filtered, and concentrated. The crude orange oil was then purified by SiO2 chromatography using a 0-40% EtOAc/hexane gradient to yield 4.42 g of the desired material.

Synthesis of 2-(5-(3,5-difluorophenyl)-2-methyl-3-(2-(phenylsulfonyl)benzyl)-1H-pyrrol-1-yl)acetic acid (compound I-43)

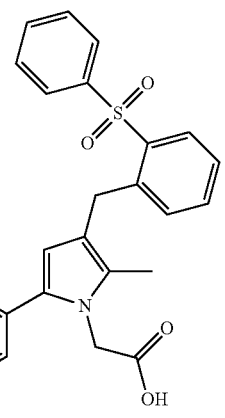

General procedure I (step 1 and 2) were carried out for the remainder of the synthesis.

2-(5-(3,5-difluorophenyl)-2-methyl-3-(2-(phenylsulfonyl)benzyl)-1H-pyrrol-1-yl)acetic acid was generated in a 74% yield. 1H NMR (400 MHz, CDCl3) δ 9.17 (bs, 1H), 8.20 (dd, 1H), 7.92-7.77 (m, 2H), 7.49-7.31 (m, 8H), 7.09 (d, 1H), 5.63 (s, 1H), 4.53 (s, 2H), 3.95 (s, 2H), 1.88 (s, 3H).

Example 20

Synthesis of 2-(3-cyano-5-methyl-2-phenyl-4-(2-(phenylsulfonyl)benzyl)-1H-pyrrol-1-yl)acetic acid and 2-(3-cyano-2-methyl-5-phenyl-4-(2-(phenylsulfonyl)benzyl)-1H-pyrrol-1-yl)acetic acid

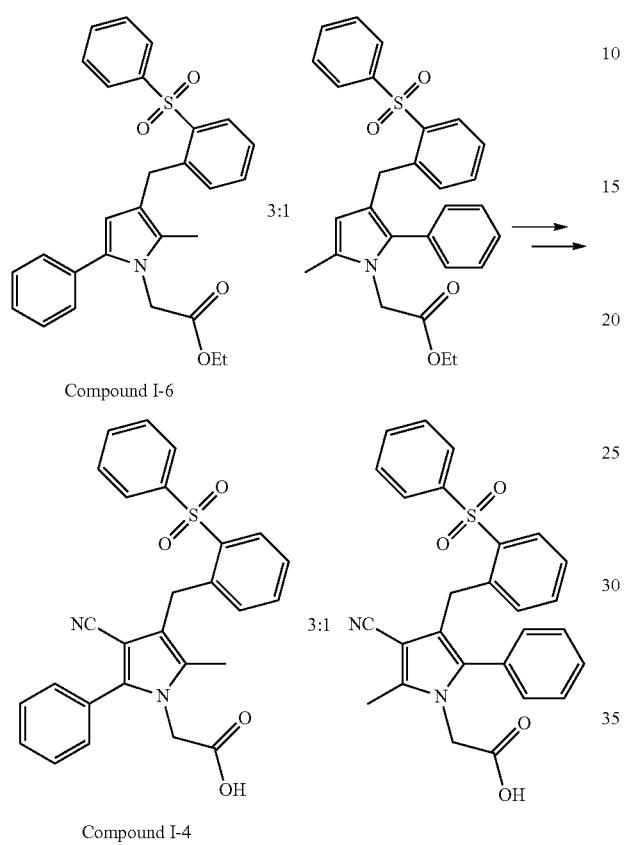

General procedure II and general procedure I (step 1 and 2) were carried out for this synthesis Compound I-4 and its side product were generated as a 3:1 mixture (respectively) in a 71% total yield.

2-(3-cyano-5-methyl-2-phenyl-4-(2-(phenylsulfonyl)benzyl)-1H-pyrrol-1-yl)acetic acid (compound I-4)

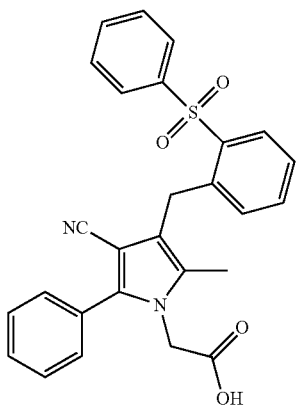 [SMILES: Cc1c(Cc2ccccc2S(=O)(=O)c2ccccc2)c(C#N)c(-c2ccccc2)n1CC(=O)O]

1H NMR (400 MHz, CDCl3) δ 8.22 (dd, 1H), 7.83 (dd, 2H), 7.52-7.27 (m, 10H), 7.03 (d, 1H), 4.50 (s, 2H), 4.08 (s, 2H), 1.86 (s, 3H).

2-(3-cyano-2-methyl-5-phenyl-4-(2-(phenylsulfonyl)benzyl)-1H-pyrrol-1-yl)acetic acid

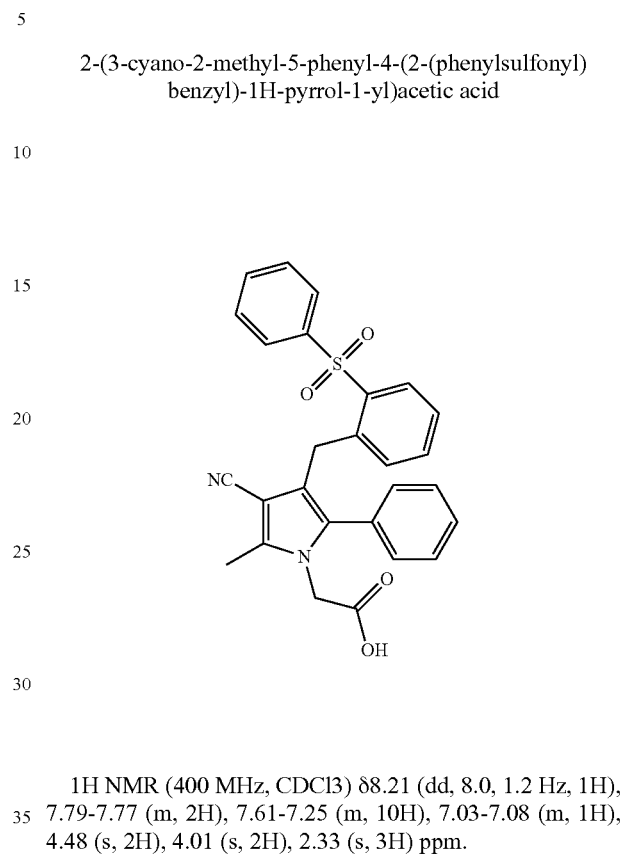

1H NMR (400 MHz, CDCl3) δ8.21 (dd, 8.0, 1.2 Hz, 1H), 7.79-7.77 (m, 2H), 7.61-7.25 (m, 10H), 7.03-7.08 (m, 1H), 4.48 (s, 2H), 4.01 (s, 2H), 2.33 (s, 3H) ppm.

Example 21

Synthesis of 2-(3-cyano-2,5-dimethyl-4-(2-(pyrrolidin-1-ylsulfonyl)benzyl)-1H-pyrrol-1-yl)acetic acid (compound number I-32, second approach)

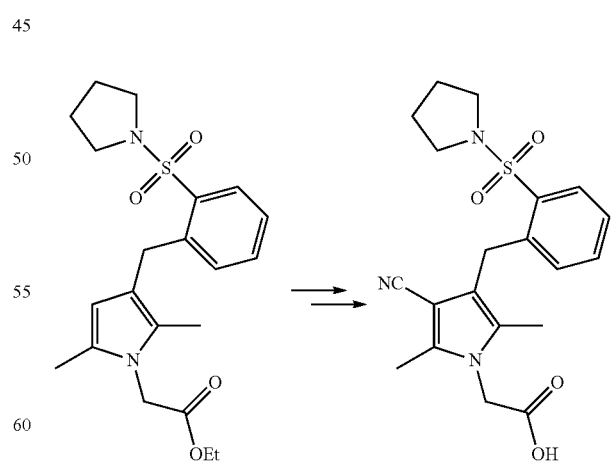

General procedure II and general procedure I (step 1 and 2) were carried out for this synthesis. The product was generated in 64% yield. 1H NMR (400 MHz, CDCl3) δ 8.76 (bs, 1H), 7.98 (dd, 1H), 7.40 (ddd, 1H), 7.30 (ddd, 1H), 7.00 (dd, 1H), 4.60 (s, 2H), 4.28 (s, 2H), 3.36-3.32 (m, 4H), 2.34 (s, 3H), 2.02 (s, 3H), 1.95-1.91 (m, 4H).

Example 22

Synthesis of 2-(3-cyano-5-methyl-4-(2-(morpholinosulfonyl)benzyl)-2-phenyl-1H-pyrrol-1-yl)acetic acid (compound I-3)

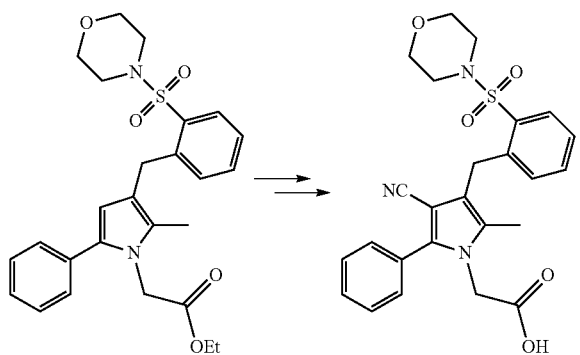 [SMILES: CCOC(=O)Cn1c(-c2ccccc2)cc(Cc2ccccc2S(=O)(=O)N2CCOCC2)c1C ; Cc1c(Cc2ccccc2S(=O)(=O)N2CCOCC2)c(C#N)c(-c2ccccc2)n1CC(=O)O]

General procedure II and general procedure I (step 1 and 2) were carried out for this synthesis. The product was generated in 39% yield. 1H NMR (400 MHz, CDCl3) δ 7.93 (dd, 1H), 7.45-7.28 (m, 7H), 7.07 (d, 1H), 4.58 (s, 2H), 4.32 (s, 2H), 3.71 (t, 4H), 3.17 (t, 4H), 2.03 (s, 3H).

Example 23

Synthesis of 2-(3-cyano-5-methyl-2-phenyl-4-(2-(pyrrolidin-1-ylsulfonyl)benzyl)-1H-pyrrol-1-yl)acetic acid (compound I-11)

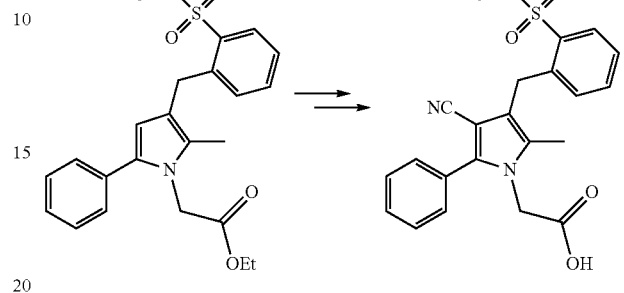

General procedure II and general procedure I (step 1 and 2) were carried out for this synthesis 2-(3-cyano-5-methyl-2-phenyl-4-(2-(pyrrolidin-1-ylsulfonyl)benzyl)-1H-pyrrol-1-yl)acetic acid was generated in 33% yield. 1H NMR (400 MHz, CDCl3) δ 7.95 (d, 1H), 7.42-7.25 (m, 7H), 7.05 (d, 1H), 4.58 (s, 2H), 4.33 (s, 2H), 3.31-3.28 (m, 4H), 2.03 (s, 3H), 1.89-1.85 (m, 4H).

Example 24

Synthesis of 2-(2-methyl-3-(2-(morpholinosulfonyl)benzyl)-5-phenyl-4-(2,2,2-trifluoroethyl)-1H-pyrrol-1-yl)acetic acid General Synthetic Scheme

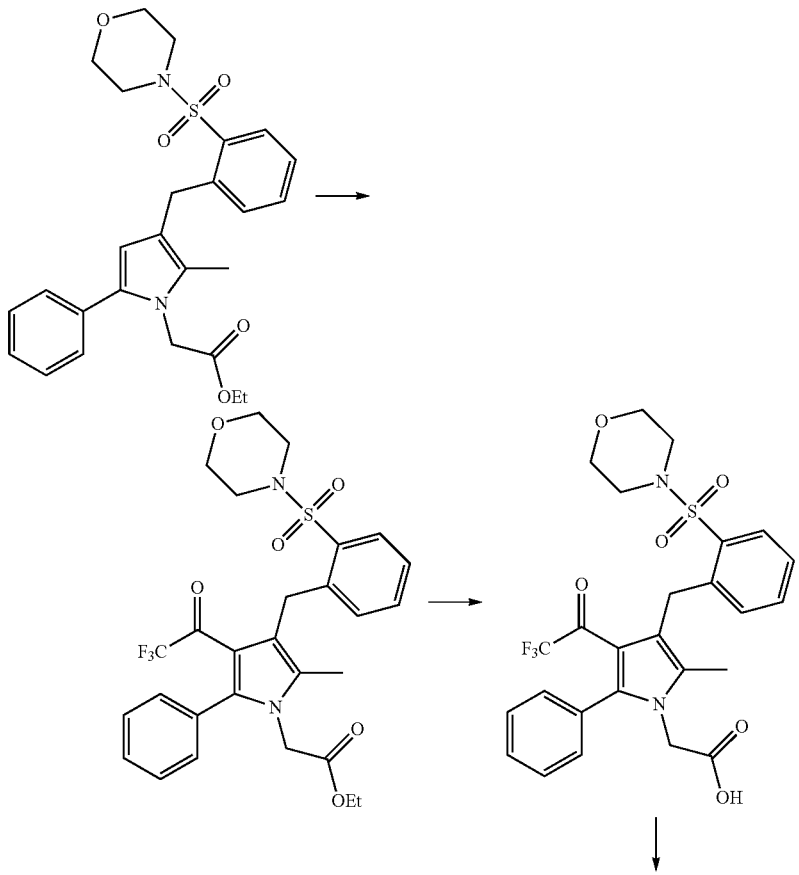

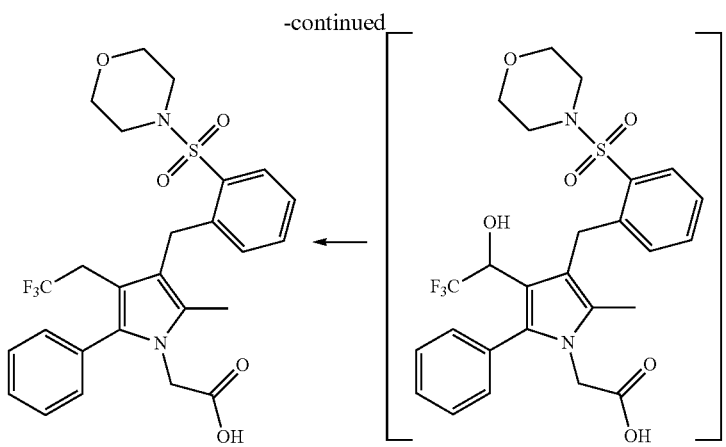

Preparation of ethyl 2-(2-methyl-3-(2-(morpholinosulfonyl)benzyl)-5-phenyl-4-(2,2,2-trifluoroacetyl)-1H-pyrrol-1-yl)acetate (compound I-21)

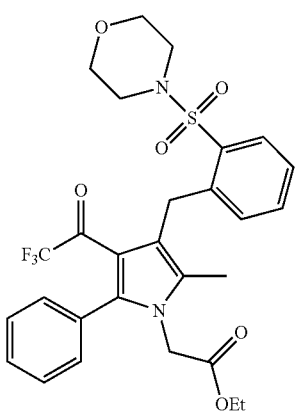 [SMILES: CCOC(=O)Cn1c(C)c(Cc2ccccc2S(=O)(=O)N2CCOCC2)c(C(=O)C(F)(F)F)c1-c1ccccc1]

Ethyl 2-(2-methyl-3-(2-(morpholinosulfonyl)benzyl)-5-phenyl-1H-pyrrol-1-yl)acetate (0.259 g, 0.537 mmol) (mixture of regioisomers—1.5:1.0) was dissolved in DCM (5.37 ml) and cooled to 0° C. DMAP (0.262 g, 2.147 mmol) was then added to the reaction in one portion, followed by TFA (0.758 ml, 5.37 mmol) in a drop-wise fashion. The ice bath was removed and the reaction was warmed to rt then refluxed for 16 h. At this time, the reaction was quenched with 1N HCl, and then diluted with 50 mL DCM. The layers were separated and the aqueous portion was then back-extracted with DCM (50 mL). The organics were combined, dried, filtered, and concentrated. The crude material ethyl 2-(2-methyl-3-(2-(morpholinosulfonyl)benzyl)-5-phenyl-4-(2,2,2-trifluoroacetyl)-1H-pyrrol-1-yl)acetate was then purified by silica gel chromatography using a 0-70% EtOAc/hexane gradient to furnish the desired material in 67% yield.

Preparation of 2-(2-methyl-3-(2-(morpholinosulfonyl)benzyl)-5-phenyl-4-(2,2,2-trifluoroacetyl)-1H-pyrrol-1-yl)acetic acid (compound I-50)

General procedure I (step 2) were carried out for this synthesis.

Preparation of 2-(2-methyl-3-(2-(morpholinosulfonyl)benzyl)-5-phenyl-4-(2,2,2-trifluoroethyl)-1H-pyrrol-1-yl)acetic acid (compound number I-45)

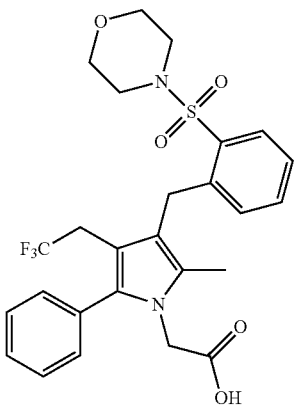 [SMILES: Cc1c(Cc2ccccc2S(=O)(=O)N2CCOCC2)c(CC(F)(F)F)c(-c2ccccc2)n1CC(=O)O]

2-(2-methyl-3-(2-(morpholinosulfonyl)benzyl)-5-phenyl-4-(2,2,2-trifluoroacetyl)-1H-pyrrol-yl)acetic acid (0.063 g, 0.114 mmol) was dissolved in THF (3 ml) and cooled to 0° C. Lithium aluminum hydride (0.114 ml, 0.228 mmol) was then added and the reaction was warmed to room temperature. At this time, LC/MS suggests reaction is complete, therefore it was quenched with ammonium chloride and extracted 3× with DCM. The organics were combined, dried, filtered, and concentrated. The crude material was taken directly on to the second reduction step without further characterization.

2-(2-methyl-3-(2-(morpholinosulfonyl)benzyl)-5-phenyl-4-(2,2,2-trifluoro-1-hydroxyethyl)-1H-pyrrol-1-yl)acetic acid (0.063 g, 0.114 mmol) was dissolved in 2 mL DCM and cooled to 0° C. 2,2,2-trifluoroacetic acid (1 ml, 0.114 mmol) was then added followed by triethylsilane (0.2 ml, 1.252 mmol). LC/MS shows reduction was instantly complete. The reaction mixture was directly concentrated to yield ~5 mg of crude material, which was purified by preparative HPLC chromatography to give 18 mg (29.4%) of the desired material.

1H NMR (400 MHz, CDCl3) δ 7.99 (dd, 1H), 7.50-7.28 (m, 7H), 7.13 (d, 1H), 4.44 (s, 2H), 4.30 (s, 2H), 3.75 (dd, 4H), 3.24 (t, 4H), 3.02 (q, 2H), 2.00 (s, 3H).

Example 25

Synthesis of 2-(3-acetyl-2,5-dimethyl-4-(2-(phenylsulfonyl)benzyl)-1H-pyrrol-1-yl)acetic acid (compound number I-52)

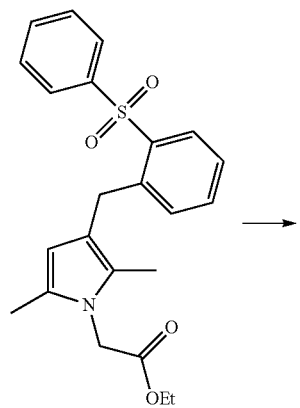

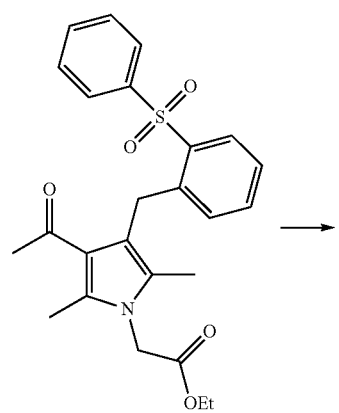

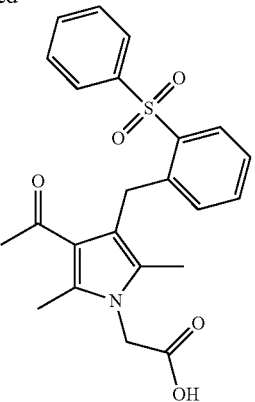

In a round-bottomed flask equipped with a magnetic stir bar, acetyl chloride (1.7 µL, 0.024 mmol) was added to a solution of ethyl 2-(2,5-dimethyl-3-(2-(phenylsulfonyl)benzyl)-1H-pyrrol-1-yl)acetate (10 mg, 0.024 mmol) in acetonitrile (0.5 mL) at room temperature. The reaction was stirred for 5 minutes, then dichloromethane (10 mL) and NaHCO3 (sat. aq. 10 mL) were added. The dichloromethane layer was separated and dried over Na2SO4, filtered and concentrated to yield ethyl 2-(3-acetyl-2,5-dimethyl-4-(2-(phenylsulfonyl)benzyl)-1H-pyrrol-1-yl)acetate (8 mgs, 72%).

To the crude mixture of ethyl 2-(3-acetyl-2,5-dimethyl-4-(2-(phenylsulfonyl)benzyl)-1H-pyrrol-1-yl)acetate (25 mg, 0.055 mmol) in MeOH:THF:water 3:3:1 (5 ml total) was added LiOH (3.96 mg, 0.165 mmol) and the resulting mixture was stirred for 30 min. To this mixture were added EtOAc (3 mL) and HCl (1N aq., 3 mL). The ethyl acetate layer was separated and dried over Na2SO4, filtered and subjected to column chromatography on silica gel (0 to 100% ethyl acetate in hexanes, followed by 0 to 20% MeOH in ethyl acetate). Collection and concentration of pertinent fractions resulted in the isolation of 2-(3-acetyl-2,5-dimethyl-4-(2-(phenylsulfonyl)benzyl)-1H-pyrrol-1-yl)acetic acid (10.5 mg, 45%) as a tan solid. 1H NMR (CDCl3/400 MHz) 8.23-8.20 (m, 1H), 7.84 (d, 2H), 7.51 (t, (t, 1H), 7.48-7.40 (m, 2H), 7.36-7.30 (m, 2H), 6.84-6.21 (m, 1H), 4.51 (s, 2H), 4.09 (s, 2H), 2.37 (s, 3H), 1.79 (s, 3H), 1.62 (s, 3H). MS m/z=426.4 (M+1).

Example 26

Synthesis of 2-(3-acetyl-2,5-dimethyl-4-(2-(pyrrolidin-1-ylsulfonyl)benzyl)-1H-pyrrol-1-yl)acetic acid (compound I-53)

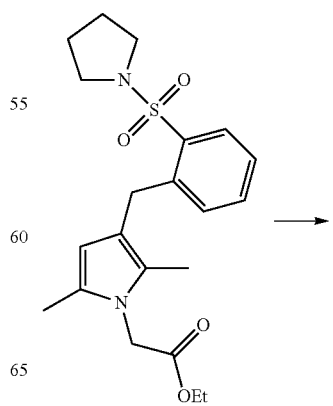

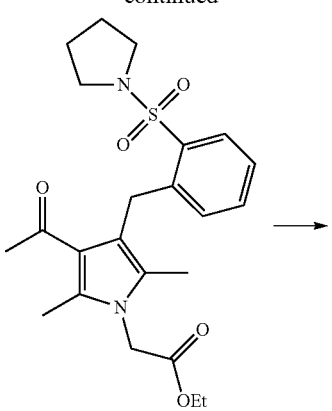

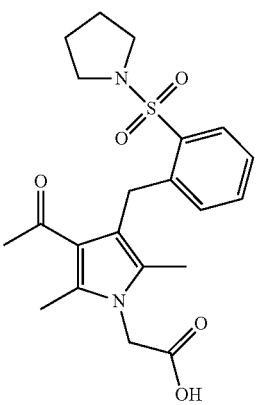

Synthesis of 2-(3-acetyl-2,5-dimethyl-4-(2-(phenylsulfonyl)benzyl)-1H-pyrrol-1-yl)acetic acid was conducted in the same fashion as that of 2-(3-acetyl-2,5-dimethyl-4-(2-(pyrrolidin-1-ylsulfonyl)benzyl)-1H-pyrrol-1-yl)acetic acid. 1H NMR (CDCl3/400 MHz) 7.95 (dd, 1H), 7.37-7.33 (m, 1H), 7.30-7.25 (m, 1H), 6.96 (d, 1H), 4.65 (s, 2H), 4.47 (s, 2H), 3.38 (t, 4H), 2.51 (s, 3H), 2.23 (s, 3H), 2.03 (s, 3H), 1.96-1.93 (m, 4H). MS m/z=519.4 (M+1).

Example 27

Synthesis of 2-(2-methyl-3-(2-(phenylsulfonyl)benzyl)-5-(pyridin-3-yl)-1H-pyrrol-1-yl)acetic acid General Synthetic Scheme

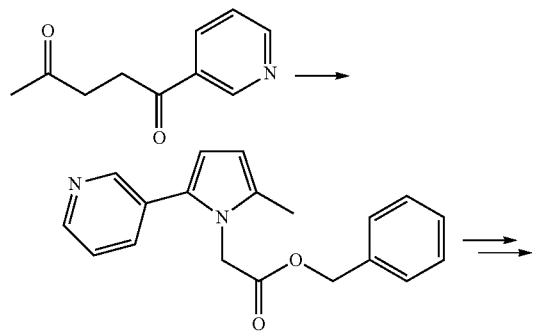

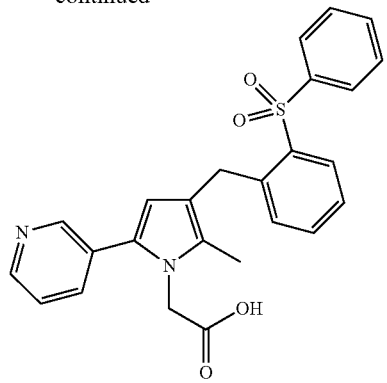

Preparation of 1-(pyridin-3-yl)pentane-1,4-dione

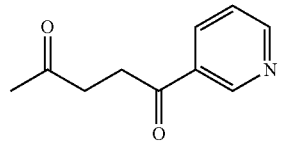

In a sealable vial were added nicotinaldehyde (4.7 g, 43.9 mmol), triethylamine (12.17 mL, 87 mmol), but-3-en-2-one (3.97 mL, 43.7 mmol), and 3-ethyl-5-(2-hydroxyethyl)-4-methylthiazol-3-ium bromide (2.202 g, 8.73 mmol) in ethanol (10 mL). The reaction mixture was heated at 80° C. for 16 h. The reaction was then concentrated. The residue was treated with 1N HCl and extracted with DCM (3×20 mL). The organic layer was dried with Na2SO4. The crude product was added to a 80 g ISCO silica gel column and was purified with a gradient of 0% to 100% ethyl acetate in hexanes. Collection and concentration of pertinent fractions resulted in isolation of 1-(pyridin-2-yl)pentane-1,4-dione (4.5 g, 58%) as a tan liquid.

Preparation of benzyl 2-(2-methyl-5-(pyridin-3-yl)-1H-pyrrol-1-yl)acetate

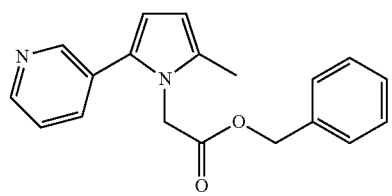 [SMILES: Cc1ccc(-c2cccnc2)n1CC(=O)OCc1ccccc1]

In a small vial, 1-(pyridin-3-yl)pentane-1,4-dione (2.26 g, 12.8 mmol) and benzyl 2-aminoacetate, HCl (5.14 g, 25.5 mmol) were dissolved in dichloromethane (15 ml). Triethylamine (5.33 mL, 38.3 mmol) was added slowly. When the reaction mixture became too viscous/chunky to stir, additional dichloromethane and ethanol (~3 mL each) were added until the mixture could resume stirring. The reaction mixture stirred overnight, then was quenched with 15 mL dichloromethane (15 mL) and NaHCO3 (sat. aq. 50 mL). The dichloromethane layer was added directly to a 120 g silica gel column and the product was eluted with 0-100% ethyl acetate in hexanes. Collection and concentration of pertinent fractions resulted in the isolation of benzyl 2-(2-methyl-5-(pyridin-3-yl)-1H-pyrrol-1-yl)acetate (3.37 g, 86%) as a colorless liquid.

Synthesis of 2-(2-methyl-3-(2-(phenylsulfonyl)benzyl)-5-(pyridin-3-yl)-1H-pyrrol-1-yl)acetic acid (compound I-2)

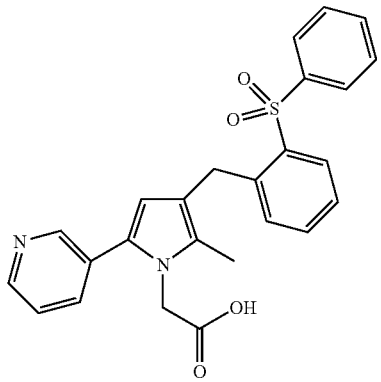 [SMILES: Cc1c(Cc2ccccc2S(=O)(=O)c2ccccc2)cc(-c2cccnc2)n1CC(=O)O]

Benzyl 2-(2-methyl-3-(2-(phenylsulfonyl)benzyl)-5-(pyridin-2-yl)-1H-pyrrol-1-yl)acetate was synthesized according to general procedure I (step 1), with the exception that 6 equivalents of triethylsilane and 4.5 equivalents of trimethylsilyl trifluoromethanesulfonate were used. The crude benzyl 2-(2-methyl-3-(2-(phenylsulfonyl)benzyl)-5-(pyridin-2-yl)-1H-pyrrol-1-yl)acetate was taken forward. In a small recovery flask, H2 was flushed over a stirring solution of benzyl 2-(2-methyl-3-(2-(phenylsulfonyl)benzyl)-5-(pyridin-3-yl)-1H-pyrrol-1-yl)acetate (350 mg, 0.652 mmol), Pd/C (20 mg, 0.019 mmol) in MeOH (2 ml) followed by subjection to 1 atm (balloon) positive pressure of H2. After 1.5 hours, the reaction vial was flushed with nitrogen gas and the mixture was filtered through a 2 micron filter. The colorless mixture was concentrated to afford 2-(2-methyl-3-(2-(phenylsulfonyl) benzyl)-5-(pyridin-3-yl)-1H-pyrrol-1-yl)acetic acid (277 mg, 95%) as a fine yellow powder. 1H NMR (CDCl3/400 MHz) 11.77 (bs, 1H), 8.7 (s, 1H), 8.44 (d, 1H), 8.25 (d, 1H), 7.86-7.82 (m, 3H), 7.54-7.37 (m, 6H), 7.17 (d, 1H), 5.76 (s, 1H), 4.46 (s, 2H), 4.03 (s, 2H), 1.99 (s, 3H). MS m/z=447.4 (M+1).

Example 28

Synthesis of 2-(2-methyl-3-(2-(phenylsulfonyl)benzyl)-5-(pyridin-4-yl)-1H-pyrrol-1-yl)acetic acid (compound I-1)

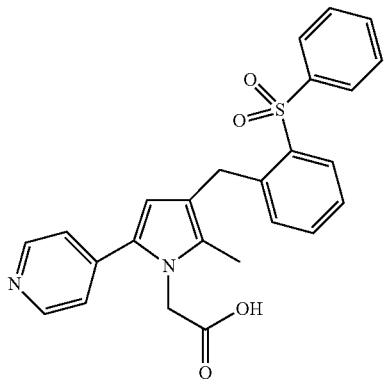 [SMILES: Cc1c(Cc2ccccc2S(=O)(=O)c2ccccc2)cc(-c2ccncc2)n1CC(=O)O]

This compound was synthesized in a similar fashion to 2-(2-methyl-3-(2-(phenylsulfonyl)benzyl)-5-(pyridin-3-yl)-1H-pyrrol-1-yl)acetic acid. 1H NMR (CDCl3/400 MHz) δ (ppm) 8.46 (d, 2H), 8.26 (dd, 1H), 7.81-7.79 (m, 2H), 7.59 (d, 2H), 7.56-7.47 (m, 5H), 7.25 (d, 1H), 6.9 (s, 1H), 4.81 (s, 2H), 4.10 (s, 2H), 2.05 (s, 3H). MS m/z=447.4 (M+1).

Example 29

Synthesis of 2-(2-methyl-3-(2-(phenylsulfonyl)benzyl)-5-(pyridin-2-yl)-1H-pyrrol-1-yl)acetic acid (compound I-17)

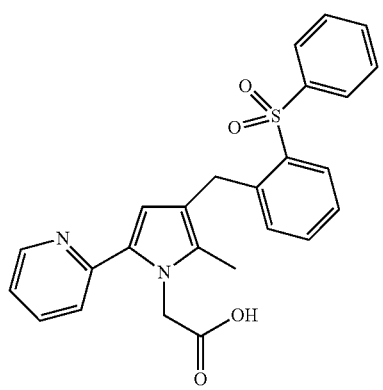 [SMILES: Cc1c(Cc2ccccc2S(=O)(=O)c2ccccc2)cc(-c2ccccn2)n1CC(=O)O]

This compound was synthesized in a similar fashion to 2-(2-methyl-3-(2-(phenylsulfonyl)benzyl)-5-(pyridin-3-yl)-1H-pyrrol-1-yl)acetic acid. 1H NMR (CDCl3/400 MHz) δ (ppm) 8.45-8.35 (m, 1H), 8.19 (d, 1H), 7.95-7.89 (m, 1H), 7.76 (d, 2H), 7.51-7.31 (m, 7H), 7.06 (d, 1H), 6.16 (s, 1H), 4.53 (s, 2H), 3.96 (s, 2H), 2.01 (s, 3H). MS m/z=447.4 (M+1).

Example 30

Synthesis of 2-(3-benzoyl-2,5-dimethyl-4-(2-(pyrrolidin-1-ylsulfonyl)benzyl)-1H-pyrrol-1-yl)acetic acid General Synthetic Scheme:

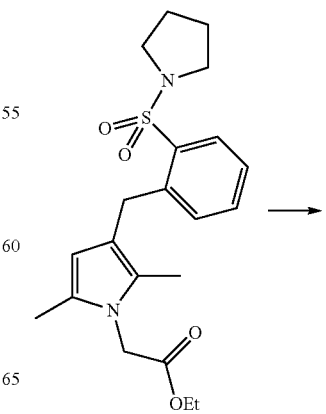

-continued

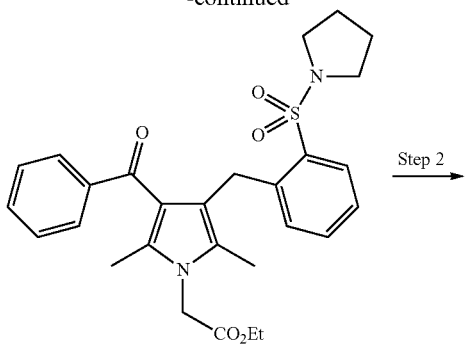

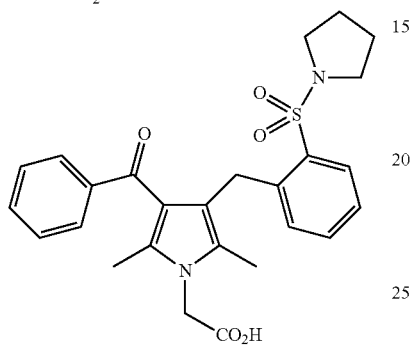

Preparation of ethyl 2-(3-benzoyl-2,5-dimethyl-4-(2-(pyrrolidin-1-ylsulfonyl)benzyl)-1H-pyrrol-1-yl) acetate (compound I-68)

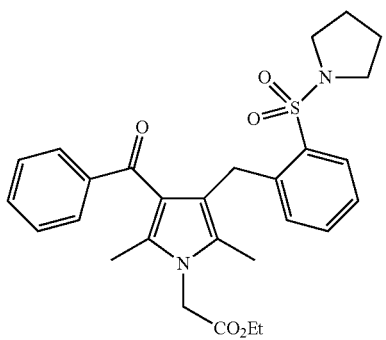 [SMILES: Cc1c(Cc2ccccc2S(=O)(=O)N2CCCC2)c(C(=O)c2ccccc2)c(C)n1CC(=O)O]

In a small vial charged with ethyl 2-(2,5-dimethyl-3-(2-(pyrrolidin-1-ylsulfonyl)benzyl)-1H-pyrrol-1-yl)acetate (143.7 mg, 0.355 mmol) in DCM (4 mL), at 0° C., was added dropwise a solution of ethylaluminum dichloride (444 µL, 0.444 mmol) in toluene. The reaction mixture turned deep rose color and benzoyl chloride (61.9 µL, 0.533 mmol) was added. The resulting mixture became orange and slowly was allowed to warm to rt. The reaction was stirred 5.25 h and then cooled once again and an additional 800 µL of EtAlCl2 and 150 µL of benzoyl chloride were added. The reaction was once again allowed to warm to room temperature slowly with stirring and stirred an additional 15.25 h at room temperature. The reaction was then quenched by the addition of water and dichloromethane and the water layer was extracted with DCM (3×). The organic layer was dried with MgSO4, and concentrated under vacuum. The crude product was added to a 40 g ISCO silica gel column and purified with a gradient of 0% to 60% EtOAc/hexanes. The product was obtained as a light orange foam (165.2 mg, 0.325 mmol, 91% yield). 1H NMR (CDCl3/400 MHz) δ (ppm) 7.92 (dd, 1H), 7.68 (dd, 2H), 7.46 (t, 1H), 7.38-7.32 (m, 3H), 7.20 (t, 1H), 7.10 (d, 1H), 4.56 (s, 2H), 4.30 (s, 2H), 4.24 (q, 2H), 3.23-3.17 (m, 4H), 2.03 (s, 3H), 1.98 (s, 3H), 1.84-1.78 (m, 4H), 1.29 (t, 3H). MS m/z: 509.40 (M+1).

Preparation of 2-(3-benzoyl-2,5-dimethyl-4-(2-(pyrrolidin-1-ylsulfonyl)benzyl)-1H-pyrrol-1-yl)acetic acid (compound I-55)

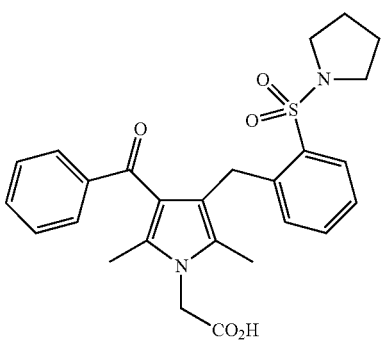

Ethyl 2-(3-benzoyl-2,5-dimethyl-4-(2-(pyrrolidin-1-yl-sulfonyl)benzyl)-1H-pyrrol-1-yl)acetate was saponified using the general procedure (step 2). 1H NMR (CDCl3/400 MHz) δ (ppm) 7.91 (dd, 1H), 7.68 (dd, 2H), 7.48-7.43 (m, 1H), 7.38-7.30 (m, 3H), 7.23-7.17 (m, 1H), 7.09 (d, 1H), 4.57 (s, 2H), 4.28 (s, 2H), 3.22-3.16 (m, 4H), 2.05 (s, 3H), 1.98 (s, 3H), 1.82-1.77 (4H). MS m/z: 481.34 (M+1).

Example 31

Synthesis of 2-(2-methyl-3-(2-(phenylsulfonyl)benzyl)-5-(4-(trifluoromethyl)phenyl)-1H-pyrrol-1-yl) acetic acid, 2-(2-methyl-3-(2-(phenylsulfonyl)benzyl)-5-(2-(trifluoromethyl)phenyl)-1H-pyrrol-1-yl) acetic acid, 2-(5-(2-fluorophenyl)-2-methyl-3-(2-(phenylsulfonyl)benzyl)-1H-pyrrol-1-yl)acetic acid, 2-(5-(3-fluorophenyl)-2-methyl-3-(2-(phenylsulfonyl)benzyl)-1H-pyrrol-1-yl)acetic acid, 2-(5-(4-fluorophenyl)-2-methyl-3-(2-(phenylsulfonyl)benzyl)-1H-pyrrol-1-yl)acetic acid Compound I-25

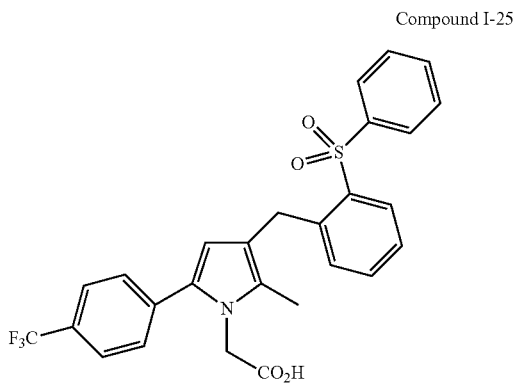

Compound I-27

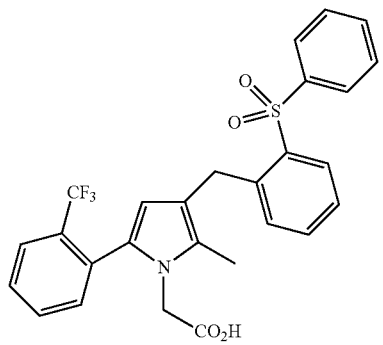

Compound I-18

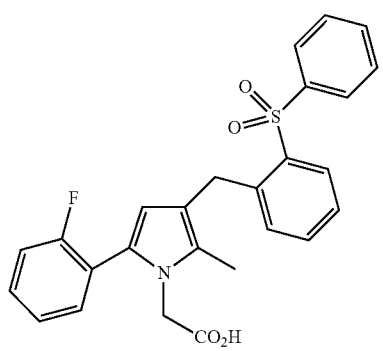

Compound I-8

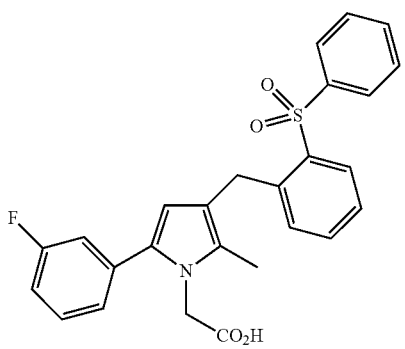

Compound I-15

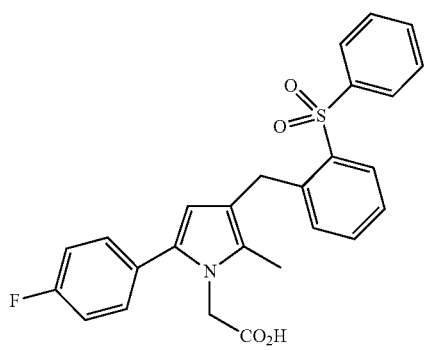

General Synthetic Scheme

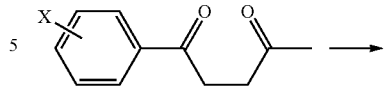

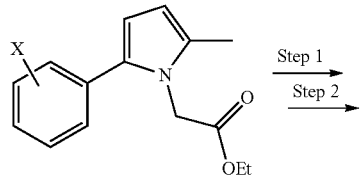

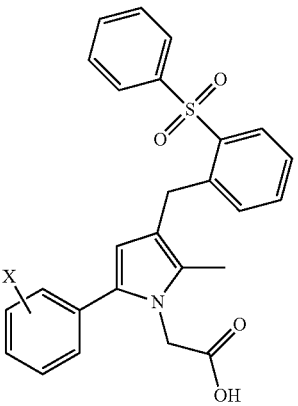

X = F (o, m, p), CF3(o, p)

The synthesis below is described for Compound I-25 and can be applied to all other examples.

Preparation of
1-(4-(trifluoromethyl)phenyl)pentane-1,4-dione

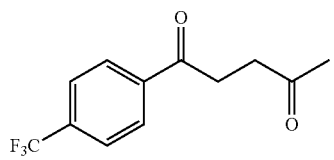 [SMILES: CC(=O)CCC(=O)c1ccc(C(F)(F)F)cc1]

In a small vial charged with 4-(trifluoromethyl)benzaldehyde (3.00 mL, 21.98 mmol) in Ethanol (Volume: 9.5 mL) was added triethylamine (6.13 mL, 44.0 mmol), but-3-en-2-one (2 mL, 21.98 mmol), and 3-ethyl-5-(2-hydroxyethyl)-4-methylthiazol-3-ium bromide (1.109 g, 4.40 mmol). The reaction mixture was heated at 80° C. for 16 h and then concentrated. The residue was treated with 1N HCl and extracted with DCM (3×). The organic layer was dried with MgSO4. The crude product was added to an 80 g ISCO silica gel column and was purified with a gradient of 0% to 40% EtOAc/hexanes. The product was obtained as a colorless crystalline solid (3.18 g, 13.02 mmol, 59.2% yield). 1H NMR (CDCl3/400 MHz) δ (ppm) 8.07 (d, 2H), 7.71 (d, 2H), 3.26 (t, 2H), 2.91 (t, 2H), 2.25 (s, 3H); MS m/z: 245.18 (M+1).

Preparation of ethyl 2-(2-methyl-5-(4-(trifluoromethyl)phenyl)-1H-pyrrol-1-yl)acetate

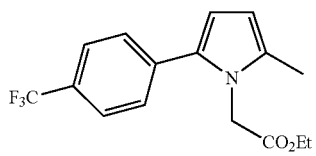 [SMILES: CCOC(=O)Cn1c(C)ccc1-c1ccc(C(F)(F)F)cc1]

In a round bottomed flask, charged with 1-(4-(trifluoromethyl)phenyl)pentane-1,4-dione (3.18 g, 13.02 mmol) in EtOH (Ratio: 2, Volume: 13 mL) and ethyl 2-aminoacetate hydrochloride (1.818 g, 13.02 mmol) was added ethyl 2-aminoacetate hydrochloride (1.818 g, 13.02 mmol) and triethylamine (10.53 mL, 76 mmol). The reaction mixture was heated at 70° C. for 15.5 h (~50% of SM remained by TLC and LCMS). The reaction was then concentrated and the residue was treated with water and extracted with DCM (3×). The organic layer was dried with MgSO4. The crude product was added to a 120 g ISCO silica gel column and was purified with a gradient of 0% to 50% EtOAc/hexanes. The product was obtained as a light yellow oil (1.8 g, 5.98 mmol, 45.9% yield). 1H NMR (CDCl3/400 MHz) δ (ppm) 7.62 (d, 2H), 7.42 (d, 2H), 6.23 (d, 1H), 6.05-6.02 (m, 1H), 4.55 (s, 2H), 4.25 (q, 2H), 2.24 (s, 3H), 1.28 (t, 3H). MS m/z: 312.22 (M+1).

Synthesis of 2-(2-methyl-3-(2-(phenylsulfonyl)benzyl)-5-(4-(trifluoromethyl)phenyl)-1H-pyrrol-1-yl)acetic acid (compound I-25)

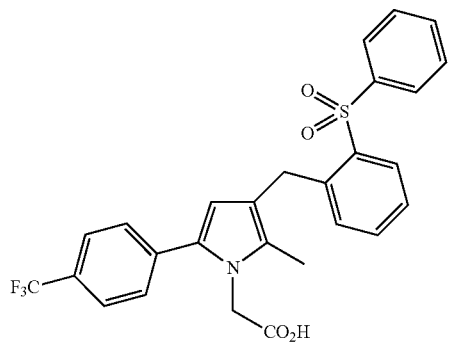 [SMILES: Cc1c(Cc2ccccc2S(=O)(=O)c2ccccc2)cc(-c2ccc(C(F)(F)F)cc2)n1CC(=O)O]

General procedure I (step 1 and 2) were carried out to generate 2-(2-methyl-3-(2-(phenylsulfonyl)benzyl)-5-(4-(trifluoromethyl)phenyl)-1H-pyrrol-1-yl)acetic acid. 1H NMR (CDCl3/400 MHz) δ (ppm) 8.27 (dd, 1H), 7.89-7.84 (m, 2H), 7.60 (d, 2H), 7.57-7.38 (m, 5H), 7.32 (d, 2H), 7.19 (d, 1H), 5.79 (s, 1H), 4.61 (s, 2H), 4.05 (s, 2H), 1.97 (s, 3H). MS m/z: 514.31 (M+1).

Synthesis of Pyrrole Precursors

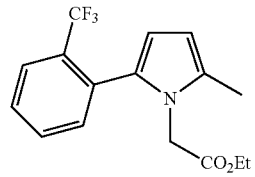 [SMILES: CCOC(=O)Cn1c(C)ccc1-c1ccccc1C(F)(F)F]

Made starting with 2-(trifluoromethyl)benzaldehyde. 1H NMR (CDCl3/400 MHz) δ (ppm) 7.74 (d, 1H), 7.56-7.44 (m, 2H), 7.36 (d, 1H), 6.10 (d, 1H), 6.01 (m, 1H), 4.45-4.20 (brm, 2H), 4.16 (q, 2H), 2.22 (s, 3H), 1.22 (t, 3H).

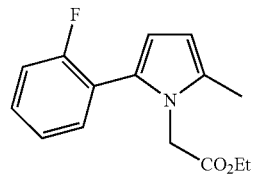

Made starting with 2-fluorobenzaldehyde. 1H NMR (CDCl3/400 MHz) δ (ppm) 7.34-7.28 (m, 2H), 7.18-7.08 (m, 2H), 6.18 (d, 1H), 6.05 (dd, 1H), 4.47 (s, 2H), 4.18 (q, 2H), 2.25 (d, 3H), 1.22 (t, 3H). MS m/z: 262.20 (M+1).

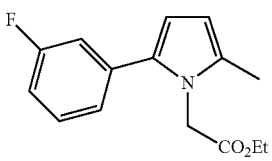 [SMILES: CCOC(=O)Cn1c(C)ccc1-c1cccc(F)c1]

Made starting with 3-fluorobenzaldehyde. 1H NMR (CDCl3/400 MHz) δ (ppm) 7.36-7.19 (m, 1H), 7.07 (app dd, 1H), 7.04-6.95 (m, 2H), 6.17 (d, 1H), 6.01 (dd, 1H), 4.55 (s, 2H), 4.25 (q, 2H), 2.23 (s, 3H), 1.28 (t, 3H)

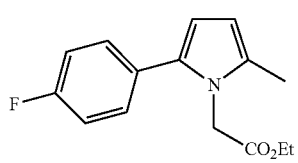 [SMILES: CCOC(=O)Cn1c(C)ccc1-c1ccc(F)cc1]

Made starting with 4-fluorobenzaldehyde. 1H NMR (CDCl3/400 MHz) δ (ppm) 7.30-7.24 (m, 2H), 7.09-7.03 (m, 2H), 6.11 (d, 1H), 5.99 (d, 1H), 4.50 (s, 2H), 4.23 (q, 2H), 2.23 (s, 3H), 1.27 (t, 3H).

Characterization of Final Compounds were Made Using General Procedure I (Step 1 and 2)

2-(2-methyl-3-(2-(phenylsulfonyl)benzyl)-5-(2-(trifluoromethyl)phenyl)-1H-pyrrol-1-yl)acetic acid (compound I-27)

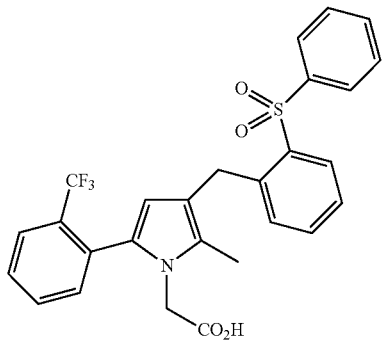 [SMILES: Cc1c(Cc2ccccc2S(=O)(=O)c2ccccc2)cc(-c2ccccc2C(F)(F)F)n1CC(=O)O]

1H NMR (CDCl3/400 MHz) δ (ppm) 8.27 (d, 1H) 7.90 (d, 2H), 7.73 (d, 1H), 7.60-7.44 (m, 6H), 7.42-7.36 (m, 1H), 7.33 (d, 1H), 7.14 (d, 1H), 5.8 (s, 1H), 4.34 (br d, 2H), 4.00 (br d, 2H), 1.87 (s, 3H). MS m/z: 514.25 (M+1).

2-(5-(2-fluorophenyl)-2-methyl-3-(2-(phenylsulfonyl)benzyl)-1H-pyrrol-1-yl)acetic acid (compound I-18)

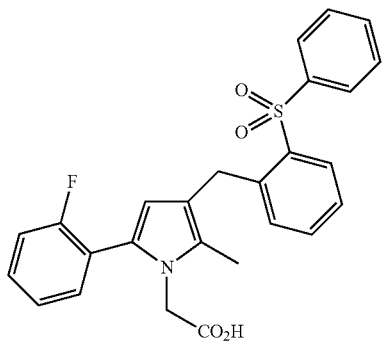 [SMILES: Cc1c(Cc2ccccc2S(=O)(=O)c2ccccc2)cc(-c2ccccc2F)n1CC(=O)O]

1 NMR (CDCl3/400 MHz) δ (ppm) 8.27 (d, 1H), 7.86 (d, 2H), 7.54-7.40 (m, 4H), 7.31-7.20 (m, 3H), 7.19-7.13 (m, 4H), 5.49 (s, 1H), 4.50 (s, 2H), 4.04 (s, 2H), 1.93 (s, 3H).

2-(5-(3-fluorophenyl)-2-methyl-3-(2-(phenylsulfonyl)benzyl)-1H-pyrrol-1-yl)acetic acid (compound I-8)

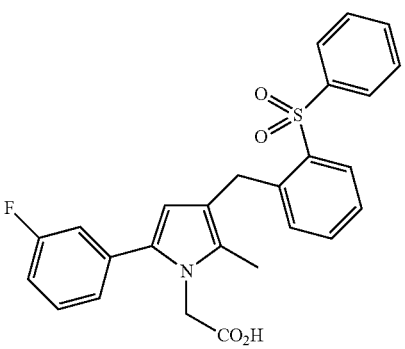 [SMILES: Cc1c(Cc2ccccc2S(=O)(=O)c2ccccc2)cc(-c2cccc(F)c2)n1CC(=O)O]

1H NMR (CDCl3/400 MHz) δ (ppm) 8.27 (d, 1H), 7.86 (d, 2H), 7.57-7.44 (m, 4H), 7.40 (t, 1H), 7.31 (dd, 1H), 7.19 (d, 1H), 7.00-6.90 (m, 3H), 5.71 (s, 1H), 4.61 (s, 2H), 4.03 (s, 2H), 1.95 (s, 3H). MS m/z: 464.22 (M+1).

2-(5-(4-fluorophenyl)-2-methyl-3-(2-(phenylsulfonyl)benzyl)-1H-pyrrol-1-yl)acetic acid (compound I-15)

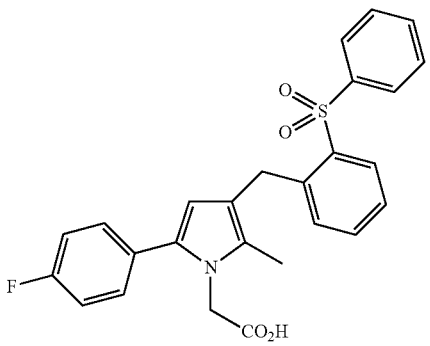 [SMILES: Cc1c(Cc2ccccc2S(=O)(=O)c2ccccc2)cc(-c2ccc(F)cc2)n1CC(=O)O]

1H NMR (CDCl3/400 MHz) δ (ppm) 8.27 (d, 1H), 7.87 (d, 2H), 7.54-7.40 (m, 4H), 7.20-7.17 (m, 4H), 7.06-7.02 (m, 2H), 5.67 (s, 1H), 4.55 (s, 2H), 4.02 (s, 2H), 1.93 (s, 3H).

Example 32

Synthesis of 2-(2,5-dimethyl-3-(2-(morpholinosulfonyl)benzoyl)-1H-pyrrol-1-yl)acetic acid General Synthetic Scheme

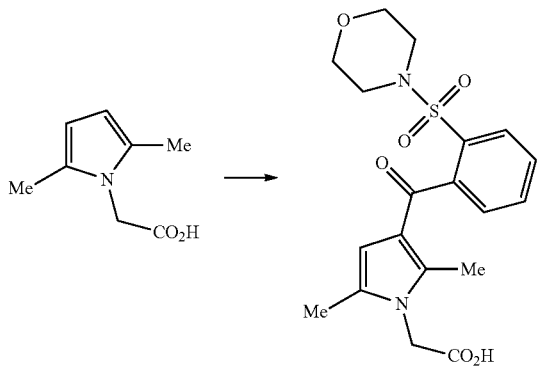

Preparation of 2-(morpholinosulfonyl)benzoyl chloride

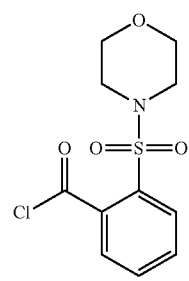 [SMILES: O=C(Cl)c1ccccc1S(=O)(=O)N1CCOCC1]

To a slurry of 2-(morpholinosulfonyl)benzoic acid (327 mg, 1.21 mmol) in dichloromethane (11 mL) was added thionyl chloride (0.220 mL, 3.01 mmol). The reaction was heated at 60° C. for 1 hour, after which LCMS analysis (sodium methoxide solution, 25% in methanol) revealed reaction completion. The reaction was concentrated to afford 2-(morpholinosulfonyl)benzoyl chloride (0.397 g, 1.37 mmol) as a viscous yellow residue and this was used in the next step without further purification.

Ethyl 2-(2,5-dimethyl-3-(2-(morpholinosulfonyl) benzoyl)-1H-pyrrol-1-yl)acetate (compound I-69)

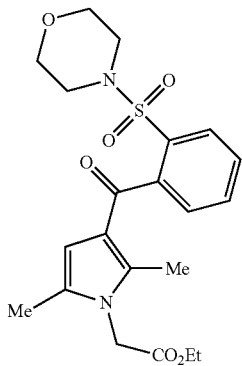

To a 0° C. solution of ethyl 2-(2,5-dimethyl-1H-pyrrol-1-yl)acetate (0.2 g, 1.10 mmol) in dichloromethane (8.0 mL) was added diethylaluminum chloride (1.66 mL, 1.66 mmol). The reaction was stirred at 0° C. for 15 minutes, after which a solution of 2-(morpholinosulfonyl)benzoyl chloride (0.384 g, 1.32 mmol) was added. The reaction was stirred for 30 minutes at 0° C., then allowed to warm to room temperature, and stirred for 3 hours at this temp. The reaction was quenched with sodium bicarbonate (15 mL), extracted with dichloromethane (3×50 mL), washed with brine, dried (sodium sulfate), filtered, and concentrated. Purification by column chromatography on silica gel using 30 to 100% ethyl acetate in hexanes afforded ethyl 2-(2,5-dimethyl-3-(2-(morpholinosulfonyl)benzoyl)-1H-pyrrol-1-yl)acetate (0.145 g, 0.334 mmol, 30% yield). 1H NMR (400 MHz, CDCl3): δ (ppm) 7.84 (d, 1H), 7.61 (app. t, 1H), 7.55 (dd, 1H), 7.39 (d, 1H), 5.72 (s, 1H), 4.51 (s, 2H), 4.23 (q, 2H), 3.68-3.71 (m, 4H), 3.14-3.17 (m, 4H), 2.44 (s, 3H), 2.07 (s, 3H), 1.29 (t, 3H).

2-(2,5-dimethyl-3-(2-(morpholinosulfonyl)benzoyl)-1H-pyrrol-1-yl)acetic acid (compound I-56)

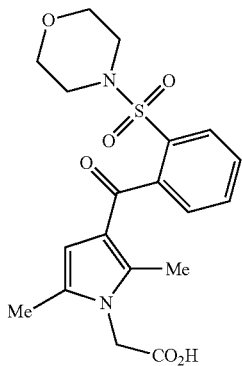

General procedure I (step 1 and 2) was followed using ethyl 2-(2,5-dimethyl-3-(2-(morpholinosulfonyl)benzoyl)-1H-pyrrol-1-yl)acetate (0.0500 g, 0.115 mmol) and 1M sodium hydroxide solution (0.345 ml, 0.345 mmol) to afford 2-(2,5-dimethyl-3-(2-(morpholinosulfonyl)benzoyl)-1H-pyrrol-1-yl)acetic acid (22.8 mg, 0.0560 mmol, 49% yield). 1H NMR (400 MHz, CDCl3): δ (ppm) 7.85 (d, 1H), 7.62 (ddd, 1H), 7.56 (app. td, 1H), 5.72 (s, 1H), 4.55 (s, 2H), 3.68-3.70 (m, 4H), 3.13-3.16 (m, 4H), 2.45 (s, 3H), 2.09 (s, 3H).

Example 33

Synthesis of 2-(2,5-dimethyl-3-phenyl-4-(2-(pyrrolidin-1-ylsulfonyl)phenylthio)-1H-pyrrol-1-yl)acetic acid Preparation of 1,2-bis(2-(pyrrolidin-1-ylsulfonyl)phenyl)disulfane

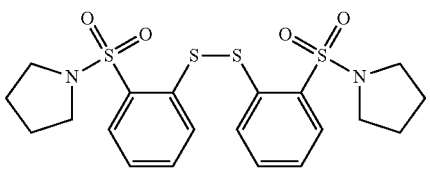 [SMILES: O=S(=O)(c1ccccc1SSc1ccccc1S(=O)(=O)N1CCCC1)N1CCCC1]

To a 0° C. solution of 1-(phenylsulfonyl)pyrrolidine (1.50 g, 7.10 mmol) in tetrahydrofuran (20 mL) was added n-butyllithium (3.00 ml, 7.81 mmol). The reaction was stirred at 0° C. for 30 minutes after which solid elemental sulfur (0.228 g, 7.10 mmol) was added in one portion. After 10 minutes, the reaction was roughly 75% converted completed, with a trace of the disulfide present by LCMS analysis. The reaction was stirred at 0° C. for an additional 30 minutes after which the starting material had been consumed. The reaction was quenched by the addition of saturated ammonium chloride solution (10 mL) and purged with oxygen. The reaction was stirred open to the air, at room temperature for 14 hours, after which it was diluted with dichloromethane, extracted with dichloromethane (3×50 mL), dried (sodium sulfate), filtered and concentrated to a brown residue. This was purified on silica gel using 5 to 75% ethyl acetate in hexanes over 60 minutes. The product, 1,2-bis(2-(pyrrolidin-1-ylsulfonyl)phenyl)disulfane (1.18 g, 2.44 mmol, 69% yield) was isolated as an off-white solid. 1H NMR (400 MHz, CDCl3): δ (ppm) 7.97 (dd, 2H), 7.84 (dd, 2H), 7.47 (app. td, 2H), 7.33 (ddd, 2H), 3.41-3.45 (m, 8H), 1.91-1.95 (m, 8H).

Preparation of ethyl 2-(3-iodo-2,5-dimethyl-4-(2-(pyrrolidin-1-ylsulfonyl)phenylthio)-1H-pyrrol-1-yl) acetate (compound I-70)

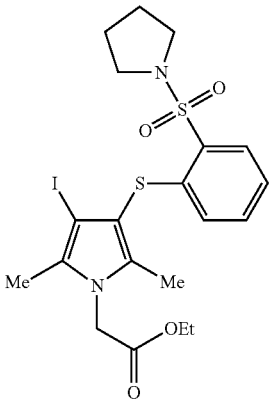 [SMILES: CCOC(=O)Cn1c(C)c(I)c(Sc2ccccc2S(=O)(=O)N2CCCC2)c1C]

To a 0° C. solution of 1,2-bis(2-(pyrrolidin-1-ylsulfonyl)phenyl)disulfane (0.241 g, 0.497 mmol) in N,N-dimethylformamide (8.3 mL), was added iodine (0.210 g, 0.828 mmol). The reaction was stirred at 0° C. for 30 minutes, after which ethyl 2-(2,5-dimethyl-1H-pyrrol-1-yl)acetate (0.150 g, 0.828 mmol) was added, and the resulting mixture was allowed to warm to room temperature. The reaction was then heated at 60° C. for 16 hours after which time additional iodine (0.210 g, 0.828 mmol) was added. The reaction was then heated at 60° C. for an additional two hours after it was allowed to cool down to room temperature, it was diluted with water and extracted with ethyl acetate (3×20 mL), dried (sodium sulfate), filtered and concentrated. Purification by column chromatography on silica gel afforded ethyl 2-(3-iodo-2,5-dimethyl-4-(2-(pyrrolidin-1-ylsulfonyl)phenylthio)-1H-pyrrol-1-yl)acetate (0.110 g, 0.201 mmol, 24% yield) as a viscous residue. 1H NMR (400 MHz, CDCl3): δ (ppm) 7.94 (d, 1H), 7.24-7.28 (m, 1H), 7.11-7.15 (m, 1H), 6.77 (d, 2H), 4.63 (s, 2H), 4.25 (q, 2H), 3.52 (m, 4H), 2.28 (s, 3H), 2.27 (s, 3H), 1.90 (m, 4H), 1.30 (t, 3H).

Methyl 2-(2,5-dimethyl-3-phenyl-4-(2-(pyrrolidin-1-ylsulfonyl)phenylthio)-1H-pyrrol-1-yl)acetate (compound I-71)

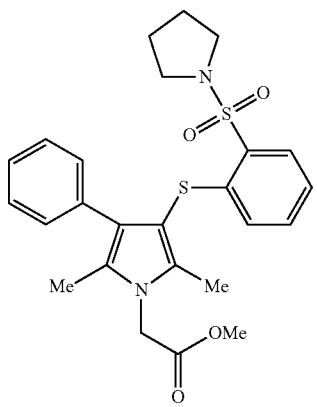 [SMILES: COC(=O)Cn1c(C)c(Sc2ccccc2S(=O)(=O)N2CCCC2)c(-c2ccccc2)c1C]

To a solution of phenylboronic acid (26.9 mg, 0.221 mmol) in methanol (1.0 mL) and toluene (1.0 mL) was added ethyl 2-(3-iodo-2,5-dimethyl-4-(2-(pyrrolidin-1-ylsulfonyl)phenylthio)-1H-pyrrol-1-yl)acetate (121 mg, 0.221 mmol), palladium tetrakistriphenylphosphine (12.8 mg, 0.0110 mmol) and sodium carbonate (0.090 mL, 0.18 mmol). The reaction mixture was heated at 100° C. for 2.5 hours, then heated at 60° C. for 16 hours, after which an additional 0.10 equiv. of both phenylboronic acid and palladium tetrakistriphenylphosphine were added. The reaction was then heated at 100° C. for one more hour, after which it was allowed to cool down to room temperature, poured over ice water (10 mL), extracted with ether (2×20 mL), and washed with water (1×30 mL). The combined organic layers were dried (sodium sulfate), filtered, and concentrated. Purification by column chromatography on silica gel afforded methyl 2-(2,5-dimethyl-3-phenyl-4-(2-(pyrrolidin-1-ylsulfonyl)phenylthio)-1H-pyrrol-1-yl)acetate (0.0246 g, 0.0510 mmol, 23% yield) as a light brown residue. LCMS: ES+ [M+H]+=485.3

2-(2,5-dimethyl-3-phenyl-4-(2-(pyrrolidin-1-ylsulfonyl)phenylthio)-1H-pyrrol-1-yl)acetic acid (compound I-30)

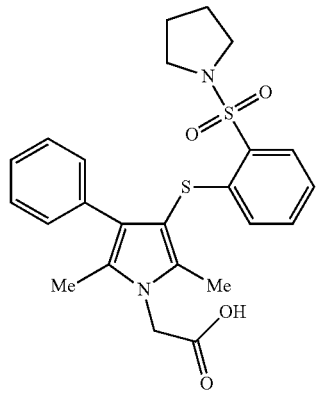 [SMILES: Cc1c(Sc2ccccc2S(=O)(=O)N2CCCC2)c(-c2ccccc2)c(C)n1CC(=O)O]

General procedure I (step 2) was followed using methyl 2-(2,5-dimethyl-3-phenyl-4-(2-(pyrrolidin-1-ylsulfonyl)phenylthio)-1H-pyrrol-1-yl)acetate (24.6 mg, 0.0510 mmol) and 1M sodium hydroxide (0.152 ml, 0.152 mmol) to afford 2-(2,5-dimethyl-3-phenyl-4-(2-(pyrrolidin-1-ylsulfonyl)phenylthio)-1H-pyrrol-1-yl)acetic acid (15.2 mg, 0.0320 mmol, 64% yield) as a tan solid. 1H NMR (400 MHz, CDCl3): δ (ppm) 7.89 (dd, 1H), 7.07-7.22 (m, 7H), 6.93 (dd, 1H), 4.73 (s, 2H), 3.19-3.23 (m, 4H), 2.27 (s, 3H), 2.23 (s, 3H), 1.61-1.64 (m, 4H).

Compound I-29 was Prepared Analogously

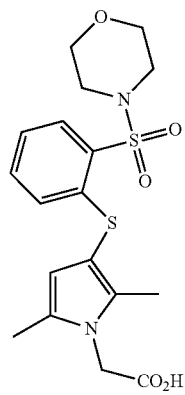 [SMILES: Cc1cc(Sc2ccccc2S(=O)(=O)N2CCOCC2)c(C)n1CC(=O)O]

2-(2,5-dimethyl-3-(2-(morpholinosulfonyl)phenylthio)-1H-pyrrol-1-yl)acetic acid same as 2-(2,5-dimethyl-3-phenyl-4-(2-(pyrrolidin-1-ylsulfonyl)phenylthio)-1H-pyrrol-1-yl)acetic acid. 1H NMR (CDCl3/400 MHz) 9.33 (s, 1H), 8.29 (d, 1H), 7.94 (d, 2H), 7.56-7.31 (m, 9H), 7.00 (d, 1H), 4.49 (s, 2H), 4.37 (s, 2H), 1.93 (s, 3H). MS m/z=474.4 (M+1).

Example 34

Synthesis of 2-(2,5-dimethyl-3-phenyl-4-(2-(pyrrolidin-1-ylsulfonyl)benzyl)-1H-pyrrol-1-yl)acetic acid General Synthetic Scheme:

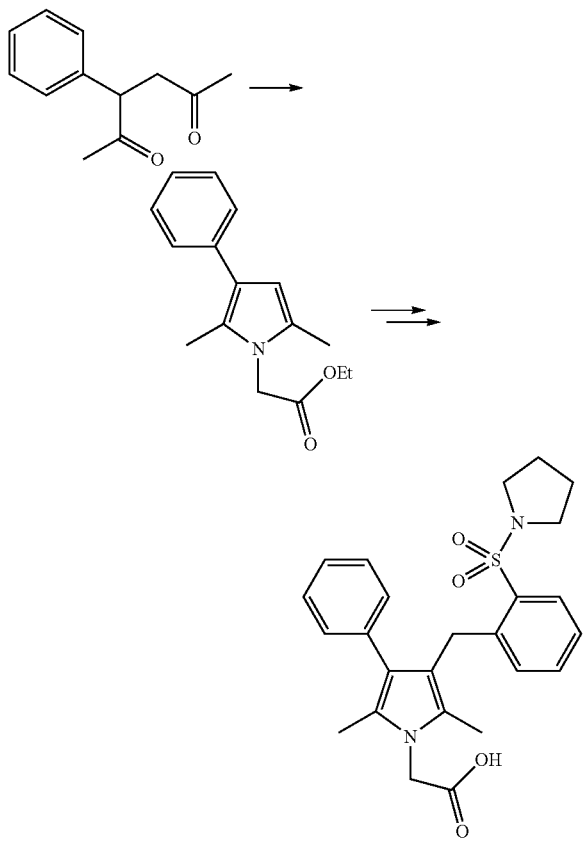

Preparation of ethyl 2-(2,5-dimethyl-3-phenyl-1H-pyrrol-1-yl)acetate

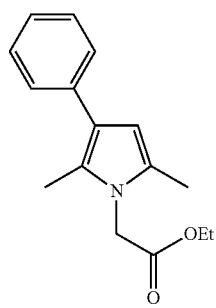 [SMILES: CCOC(=O)Cn1c(C)cc(-c2ccccc2)c1C]

To a stirring solution of 3-phenylhexane-2,5-dione (0.330 g, 1.735 mmol) in dichloroethane (5 ml) was added triethylamine (0.725 ml, 5.20 mmol), followed by ethyl 2-aminoacetate hydrochloride (0.291 g, 2.082 mmol). The reaction was stirred overnight at room temperature, after which LCMS showed formation of the desired product. The reaction mixture was purified directly on an ISCO automated chromatography system (silica gel) using an EtOAc/hexane gradient. The desired fractions were collected and concentrated in vacuum and the crude mixture was taken directly to the next step without further purification.

Synthesis of 2-(2,5-dimethyl-3-phenyl-4-(2-(pyrrolidin-1-ylsulfonyl)benzyl)-1H-pyrrol-1-yl)acetic acid (compound I-57)

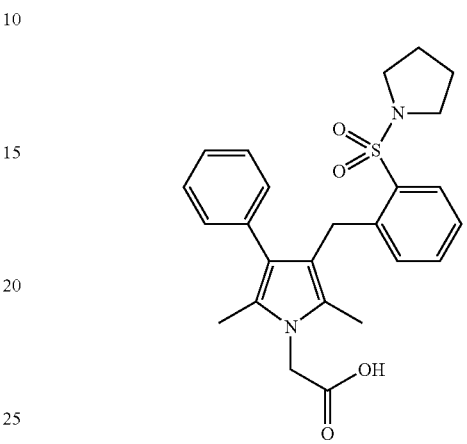

Crude ethyl 2-(2,5-dimethyl-3-phenyl-1H-pyrrol-1-yl)acetate (0.132 g, 0.513 mmol) was dissolved in DCM (5 ml) and stirred in a 250 ml round bottomed flask. The reaction temperature was lowered to −78° C. Trimethylsilyl trifluoromethylsulfonate (0.232 ml, 1.282 mmol) was then added, followed by triethylsilane (0.246 ml, 1.539 mmol) and the reaction mixture was stirred under a positive nitrogen atmosphere for 30 minutes. 2-(pyrrolidin-1-ylsulfonyl)benzaldehyde (0.123 g, 0.513 mmol), dissolved in 1 ml of DCM was added dropwise to the stirring reaction mixture and stirring continued at −78° C. LCMS showed formation of product. Aldehyde reduction was also an evident by-product by LCMS. The reaction was allowed to warm up to 0° C. and another equivalent of aldehyde was added. The crude reaction mixture was concentrated and purified directly by reverse phase HPLC. After concentration, the resulting product was a slightly pink oil. This material was taken forward without any further characterization.

To a stirring solution of ethyl 2-(2,5-dimethyl-3-phenyl-4-(2-(pyrrolidin-1-ylsulfonyl)benzyl)-1H-pyrrol-1-yl)acetate (0.029 g, 0.060 mmol) in tetrahydrofuran (1 ml) and water (1 ml) was added 1N sodium hydroxide (0.121 ml, 0.121 mmol). Upon addition, the reaction changed color from pink to yellow. The mixture was stirred overnight, after which LCMS analysis indicated reaction completion. The reaction was quenched with 0.050 ml of 3N HCl and stirred to afford a pink color. The crude mixture was concentrated and taken up in acetonitrile and purified by reverse phase HPLC chromatography. Acetonitrile and water spiked with 0.1% TFA were used as eluents. The desired fractions were collected and quenched with aqueous saturated sodium bicarbonate solution and washed with ether. The aqueous layer was then acidified with 3N HCl to pH=1 and this aqueous layer was extracted 3 times with ether. The combined organic layers were washed with brine, dried over sodium sulfate and concentrated to afford a purple solid (0.0203 g, 0.045 mmol, 74.3% yield). 1H NMR (CDCl3/400 MHz)δ ppm) 7.91 (d, 1H), 7.37-7.33 (m, 1H), 7.23-7.17 (m, 1H), 7.15-7.11 (m, 3H), 7.08-7.05 (m, 1H), 6.99-6.97 (m, 2H), 4.63 (s, 2H), 4.07 (s, 2H), 3.08-3.04 (m, 4H), 2.14 (s, 3H), 1.98 (s, 3H), 1.61-1.58 (m, 4H). LCMS (M+1): 453.3.

LCMS (M−1): 451.3.

Example 35

Preparation of 2-(3,5-dimethyl-4-(2-(pyrrolidin-1-ylsulfonyl)benzyl)-1H-pyrazol-1-yl)acetic acid (I-72)

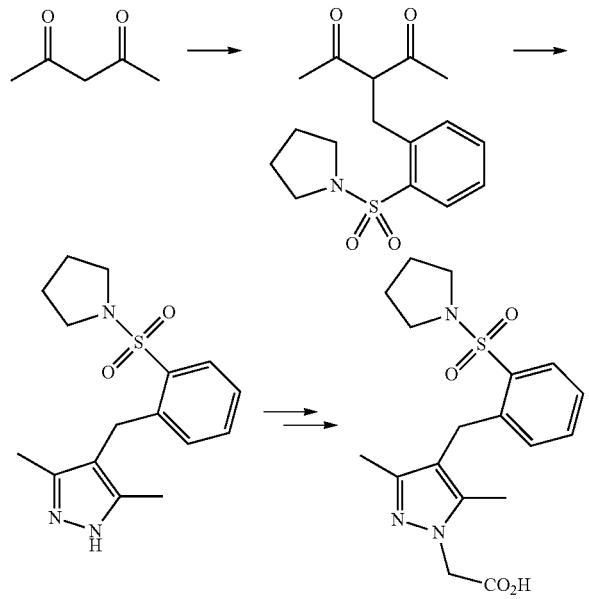

Dione Benzylation

Pentane-2,4-dione (0.155 ml, 1.517 mmol) was dissolved in THF (3 ml) and cooled to −10° C. Sodium hydride (60% in dispersion oil, 0.061 g, 1.517 mmol) was then added and the bubbly mixture was allowed to warm to rt and stirred for 10 min. Because it was quite thick at this point, DMF (3 ml) was added and complete homogeneity was achieved. At this time, 2-(pyrrolidin-1-ylsulfonyl)benzyl 4-methylbenzenesulfonate (0.2 g, 0.506 mmol) was added dropwise and the reaction was stirred at rt for 1 hour. LC/MS at this juncture suggests a clean reaction, but a sluggish one. Therefore, the reaction was moved to a hot plate set at 50° C. and stirred overnight. The reaction was quenched with NH4Cl and extracted with EtOAc (2×). The organics were combined, dried, filtered, and concentrated. The crude material was carried directly on to pyrazole formation step.

Pyrazole Formation 3-(2-(Pyrrolidin-1-ylsulfonyl)benzyl)pentane-2,4-dione (0.164 g, 0.506 mmol) (crude) was dissolved in ethanol (12 ml) and charged with hydrazine hydrate (0.2 ml, 6.37 mmol). Reaction is heated to 50° C. and analyzed by LC/MS. After 15 minutes, LC/MS suggests reaction is complete. Therefore, reaction is concentrated and carried directly on to alkylation reaction without further purification.

Pyrazole Alkylation 3,5-Dimethyl-4-(2-(pyrrolidin-1-ylsulfonyl)benzyl)-1H-pyrazole (0.075 g, 0.235 mmol) was dissolved in acetonitrile and consecutively charged with potassium carbonate (0.097 g, 0.704 mmol) and ethyl bromoacetate (0.033 ml, 0.293 mmol). Reaction vessel (scintillation vial) was moved to a 90° C. hot plate and stirred for 2 hours. After about 2 hours, reaction is clean, and has progressed about 50%. A single, small crystal of NaI was added and the reacting mixture was moved back to hot plate and stirred at 90° C. After 4 h, reaction was quenched with NH4Cl and extracted with DCM (2×). Organics are combined, dried, filtered, and concentrated. The crude oil was purified using a 0-100% EtOAc/hexane gradient to give desired product in 67% yield (three steps).

Saponification

General saponification conditions were employed to generate 1-72 in 87% yield. 1H NMR (400 MHz, CDCl3) δ 7.96 (dd, J=7.6, 1.2 Hz, 1H), 7.48-7.26 (m, 2H), 6.98 (d, J=7.6, 1H), 4.97 (s, 2H), 4.20 (s, 2H), 3.31-3.27 (m, 4H), 2.14 (s, 3H), 2.11 (s, 3H), 1.86-1.82 (m, 4H) ppm.

Example 36

Synthesis of 2-(4-cyano-2,5-dimethyl-1-(2-(pyrrolidin-1-ylsulfonyl)benzyl)-1H-pyrrol-3-yl)acetic acid (I-73)

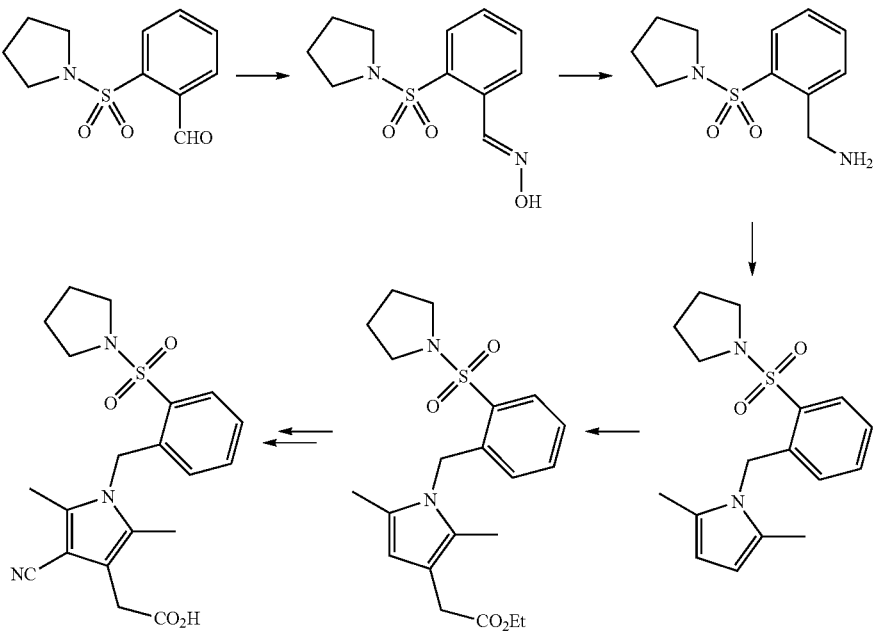

Oxime Formation 2-(Pyrrolidin-1-ylsulfonyl)benzaldehyde (1.0 g, 4.18 mmol) and hydroxylamine hydrochloride (0.290 g, 4.18 mmol) were dissolved in 25 mL EtOH and charged with sodium carbonate (0.886 g, 8.36 mmol) and sodium acetate (0.686 g, 8.36 mmol). Reaction is moved to a 60° C. hot plate and stirred overnight. After 14 hours, the reaction is quenched with ammonium chloride and extracted 3×DCM. The combined organics were dried, filtered, and concentrated. The crude material was chromatographed using ISCO (0-100% EtOAc/hexanes) to yield 1.063 g of product (100%) as a clear viscous oil.

Reduction/Amine Formation (E)-2-(Pyrrolidin-1-ylsulfonyl)benzaldehyde oxime (1.063 g, 4.18 mmol) was dissolved in THF (Volume: 30 ml) and cooled to 0° C. LAH (1.0M solution, 6.27 ml, 12.54 mmol) was added dropwise (bubbling at first), which ultimately caused the reaction to turn red in color. Reaction is then warmed to rt, stirred for 1 h, then re-cooled to 0° C. Carefully, reaction is quenched with a saturated solution of Rochelle salt, then filtered. The filtrate was diluted with water (50 mL) and DCM (30 mL) and the layers were separated. The aqueous portion was washed with two additional portions of DCM (25 mL), and then the organic portions were combined, dried, filtered, and concentrated. The crude amine was taken directly on to pyrrole formation without any further purification.

Pyrrole Formation (2-(Pyrrolidin-1-ylsulfonyl)phenyl)methanamine (1.005 g, 4.18 mmol) was dissolved in ethanol (Volume: 15 ml) and consecutively charged with TEA (0.874 ml, 6.27 mmol) and hexane-2,5-dione (0.560 ml, 4.60 mmol). Reaction is then heated to 70° C. and stirred overnight. After 14 hours, the reaction is concentrated and directly purified using SiO2 chromatography with a 0-75% EtOAc/hexane gradient to afford 496 mg (37.3%, two steps) of desired material as a viscous, clear oil.

Reductive Alkylation

In a scintillation vial, 2,5-dimethyl-1-(2-(pyrrolidin-1-ylsulfonyl)benzyl)-1H-pyrrole (0.250 g, 0.785 mmol) was dissolved in 6 mL DCM and cooled to −78° C. TMSOTf (0.319 ml, 1.766 mmol) was added followed by TRIETHYLSILANE (0.376 ml, 2.355 mmol) and the reaction mixture was stirred at −78° C. for 30 minutes. At this time, ethyl 2-oxoacetate (0.200 g, 0.785 mmol) and then the reaction was stirred at −78° C. for 10 minutes, warmed to rt, and stirred overnight. After 14 hours, it doesn't appear the reduction was taking place, therefore an additional equivalent of TMSOTf and TES were added and the reaction was heated to 40° C. for 10 hours. LC/MS shows mostly product, therefore reaction is quenched with sodium bicarbonate solution, moved to a separatory funnel, and the layers were separated. The aqueous portion was washed two additional times with DCM (20 mL), then the organic portions were combined, dried, filtered, and concentrated. The crude was purified using SiO2 chromatography with a 0-80% EtOAc/hexanes gradient to afford 101 mg (32%) of desired compound.

Cyanylation/Saponification

Following general cyanylation conditions followed by general saponification conditions, Example B was generated in 70% yield. 2-(4-cyano-2,5-dimethyl-1-(2-(pyrrolidin-1-ylsulfonyl)benzyl)-1H-pyrrol-3-yl)acetic acid (1-73): 1H NMR (400 MHz, CDCl3) δ 10.88 (bs, 1H), 7.92 (dd, J=7.6, 1.2 Hz, 1H), 7.48 (ddd, J=7.6, 7.6, 1.6 Hz, 1H), 7.42 (dd, J=7.6, 7.6 Hz, 1H), 6.33 (d, J=7.6 Hz, 1H), 5.43 (s, 2H), 3.59 (s, 2H), 3.39-3.35 (m, 4H), 2.22 (s, 2H), 2.00 (s, 3H), 1.99-1.96 (m, 4H) ppm.

Example 37

Biological Activity Measurements

Animal Models Related to Allergic Response

Any of a variety of animal models and in vitro assays can be used to test the compounds for their effectiveness in reducing allergic and inflammatory activity. Useful compounds can exhibit effectiveness in reducing allergic response and inflammation in one or more animal models or in vitro assays.

Induction of Contact Hypersensitivity.

In this model, induction of contact hypersensitivity (CHS) is created as described by Takeshita et al. (2004. Int. Immunol. 16(7):947-59). On days 0 and 1, female Balb/c mice, 7-8 weeks of age are painted onto the shaved abdominal skin with 400 μl of 0.5% fluorescein isothiocyanate (FITC) dissolved in acetone:dibutylpthalate (1:1, DBP). Six days later, mice are challenged by application of 20 μl of 0.5% FITC in DBP onto both sides of the right ear. The solvent control (DBP) is applied to the left ear. Challenge-induced increases in ear thickness are measured by an engineer's micrometer at 0, 24, 48 and 72 hours post-challenge. The CHS response is determined by challenge-induced increases in ear thickness. CHS response=[(right ear thickness post challenge−left ear thickness post challenge)−(right ear thickness pre challenge−left ear thickness pre challenge)].

To determine the presence of leukocyte infiltration, ears and back skins are fixed for 30 hours in zinc fixative at room temperature and embedded in paraffin for histological and immunohistochemical evaluation. For assessment of eosinophil peroxidase activity (EPO), skin sections are homogenized in 1 ml of ice cold buffer (0.05 M Tris-HCl pH 8.0 containing 0.1% Triton X-100). The tissue samples are centrifuged at 10,000 g for 20 minutes at 4° C. and supernatants are collected for measurement of EPO activity. In a 96 well microtiter plate, the substrate solution (100 μl of 10 mM o-phenylenediamine in 0.05 M Tris-HCl and 4 mM $H_2O_2$) is added to the 20-fold diluted homogenate in buffer (100 μl). The reaction mixture is incubated at room temperature for 1 hour before the reaction is stopped by the addition of 100 μl of 2M sulfuric acid. The microtiter plate is measured for absorbance.

Evan's Blue Test. Complete protocol details can be found in Takeshita et al. (2004. Int. Immunol. 16(7):947-59). Briefly, female Balb/c mice, 7 weeks of age are injected at two locations intradermally on their shaved backs with increasing concentrations of 0.1-10 μg/site of DK-PGD$_2$. This is followed by an intravenous injection of 0.25 ml of saline containing 1.25 mg of Evan's blue dye. Four hours post-dye injection, mice are euthanized and the back skin is collected. Edema severity is assessed by measuring the density of the extravasated dye. Effects of pharmacological inhibition of the inflammatory reaction to DK-PGD$_2$ will also be assessed by treatment with CRTH2 antagonists, such as Ramatroban.

Ovalbumin-Induced Airway Cell Proliferation and Inflammation.

Complete protocol details can be found in Eynott et al. (2003. J. Pharmacol. Ther. 304:22-29). Briefly, Brown Norway rats are sensitized on days 1, 2, and 3 with intraperitoneal (i.p.) injections of 1 mg ovalbumin (OVA) and 100 mg Al(OH)$_3$ in 1 mL 0.9% NaCl saline. They are then exposed to either 0.9% NaCl saline or 1% OVA aerosol every 3rd day (days 6, 9, & 12) for 30 minutes. 2 mg/kg dexamethasone is used as a positive control and is dosed i.p. once a day on days 4, 5, 6, 9, & 12. Vehicle (15% β-cyclodextrins in DMSO) and test compounds are dosed orally twice a day on days 5-12. On challenge days, all animals are treated 1 hour prior to OVA allergen exposure and, if required for twice a day treatment, ~4-8 hours after allergen exposure. Samples are collected 24 hours after the last OVA challenge. For sample collection, rats are anaesthetized by administration of 10 mg/kg xylazine and 60 mg/kg ketamine intraperitoneally. Once the rats were fully anesthetized, blood is collected for serum via the retro-orbital route. The rats are subsequently perfused by injecting 30 mL PBS through the right ventricle of the heart after the abdominal aorta is severed. A tracheostomy is then performed and bronchoalveolar lavage fluid (BAL) is collected through five 5 mL rinses using Hank's Balanced Salt Solution, which was kept on ice. Airway inflammatory cell accumulation and proliferation of cells are measured through the BAL fluid collection and subsequent cell counts. Cytospin slides are prepared and eosinophil % are determined by counting ~400 cells per slide. The test compounds are dosed at 5 mg/kg twice daily at various concentrations. Activity is scored based on the ability of the test compound to prevent ovalbumin-induced eosinophil induction (as determined by percentage of eosinophils in BAL fluid).

Ovalbumin-Induced Airway Inflammation in Sensitized Brown Norway Rats

The assay assesses the effect of test compounds on cellular recruitment into the lung after antigen challenge in the sensitized Brown Norway rat. The model is a slightly modified protocol based on that disclosed in Underwood et al. 2002 British Journal of Pharmacology 137: 263-275. Briefly, male Brown Norway rats (200-225 g, from Harlan) are be sensitized on days 0, 14 and 21 with ovalbumin (100 µg/rat, i.p.) administered with Alum™ (20 mg/rat aluminum hydroxide and 20 mg/rat magnesium hydroxide, i.p.). Rats are challenged with inhaled ovalbumin (10 g/l, 30 minutes) or saline aerosol on day 28. Vehicle (5 ml/kg) or test compound (1 or 10 mg/kg, 5 ml/kg) are dosed orally 16 and 1 hour(s) before and 1 and 6 hours after antigen challenge. Budesonide (3 mg/kg) is included as a positive control and dosed at the same time points. End point measurements are as follows; one hour after the challenge the rats have Enhanced Pause (PenH) levels monitored for 5 hours to assess late asthmatic reaction.

Cellular burden and inflammatory status are assessed. Twenty-four hours after ovalbumin challenge, rats are euthanized with an overdose of pentobarbitone i.p. A heparinized blood sample is taken via cardiac puncture and the resulting plasma kept frozen. Bronchoalveolar lavage (BAL) is carried out (2×3 ml RPMI media, 30 seconds each). Immediately after BAL, the left lobe is removed, perfused with RPMI to remove the blood pool of cells and 300 mg of lung is chopped and stored in RPMI/FCS (fetal calf serum) containing penicillin/streptomycin. The remaining perfused, chopped lung tissue is flash frozen and stored at −80° C. The remaining lung lobes are insufflated with formalin to a pressure of 20 mmHg, the lungs tied off and stored in formalin until required.

The 300 mg of tissue undergoes collagenase digestion and the cells are recovered (For method see Underwood et al., (1997) Br. J. Pharm., 122, 439-446). Total cell counts recovered from the airway lumen and lung tissue are quantified using a Sysmex cell counter. Differential cell counts (200 cells counted which comprise eosinophils, neutrophils, lymphomononuclear cells expressed as percentage and absolute cell counts) of cells recovered from the airway lumen and lung tissue are made by light microscopy from cytocentrifuge preparations stained with Wright-Giemsa stain. Remaining BAL samples are spun down and supernatant retained at −20° C. Additionally, this model can be used to assess the effect of agents described herein on airway resistance.

Sephadex induced-Pulmonary Eosinophilia in Rodents. Male Swiss Webster mice are used in a model of Sephadex induced-Pulmonary Eosinophilia. In brief, test groups receive vehicle, test compound (10 mg/kg) or positive control, dexamethasone (0.5 mg/kg), by oral gavages, twice per day (p.o., b.i.d.) at a dosing volume of 10 ml/kg, on days −1, 0, 1 and once, 4 hours pre-sacrifice, on day 2. On day 0, test groups are each intravenously administered 3 mg/kg Sephadex beads G-100-120 (Sigma) at a dosing volume of 5 ml/kg or no Sephadex. On day 2, four hours post vehicle/test compound/dexamethasone administration, animals are euthanized by inhalation of $CO_2$ and subsequently undergo histopathology and lavage evaluation of lungs for severity of eosinophilic infiltrate in peribronchiolar locations. Bronchoalveolar lavage fluid is collected by flushing the lung via the trachea 3 times with 1 ml aliquots of cold saline, and then the lungs are harvested by filling with formalin and allowed fixation a minimum of 1 day. White blood cell counts are prepared from lavage fluids. In addition, lavage fluids are immediately prepared for cytospin and cell differential counts performed. Cytospin slides are stained with a Wrights-Giemsa stain. Whole lung sections are stained with Hematoxylin and eosin stain for morphometry evaluation of severity of inflammatory cell infiltrate in peribronchiolar locations around Sephadex beads. Three sections (initial and 2 steps at 100 µm intervals) are prepared from each animal for analysis of area or diameter of inflammation around 5-8 Sephadex beads/mouse. Morphometric digital imaging analysis is performed to score inflammation. A similar experimental protocol can be performed using Lewis rats with the modification that animals are euthanized on day 1.

Mouse Model of Allergic Airways Disease Using the FlexiVent System.

In this model, animals in groups of 10 (8-10 wk old male BALB/c mice) are used to assess allergic airway disease. Mice are quarantined for 14 days. On days 0 (the first day following the end of the 14 day quarantine) and day 7, experimental animals are immunized by intraperitoneal (i.p.) injection with a mixture of ovalbumin (OVA; 10 µg) and aluminum hydroxide (Alum; 2 mg) in sterile water. A second group of animals is immunized with sterile water only and serves as a nonimmunized (negative) control. On days 13, 14, 15, and 16, dexamethasone (positive control), test compound or vehicle only is delivered by oral gavages (all at 10 mg/kg and a dosing volume of 10 ml/kg) twice a day. Animals are exposed to ovalbumin on days 14 and 15. Ovalbumin exposures are generated by aerosolizing 1% heat-aggregated ovalbumin (chicken egg, grade V; Sigma, St. Louis, Mo.), diluted with filtered air, and then delivered to the exposure chambers for 3 hours (H2000, Hazelton Systems). The total mass concentration of ovalbumin is determined by gravimetric analysis of filter samples taken every hour during exposure. The target mass concentration of ovalbumin is 4 mg/m$^3$. Chamber temperatures are maintained at 26±2° C. and lights on a 12 hour on/off cycle. Animals are given food (Teklad™ certified rodent diet (Harlan Teklad, Madison, Wis.)), ad libitum except during the 3 hour exposure period. Water is available ad libitum throughout the duration of the study.

On day 17, animals are anesthetized and tested for pulmonary function (response to methacholine challenge) by forced oscillation techniques (FlexiVent). Airway hyper responsiveness (AHR) to increasing concentrations of aerosolized methacholine (MCh) is measured using a FlexiVent analyzer (SCIREQ, Montreal, Canada). Briefly, each mouse is anesthetized with Avertin (250 mg/kg; 0.02 ml/g; 1.2% (w/v)

solution of 2,2,2 tribromoethanol in 0.8% tert-amyl ethanol (2 methyl, 2 butanol)) i.p. and placed on a heating pad. The neck fur is shaved and a small superficial incision made in the skin above the trachea. After the lobes of the salivary gland are separated, a small incision is made in the trachea, and the trachea is cannulated with a blunt-end 20 gauge needle hub. The cannula is secured by suture thread and the skin is pulled back and secured by cyanoacrylate adhesive. Ventilation is performed through the cannula by positive pressure maneuvers on the Flexivent apparatus. Once on the ventilator, pancuronium, (paralytic, 0.5 mg/kg) is administered i.p. Heart rate is monitored via a Grass Instruments Recorder w/Tachograph. Changes in heart rate greater than 50 bpm from baseline require supplementing the anesthesia (Avertin, ip). Additional doses of Avertin are given at a dose of 100 mg/kg and the animal's heart rate is monitored for at least 60 sec to determine if additional doses are needed. After baseline measurements of resistance and compliance, increasing doses of methacholine (Mch; 3, 6, 12, 25, 50 mg/ml nebulizer) are delivered via aerosol and resistance and compliance are measured. Airway resistance is calculated for each concentration of methacholine and the average+SEM is plotted for all treatment groups. Changes in pulmonary resistance (i.e., Mch dose-response curves) are assessed by repeated measures two way analysis of variance (ANOVA) with Bonferroni post-test. All other statistical comparisons are made using ANOVA with the Dunnetts multiple comparison test. A value of $p<0.05$ is considered significant.

Following AHR measurements, blood is collected and saved for further evaluation. The animals are then euthanized by injection with a lethal dose of a pentobarbital-based euthanasia solution. Bronchoalveolar lavage (BAL) cells are obtained from 7 animals per experimental or control group by inserting a catheter into the trachea and lavaging the lung 3 times with 0.8 ml of PBS (without calcium chloride and magnesium chloride). Total BAL cells are determined using a hemacytometer. BAL cells are spun onto slides by cytocentrifugation and stained with a modified Wright-Giemsa stain. Four hundred cells are counted and the percentage of specific cell types determined for each animal. The first lavage fluid sample (after centrifugation) is frozen separately for future cytokine analysis. The whole lung is snap frozen dry for future analyses.

Three animals from each group which are not subjected to BAL are used for histopathology analysis and have their lungs instilled via the trachea with 10% buffered formalin, removed and fixed in the same solution. Generally, three specimens per treatment, each consisting of multiple axial sections of lung, are examined. All sections are stained with alcian blue-H&E. Lesions are graded on a subjective basis. Lesions are graded as minimal, mild, moderate, and marked (corresponding to severity scores of 1, 2, 3, and 4, respectively) and given a distribution designation of either focal, locally extensive, multifocal, multifocal and coalescing, or diffuse (corresponding to distribution scores of 1, 2, 3, 4 and 5, respectively). The product of the severity and distribution scores is averaged for each treatment group.

Prostaglandin $D_2$-induced Eosinophilic Airway Inflammation.

Complete protocol details can be found in Shiraishi et al (2004. J. Pharmacol. Ther. epub as DOI:10:1124/jpet.104.078212). Briefly, Brown Norway rats are intravenously injected with rat interleukin-5 or PBS, one hour prior to intratracheal administration of prostanoid receptor agonists. These agonists can include the following; $PGD_2$, two $CRTH_2$-specific agonists, DK-$PGD_2$, 15R-methyl $PGD_2$, and 11-deoxy-11-methylene-15-keto-$PGD_2$ (MK-$PGD_2$), a DP receptor-specific agonist BW 245C, a thromboxane $A_2$ receptor (TP)-specific agonist, -BOP and Indomethacin. In some experiments, an orally delivered CRTH2/TP antagonist, Ramatroban, an intravenously delivered DP antagonist, BW A868C, or an intravenously delivered TP antagonist are administered two hours prior to administration of agonists. Rats are euthanized at 2, 8 and 24 hours post-agonist administration. Inflammatory cell accumulation in the trachea and lungs is recovered by bronchoalveolar lavage for cell counts and lungs are evaluated by histological examination. In a separate experiment, rats receive intravenous injection of IL-5 (0.2 ng/kg) or PBS one hour prior to intratracheal administration of $PGD_2$ (100 nmoles/animal) or vehicle. A peripheral blood sample is collected hourly post-dose of IL-5 for hematological evaluation.

Murine Allergic Inflammation.

Complete protocol details are described in Fujitani et al. (2002 J. Immunol 168:443-449) and Matsuoka et al. (2000. Science 287: 2013-2017). Briefly, transgenic and wild type mice are immunized with 10 µg ovalbumin (OVA) in 0.2 ml aluminum hydroxide (Alum) on days 0 and 14. On day 21, the mice are exposed to aerosolized OVA (50 mg/ml in sterile saline) for 20 minutes. On days 1 and 3 post-OVA challenge, mice are euthanized, bronchoalveolar lavaged, and the lavage fluid is assessed by differential cell counting.

Allergic Rhinitis in Anesthetized Rodents.

In this model described, for example, by Arimura et al. (2001 J. Pharmacol. Ther. 298:411-419) guinea pigs are sensitized to OVA twice by inhalation of an aerosol solution of 1% OVA for 10 minutes. At 7 days after the second sensitization, the animals are anesthetized and artificially ventilated through a tracheal cannula using a respirator. Another glass cannula is inserted into the nasopharynx from the side of the larynx, and a fixed amount of air is continuously insufflated into the nasal cavity via the nasal cannula using another respirator. Insufflation pressure is monitored by a pressure transducer connected to the side arm of the nasal cannula as an indication of intranasal pressure. Nasal antigen challenge is performed by generating an aerosol of 3% OVA between the nasal cannula and the animal respirator for 3 minutes using an ultrasonic nebulizer, and then the intranasal pressure is measured for 30 minutes. Nasal secretion and the nose are collected for further evaluation.

A biphasic allergic rhinitis model in conscious guinea pigs is also fully described in Arimura et al. (2001 J. Pharmacol. Ther. 298:411-419).

Allergic Conjunctivitis Model.

Complete protocol details are described in Arimura et al. (2001 J. Pharmacol. Ther. 298:411-419). Briefly, a 2.5% OVA solution is applied topically to both eyes (10 µl/eye) of conscious guinea pigs that have been sensitized as described in the "Allergic Rhinitis Model in Anesthetized Rodents" protocol above. Immediately following OVA application, Evan's blue dye (20 mg/kg i.v.) is injected as a marker of plasma exudation. The amount of Evan's blue extravasated in the conjunctiva and eyelid for 30 minutes is quantified. Independently, histamine 0.001%, PGD2 0.01%, or a combination of the two are applied to the eyes of non-sensitized guinea pigs, and dye exudation is determined.

Determination of Interleukin-13 Levels in Bronchial Alveolar Lavage Fluid.

A commercially available ELISA kit (Biosource, Catalog #KRC0132) is used to determine the effects of compounds on the Interleukin-13 (IL-13) levels of bronchial alveolar lavage fluid (BALF) taken from rats that have undergone certain allergen induced (e.g. ovalbumin, sephadex, prostaglandin $D_2$) airway cell proliferation and inflammation.

After collection, BALF samples are concentrated 5-fold with Microcon YM-3 centrifugal devices (Millipore, Catalog #42404) and stored at −80° C. until use. A 500 pg/mL standard stock is prepared by reconstituting the IL-13 standard provided in the kit with the amount of standard diluent specified on the standard vial. A standard curve is then prepared by serially the standard stock down to 7.8 pg/mL. 50 μL of each point of the standard curve and 50 μL of concentrated BALF sample are added to the ELISA plate. Added to these samples is 150 μL of anti-rat IL-13 biotin conjugate. The plate is then incubated at room temperature for 2 hours. The plate is then washed 4 times with wash buffer and 100 μL of 1-x streptavidin-peroxidase is added to all wells. The samples are then incubated at room temperature for 30 minutes. Again, the plate is washed 4 times with wash buffer. 100 μL of stabilized chromogen are added to each well and the plate is incubated at room temperature for 45 minutes. To stop the reaction, 100 μL of stop solution is added and the plate is read at 450 nm. Levels of other cytokines including IL-1β, IL-4, IL-5 and the chemokine, eotaxin can be similarly assessed in BALF samples to determine the effect of test compounds on Th-2 related function.

Determination of Ovalbumin Specific Immunoglobulin E in Serum.

The effects of compounds on serum immunoglobulin E (IgE) levels in rodents that have undergone allergen-induced (e.g. ovalbumin) airway cell proliferation and inflammation can be measured using an assay developed with reference to Salgado et al., Allergol. et Immunopathol., 16, 2 (95-98), 1988. Serum samples are taken from rats suffering from asthma, induced by the inhalation of ovalbumin, and stored at −80° C. until use. The ELISA plate is coated with 1.25 mg/mL ovalbumin prepared in coating buffer (0.5M Carbonate-Bicarbonate, pH 9.6, Bethyl Labs, Catalog #E107) and incubated overnight at 4° C. After 18 hours, the plate is washed one time with wash buffer (50 mM Tris, 0.14 M NaCl, 0.05% Tween 20, pH 8.0, Bethyl Labs, Catalog #E106). 200 μL of blocking solution (5% skim milk/PBS) is added and the plate is incubated at 4° C. for 1 hour. Serum samples are diluted 1:3000 in sample diluent (Post coat solution containing 50 mM Tris, 1% BSA, pH 8.0 0.05% Tween 20, Bethyl Labs, Catalog #E104). After the one hour incubation with blocking solution, the plate is washed three times with wash solution and 100 μL of diluted sample is added to the appropriate well. Samples are then incubated at room temperature for 3 hours. Once the 3 hour incubation is complete, the plate is washed five times with wash buffer. The sheep anti-rat IgE HRP conjugate detection antibody (Bethyl Labs, Catalog #A110-117P) is diluted 1:100 in a 1% skim milk/PBS solution. 100 μL of this solution is then added to the plate and the plate is incubated for 1 hour at 4° C. The plate is then washed another five times with wash buffer. The TMB peroxidase substrate (Bethyl Labs, Catalog #E102) is prepared by adding equal volumes of TMB peroxidase substrate with Peroxidase solution B. 100 μL of substrate is added to plate and incubated at room temperature for 15 minutes. The enzymatic reaction is stopped by adding 100 μL of 2 M sulfuric acid (Sigma Aldrich). The plate is then read at a wavelength of 450 nm.

Determination of Methacholine Responsiveness in Mice 2-8 Weeks of Age

Complete protocol details for this model can be found in Bozanich et al. (J Appl Physiol 103: 542-546, 2007). Briefly, the animals are prepared, anaesthetized, tracheotimized, connected to a ventilator, and cannulated as described. Two small electrodes are placed into the intercostal muscles of the mouse and connected to an electrical stimulator (Grass Instruments, Quincy, Mass.). Ventilation is paused, the positive end-expiratory pressure is removed with the airway, and the plethysmograph is opened to atmosphere to allow the lungs to reach the elastic equilibrium volume at transrespiratory pressure of 0 hPa, defined as functional residual capacity (FRC). With the plethysmograph closed and the airway occluded, five to eight stimulated breathing efforts are induced over a 10 sec period. FRC is then calculated using Boyle's principle. Lung volume (VL) is then increased by lowering the plethysmograph pressure from 0 to −20 hPa in a quasi-linear fashion during 15-20 sec. The increase in VL from FRC to transrespiratory pressure=20 hPa (VL20) achieved during the slow deep inflation (sDI) maneuver is determined by integrating the flow into the animal through the wave tube as described. The inflation phase is followed by a slow passive expiration to transrespiratory pressure=0 hPa, where the measurement of FRC is repeated in a subgroup of animals. Respiratory system impedance (Zrs) is measured using a low-frequency (4-38 Hz) forced oscillation technique and a wave-tube system as described. Doubling doses (6-48 ug/min-kg) of beta-methacholine chloride (MCh; Sigma-Aldrich) are delivered for 5 min by constant infusion via the jugular vein cannula. A steady-state constriction is achieved by 5 min and is verified by monitoring tracheal pressure during mechanical ventilation. FRC is measured, and a single slow deep inhalation (sDI) maneuver is performed with the infusion continuing to run. Test compound or vehicle alone is administered, for example, orally, twice daily for 1-4 days prior to receiving the MCh treatment and may also include dosing approximately 4 hours before MCh treatment. Differences in FRC before and after an sDI maneuver performed at baseline and the maximum MCh dose in a mice subgroups (for example, 3-10 mice from each age group) are determined using paired t-tests. MCh responsiveness in the presence and absence of test compound is calculated as described for each animal group.

Murine Model of Atopic Dermatitis.

This model is described, for example, by Spergel et. al. (1998 J. Clin. Invest. 101: 1614-1622). Epicutaneous (EC) sensitization of mice was performed as described by Wang et al. (1996 J. Immunol. 156:4079-4082). Briefly, 4-6 week old BALB/c mice were anesthetized with methoxyflurane (Metofane; Mallinckrodt Veterinary, Mundelein, Ill.), then shaved with an electric razor. 100 μg of OVA (grade V; Sigma Chemical Co., St. Louis, Mo.) in 100 μl of normal saline or placebo (100 μl of normal saline) was placed on a 1×1 cm patch of sterile gauze, which was secured to the skin with a transparent bioocclusive dressing (Johnson and Johnson Medical Inc., Arlington, Tex.). The patch was placed for a 1-wk period and then removed. 2 wk later, an identical patch was reapplied to the same skin site. Each mouse had a total of three 1-wk exposures to the patch separated from each other by 2-wk intervals. Inspection confirmed that the patch remained in place at the end of each sensitization period. For a positive control, intraperitoneal (IP) sensitization of another group of mice was performed with OVA (100 μg)-alum and boosted 2 wk later with the same dose of OVA in alum.

Mice are bled and sera collected 1 hour following the end of the series of three EC sensitizations by the standard PharMingen ELISA protocol used to quantify the total amount of IgE in serum. OVA specific antibodies in the serum can also be assessed, as well as cellular infiltrate into the skin by histological and immunohistochemical analysis. Also, the presence of mRNA for cytokines in skin sites sensitized with OVA can be detected via RT-PCR (protocol details are fully described in Spergel et. al., 1998 J. Clin. Invest. 101: 1614-162).

BAL fluid can also be examined in this model. EC sensitized mice are challenged with a single exposure to inhaled 1% OVA via a nebulizer for 20 minutes, and 24 hours later BAL fluid is examined for the presence of eosinophils and other cellular infiltrate (protocol details are fully described in Spergel et. al., 1998 J. Clin. Invest. 101: 1614-162).

Airway hyper responsiveness can also be assessed in this model described by Spergel et. al., 1996. Briefly, 24 hours after one dose of nebulized 1% OVA, airway measurements are measured plethysmographically in sedated, ventilated mice in response to graded doses of intravenous methacholine.

DK-PGD2-Induced Systemic Eosinophilia in Rats.

Female Sprague-Dawley rats (175-250 g) were dosed orally with test compound (or vehicle). Thirty minutes after dosing, animals were anaesthetized with isoflurane. Following induction of anesthesia, animals received an intracardiac injection of 10 μg DK-PGD2 in 0.3 ml heparinized (10 U/ml) saline. Control animals received an injection of 0.3 ml heparinized saline. Sixty minutes after the intracardiac injection, animals were again anesthetized with isoflurane and a blood sample was drawn from the abdominal aorta (into heparin) while the rat was anaesthetized but not dead. An aliquot of blood (500 μL) was mixed with an equal volume of 4% dextran (mw 500,000) and the erythrocytes were allowed to settle. A cytospin preparation was made from the resulting leukocyte rich fraction (top) and the cytospin was fixed and stained with Diff-Quick Stain kit (Dade Behring Inc, Newark, Del.). An aliquot of the leukocyte rich fraction was taken for total leukocyte count using flow cytometer (Guava EasyCyte Mini system). Differential leukocyte counts were obtained from the cytospin preparations. Blood eosinophil numbers were determined from the total leukocyte count and the percentage eosinophils.

Human Whole Blood CD11B Antagonist Assay (Modified from Nicholson, et al. Pulmonary Pharmacology and Therapeutics: 20 (2007); 52-59).

The potential CRTH2 antagonist activity of certain compounds was tested in human whole blood using an assay that tests the ability of the compounds to block the CD11b expression in eosinophils by 15-R-methyl-PGD2. A CRTH2 antagonist should block CD11b expression by subsequently added 15-Methyl-PGD2. Human whole blood (200 μL) was incubated at 37° C. for 10 minutes in the presence of various concentrations of test compounds before being challenged with the agonist 15R-Methyl-PGD2 (10 nM). Reactions were terminated by the addition of ice-cold PBS+0.5% BSA+2 mMEDTA (1 mL) and centrifugation (300×g for 5 minutes at 4° C.) Cells were then incubated at 4° C. for 10 min in the presence of human IgG. Cells were then incubated for 30-45 min with a mixture of PE-Cy5-labeled mouse anti-human CD16 (10 ul; BD Biosciences) and FITC-labeled mouse anti-human CD11b (10 μL; Beckman Coulter.) After rinsing (1 mL ice-cold PBS+0.5% BSA+2 mMEDTA), red blood cells were lysed by the addition of 1 mL ice-cold $H_2O$ to the cell pellet for 30 sec-1 min immediately followed by the addition of 3.5% NaCl (300 μL.) Cells were then rinsed (2×-1 ml ice cold PBS+0.5% BSA+2 mMEDTA) and fixed in PBS containing 1% formaldehyde. The distribution of fluorescence intensities was measured by flow cytometry. Eosinophils were gated out on the basis of their granularity (high side scatter) and absence of CD-16. CD11b was then measured on this eosinophil population on the basis of fluorescence due to FITC.

DPBS CD11b Antagonist Assay.

The potential CRTH2 antagonist activity of certain compounds was tested using a CD11b expression assay using essentially the method described by Monneret et al. (J Pharmacol Exp Ther 304:349-55, 2003). Briefly, polymorphonuclear cells (0.5 ml; $10^6$/ml cells) in PBS containing 0.9 mM $CaCl_2$ and 0.5 mM $MgCl_2$) were preincubated with various concentrations of test compounds at room temperature for 10 minutes before they were challenged with the agonist 15R-Methyl-PGD2 (10 nM). The incubations were terminated by the addition of ice-cold FACSFlow (BD Biosciences; Cat# 342003) and centrifugation (400 g for 5 minutes at 4° C.). The cells were then incubated for 30 minutes at 4° C. with a mixture of PE-labeled mouse anti-human VLA-4 (5 μl; BD Biosciences) and FITC-labeled mouse anti-human CD11b (10 μl; Beckman Coulter). The cells were then incubated with Optilyse C (0.25 ml; Beckman Coulter) for 15 minutes, centrifuged, and then fixed in PBS (0.4 ml; calcium and magnesium free) containing 1% formaldehyde. The distribution of fluorescence intensities among 60,000 cells was measured by flow cytometry. Eosinophils were gated out on the basis of their granularity (high side scatter) and labeling with VLA-4 (PE fluorescence). CD11b was then measured in the eosinophil region on the basis of fluorescence due to FITC. All data were corrected for the value obtained for the corresponding isotope control antibody.

Data for compounds of the invention are summarized in Table 2.

TABLE 2

| compound number | CD11b Antag IC50(nM) [HuEos-DPBS-vs10nM15R] | CD11b Antag IC50(nM) [HuEos-HuWB-vs10nM15R] |
|---|---|---|
| I-20 | D | |
| I-9 | B | B |
| I-72 | C | D |
| I-32 | A | B |
| I-6 | A | C |
| I-4 | A | B |
| I-53 | A | B |
| I-23 | A | B |
| I-56 | D | C |
| I-55 | A | B |
| I-52 | A | B |
| I-29 | A | B |
| I-46 | B | B |
| I-63 | D | D |
| I-57 | A | B |
| I-25 | B | D |
| I-73 | | D |
| I-16 | | C |
| I-13 | | B |
| I-18 | | D |
| I-15 | | C |
| I-8 | | B |
| I-2 | | B |
| I-12 | | B |
| I-1 | | A |
| I-17 | | C |
| I-27 | | D |
| I-14 | | C |
| I-3 | | B |
| I-11 | | B |

Activity for CD11b Antagonist Activity (DPBS or Human Whole Blood):
A: Less than 5 nM
B: From 5 nM to less than 100 nM
C: From 100 nM to less than 500 nM
D: Greater than 500 nM
Empty cells indicate that the test was not done.

A number of embodiments have been described. Nevertheless, it will be understood that various modifications may be made without departing from the spirit and scope of the invention.

We claim:
1. A compound having Formula I, or a pharmaceutically acceptable salt thereof;

Formula I with the proviso that the compound having Formula I is not a compound selected from 5[[6-methoxy-3-(4-methoxybenzoyl)-2-methyl-1H-pyrrolo[2,3-b]pyridin-1-yl] methyl]-α,α-dimethyl-2H-Tetrazole-2-acetic acid [CAS Registry No. 1097838-63-5], 5-[[5-(benzoylamino)-2-thiazolyl]thio]-2H-tetrazole-2-acetic acid [CAS Registry No. 1099441-56-1], 2-butyl-1-[[4-[(2-carboxybenzoyl)amino]phenyl]methyl]-5-chloro-1H-imidazole-4-acetic acid [CAS Registry No. 114798-40-2], and 2-butyl-1-[[4-[(2-carboxybenzoyl)amino] phenyl]methyl]-5-chloro-1H-imidazole-4-acetic acid [CAS Registry No. 114773-45-4],
wherein:
ring A is a phenyl or pyrrolidinyl;
ring B is a phenyl;
ring D is an optionally substituted pyrrolyl; wherein
   $x^1$ is N;
   $x^2$ is C—$R^2$;
   $x^3$ is C;
   $x^4$ is C—$R^4$; and
   $x^5$ is C—$R^5$;
$R^2$ is selected from —H, a halogen, —CN, a $C_{1-6}$ aliphatic radical, a $C_{1-6}$ alkoxy and a cyclopropyl ring, wherein $R^2$ is independently substituted with from 0 to 3 instances of $R^A$; wherein
   each $R^A$ is independently selected from a halogen, —OH, a $C_{1-2}$ alkoxy and a $C_{1-2}$ haloalkoxy;
$R^4$ is selected from a halogen, —CN, —$R^6$, —O$R^6$, —C(O)$R^6$, —C(O)O$R^6$, —N($R^6$)$_2$;
$R^5$ is selected from a halogen, —CN, —$R^6$, —O$R^6$, —C(O)$R^6$, —N($R^6$)$_2$;
p is an integer selected from 0, 1 and 2;
each $R^6$ is independently selected from —H, a $C_{1-6}$ aliphatic radical,
   a 6 membered aryl ring, a 5 or 6 membered heteroaryl ring, and a $C_{3-10}$ cycloaliphatic ring;
   wherein
      when $R^6$ is a $C_{1-6}$ aliphatic radical, it is independently substituted with from 0 to 6 instances of $R^7$,
      when $R^6$ is a $C_{3-10}$ cycloaliphatic ring or a 5 or 6-membered heteroaryl, it is independently substituted with from 0 to 6 instances of $R^8$, and
      when $R^6$ is 6-membered aryl, it is independently substituted with from 0 to 6 instances of $R^{8'}$;
      each $R^7$ is independently selected from a halogen, —CN, oxo, —O$R^9$ and —C(O)$R^9$;
      each $R^8$ is independently selected from a halogen, —CN, oxo, a $C_{1-6}$ aliphatic radical, and —C(O)$R^9$;
      each $R^{8'}$ is independently selected from a halogen, —CN, a $C_{1-6}$ aliphatic radical, and —C(O)$R^9$;
      each $R^9$ is independently selected from hydrogen, a $C_{1-6}$ aliphatic radical,
         a 6 membered aryl, a 5 or 6 membered heteroaryl, and a $C_{3-10}$ cycloaliphatic; wherein
         when $R^9$ is a $C_{1-6}$ aliphatic radical, it is independently substituted with from 0 to 6 instances of $R^{11}$, and
         when $R^9$ is a 6-membered aryl, a 5 or 6-membered heteroaryl, or a $C_{3-10}$ cycloaliphatic ring, it is independently substituted with from 0 to 3 instances of $R^{12}$;
      each $R^{11}$ is independently selected from a halogen, —CN, —OH, a $C_{1-4}$ alkoxy and a $C_{1-4}$ haloalkoxy;
      each $R^{12}$ is independently selected from a halogen, —CN, —OH, a $C_{1-4}$ alkyl, a $C_{1-4}$ haloalkyl, a $C_{1-4}$ alkoxy and a $C_{1-4}$ haloalkoxy;
$R^{13}$ is selected from —H, a $C_{1-6}$ aliphatic radical, and a monocyclic or bicyclic ring, wherein the ring is selected from a 6 to 10-membered aryl, a 5 to 10-membered heteroaryl, a $C_{3-10}$ cycloaliphatic and a 4 to 10-membered heterocycle; wherein
   when $R^{13}$ is a $C_{1-6}$ aliphatic radical, it is independently substituted with from 0 to 6 instances of $R^{14}$;
   when $R^{13}$ is a non-aromatic ring or a heteroaryl, it is independently substituted with from 0 to 6 instances of $R^{15}$; and
   when $R^{13}$ is an aryl, it is independently substituted with from 0 to 6 instances of $R^{15'}$;
      each $R^{14}$ is independently selected from a halogen, —CN, oxo, —O$R^9$, —$R^{10}$, —C(O)$R^9$, —C(O) O$R^9$, —S(O)$_m R^9$, —N($R^9$)$_2$, —S(O)$_2$N($R^9$)$_2$, —N$R^9$S(O)$_2 R^9$, —C(O)N($R^9$)$_2$ and —N$R^9$C(O) $R^9$;
      each $R^{15}$ is independently selected from a halogen, —CN, —NO$_2$, oxo, a $C_{1-6}$ aliphatic radical, —$R^{10}$, —C(O)$R^9$, —C(O)O$R^9$, —O$R^9$, —S(O)$_m R^9$, —N($R^9$)$_2$, —S(O)$_2$N($R^9$)$_2$, —N$R^9$S(O)$_2 R^9$, —C(O)N($R^9$)$_2$ and —N$R^9$C(O)$R^9$; and
      each $R^{15'}$ is independently selected from a halogen, —CN, —NO$_2$, a $C_{1-6}$ aliphatic radical, —$R^{10}$, —C(O)$R^9$, —C(O)O$R^9$, —O$R^9$, —S(O)$_m R^9$, —N($R^9$)$_2$, —S(O)$_2$N($R^9$)$_2$, —N$R^9$S(O)$_2 R^9$, —C(O)N($R^9$)$_2$ and —N$R^9$C(O)$R^9$;
$R^{16}$ and $R^{17}$ are each independently selected from —H, deuterium, a $C_{1-6}$ alkyl, a $C_{1-6}$ haloalkyl and a halogen, or
alternatively, $R^{16}$ and $R^{17}$ are independently selected from a $C_{1-6}$ alkyl and a $C_{1-6}$ haloalkyl, and $R^{16}$ and $R^{17}$ taken together with the atom to which they are attached form a cyclopropyl or halocyclopropyl ring;
L is a linker selected from a methylene, —O—, —S(O)$_m$— and —N$R^1$—; wherein
   when L is a methylene, it is independently substituted with from 0 to 2 instances of $R^{18}$;
m is 0, 1 or 2;
$R^1$ is selected from —H, a $C_{1-6}$ aliphatic radical, a $C_{3-6}$ cycloaliphatic, —CO($C_{1-6}$ aliphatic), —CO($C_{3-6}$ cycloaliphatic), —CO—(phenyl), a benzyl and —CO—(benzyl); wherein
   when $R^1$ is selected from a $C_{1-6}$ aliphatic radical, —CO—(phenyl), a benzyl and —CO—(benzyl), it is independently substituted with from 0 to 3 instances of $R^B$; wherein each $R^B$ is independently selected from a halogen, a $C_{1-2}$ alkyl and a $C_{1-2}$ alkoxy;

each $R^{18}$ is independently selected from a halogen, —CN, a $C_{1-6}$ aliphatic radical, a $C_{1-6}$ haloaliphatic radical, and a $C_{3-6}$ cycloaliphatic; or alternatively, each $R^{18}$ is independently selected from a $C_{1-6}$ aliphatic radical and a $C_{1-6}$ haloaliphatic radical, and two $R^{18}$ groups, taken together with the atom to which they are attached form a cyclopropyl or halocyclopropyl ring;

o is an integer selected from 0, 1 and 2;

each $J^B$ is independently selected from a halogen, —$NO_2$, —CN, —$R^{19}$, —C(O)H, —C(O)OH, —C(O)$NH_2$, —OH, —SH, —$NH_2$, —C(O)$R^{19}$, —C(O)$OR^{19}$, —C(O)N($R^{20}$)$R^{19}$, —N($R^{20}$)C(O)$R^{19}$, —$OR^{19}$, —$SR^{19}$ and —$NR^{19}R^{20}$;

each $R^{20}$ is independently selected from a —H and a $C_{1-6}$ aliphatic radical;

each $R^{19}$ is independently selected from a $C_{1-6}$ aliphatic radical, a $C_{3-6}$ cycloaliphatic, a phenyl, a benzyl; wherein when $R^{19}$ is a $C_{1-6}$ aliphatic radical, it is independently substituted with from 0 to 3 instances of $R^C$, wherein each $R^C$ is independently selected from a halogen, —CN, —OH, —$NH_2$, a $C_{3-4}$ cycloalkyl, a $C_{3-4}$ halocycloalkyl, a —O ($C_{1-4}$ alkyl), a —O($C_{3-4}$ cycloalkyl), a —O($C_{3-4}$ halocycloalkyl), a —O($C_{1-4}$ haloalkyl), a —NH($C_{1-4}$ alkyl), and a —N($C_{1-4}$ alkyl)$_2$; wherein when $R^{19}$ is a phenyl, it is independently substituted with from 0 to 3 instances of $R^D$, wherein each $R^D$ is independently selected from a halogen, a $C_{1-4}$ aliphatic radical, —CN, —OH, —$NH_2$, a —O($C_{1-4}$ alkyl), a —NH($C_{1-4}$ alkyl) and a —N($C_{1-4}$ alkyl)$_2$; and when $R^{19}$ is a $C_{3-6}$ cycloaliphatic, it is independently substituted with from 0 to 3 instances of $R^{D'}$, wherein each $R^{D'}$ is independently selected from a halogen, oxo, a $C_{1-4}$ aliphatic radical, —CN, —OH, —$NH_2$, a —O($C_{1-4}$ alkyl), a —NH($C_{1-4}$ alkyl) and a —N($C_{1-4}$ alkyl)$_2$;

L' is a linker selected from —Y—$SO_2$—, —$NR^{21}SO_2$—, —$SO_2NR^{21}$—, —Y—C(O)—, —$NR^{21}$C(O)— and —C(O)$NR^{21}$—; wherein Y is selected from a single bond, a straight $C_{1-2}$ alkylene linker, and a branched $C_2$ alkylene linker, wherein the $C_{1-2}$ alkylene linker is independently substituted with from 0 to 3 halogen atoms;

$R^{21}$ is selected from hydrogen, a $C_{1-6}$ alkyl, and a $C_{1-6}$ haloalkyl; n is an integer selected from 0, 1, 2 and 3;

each $J^A$ is independently selected from a halogen, —CN, —$R^{22}$, —C(O)H, —C(O)OH, —C(O)$NH_2$, —OH, —SH and —$NH_2$, —C(O)$R^{22}$, —C(O)$OR^{22}$, —C(O)N($R^{23}$)$R^{22}$, —N($R^{23}$)C(O)$R^{22}$, —$OR^{22}$, —$SR^{22}$ and —$NR^{22}R^{23}$;

each $R^{23}$ is independently selected from a —H and a $C_{1-6}$ aliphatic radical;

each $R^{22}$ is independently selected from a $C_{1-6}$ aliphatic radical, a $C_{3-6}$ cycloaliphatic ring, a phenyl, and a benzyl; wherein when $R^{22}$ is a $C_{1-6}$ aliphatic radical, it is independently substituted with from 0 to 3 instances of $R^F$, wherein each $R^F$ is independently selected from a halogen, —CN, —OH, —$NH_2$, a $C_{3-4}$ cycloalkyl, a $C_{3-4}$ halocycloalkyl, a —O($C_{1-4}$ alkyl), a —O($C_{3-4}$ cycloalkyl), a —O($C_{3-4}$ halocycloalkyl), a —O($C_{1-4}$ haloalkyl), a —NH($C_{1-4}$ alkyl), and a —N($C_{1-4}$ alkyl)$_2$;

when $R^{22}$ is a $C_{3-4}$ cycloalkyl ring, it is independently substituted with from 0 to 3 instances of $R^G$, wherein each $R^G$ is independently selected from a halogen, oxo, a $C_{1-4}$ aliphatic radical, —CN, —OH, —$NH_2$, a —O($C_{1-4}$ alkyl), a —NH($C_{1-4}$ alkyl) and a —N($C_{1-4}$ alkyl)$_2$; and when $R^{22}$ is a phenyl, it is independently substituted with from 0 to 3 instances of $R^{G'}$, wherein each $R^{G'}$ is independently selected from a halogen, a $C_{1-4}$ aliphatic radical, —CN, —OH, —$NH_2$, —O($C_{1-4}$ alkyl), —NH($C_{1-4}$ alkyl) and —N($C_{1-4}$ alkyl)$_2$.

2. The compound of claim 1, wherein $R^{16}$ and $R^{17}$ are each independently selected from —H and a methyl or, alternatively, $R^{16}$ and $R^{17}$ taken together with the carbon to which they are attached, form a cyclopropyl ring.

3. The compound according to claim 2, wherein $R^{16}$ and $R^{17}$ are both —H.

4. The compound according to claim 1, wherein the compound is selected from compounds having formula IA:

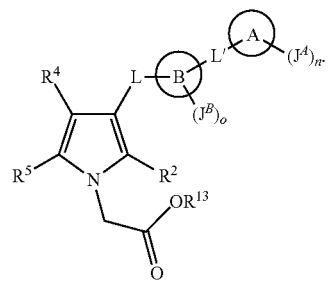

IA

5. The compound according to claim 1, wherein L is selected from a methylene, and —S—.

6. The compound according to claim 5, wherein L is selected from a methylene and —S—.

7. The compound according to claim 6, wherein the compound is selected from compounds having formula IIA or formula IIB:

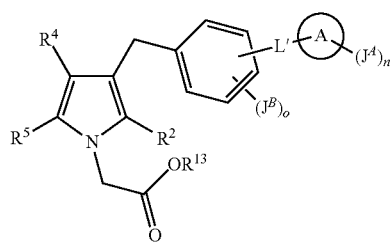

IIA

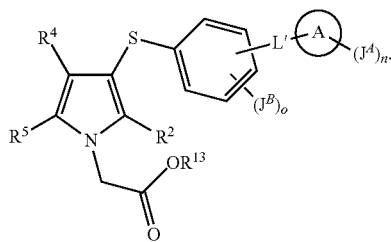

IIB

8. The compound of claim 1, wherein $R^2$ is selected from a halogen, —H, a cyclopropyl ring, a $C_{1-4}$ alkyl and a $C_{1-4}$ haloalkyl.

9. The compound according to claim 8, wherein R² is selected from a C₁₋₄ alkyl and —H.

10. The compound according to claim 9, wherein R² is a methyl.

11. The compound according to claim 10, wherein the compound is selected from compounds having structural formula IIIA or structural formula IIIB:

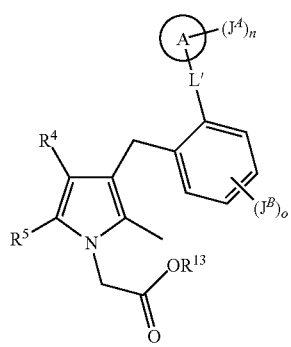

IIIA

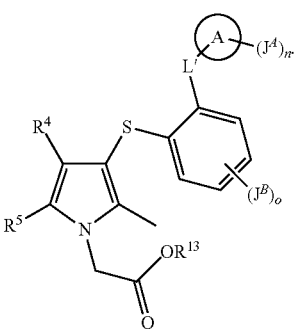

IIIB

12. The compound according to claim 1, wherein L' is selected from —SO₂— and —CH₂SO₂—.

13. The compound according to claim 12, wherein L' is —SO₂—.

14. The compound of claim 1, wherein o is 0.

15. The compound according to claim 14, wherein the compound is selected from compounds having structural formula IVA or structural formula IVB:

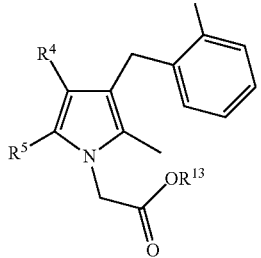

IVA

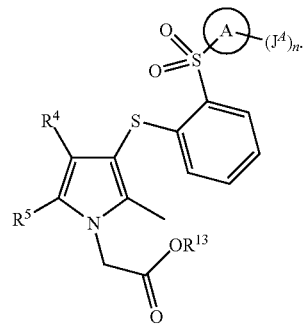

IVB

16. The compound of claim 1, wherein ring A is phenyl.

17. The compound of claim 1, wherein ring A is pyrrolidinyl.

18. The compound of claim 1, wherein ring A is selected from a phenyl and an N-linked pyrrolidinyl.

19. The compound of claim 18, wherein the compound is selected from compounds having structural formula VA, VC, VD or VF:

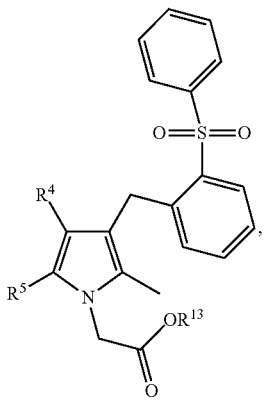

VA

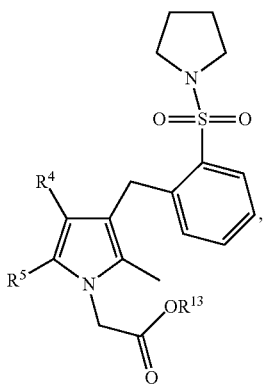

VC

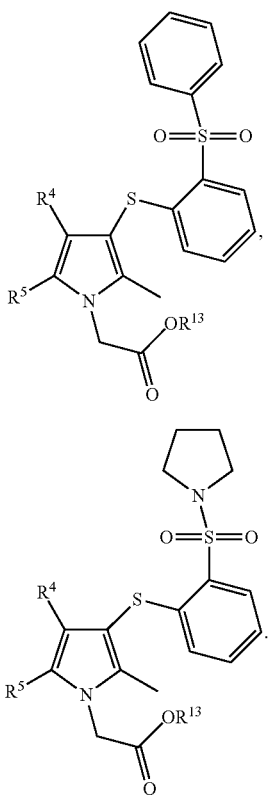

20. The compound of claim 1, wherein $R^4$ is selected from a halogen, —CN, —$R^6$, —$OR^6$, —$C(O)R^6$, —$C(O)OR^6$, —$N(R^6)_2$, —$S(O)_pR^6$, —$S(O)_2N(R^6)_2$, —$NR^6S(O)_2R^6$, —$C(O)N(R^6)_2$ and —$NR^6C(O)R^6$.

21. The compound of claim 20, wherein $R^4$ is selected from a —H, a halogen, —CN, a $C_{1-6}$ aliphatic radical, a $C_{3-6}$ cycloaliphatic ring, a $C_{1-6}$ haloaliphatic radical, a phenyl which is optionally substituted by $R^{8'}$, a benzyl which is optionally substituted by $R^{8'}$, —$OR^6$ and —$C(O)R^6$.

22. The compound of claim 21, wherein $R^4$ is selected from —H, a halogen, —CN, a $C_{1-4}$ alkyl, a $C_{1-4}$ haloalkyl, a $C_{3-6}$ cycloalkyl, a —$O(C_{1-4}$ alkyl), a —$O(C_{1-4}$ haloalkyl), a —$O(C_{3-6}$ cycloalkyl), a —O(phenyl), a —O(substituted phenyl), a —O(benzyl), a —O(substituted benzyl), a —C(O)($C_{1-4}$ alkyl), a —C(O)($C_{1-4}$ haloalkyl), a —C(O)($C_{3-6}$ cycloalkyl), a —C(O)(phenyl), a —C(O)(substituted phenyl), a —C(O)(benzyl), —C(O)(substituted benzyl) and —C(O)H; wherein each of said substituted phenyl or benzyl rings, is substituted by from 0 to 4 instances of $R^{8'}$.

23. The compound of claim 22, wherein $R^4$ is selected from —H, a halogen, —CN, an ethyl, a methyl, a propyl, a trifluoroethyl, a trifluoromethyl, a cyclopropyl, a cyclopentyl, a cyclohexyl, a cyclopropyloxy, a cyclopentyloxy, a cyclohexyloxy, an ethoxy, a methoxy, a propyloxy, a trifluoromethoxy, a trifluoroethoxy, a benzoyl, a phenyl, a phenyloxy, a methylcarbonyl, an ethylcarbonyl, a trifluoromethylcarbonyl, a trifluoroethylcarbonyl, and —C(O)H; wherein each of said benzoyl, phenyl or phenyloxy is independently substituted by from 0 to 4 instances of $R^{8'}$.

24. The compound of claim 23, wherein $R^4$ is selected from a —H, a halogen, —CN, an ethyl, a methyl, a propyl, a trifluoroethyl, a trifluoromethyl, a cyclopropyl, a cyclopentyl, a cyclohexyl, phenyl, a benzoyl, a methylcarbonyl, an ethylcarbonyl, a trifluoromethylcarbonyl, a trifluoroethylcarbonyl and —C(O)H; wherein each of said phenyl and benzoyl groups is independently substituted by from 0 to 4 instances of $R^{8'}$.

25. The compound of claim 24, wherein $R^4$ is selected from a —H, iodo, —CN, methyl, 2,2,2-trifluoroethyl, benzoyl, methylcarbonyl, trifluoromethylcarbonyl, —C(O)H and phenyl; wherein said phenyl is independently substituted with from 0 to 2 instances of halogen.

26. The compound of claim 25, wherein $R^4$ is a phenyl substituted with from 0 to 2 instances of halogen.

27. The compound of claim 26, wherein $R^4$ is a phenyl substituted with from 0 to 2 instances of fluoro.

28. The compound of claim 25, wherein $R^4$ is selected from a —H, —CN, a methyl, 2,2,2-trifluoroethyl, a benzoyl, a methylcarbonyl, a trifluoromethylcarbonyl, —C(O)H, a phenyl and a fluorophenyl; wherein said fluorophenyl is substituted with from 0 to 2 additional instances of fluoro.

29. The compound of claim 1, wherein $R^5$ is selected from a halogen, —CN, a $C_{1-6}$ aliphatic radical independently substituted with from 0 to 4 instances of $R^7$, a $C_{3-6}$ cycloaliphatic, a phenyl independently substituted with from 0 to 4 instances of $R^{8'}$, and a 6-membered heteroaryl independently substituted with from 0 to 4 instances of $R^{8'}$.

30. The compound of claim 29, wherein $R^5$ is selected from a halogen, —CN, a $C_{1-6}$ alkyl independently substituted with from 0 to 4 instances of $R^7$, a $C_{3-6}$ cycloaliphatic, a phenyl independently substituted by from 0 to 4 instances of $R^{8'}$, and a 6-membered heteroaryl independently substituted by from 0 to 4 instances of $R^{8'}$.

31. The compound of claim 30, wherein $R^5$ is selected from the group consisting of: a halogen, —CN; a $C_{1-6}$ alkyl substituted with from 0 to 2 instances of a substituent independently selected from halogen and —OH; a 3-6 membered cycloalkyl, a phenyl and a 6-membered heteroaryl; wherein each of said phenyl and 6-membered heteroaryl rings is substituted by from 0 to 3 instances of a substituent independently selected from a halogen, a $C_{1-4}$ alkyl, a $C_{1-4}$ haloalkyl, a $C_{1-4}$ alkoxy, a $C_{1-4}$ haloalkoxy and —CN.

32. The compound of claim 31, wherein $R^5$ is selected from a halogen, —CN, an ethyl, a methyl, a propyl, a 3-6 membered cycloalkyl, a phenyl, a pyridine and a pyrimidine; wherein each said methyl, ethyl and propyl is independently substituted with from 0 to 4 instances of a halogen or —OH; and wherein each said phenyl, pyridine and pyrimidine is substituted with from 0 to 4 instances of a substituent independently selected from a halogen, a $C_{1-2}$ alkyl, a $C_{1-2}$ haloalkyl, an $C_{1-2}$ alkoxy and a $C_{1-2}$ haloalkoxy.

33. The compound of claim 32, wherein $R^5$ is selected from —CN, an ethyl, a methyl, a propyl, a cyclopropyl, a cyclopentyl, a cyclohexyl, a phenyl and a pyridine; wherein each said methyl, propyl and ethyl is independently substituted with from 0 to 2 instances of a halogen or —OH; wherein said phenyl is independently substituted by from 0 to 2 instances of halogen or —$CF_3$; and wherein said pyridine is substituted by from 0 to 4 instances of a substituent independently selected from a halogen, a $C_{1-2}$alkoxy, a $C_{1-2}$haloalkoxy and $CF_3$.

34. The compound of claim 33, wherein $R^5$ is selected from a —CN, a 2-hydroxyethyl, a methyl, a cyclopropyl, a cyclopentyl, a cyclohexyl, a phenyl and a pyridine; wherein said phenyl is independently substituted by from 0 to 2 instances of fluorine or —$CF_3$; and wherein said pyridine is independently substituted by from 0 to 1 instances of fluoro or chloro.

35. The compound of claim 34, wherein $R^5$ is selected from —CN, a methyl, a cyclopropyl, a cyclopentyl, a cyclohexyl, a phenyl, pyridine, a 3-chloro-4-pyridinyl and a 3-chloro-2- pyridinyl; wherein said phenyl is independently substituted by from 0 to 2 instances of fluorine or from 0 to 1 instances of —CF$_3$.

36. The compound of claim 1, wherein R$^{13}$ is selected from a —H and a C$_{1-6}$ alkyl.

37. The compound of claim 36, wherein R$^{13}$ is a —H.

38. The compound of claim 1, wherein o is 1 or 2 and J$^B$ is a halogen.

39. A compound according to claim 1 selected from those depicted in Table 1.

40. A composition comprising a pharmaceutically acceptable carrier and a compound according to claim 1 or 39.

41. A composition comprising a compound according to claim 1 or 39, in combination with one or more therapeutic agents seleted from: inactivating antibodies to interleukins; soluble chemokine receptors; a chemokine receptor modulators; histamine H1 receptor antagonists or antihistamines; leukotriene D4 receptor antagonists or leukotriene antagonists or a LTD4 antagonists; PGD2 receptor antagonists; VLA-4 antagonists; corticosteroids; immunosuppressants; non-steroidal anti-asthmatics, non-steroidal antiinflammatory agents (NSAIDs); cyclooxygenase-2 (COX-2) inhibitors; inhibitors of phosphodiesterase type IV (PDE-IV); opioid analgesics; antithrombotic agents; warfarin derivatives, β-blockers; β-adrenergic agonists; ACE inhibitors; vasodilators; anti-diabetic agents; preparations of interferon beta; gold compounds such as auranofin and aurothioglucose; TNF inhibitors; multiple sclerosis therapeutic agents; 5-aminosalicylic acid and prodrugs thereof; DNA-alkylating agents; antimetabolites; microtubule disruptors; DNA intercalators; DNA synthesis inhibitors; DNA cross-linking agents; hormone therapy; or cytostatic agents; and a pharmaceutically acceptable carrier.

42. The compound of claim 1, having the following formula,

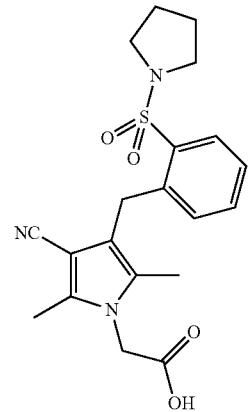 [SMILES: Cc1c(C#N)c(Cc2ccccc2S(=O)(=O)N2CCCC2)c(C)n1CC(=O)O]

or a pharmaceutically acceptable salt thereof.

* * * * *